(12) United States Patent
Zhu et al.

(10) Patent No.: US 12,247,089 B2
(45) Date of Patent: *Mar. 11, 2025

(54) PHOTO-COUPLED SYNERGISTICALLY CROSSLINKED HYDROGEL MATERIAL AND ITS COMPOSITION, PREPARATION METHOD, USE, PRODUCT, AND PREPARATION KIT

(71) Applicant: Zhongshan Guanghe Medical Technology Co., Ltd., Guangdong (CN)

(72) Inventors: Linyong Zhu, Shanghai (CN); Yujie Hua, Shanghai (CN); Qiuning Lin, Shanghai (CN); Yiqing Zhang, Shanghai (CN); Chunyan Bao, Shanghai (CN); Xuepeng Zhong, Shanghai (CN)

(73) Assignee: ZHONGSHAN GUANGHE MEDICAL TECHNOLOGY CO., LTD., Guangdong (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/848,352

(22) Filed: Apr. 14, 2020

(65) Prior Publication Data
US 2020/0262939 A1  Aug. 20, 2020

Related U.S. Application Data

(63) Continuation of application No. PCT/CN2018/080174, filed on Mar. 23, 2018.

(30) Foreign Application Priority Data

Nov. 15, 2017 (CN) .......................... 201711132436.6

(51) Int. Cl.
*C08B 37/08* (2006.01)
*A61K 31/722* (2006.01)
(Continued)

(52) U.S. Cl.
CPC ........ *C08B 37/0072* (2013.01); *A61K 31/722* (2013.01); *A61K 31/727* (2013.01);
(Continued)

(58) Field of Classification Search
CPC ... C08B 37/0072; C08B 11/12; C08B 37/003; C08B 37/0069; C08B 37/0075;
(Continued)

(56) References Cited

U.S. PATENT DOCUMENTS 6,020,480 A    2/2000  Cohen et al.
10,294,335 B2*  5/2019  Zhu ..................... A61L 27/28
(Continued)

FOREIGN PATENT DOCUMENTS

CA    2941395      9/2015
CN    102531910    7/2012
(Continued)

OTHER PUBLICATIONS

Oommen et al., "Smart Design of Stable Extracellular Matrix Mimetic Hydrogel: Synthesis, Characterization, and in Vitro and in Vivo Evaluation for Tissue Engineering", Advanced Functional Materials, first published Oct. 12, 2012, pp. 1273-1280, discussed in Specification.
(Continued)

*Primary Examiner* — Blessing M Fubara
(74) *Attorney, Agent, or Firm* — HSML P.C.

(57) ABSTRACT

This invention provides a preparation, composition, product, and application of a photo-coupled synergistically crosslinked hydrogel material. The preparation includes dissolving Component A including a photosensitive polymer
(Continued)

derivative having o-nitrobenzyl phototriggers and Component B including a polymer derivative having amine or alkene (double group) or sulfhydryl group in a biocompatible medium to obtain solution A and solution B, respectively; mixing the solution A and solution B homogeneously to obtain a hydrogel precursor solution; initiating photocoupled synergistic crosslinking under an irradiation of a UV light to form the hydrogel. The irradiation causes the o-nitrobenzyl phototriggers to generate an aldehyde group/keto group or a nitroso group to initiate photo-coupled synergetic crosslinking. The photo-coupled synergistically crosslinked hydrogel has applications in tissue engineering, regenerative medicine, 3D printing and as a carrier of cell, protein or drug.

16 Claims, 5 Drawing Sheets

(51) Int. Cl.
| | | |
|---|---|---|
| A61K 31/727 | (2006.01) | |
| A61K 31/728 | (2006.01) | |
| A61K 31/737 | (2006.01) | |
| A61K 31/738 | (2006.01) | |
| A61K 31/77 | (2006.01) | |
| A61K 31/785 | (2006.01) | |
| A61L 24/00 | (2006.01) | |
| A61L 24/04 | (2006.01) | |
| A61L 24/08 | (2006.01) | |
| A61L 26/00 | (2006.01) | |
| A61L 27/18 | (2006.01) | |
| A61L 27/20 | (2006.01) | |
| A61L 27/52 | (2006.01) | |
| B33Y 70/00 | (2020.01) | |
| C07D 273/01 | (2006.01) | |
| C07D 291/08 | (2006.01) | |
| C08B 11/12 | (2006.01) | |
| C08B 37/00 | (2006.01) | |
| C08G 65/334 | (2006.01) | |
| C08G 69/48 | (2006.01) | |
| C08J 3/075 | (2006.01) |

(52) U.S. Cl.
CPC .......... *A61K 31/728* (2013.01); *A61K 31/737* (2013.01); *A61K 31/738* (2013.01); *A61K 31/77* (2013.01); *A61K 31/785* (2013.01); *A61L 24/0031* (2013.01); *A61L 24/046* (2013.01); *A61L 24/08* (2013.01); *A61L 26/0019* (2013.01); *A61L 26/0023* (2013.01); *A61L 26/008* (2013.01); *A61L 27/18* (2013.01); *A61L 27/20* (2013.01); *A61L 27/52* (2013.01); *B33Y 70/00* (2014.12); *C07D 273/01* (2013.01); *C07D 291/08* (2013.01); *C08B 11/12* (2013.01); *C08B 37/003* (2013.01); *C08B 37/0069* (2013.01); *C08B 37/0075* (2013.01); *C08G 65/3348* (2013.01); *C08G 69/48* (2013.01); *C08J 3/075* (2013.01); *C08J 2301/28* (2013.01); *C08J 2305/00* (2013.01); *C08J 2305/08* (2013.01); *C08J 2305/10* (2013.01); *C08J 2371/02* (2013.01); *C08J 2377/04* (2013.01)

(58) Field of Classification Search
CPC .... B33Y 70/00; A61K 31/722; A61K 31/727; A61K 31/728; A61K 31/737; A61K 31/738; A61K 31/77; A61K 31/785; A61L 24/0031; A61L 24/08; A61L 26/0019; A61L 26/0023; A61L 26/008; A61L 27/18; A61L 27/20; A61L 27/52; C07D 273/01; C07D 291/08; C08G 65/3348; C08G 69/48; C08J 3/075; C08J 2301/28; C08J 2305/00; C08J 2305/08; C08J 2305/10; C08J 2371/02; C08J 2377/04

See application file for complete search history.

(56) References Cited

U.S. PATENT DOCUMENTS

| | | | |
|---|---|---|---|
| 11,117,879 B2 * | 9/2021 | Zhu | C08F 220/68 |
| 2016/0108172 A1 | 4/2016 | Sivaguru et al. | |
| 2017/0313827 A1 * | 11/2017 | Zhu | A61K 8/73 |

FOREIGN PATENT DOCUMENTS

| | | | | |
|---|---|---|---|---|
| CN | 105131315 | * | 12/2015 | ........ A61K 31/728 |
| CN | 105131315 A | | 12/2015 | |
| CN | 105153362 | | 12/2015 | |
| CN | 106349465 | | 1/2017 | |
| CN | 106822183 A | | 6/2017 | |
| WO | 2016082725 A1 | | 6/2016 | |

OTHER PUBLICATIONS

Peng et al., "Cyclodextrin-Dextran Based in Situ Hydrogel Formation: A Carrier for Hydrophobic Drugs", Soft Matter, first published Oct. 23, 2009, pp. 85-87, discussed in Specification.
Li et al., "Biodegradable and Injectable in situ Cross-linking Chitosan-Hyaluronic Acid Based Hydrogels for Postoperative Adhesion Prevention", Biomaterials, first published Feb. 4, 2014, pp. 3903-3917, discussed in Specification.
Delaittre et al., "Acrylamide-Based Copolymers Bearing Photoreleasable Thiols for Subsequent Thiol-Ene Functionalization", Macromolecules, first published Feb. 8, 2012, pp. 1792-1802, discussed in Specification.
Fu et al., "Visible-Light-Initiated Thiol-Acrylate Photopolymerization of Heparin-Based Hydrogels", BioMacromolecules, first published Dec. 23, 2014, pp. 497-506, discussed in Specification.
Ozdemir et al., "Tuning Hydrogel Properties to Promote the Assembly of Salivary Gland Spheroids in 3D", ACS Biomaterials Science & Engineering, first published Oct. 18, 2016, pp. 2217-2230, discussed in Specification.
Choi et al., "Thiolated Dextran-Coated Gold Nanorods for Photothermal Ablation of Inflammatory Macrophages", Langmuir Article, first published Oct. 7, 2010, pp. 17520-17527, discussed in Specification.
Zhang et al., "In Situ Gelable Interpenetrating Double Network Hydrogel Formulated from Binary Components: Thiolated Chitosan and Oxidized Dextran", BioMacromolecules, first published Mar. 16, 2011, pp. 1428-1437, discussed in Specification.
Cameron et al., "Photogeneration of Organic Bases from o-Nitrobenzyl-Derived Carbamates", J. Am. Chem. Soc., first published in 1991, pp. 4303-4313, discussed in Specification.
Pirrung et al., "Pentadienylnitrobenzyl and Pentadienylnitropiperonyl Photochemically Removable Protecting Groups", J. Org. Chem., first published Jun. 17, 1999, pp. 5042-5047, discussed in Specification.
Aujard et al., "o-Nitrobenzyl Photolabile Protecting Groups with Red-Shifted Absorption: Syntheses and Uncaging Cross-Sections for One- and Two-Photon Excitation", Chemistry a European Journal, first published Jun. 8, 2006, pp. 6865-6879, discussed in Specification.
Russell et al., "alpha-Carboxy-6-nitroveratryl: A Photolabile Protecting Group for Carboxylic Acids", J. Org. Chem., first published Jun. 10, 2010, pp. 4648-4651, discussed in Specification.
Specht et al., "1-(o-Nitrophenyl)-2,2,2-trifluoroethyl Ether Derivatives as Stable and Efficient Photoremovable Alcohol-Protecting Groups", Angew. Chem. Int. Ed., first published 2004, pp. 2008-2012, discussed in Specification.

(56) References Cited

OTHER PUBLICATIONS

Baldwin et al., "New Photolabile Phosphate Protecting Groups", Tetrahedron, first published 1990, pp. 6879-6884, discussed in Specification.
Pauloehrl et al., "(Bio)Molecular Surface Patterning by Phototriggered Oxime Ligation", Angewandte Chem. Int. Ed., first published 2012, pp. 9181-9184, discussed in Specification.
Patchornik et al., "Photosensitive Protecting Groups", Journal of the American Chemical Society, first published Oct. 21, 1970, pp. 6333-6335, discussed in Specification.
Kalbag et al., "A Photolabile Protecting Group for Histidine", Journal of the American Chemical Society, first published Jan. 22, 1975, pp. 440-441, discussed in Specification.
Engels et al., "Synthesis, Structure, and Reactivity of Adenosine Cyclic S"-Phosphate Benzyl Triesters", Journal of Medicinal Chemistry, first published 1977, pp. 907-911, discussed in Specification.
Riguet et al., "New Safety-Catch Photolabile Protecting Group", Organic Letters, first published Nov. 30, 2007, pp. 5453-5456, discussed in Specification.
Bley et al., "Photoprocesses of Molecules with 2-Nitrobenzyl Protecting Groups and Caged Organic Acids", Photochemistry and Photobiology, first published in 2008, pp. 162-171, discussed in Specification.
Singh et al., "3-Nitro-2-naphthalenemethanol: a photocleavable protecting group for carboxylic acids", Tetrahedron, first published in 2005, pp. 10007-10012, discussed in Specification.
Friedrich et al., "A two-photon activatable amino acid linker for the induction of fluorescence", Chem. Commun., first published in 2015, pp. 15382-15385, discussed in Specification.
Groszek et al., "Synthesis and adrenolytic activity of 1-(1H-indol-4-yloxy)-3-(2-(2-methoxyphenoxy)ethylamino)propan-2-ol analogs and its enantiomers. Part 2", European Journal of Medicinal Chemistry, first published Jul. 21, 2009, pp. 5103-5111, discussed in Specification.
Greene et al., "Synthesis and Biochemical Evaluation of 3-Phenoxy-1,4-diarylazetidin-2-ones as Tubulin-Targeting Antitumor Agents", Journal of Medicinal Chemistry, first published Dec. 3, 2015, pp. 90-113, discussed in Specification.
Wu et al., "Synthesis and Evaluation of 3-Aroylindoles as Anticancer Agents: Metabolite Approach", Journal of Medicinal Chemistry, first published Jul. 8, 2009, pp. 4941-4945, discussed in Specification.
Agasti et al., "Photoregulated Release of Caged Anticancer Drugs from Gold Nanoparticles", J. Am. Chem. Soc. first published in 2009, pp. 5728-5729, discussed in Specification.
Subramani et al., "Direct photopatterning of light-activated gold nanoparticles", Journal of Materials Chemistry, first published in 2011, pp. 14156-14158, discussed in Specification.
Muraoka et al., "Quadruple Helix Formation of a Photoresponsive Peptide Amphiphile and Its Light-Triggered Dissociation into Single Fibers", J. Am. Chem. Soc., first published in 2008, pp. 2946-2947, discussed in Specification.
Morihiro et al., "Photoinduced changes in hydrogen bonding patterns of 8-thiopurine nucleobase analogues in a DNA strand", Organic & Biomolecular Chemistry, first published in 2014, pp. 2946-2952.
Peng et al.,"Dextran based photodegradable hydrogels formed via a Michael addition", Soft Matter, Issue 10, 2011, pp. 4881-4887.
Ye et al., "Photo-responsive shell cross-linked micelles based on carboxymethyl chitosan and their application in controlled release of pesticide", Carbohydrate Polymers 132, 2015, pp. 520-528.
Office Action issued in Chinese Application No. 201711132472.2, dated Apr. 27, 2020, with English machine translation, 16 pages provided.
Search Report issued in Chinese Application No. 201711132472.2, dated Apr. 16, 2020 with English machine translation, 4 pages provided.
Office Action issued in corresponding Chinese Application No. 201711132436.6, dated Apr. 15, 2020, with English machine translation, 15 pages provided.
Search Report issued in corresponding Chinese Application No. 201711132436.6, with English translation; 3 pages provided.
Yang et al., "Tissue-Integratable and Biocompatible Photogelation by the Imine Crosslinking Reaction", Advanced Materials, first published Feb. 3, 2016, pp. 2724-2730.
STNext, available at https://www.stn.org, RN842150-25-8 (Mar. 4, 2005), RN107573-91-1(Apr. 11, 1987), RN59945-42-5 (Nov. 16, 1984), total 4 pages provided.
International Search Report (in Chinese and English) published in PCT/CN2018/080174, mailed Aug. 8, 2018, 7 pages provided.
Bao et al., "Long conjugated 2-nitrobenzyl derivative caged anticancer prodrugs with visible light regulated release: preparation and functionalizations", Organic & Biomolecular Chemistry, Dec. 31, 2012, Royal Society of Chemistry, vol. 10, pp. 5238-5244, cited in International Search Report.
Lin et al., "Phototriggers: Work mechanisms and applications", Imaging science and photochemistry, vol. 32 No. 1, Jan. 31, 2014, with English Abstract, 25 pages provided; cited in International Search Report.

* cited by examiner

PHOTO-COUPLED SYNERGISTICALLY CROSSLINKED HYDROGEL MATERIAL AND ITS COMPOSITION, PREPARATION METHOD, USE, PRODUCT, AND PREPARATION KIT

FIELD OF THE INVENTION

The invention belongs to the field of biological materials, and particularly relates to the preparation, composition, product, and application of a photo-coupled synergistically crosslinked hydrogel material.

BACKGROUND OF THE INVENTION

Hydrogel are designed as highly hydrated and crosslinked 3D polymeric networks. Due to its excellent biocompatibility and certain mechanical strength, it can highly fit the micro-environment of biological tissues and is widely used in tissue engineering and regenerative medicine. In clinical applications, in-situ forming hydrogels have excellent tissue integration ability. Currently, in-situ forming hydrogels are mainly divided into temperature-sensitive hydrogel, two-component injectable hydrogel, and photosensitive hydrogel according to the gelation mechanism. The mechanism of temperature-sensitive hydrogel is that a gel precursor which is a liquid phase at a low temperature undergoes phase-change gelation under body temperature after reaching the body to realize in-situ forming (such as LeGoo, hydroxybutyl chitosan, etc.). This kind of hydrogels generally has problems such as weak gel strength, slow temperature response, and slow degradation in the body. The two-component injectable hydrogel mainly implements in-situ forming by injecting while mixing gel precursor containing reactive functional group by a two-component syringe (for example, Fibrin Glue, Adherus AutoSpray, etc.). Thus there is a high requirement for the crosslinking speed of the reactive functional groups. If the gelation rate is too slow, the gel precursor will be diluted or washed away by the blood or exudate in the body. If the gelation rate is too fast, it is unfavorable to clinical operation and the gel precursor is easy to block needles. And the two-component syringe is relatively expensive which greatly increase application cost. The above drawbacks limit the wide application of these materials.

Compared to temperature-sensitive hydrogel and two-component injectable hydrogel, photosensitive hydrogel is more practical in clinical operation due to precise controllable ability in time and space. For the current method of preparing hydrogels by photo-crosslinking, unsaturated biomacromolecule polymerization crosslinking by free radical crosslinking is the most common method. Although the photo-initiated radical polymerization crosslinking method has a fast cure rate (about 2 s), free radicals inevitably cause damage to cells or biological tissues, and the intrinsic oxygen inhibition of free radicals makes it difficult to construct a thin layer of hydrogel in situ by this method. Meanwhile, the lack of adhesion ability of such hydrogels to tissue has also been a barrier to the clinical application of this technique. So far, the FDA has approved the only one case of photosensitive hydrogel named FocalSeal to prevent hernia formation after pneumonectomy. Recently, Biomet has acquired the in situ hydrogel construction technology from John Hopkins University for cartilage repair. Although the above techniques have achieved excellent clinical effects, they must be used by combining with additional prime coat to promote the integration between gel and tissue, which complicates the clinical use of photosensitive hydrogels.

In view of the deficiency of photoinitiating free radical polymerization crosslinking technology to prepare hydrogel, Linyong Zhu et. proposed non-free radical photocoupling crosslinking technology in 2014 (Yunlong Yang; Jieyuan Zhang; Zhenzhen Liu; Qiuning Lin; Xiaolin Liu; Chunyan Bao; Yang Wang; Linyong Zhu. Adv. Mater. 2016, 28, 2724.; Linyong Zhu et. al. PCT. No. WO2016082725 A1, issued Jun. 2, 2016), the technology is based on the imine crosslinking reaction between aldehyde group produced by o-nitrobenzyl alcohol under irradiation of ultraviolet light and amine group in polymer derivatives containing amines. This completely avoided the generation of free radicals and effectively solve problem of the toxicity of free radicals and oxygen inhibition, and the thickness of the gel layer can be adjusted. Meantime, the aldehyde group produced by o-nitrobenzyl phototrigger under irradiation of light can further react with the amine group of the protein in the surface of tissue. Thereby, this can realize the chemical bond linking between the gel layer and the tissue and solve the problem of tissue adhesion and integration in conventional photosensitive hydrogel. However, the crosslinking speed of the aldehyde group with the amine group is greatly slower than that of the free radical crosslinking (the initial gelation time is about 30 s, and the complete gelation time is about 2 min), which is not conducive to clinical operation, thus limiting clinical transformation of this non-free radical photo-coupling crosslinking technology.

CONTENT OF THE INVENTION

The first objective of the present invention is to provide a cyclic o-nitrobenzyl phototrigger, as shown in Formula I-2.

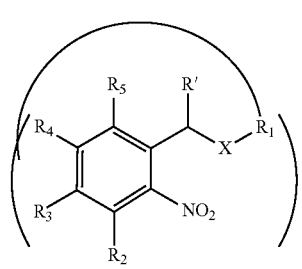

Formula I-2

Among this structure,

X=O, S or N; when X=O, it is a cyclic o-nitrobenzyl alcohol phototriggers; when X=S, it is a cyclic o-nitrobenzyl sulfide phototriggers; when X=N, it is a cyclic o-nitrobenzyl amine phototriggers.

One end of $R_1$ is connected with X, and the other end is connected optionally with one of $R_2$, $R_3$, $R_4$ or $R_5$ to form a cyclic structure.

R' is selected from the group consisting of a hydrogen atom, a halogen atom, a hydroxyl group, a sulphydryl group, an amine group, a nitro group, a cyano group, an aldehyde group, a ketone group, an ester group, an amide group, a phosphonic acid group, a phosphonate group, a sulfonate group, a sulfonic acid ester group, a sulfoxide group, an aryl group, a heteroaryl group, an alkyl group, an alkylene group, a modified alkyl group, and a modified alkylene group.

$R_1$ is selected from the group consisting of a hydrogen atom, an ether group, an ester group, a carbonate group, an amino formate ester group, a mercaptoformic ester group, and phosphoric acid ester group.

$R_2$, $R_3$, $R_4$, and $R_5$ are independently selected from the group consisting of a hydrogen atom, a halogen atom, a hydroxyl group, a mercapto group, an amine group, a nitro group, a cyano group, an aldehyde group, a ketone group, a carboxyl group, an ester group, an amide group, a phosphonic acid group, a phosphonate group, a sulfonic acid group, a sulfonate group, a sulfone group, a sulfoxide group, an aryl group, a heteroaryl group, an alkyl group, an alkylene group, a modified alkyl group, and a modified alkylene group.

$R_2$, $R_3$, $R_4$ and $R_5$ can be interconnected with each other and form saturated or unsaturated alicyclic or heteroalicyclic ring(s), aromatic ring(s), or aromatic heterocyclic ring(s), together with carbon atom(s).

Further, the alkyl group is a saturated or unsaturated aliphatic linear or branched alkyl group having 1 to 30 carbon atoms.

The alkylene group is a saturated or unsaturated aliphatic linear chain or branched alkylene group with 1-30 carbon atoms.

The modified alkyl group is a group modified from an alkyl group, in which any carbon atom is attached with at least one group selected from the group consisting of halogen atom, —OH, —SH, —$NO_2$, —CN, —CHO, —COOH, ester, amide, aromatic, arylidene, —CO—, —O—, —S—, —SO—, —$SO_2$—, amino, secondary amine, tertiary amine, quaternary ammonium salt, saturated or unsaturated single or double cyclic alkylene, and bridged aliphatic heterocyclic. The modified alkyl group has 1~30 carbon atoms, and its carbon-carbon single bond can be optionally and independently replaced with a carbon-carbon double bond or a carbon-carbon triple bond.

The modified alkylene group is a group modified from an alkylene group, in which any carbon atom is attached with at least one group selected from the group consisting of halogen atom, —OH, —SH, —$NO_2$, —CN, —CHO, —COOH, ester, amide, aromatic, arylidene, —CO—, —O—, —S—, —SO—, —$SO_2$—, amino, secondary amine, tertiary amine, quaternary ammonium salt, saturated or unsaturated single or double cyclic alkylene, and bridged aliphatic heterocyclic. The modified alkyl group has 1~30 carbon atoms, and its carbon-carbon single bond can optionally and independently be replaced with a carbon-carbon double bond or a carbon-carbon triple bond.

The ether group is selected from the following structures:
—$(CH_2)_xCH_3$, —$(CH_2CH_2O)_xCH_3$, —$(CH_2)_x(CH_2CH_2O)_yCH_3$, or

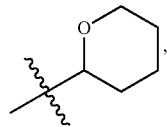

where x and y≥0 and are integers.

The ester group is selected from the following structures:
—$CO(CH_2)_xCH_3$, —$CO(CH_2CH_2O)_xCH_3$, —$CO(CH_2)_x(CH_2CH_2O)_yCH_3$, where x and y?0 and are integers.

The carbonate group is selected from the following structures:
—$COO(CH_2)_xCH_3$, —$COO(CH_2CH_2O)_xCH_3$, —$COO(CH_2)_x(CH_2CH_2O)_yCH_3$, where x and y?0 and are integers.

The amino formate ester group is selected from the following structures:
—$CONH(CH_2)_xCH_3$, —$CONH(CH_2CH_2O)_xCH_3$, —$CONH(CH_2)_x(CH_2CH_2O)_yCH_3$, where x and y≥0 and are integers.

The mercapto formate ester group is selected from the following structures:
—$COS(CH_2)_xCH_3$, —$COS(CH_2CH_2O)_xCH_3$, —$COS(CH_2)_x(CH_2CH_2O)_yCH_3$, where x and y≥0 and are integers.

The phosphate ester group is selected from the following structures:
—$POOO(CH_2)_xCH_3$, —$POOO(CH_2CH_2O)_xCH_3$, —$POOO(CH_2)_x(CH_2CH_2O)_yCH_3$, where x and y≥0 and are integers.

The aryl ring is a monocyclic or fused bicyclic ring of 5-10 atoms.

The heteroaryl is a monocyclic or fused bicyclic ring containing 5 to 10 atoms, and its ring contains at least one hetero atom selected from the group consisting of N, O, S, and Si.

The halogen atom is independently selected from the group consisting of F, Cl, Br, and I.

The alicyclic ring is a saturated or unsaturated monocyclic or polycyclic alicyclic ring of 3 to 10 atoms.

The alicyclic ring is a saturated or unsaturated monocyclic or polycyclic alicyclic ring of 3 to 10 atoms, and its ring contains at least one hetero atom selected from N, O, S and Si. When the heteroalicyclic ring contains an S atom, it is selected from —S—, —SO— and —$SO_2$—; H on the alicyclic or alicyclic ring can be optionally substituted with a halogen atom, a nitro group, an aryl group, an alkyl group, or a modified alkyl group.

The aromatic ring is a monocyclic or fused bicyclic ring of 5-10 atoms.

The aromatic heterocycle is a monocyclic or fused bicyclic ring containing 5 to 10 atoms, and its ring contains at least one hetero atom selected from N, O, S, or Si. H on the aromatic ring or the aromatic heterocyclic ring can be optionally substituted with a halogen atom, a nitro group, an aryl group, an alkyl group, or a modified alkyl group.

The above cyclic o-nitrobenzyl phototriggers are preferably selected from the following cyclic structures:

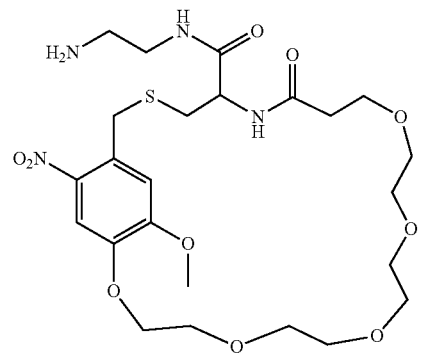

Compound 93

Compound 94
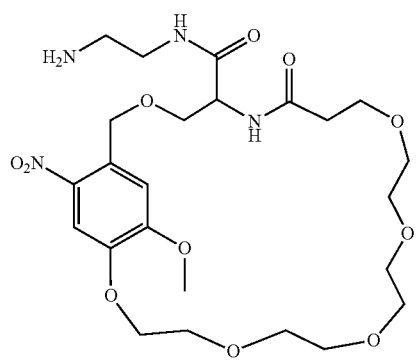
Compound 95
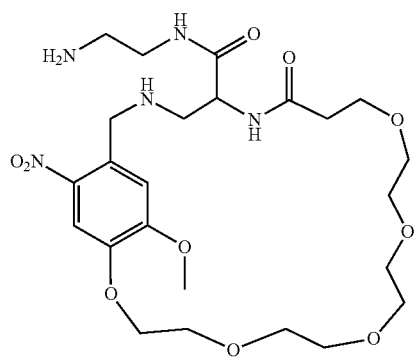
Compound 96
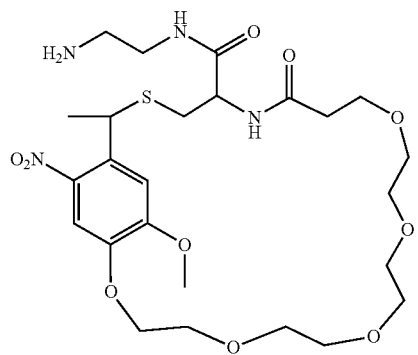
Compound 97
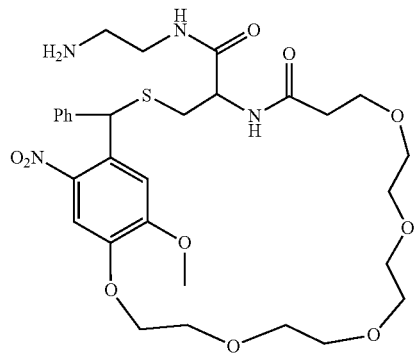
Compound 98
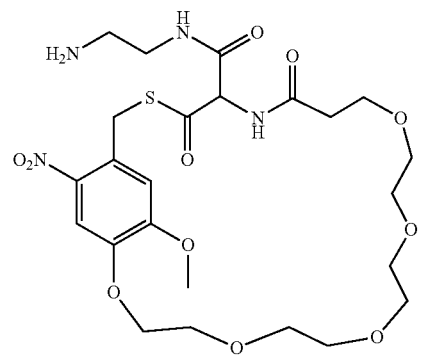
Compound 99
Compound 100
Compound 103
Compound 104

Compound 105

Compound 106

Compound 107

Compound 108

Compound 109

The second objective of the present invention is to provide a series of novel structures of polymer derivatives modified with o-nitrobenzyl phototriggers.

The structure of the polymer derivatives modified with o-nitrobenzyl phototriggers is shown in Formula A:

Formula A

The polymer derivatives modified with the o-nitrobenzyl phototriggers specifically have the following structures:

1. the polymer derivatives modified with o-nitrobenzyl sulfide phototriggers as shown in Formula A-I,
2. the polymer derivatives modified with o-nitrobenzylamine phototriggers as shown in Formula A-II,
3. the polymer derivatives modified with cyclic o-nitrobenzyl, cyclic o-nitrobenzyl sulfide or cyclic o-nitrobenzylamine phototriggers as shown in Formula A-III, Formula A-I

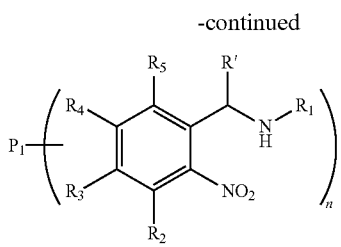

Formula A-II

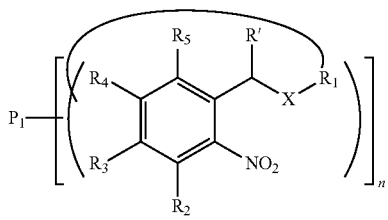

Formula A-III

In Formula A, Formula A-I, Formula A-II and Formula A-III, R' is selected from the group consisting of a hydrogen atom, a halogen atom, a hydroxyl group, a sulphydryl group, an amine group, a nitro group, a cyano group, an aldehyde group, a ketone group, an ester group, an amide group, a phosphonic acid group, a phosphonate group, a sulfonate group, a sulfonic acid ester group, a sulfoxide group, an aryl group, a heteroaryl group, an alkyl group, an alkylene group, a modified alkyl group, and a modified alkylene group.

In Formula A-I, Formula A-II and Formula A-III, $R_1$ is selected from the group consisting of a hydrogen atom, an ether group, an ester group, a carbonate group, an amino formate ester group, a mercaptoformic ester group and phosphoric acid ester group.

In Formula A-I, Formula A-II and Formula A-III, $R_2$, $R_3$, $R_4$ and $R_5$ are independently selected from the group consisting of a hydrogen atom, a halogen atom, a hydroxyl group, a mercapto group, an amine group, a nitro group, a cyano group, an aldehyde group, a ketone group, a carboxyl group, an ester group, an amide group, a phosphonic acid group, a phosphonate group, a sulfonic acid group, a sulfonate group, a sulfone group, a sulfoxide group, an aryl group, a heteroaryl group, an alkyl group, an alkylene group, a modified alkyl group, and a modified alkylene group.

In Formula A-I, Formula A-II and Formula A-III, $R_2$, $R_3$, $R_4$ and $R_5$ are preferably interconnected with each other to form a saturated or unsaturated alicyclic or heteroalicyclic ring, or an aromatic ring or an aromatic heterocyclic ring, together with carbon atom(s).

In Formula A, Formula A-I, Formula A-II and Formula A-III, $P_1$ can connect with one or more of $R_2$, $R_3$, $R_4$ and $R_5$ groups or connect with the formed saturated or unsaturated alicyclic ring or heterocyclic ring, or aromatic ring or heterocyclic ring.

In Formula A-III, X can be O, S or NH, etc. $R_1$ is connected with X and any one of $R_2$, $R_3$, $R_4$ and $R_5$ groups to form a cyclic structure. $P_1$ can connect with one or more of $R_2$, $R_3$, $R_4$ and $R_5$ groups, or directly connects with the ring chain.

$P_1$ connects with one or more of $R_2$, $R_3$, $R_4$ and $R_5$ groups, or connects with the formed saturated or unsaturated alicyclic ring or heterocyclic ring, or aromatic ring or heterocyclic ring, or directly connects with the ring chain, via a linkage bond. The linkage bond is represented by —O—, —S—, —NH—, -alkyl group-, —COO— and —CONH—.

In the Formula A, Formula A-I, Formula A-II and Formula A-III, n≥2. This means the average number of o-nitrobenzyl phototriggers on a single $P_1$ polymer chain is more than or equal to 2.

In the Formula A, Formula A-I, Formula A-II and Formula A-III, $P_1$ is a hydrophilic or water-soluble natural polymer or synthetic polymer, or independently selected from a various of hydrophilic or water-soluble natural polymers or synthetic polymers.

Further, the alkyl group is a saturated or unsaturated aliphatic linear or branched alkyl group having 1 to 30 carbon atoms.

The alkylene group is a saturated or unsaturated aliphatic linear chain or branched alkylene group with 1-30 carbon atoms.

The modified alkyl group is an alkyl group whose any carbon atom is at least substituted by one of the groups consisting of a halogen atom, —OH, —SH, —NO$_2$, —CN, —CHO, —COOH, ester, amide, aromatic, arylidene, —CO—, —O—, —S—, —SO—, —SO$_2$—, amino, secondary amine, tertiary amine, quaternary ammonium salt, saturated or unsaturated single or double cyclic alkylene, bridged aliphatic heterocyclic. And the modified alkyl group has 1~30 carbon atoms whose carbon-carbon single bond is replaced optionally and independently by a carbon-carbon double bond or a carbon-carbon triple bond.

The modified alkylene group is an alkylene group in which any carbon atom is attached with at least one group selected from the group consisting of halogen atom, —OH, —SH, —NO$_2$, —CN, —CHO, —COOH, ester, amide, aromatic, arylidene, —CO—, —O—, —S—, —SO—, —SO$_2$—, amino, secondary amine, tertiary amine, quaternary ammonium salt, saturated or unsaturated single or double cyclic alkylene, bridged aliphatic heterocyclic. The modified alkyl group has 1~30 carbon atoms whose carbon-carbon single bond is replaced optionally and independently by a carbon-carbon double bond or a carbon-carbon triple bond.

The ether group is selected from the following structures:
—(CH$_2$)$_x$CH$_3$, —(CH$_2$CH$_2$O)$_x$CH$_3$, —(CH$_2$)$_x$(CH$_2$CH$_2$O)$_y$CH$_3$, or

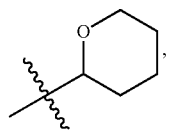

wherein x and y≥0 and are integers.

The ester group is selected from the following structures:
—CO(CH$_2$)$_x$CH$_3$, —CO(CH$_2$CH$_2$O)$_x$CH$_3$, —CO(CH$_2$)$_x$(CH$_2$CH$_2$O)$_y$CH$_3$, wherein x and y≥0 and are integers.

The carbonate group is selected from the following structures:
—COO(CH$_2$)$_x$CH$_3$, —COO(CH$_2$CH$_2$O)$_x$CH$_3$, —COO(CH$_2$)$_x$(CH$_2$CH$_2$O)$_y$CH$_3$, wherein x and y≥0 and are integers.

The amino formate ester group is selected from the following structures:
—CONH(CH$_2$)$_x$CH$_3$, —CONH(CH$_2$CH$_2$O)$_x$CH$_3$, —CONH(CH$_2$)$_x$(CH$_2$CH$_2$O)$_y$CH$_3$, wherein x and y≥0 and are integers.

The mercapto formate ester group is selected from the following structures:
—COS(CH$_2$)$_x$CH$_3$, —COS(CH$_2$CH$_2$O)$_x$CH$_3$, —COS(CH$_2$)$_x$(CH$_2$CH$_2$O)$_y$CH$_3$, wherein x and y≥0 and are integers.

The phosphate ester group is selected from the following structures:

—POOO(CH$_2$)$_x$CH$_3$, —POOO(CH$_2$CH$_2$O)$_x$CH$_3$, —POOO(CH$_2$)$_x$(CH$_2$CH$_2$O)$_y$CH$_3$, wherein x and y≥0 and are integers.

The aryl ring is a monocyclic or fused bicyclic ring of 5-10 atoms.

The heteroaryl is a monocyclic or fused bicyclic ring containing 5 to 10 atoms, the ring contains at least one hetero atom selected from N, O, S, and Si.

The halogen atom is independently selected from F, Cl, Br, and I.

The alicyclic ring is a saturated or unsaturated monocyclic or polycyclic alicyclic ring of 3 to 10 atoms.

The heteroalicyclic ring is a saturated or unsaturated monocyclic or polycyclic alicyclic ring of 3 to 10 atoms, and the ring contains at least one hetero atom selected from N, O, S, and Si. When the heteroalicyclic ring contains an S atom, it is selected optionally from —S—, —SO— or —SO$_2$—; H on the alicyclic or alicyclic ring may be optionally substituted by a halogen atom, a nitro group, an aryl group or an alkyl group or a modified alkyl group.

The aromatic ring is a monocyclic or fused bicyclic ring of 5-10 atoms.

The aromatic heterocycle is a monocyclic or fused bicyclic ring containing 5 to 10 atoms, the ring contains at least one hetero atom selected from N, O, S or Si; H on the aromatic ring or the aromatic heterocyclic ring may also be optionally substituted by a halogen atom, a nitro group, an aryl group, an alkyl group or a modified alkyl group.

Further, the alicyclic or heteroalicyclic ring are preferably selected from:

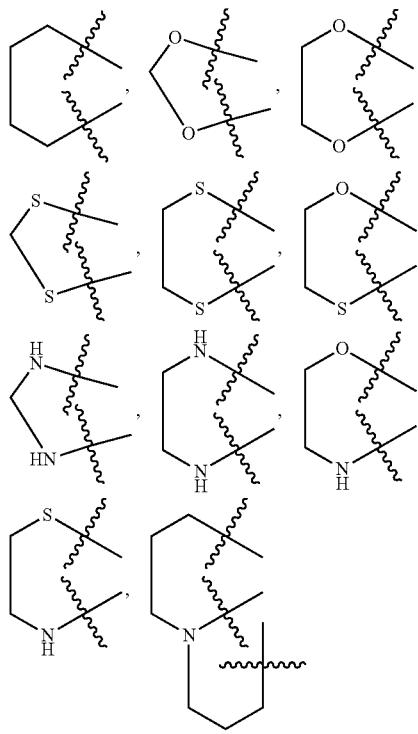

etc.;

Further, the aromatic ring or the aromatic heterocyclic ring are preferably selected from:

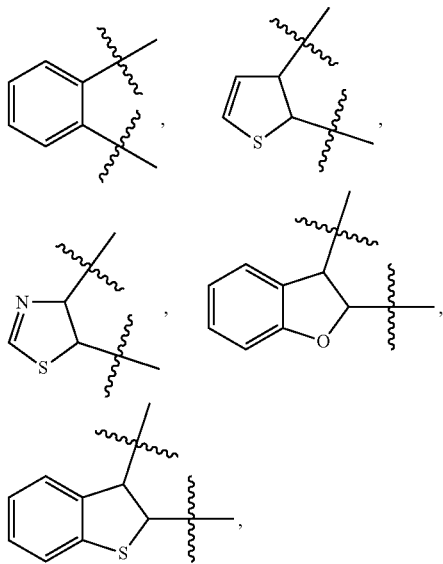

etc.;

R' is preferably selected from:
—H, —CH$_3$, —CH$_2$CH$_3$, —CH═CH—CH═CH—CH$_3$, —F, —Cl, —Br, —I, —CF$_3$, —CCl$_3$, —CBr$_3$, —CI$_3$, —CN, —COOH, -Ph,

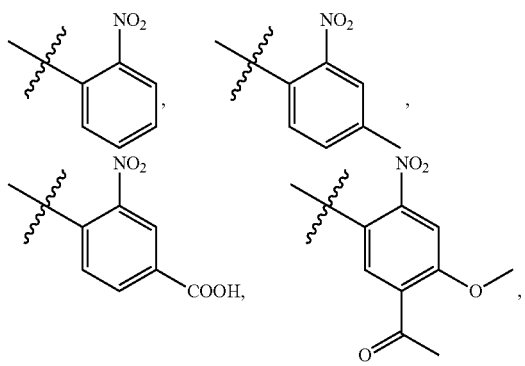

etc.;

R$_2$, R$_3$, R$_4$ and R$_5$ are preferably selected from:
—H, —OH, —SH, —NH$_2$, —F, —Cl, —Br, —I, —CF$_3$, —CCl$_3$, —CBr$_3$, —CI$_3$, —NO$_2$, —CN, —CHO, —COOH, —COONH$_2$, —SO$_3$H, etc.;

Alkyl substituent is preferably selected from linear alkyl as —(CH$_2$)$_x$CH$_3$, branched alkyl as —(CH$_2$)$_x$(CY'Y")$_y$CH$_3$ (Y', Y" is hydrogen, alkyl or modified Alkyl), etc., where x and y≥0, x and y are integers;

The ether substituent is preferably selected from —O(CH$_2$)$_x$CH$_3$, —O(CH$_2$CH$_2$O)$_x$CH$_3$, —O(CH$_2$)$_x$(CH$_2$CH$_2$O)$_y$CH$_3$, etc., where x and y≥0, x and y are integers;

The thioether substituent is preferably selected from —S(CH$_2$)$_x$CH$_3$, —S(CH$_2$CH$_2$O)$_x$CH$_3$, —S(CH$_2$)$_x$(CH$_2$CH$_2$O)$_y$CH$_3$, etc., where x and y≥0, x and y are integers;

Amino substituent is preferably selected from —NH(CH$_2$)$_x$CH$_3$, —NH(CH$_2$)$_x$(CY'Y")$_y$CH$_3$, —N(CY'Y")$_x$(CY'Y")$_y$,

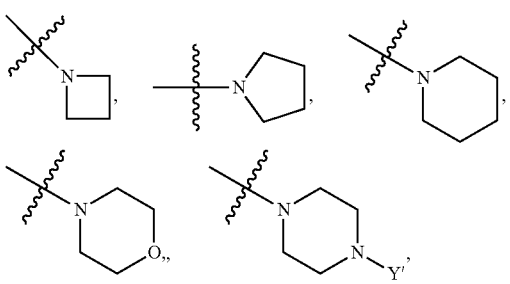

(Y, Y' is hydrogen, alkyl or modified alkyl), etc., wherein x and y≥0, x and y are integers;

The ester substituent is preferably selected from —COO(CH$_2$)$_x$CH$_3$, —COO(CH$_2$CH$_2$O)$_x$CH$_3$, —COO(CH$_2$)$_x$(CH$_2$CH$_2$O)$_y$CH$_3$ or the like, wherein x and y≥0, x and y are integers;

The amide substituent is preferably selected from —CONH(CH$_2$)$_x$CH$_3$, —CONH(CH$_2$CH$_2$O)$_x$CH$_3$, —CONH(CH$_2$)$_x$(CH$_2$CH$_2$O)$_y$CH$_3$ or the like, wherein x and y≥0, x and y are integers;

The aromatic substituent is preferably selected from -Ph,

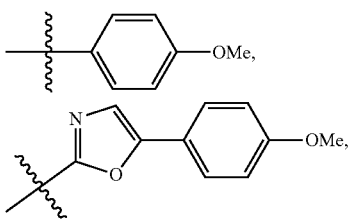

etc.

The polymer P$_1$ in the polymer derivatives modified with the o-nitrobenzyl phototriggers may be a hydrophilic or water-soluble natural polymer including natural polysaccharides and their modifications or degradants, proteins and their modifications or degradants and etc. The natural polysaccharides include hyaluronic acid, carboxymethyl cellulose, methyl cellulose, hydroxyethyl cellulose, hydroxypropyl cellulose, alginate, dextran, agarose, heparin, chondroitin sulfate, glycol chitosan, propylene glycol chitosan, chitosan lactate, carboxymethyl chitosan or quaternary ammonium salt of chitosan. The protein includes various hydrophilic or water-soluble animal and plant proteins, collagen, serum proteins, silk fibroin proteins and elastin, and the protein degradations include gelatin or polypeptides. Hydrophilic or water-soluble synthetic polymers include two-arm or multi-arm poly (ethylene glycol), poly (ethylene imine), dendrites, synthetic peptides, polylysine, poly (glutamic acid), poly (acrylic acid), poly (methacrylic acid), polyacrylate, poly (methacrylate), poly (acrylamide), poly (methacrylamide), poly (vinyl alcohol), poly (vinyl pyrrolidone).

In the above grafted or polymerized water-soluble or hydrophilic polymer derivative, the average number of o-nitrobenzyl phototriggers on a single polymer chain is greater than or equal to 2 (n≥2).

The polymer derivative modified with the o-nitrobenzyl phototriggers may be a hydrophilic or water-soluble polymer simultaneously containing one or more different groups, or a mixture of hydrophilic or water-soluble polymers with one or more different groups. The hydrophilic or water-soluble polymer refers to a hydrophilic or water-soluble natural polymer, or a hydrophilic or water-soluble synthetic polymer.

Alternatively, the Formula A-I may be selected from the following Component A-1 to Component A-45:

Component A-1

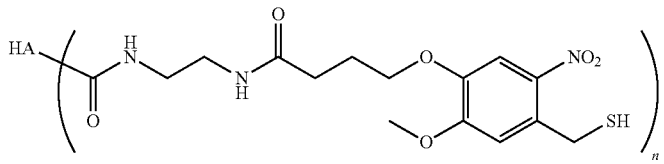

Component A-2

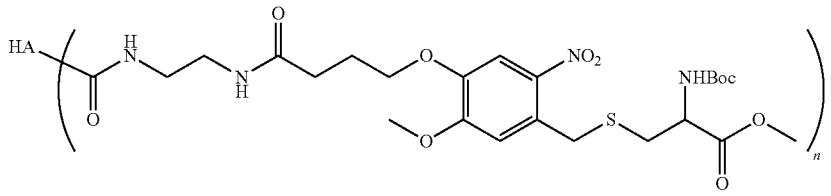

Component A-3

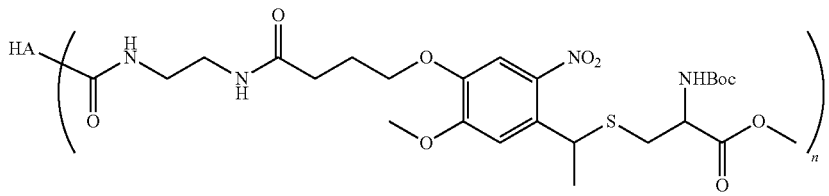

-continued
Component A-5
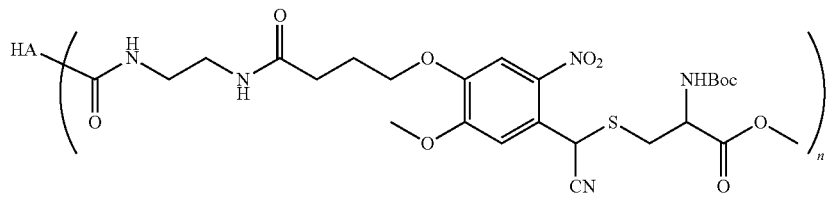
Component A-6
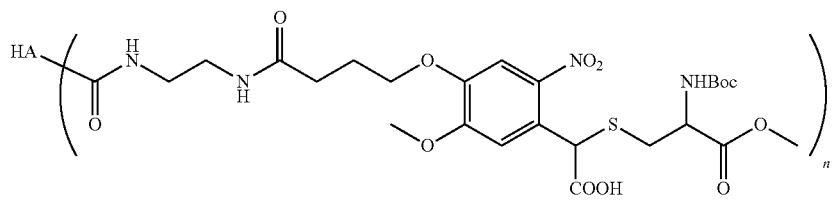
Component A-7
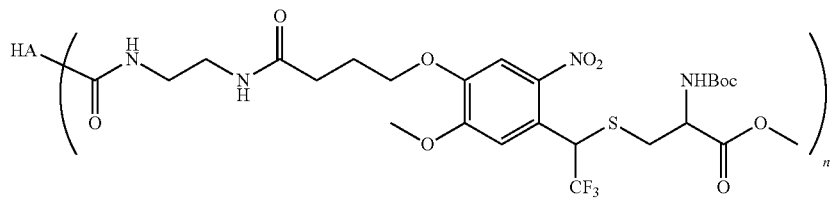
Component A-9                            Component A-10
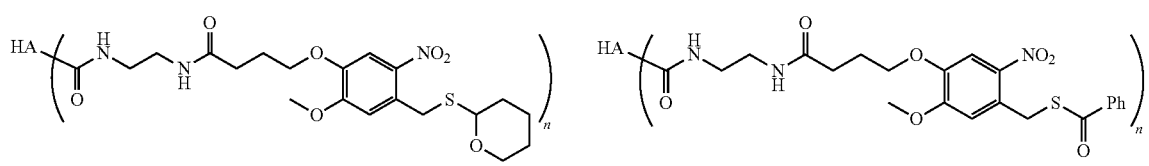
Component A-11
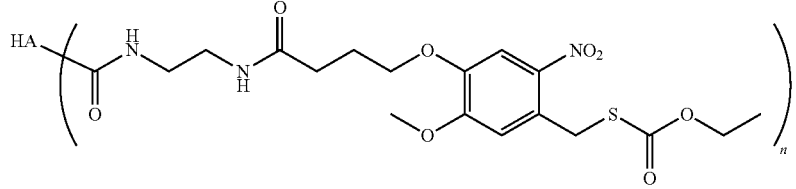
Component A-12
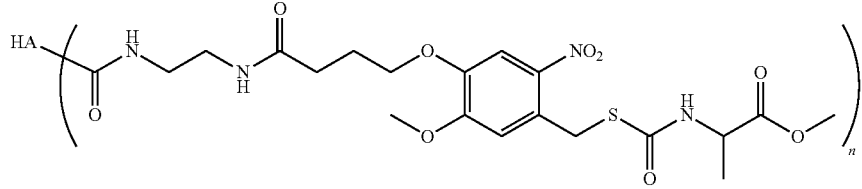
Component A-13
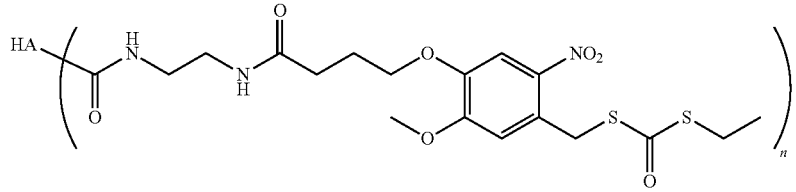
Component A-14
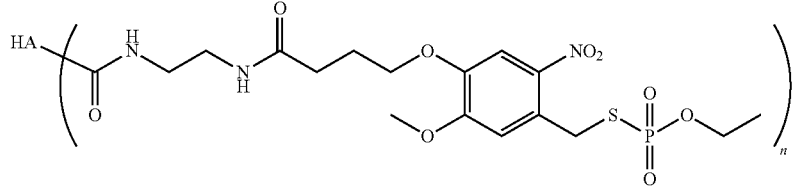

-continued
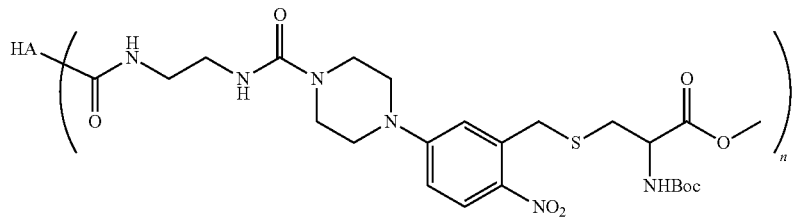
Component A-16
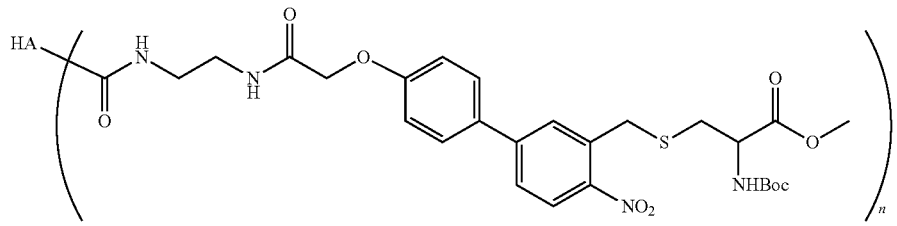
Component A-17
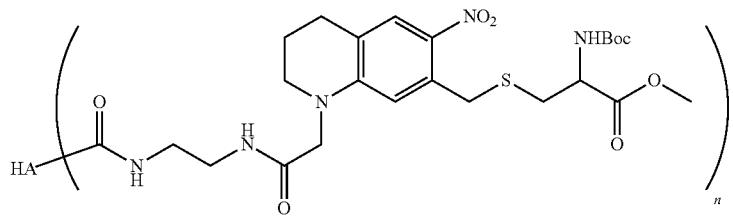
Component A-20
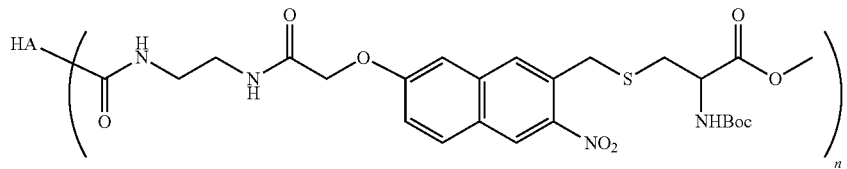
Component A-21
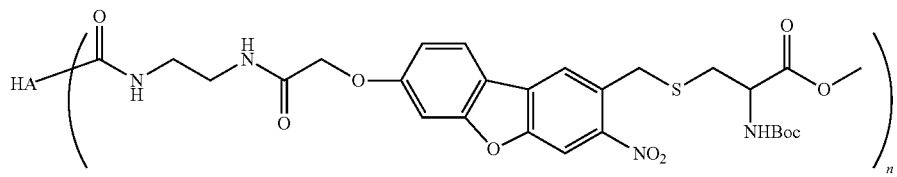
Component A-22
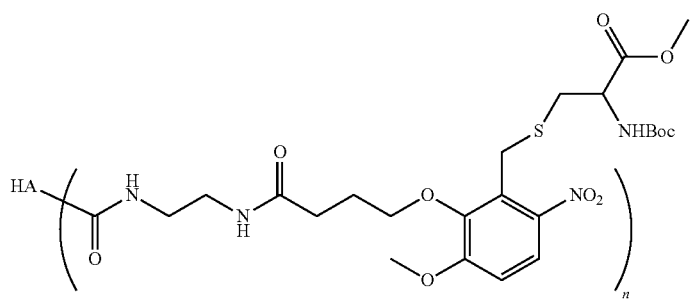
Component A-23
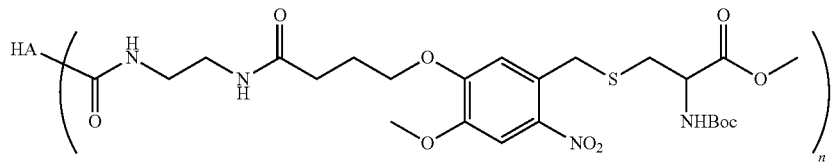
Component A-24

Component A-25
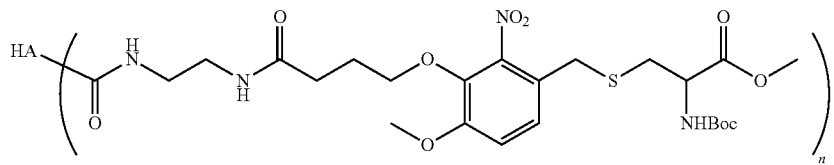
Component A-26
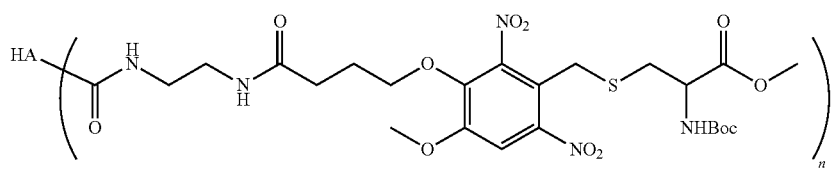
Component A-28
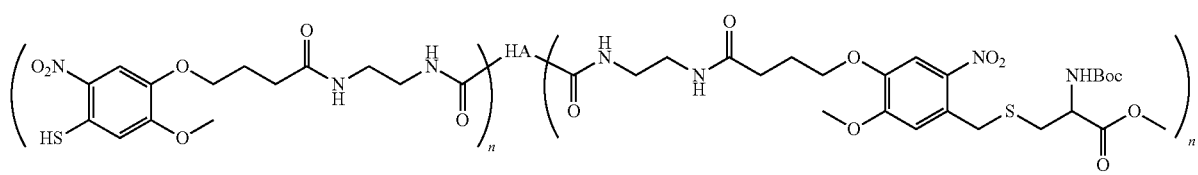
Component A-29
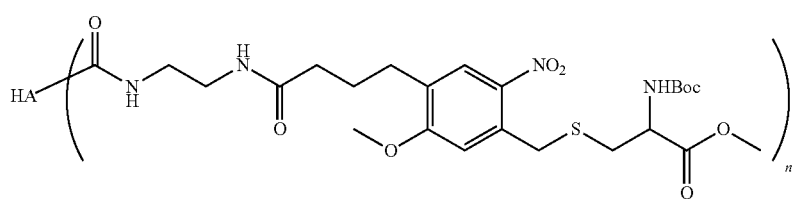
Component A-30
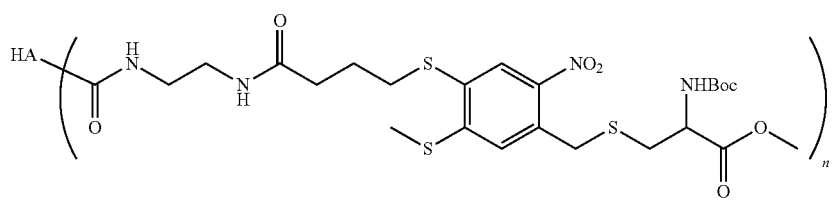
Component A-31
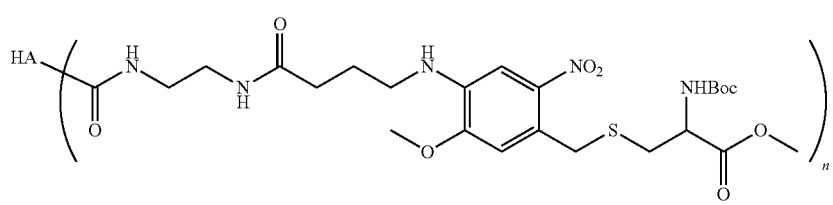
Component A-32
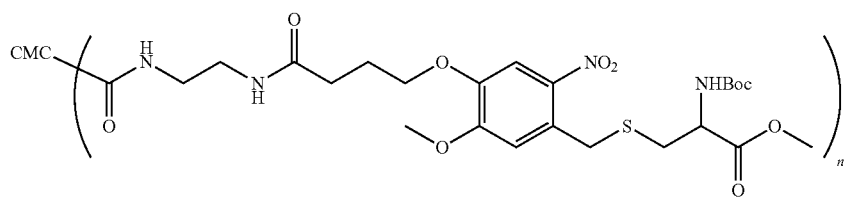
Component A-33
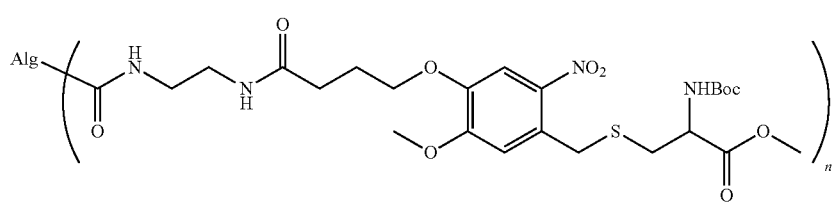

-continued
Component A-34
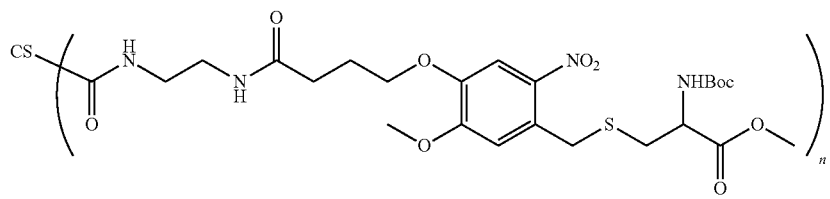
Component A-35
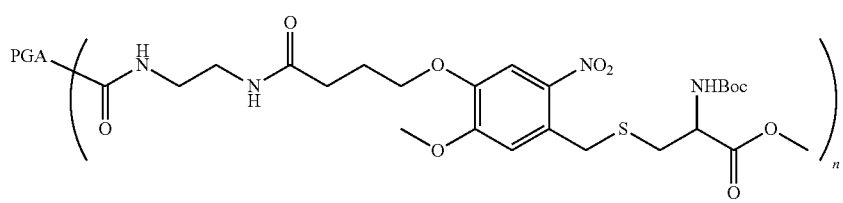
Component A-36
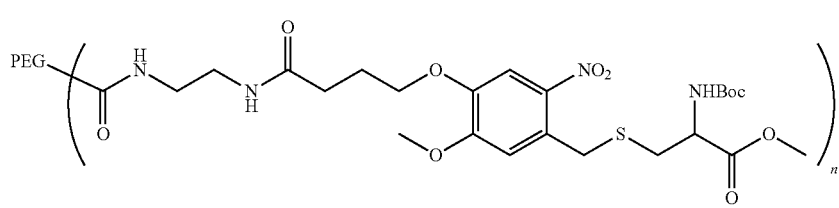
Component A-37
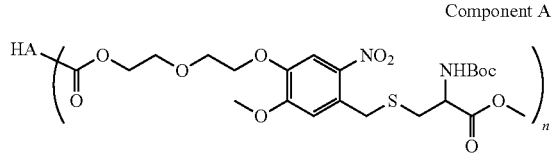
Component A-38
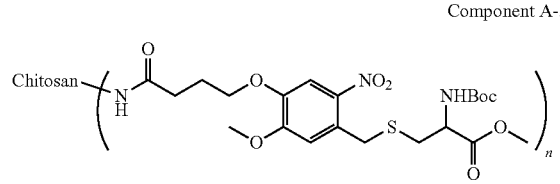
Component A-39
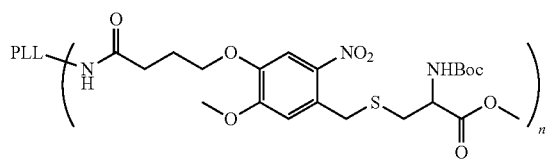
Component A-40
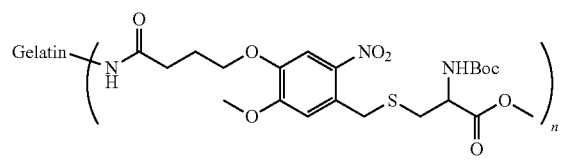
Component A-41
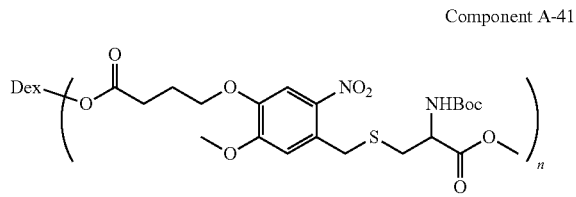
Component A-42
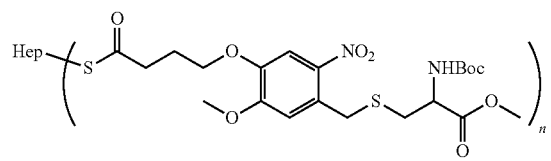
Component A-43
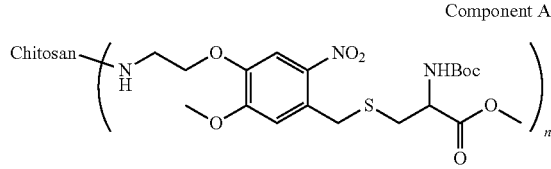
Component A-44
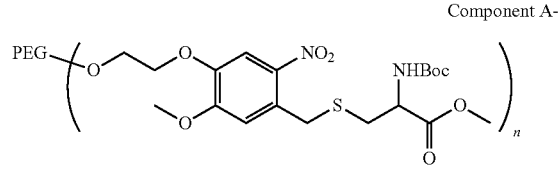

Component A-45
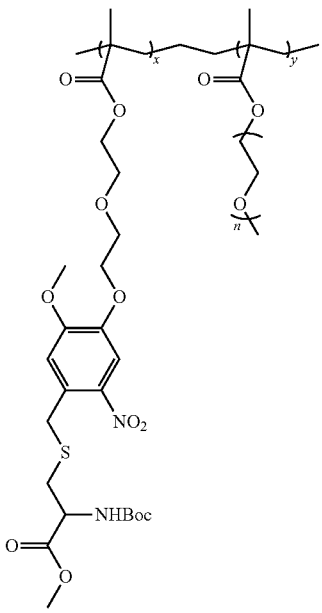
Alternatively, the Formula A-II may be selected from the structures of the following Component A-46 to Component A-63:
Component A-46
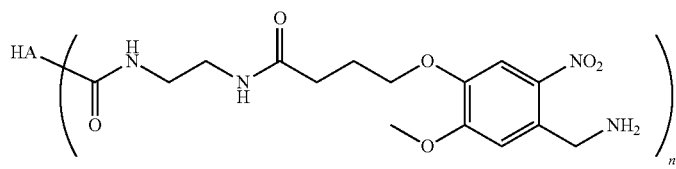
Component A-47
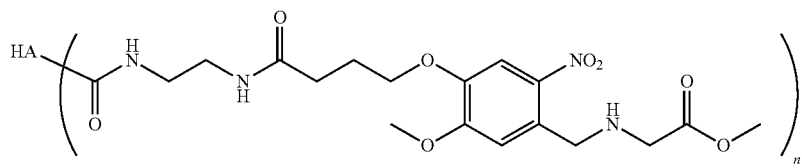
Component A-48
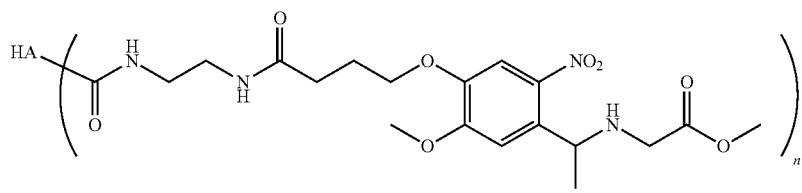
Component A-49
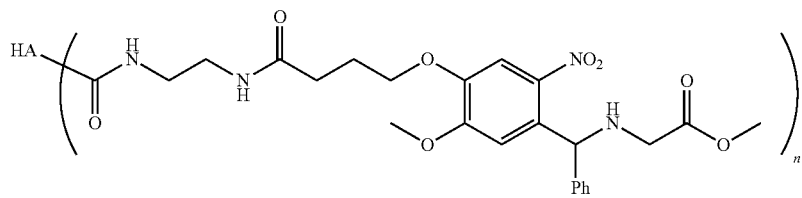

-continued
Component A-50
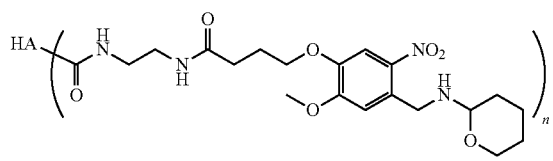
Component A-51
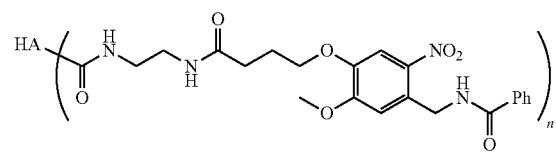
Component A-52
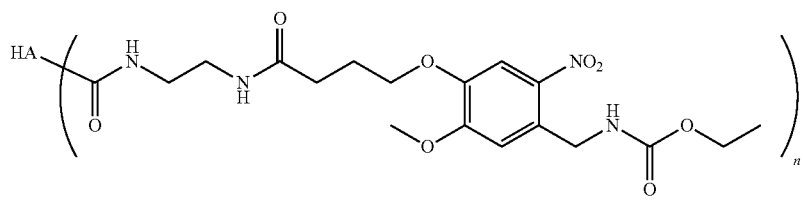
Component A-53
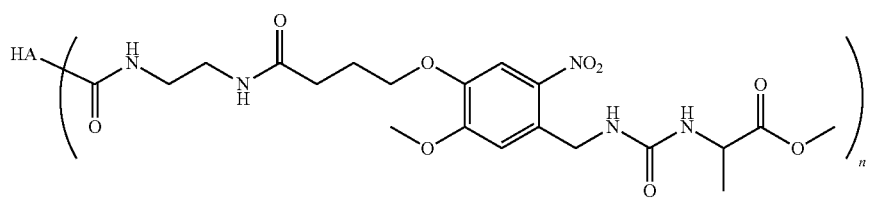
Component A-56
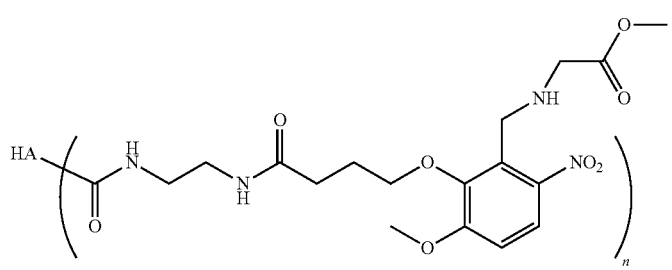
Component A-57
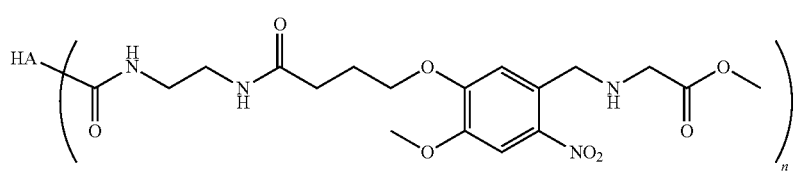
Component A-58
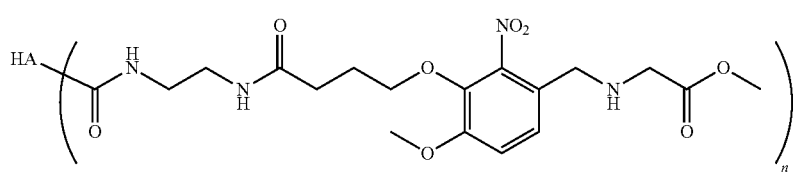
Component A-59
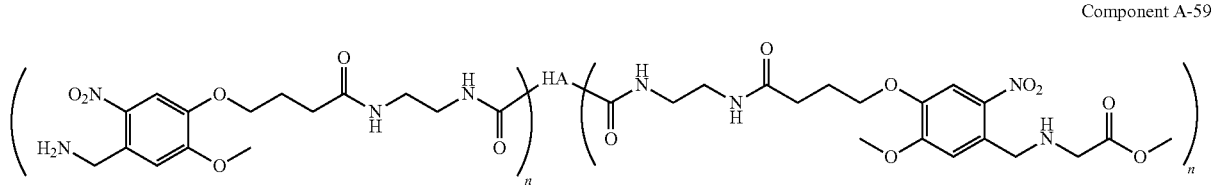
Component A-60
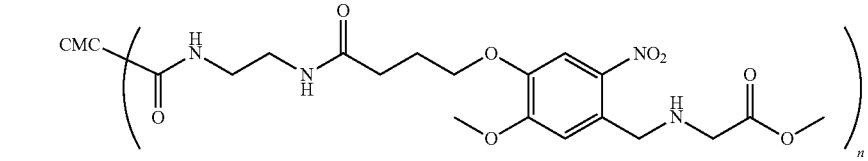

Component A-61
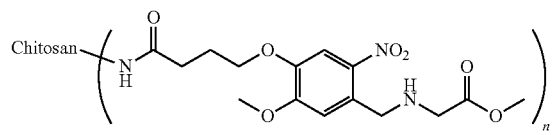
Component A-62
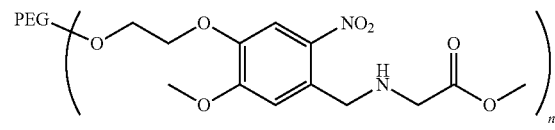
Component A-63
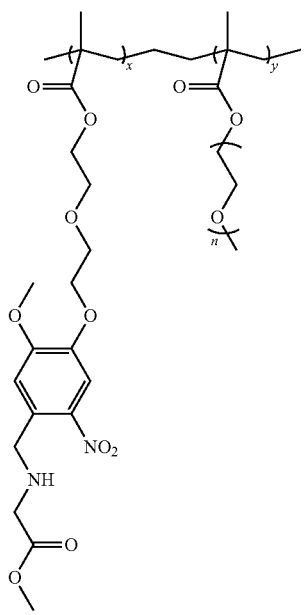
Alternatively, the Formula A-III may be selected from the structures of the following Component A-64 to Component A-82:
Component A-64
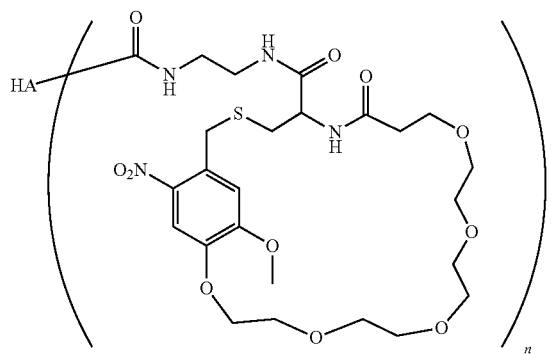
Component A-65
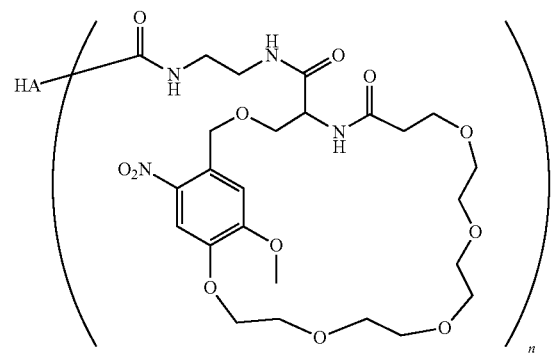

-continued
Component A-66
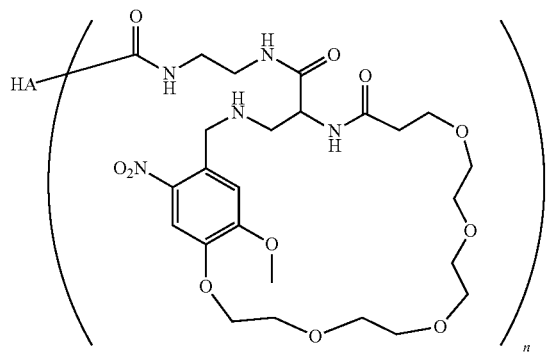
Component A-67
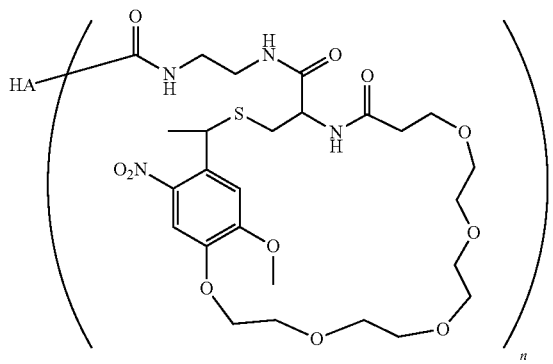
Component A-68
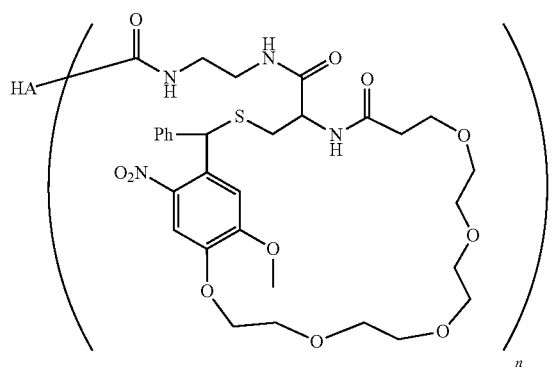
Component A-69
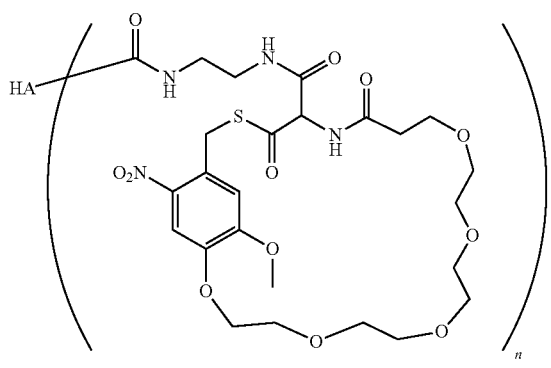
Component A-70
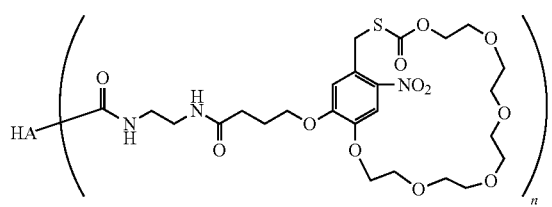
Component A-71
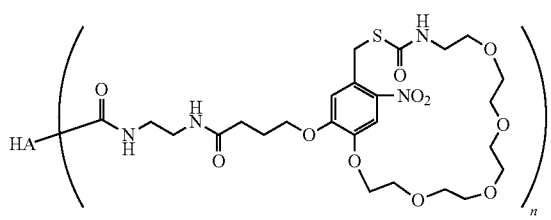
Component A-74
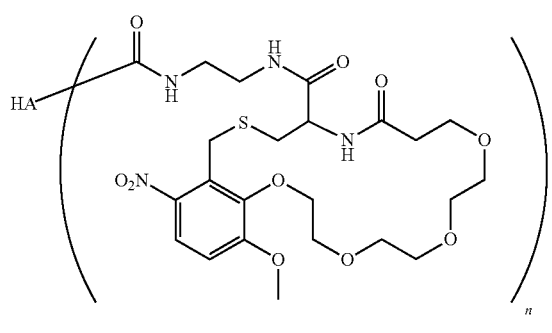
Component A-75
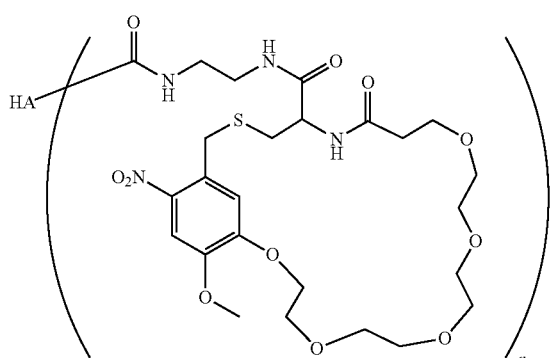

-continued
Component A-76
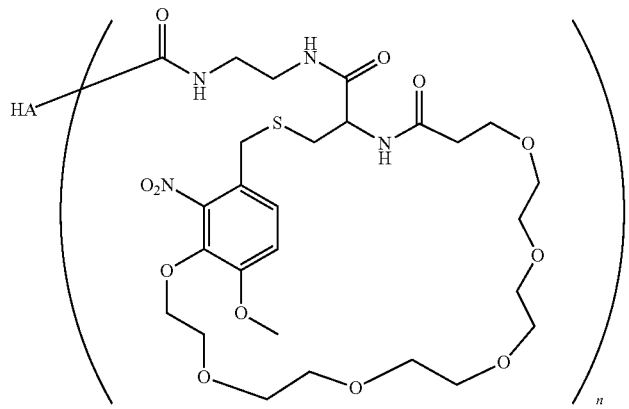
Component A-77
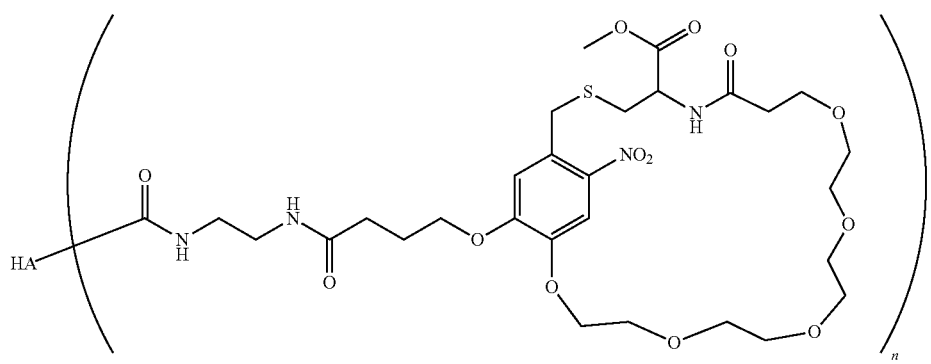
Component A-78
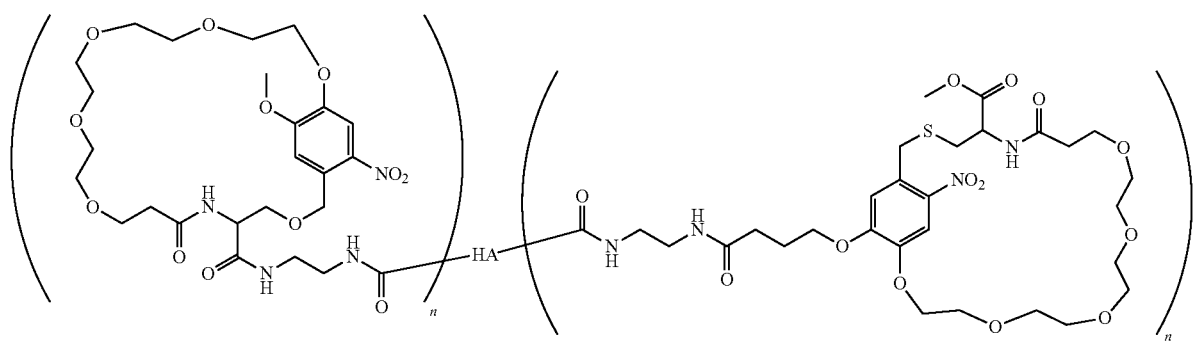
Component A-79
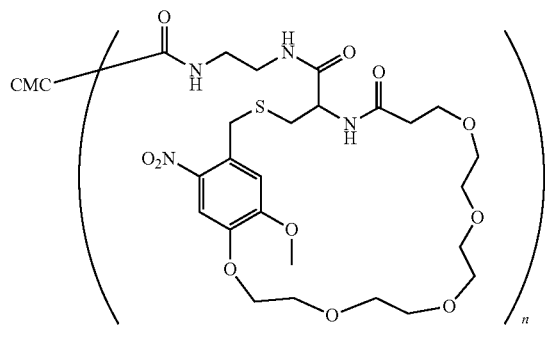
Component A-80
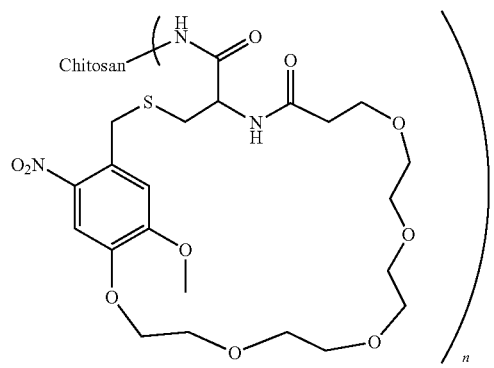

Component A-81

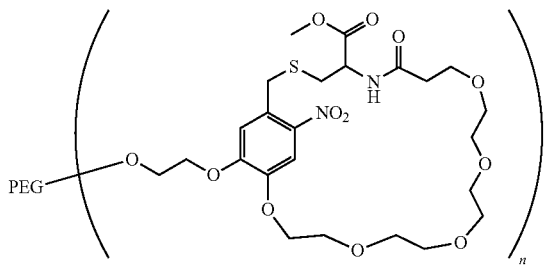

Component A-82

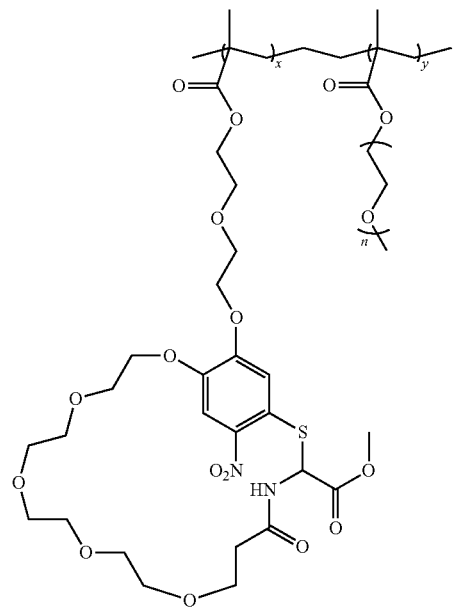

In the molecules of Component A-1 to Component A-82, n≥2, HA stands for hyaluronic acid; CMC stands for carboxymethyl cellulose; Alg stands for alginic acid; CS stands for chondroitin sulfate; PGA stands for polyglutamic acid; PEG stands for polyethylene glycol; Chitosan is chitosan; Gelatin is gelatin; PLL stands for polylysine; Dex is dextran; Hep stands for heparin.

In the polymer derivatives modified with o-nitrobenzyl sulfide phototriggers as shown in Formula A-I, the oxygen atom (O) is replaced by a sulfur atom (S). Because the 3 d empty orbit of the sulfur atom could facilitate intramolecular charge transfer to speed up the photolysis rate and photolysis efficiency of the phototriggers. That is, the aldehyde group/keto group or nitroso group can be released more rapidly and more completely under irradiation which accelerates its crosslinking speed as crosslinking sites. And the released aldehyde/ketone group or nitroso can be connected to the active group on the surface of the tissue, which can greatly improve the adhesion strength between the material and the tissue. In addition, the simultaneous release and crosslinking of various reactive functional groups (single aldehyde-amine photocoupled crosslinking is only the release and crosslinking of a single reactive functional group) greatly improve the crosslinking efficiency and crosslinking density, which further improve the mechanical properties of the material. Therefore, the optimization of the molecular structure make it as a photosensitive group modification of polymer derivatives to exhibit more excellent material performance, such as the crosslinking speed increases from 30 s in the aldehyde-amine photocoupled crosslinking to less than 5 s, the tissue adhesion strength increases to about 78 kPa, the mechanical properties increases to about 700 kPa, specific data are shown in Example 102, Example 103, Example 104.

In the polymer derivatives modified with o-nitrobenzylamine phototriggers as shown in Formula A-II, the oxygen atom (O) is replaced by a nitrogen atom (N). Because nitrogen as a strong electron donor could facilitate intramolecular charge transfer to speed up the photolysis rate and photolysis efficiency of the phototriggers. That is, the aldehyde group/keto group or nitroso group can be released more rapidly and more completely under irradiation which accelerates its crosslinking speed as crosslinking sites. And the released aldehyde/ketone group or nitroso can be connected to the active group on the surface of the tissue, which can greatly improve the adhesion strength between the material and the tissue. In addition, the simultaneous release and crosslinking of various reactive functional groups (single aldehyde-amine photocoupled crosslinking is only the release and crosslinking of a single reactive functional group) greatly improve the crosslinking efficiency and crosslinking density, which further improve the mechanical properties of the material. Therefore, the optimization of the molecular structure make it as a photosensitive groups modification of polymer derivatives to exhibit more excellent material performance, such as the crosslinking speed increases from 30 s in the aldehyde-amine photocoupled crosslinking to less than 5 s, the tissue adhesion strength increases to about 48 kPa, the mechanical properties increases to about 450 kPa, specific data are shown in Example 102, Example 103, Example 104.

In the polymer derivatives modified with cyclic o-nitrobenzyl phototriggers or cyclic o-nitrobenzyl sulfide phototriggers or cyclic o-nitrobenzylamine phototriggers as shown in Formula A-III, it has an intramolecular ring structure. The phototriggers is designed to release another reactive functional group (such as a sulphydryl group) under irradiation which can be retained on the precursor of o-nitrobenzyl (another reactive functional group released from simple aldehyde-amine photocoupled crosslinking will be removed from the precursor of o-nitrobenzyl), thereby the additional release of the sulphydryl group on the basis of simultaneously release of the aldehyde group/keto group or nitroso group could further increase the effective crosslinking. In addition, in the cyclic o-nitrobenzyl sulfide phototriggers, the 3 d empty orbital of the sulfur atom (S) facilitates intramolecular charge transfer; in the cyclic o-nitrobenzylamine phototriggers, nitrogen atom (N) is a strong electron donor, which is conducive to intramolecular charge transfer and accelerates the photolysis rate and photolysis efficiency of the phototriggers. That is, the aldehyde group/keto group or nitroso group can be released more rapidly and more completely under irradiation which accelerates its crosslinking speed as crosslinking sites. And the released aldehyde/ketone group or nitroso can be connected to the active group on the surface of the tissue, which can greatly improve the adhesion strength between the material and the tissue. In addition, the simultaneous release and crosslinking of various reactive functional groups (single aldehyde-amine photocoupled crosslinking is only the release and crosslinking of a single reactive functional group) greatly improve the crosslinking efficiency and crosslinking density, which further improve the mechanical properties of the material. Therefore, the optimization of the molecular structure make it as a photosensitive groups modification of polymer derivatives to exhibit more excellent material performance, such as the crosslinking speed increases from 30 s in the aldehyde-amine photocoupled crosslinking to less than 5 s, the tissue adhesion strength increases to about 122 kPa, the mechanical properties increases to about 800 kPa, specific data are shown in Example 102, Example 103, Example 104.

In the polymer derivatives modified with o-nitrobenzyl sulfide phototriggers as shown in Formula A-I or the polymer derivatives modified with o-nitrobenzylamine phototriggers as shown in Formula A-II, the aldehyde or keto group generated by o-nitrobenzyl under illumination can react with primary amine, diamine, hydrazide or hydroxylamine by Schiff's base, the generated nitroso can react with itself, or react with other reactive group (e.g. sulfhydryl, hydroxyl, carboxyl, sulfonate, carbonyl, double bond, etc.) to form hydrogel. This crosslinking mode of simultaneously producing aldehyde/ketone or nitroso under illumination is a multiple photo-coupling crosslinking mode which has synergistic cross-linking effect, and can be called the photo-coupling synergistic crosslinking. The following diagram is schematic diagram of the photo-coupling synergistic crosslinking (o-nitrobenzyl phototriggers as shown in Formula A-I or Formula A-II).

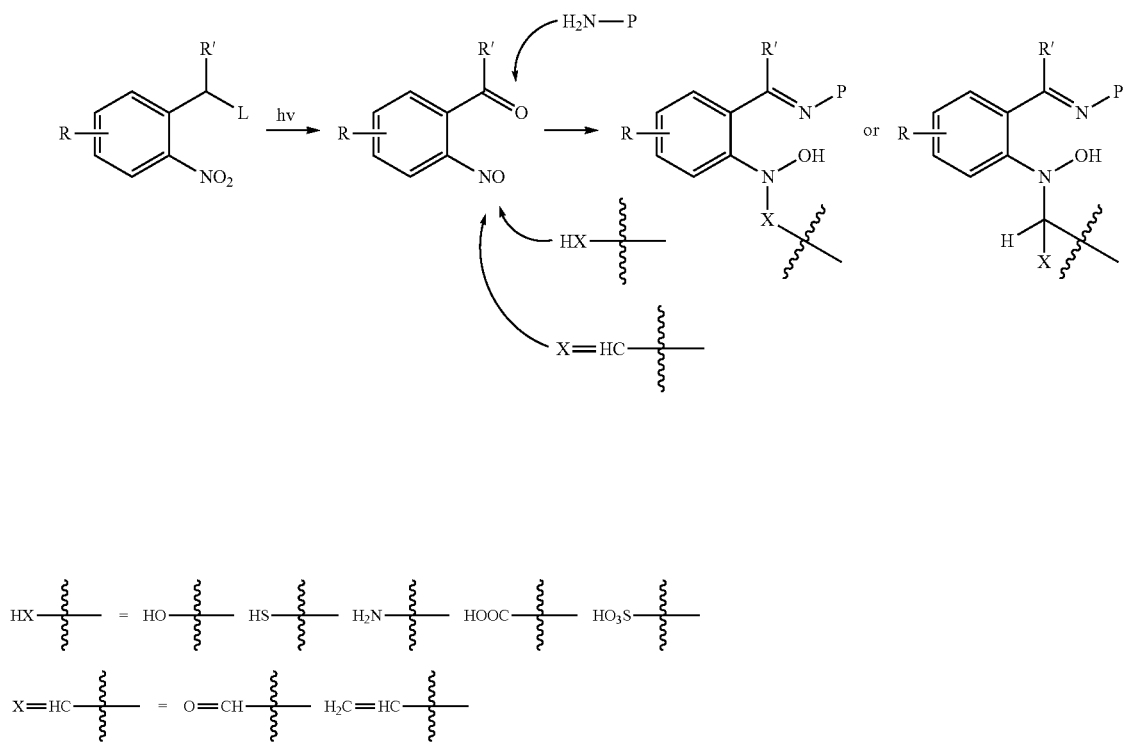

The polymer derivatives modified with cyclic o-nitrobenzyl sulfide phototriggers as shown in Formula A-III has an intramolecular cyclic structure. Except for the above crosslinking, the additionally released sulfhydryl group can react with nitroso generated by its own, or react with the double bond group in Component B by Michael addition, or react with thiol group by disulfide bond to form a hydrogel. This crosslinking mode of simultaneously producing aldehyde/ketone or nitroso and releasing mercapto group under illumination to produce further crosslinking is a multiple photo-coupling crosslinking mode which has synergistic cross-linking effect, and can be called the photo-coupling synergistic crosslinking. The following diagram is schematic diagram of the photo-coupling synergistic crosslinking (o-nitrobenzyl phototriggers as shown in Formula A-III):

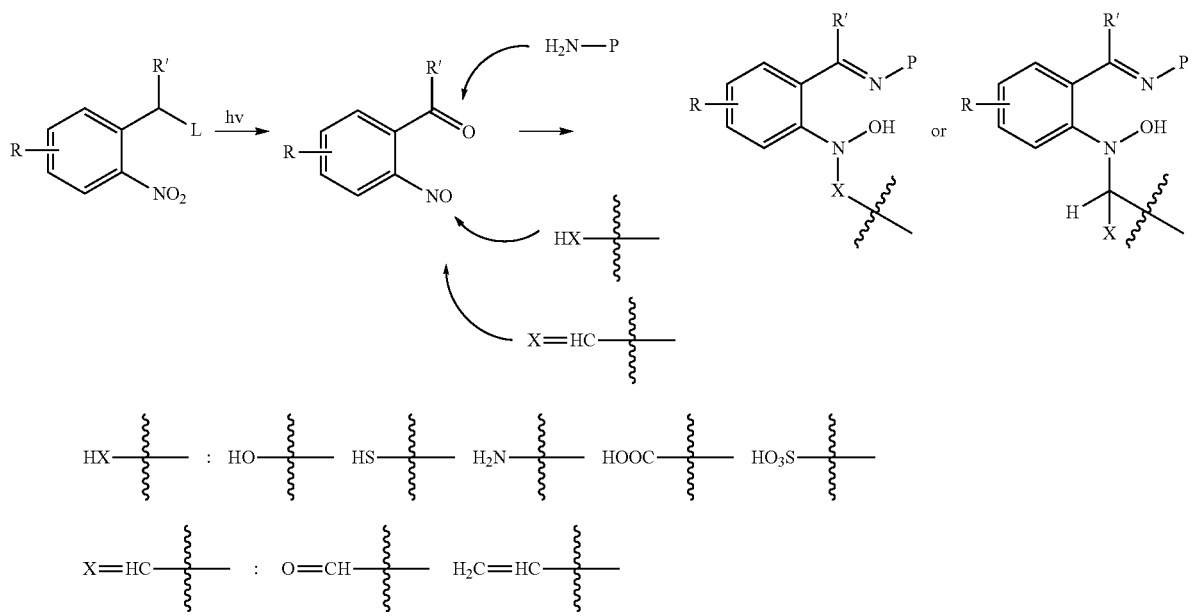

The third purpose of the present invention is to provide methods for preparing the polymer derivatives modified with the o-nitrobenzyl phototriggers.

In the present invention, the preparation methods of the polymer derivatives modified with the o-nitrobenzyl phototriggers are chemical labeling methods or manual polymerization methods.

Among them, the chemical labeling method is a chemical reaction between a polymer and a chemical group in an o-nitrobenzyl phototriggers, including labeling method between a polymer containing carboxyl group and an o-nitrobenzyl molecule containing hydroxyl group, mercapto group or amino group (O. P. Oommen, S. Wang, M. Kisiel, M. Sloff, J. Hilborn, O. P. Varghese, Adv. Funct. Mater. 2013, 23, 1273.); labeling method between a polymer containing hydroxyl group and an o-nitrobenzyl molecule containing carboxyl group or bromine group (Reference K. Peng, I. Tomatsu, A V Korobko, A. Kros, Soft Matter 2010, 6, 85; L. Li, N. Wang, X. Jin, R. Deng, S. Nie, L. Sun, Q. Wu, Y. Wei, C. Gong, Biomaterials 2014, 35, 3903.); labeling method between a polymer containing amine group and an o-nitrobenzyl molecule containing carboxyl group or bromine group (reference L. Li, N. Wang, X. Jin, R. Deng, S. Nie, L. Sun, Q. Wu, Y. Wei, C. Gong, Biomaterials 2014, 35, 3903.) and so on.

The method of artificial polymerization is copolymerization of functional monomer of o-nitrobenzyl derivative with other comonomer, and the method can be random free radical polymerization or control free radical polymerization (such as ATRP and RAFT polymerization) and so on.

The polymer derivatives modified with the o-nitrobenzyl phototriggers are specifically as follows:
1. polymer derivatives modified with o-nitrobenzyl sulfide phototriggers having the structure of Formula A-I;
2. polymer derivatives modified with o-nitrobenzylamine phototriggers having the structure of Formula A-II;
3. polymer derivatives modified with cyclic o-nitrobenzyl phototriggers, cyclic o-nitrobenzyl sulfide phototriggers or cyclic o-nitrobenzylamine phototriggers having the structure of Formula A-III.

In the invention, some of implementable preparation methods of the polymer derivatives modified with o-nitrobenzyl phototriggers (o-nitrobenzyl sulfide, o-nitrobenzylamine, cyclic o-nitrobenzyl, cyclic o-nitrobenzyl sulfide, cyclic o-nitrobenzylamine) are as follows:

The first implementable preparation method is: The solution of a water-soluble polymer or a polymer containing a carboxyl group in distilled water is added o-nitrobenzyl molecule containing reactive functional group hydroxyl group or mercapto group or amine group, and then added condensing agent 1-ethyl-(3-dimethyl amine propyl) carbodiimine hydrochloride (EDC-HCl) and the activator hydroxybenzotriazole (HOBt), then the mixture is stirred at room temperature for 24-48 h. After the reaction is completed, the reaction solution is added to a dialysis bag and dialyzed against a dilute hydrochloric acid solution for 2-3 d, and then freeze-dried to obtain the o-nitrobenzyl modified photosensitive polymer derivative.

The second implementable preparation method is: The solution of a water-soluble polymer or a polymer containing a carboxyl group in 0.01 mol/L 2-(N-morpholine) ethylsulfonic acid (MES) buffer solution (pH=5.2) is added in o-nitrobenzyl molecule dissolved in dimethyl sulfoxide. Then, 4-(4,6-dimethoxytriazin-2-yl)-4-methylmorpholine hydrochloride (DMTMM) dissolved in MES buffer solution is added in the above reaction solution in three times (every 1 h), and the mixture is reacted at 35° C. for 24 h. Then, the reaction solution is poured into a dialysis bag, dialyzed against deionized water for 2-3 d, and then freeze-dried to obtain the o-nitrobenzyl modified photopolymer derivative.

In the first implementable preparation method and the second implementable preparation method, the above water-soluble polymer or polymer containing carboxyl group may be polyethylene glycol, polysaccharide containing carboxyl group (e.g., hyaluronic acid, carboxymethyl cellulose, alginic acid, etc.), protein or polypeptide containing carboxyl group (e.g., gelatin, etc.), preferably be multi-arm carboxyl polyethylene glycol, hyaluronic acid, carboxymethyl cellulose, and gelatin. More preferably, it is hyaluronic acid.

The third implementable preparation method is: The solution of water-soluble polymer containing hydroxyl group or amine group dissolved in distilled water is added o-nitrobenzyl molecule containing a reactive functional group of carboxyl group. And the mixture is added a condensing agent of 1-ethyl-(3-dimethylaminopropyl) carbodiimide hydrochloride (EDC-HCl) and a catalyst of toluene pyridinium p-toluenesulfonate (DPTS) and stirred at room temperature for 24-48 h. Then the reaction solution is poured into an insoluble solvent to reprecipitate (for example, the modified polyethylene glycol derivative can be poured into diethyl ether to reprecipitate, the polysaccharide polymer derivative can be poured into ethanol to reprecipitate). The obtained sediment is dissolved in water and dialyzed for 2-3 days in a dialysis bag, and freeze-dried to obtain o-nitrobenzyl modified photosensitive polymer derivative.

The fourth implementable preparation method is: The solution of water-soluble polymer containing hydroxyl group or amine group dissolved in distilled water is added o-nitrobenzyl molecule containing a reactive functional group of bromine and potassium carbonate as a base, and the mixture is stirred at room temperature for 24-48 hours. Then the reaction solution is poured into an insoluble solvent to reprecipitate (for example, the modified polyethylene glycol derivative can be poured into diethyl ether to reprecipitate, the polysaccharide polymer derivative can be poured into ethanol to reprecipitate). The obtained sediment is dissolved in water and dialyzed for 2-3 days in a dialysis bag, and freeze-dried to obtain o-nitrobenzyl modified photosensitive polymer derivative.

In the third implementable preparation method and the fourth implementable preparation method, the above water-soluble polymer or polymer containing hydroxyl group or amine group may be polyethylene glycol or natural polysaccharide or protein/polypeptide containing hydroxyl group or amine group, preferably multi-arm hydroxyl polyethylene glycol, multi-arm amine polyethylene glycol, ethylene glycol chitosan, propylene glycol chitosan, carboxymethyl chitosan, chitosan lactate, natural polysaccharide, polylysine or gelatin, etc., further preferably ethylene glycol chitosan, multi-arm hydroxyl polyethylene glycol.

In the above reaction, the molar ratio of the carboxyl group, the hydroxyl group or the amine group in the water-soluble polymer to the molecule of o-nitrobenzyl derivative is preferably 1:0.1-2; the molar ratio of amine-modified o-nitrobenzyl molecule to 1-ethyl-(3-dimethylamine-propyl) carbodiimine hydrochloride (EDC-HCl) and the activator of hydroxybenzotriazole (HOBt) is 1:2:1; the molar ratio of amine-modified o-nitrobenzyl molecule to 4-(4,6-dimethoxytriazine-2-group)-4-methyl morpholine hydrochloride (DMTMM) is 1:7.5; the molar ratio of carboxyl-modified o-nitrobenzyl molecule to 1-ethyl-(3-dimethylamine-propyl) carbodiimine hydrochloride (EDC-HCl) and the catalyst of DPTS is 1:2:1; the molar ratio of o-nitrobenzyl bromide molecule to potassium carbonate is 1:2.

The fifth implementable preparation method is: The o-nitrobenzyl modified synthetic copolymer can be obtained by polymerization between an o-nitrobenzyl polymerizable monomer derivative and one or more polymerizable co-monomers. It is purified by multiple dissolution-re-precipitation methods.

The above o-nitrobenzyl polymerizable monomer derivative may be acrylate ester, methacrylate, acrylamide or methacrylamide, preferably methacrylate and acrylamide, more preferably methacrylate.

At least one of the above polymerizable comonomers must be water-soluble comonomer selected from the water-soluble polymerizable comonomer of polyethylene glycol methacrylate (PEG-MA), polyethylene glycol acrylate, methacrylic acid (MAA), acrylic acid (AA), hydroxyethyl acrylate, acrylamide (AM), etc. The polymerizable monomer is preferably polyethylene glycol methacrylate (PEG-MA). Other co-monomers are selected for different applications.

The polymerization molar ratio of the above o-nitrobenzyl polymerizable monomer derivative to the water-soluble comonomer may be from 1:20 to 1:2, preferably from 1:9 to 1:3, further preferably 1:4.

The above polymerization method may be random radical polymerization or controlled radical polymerization (such as RAFT polymerization, ATRP polymerization, etc.). It is preferably a random radical polymerization. That is, the o-nitrobenzyl polymerizable monomer derivative and the comonomer are co-dissolved in a certain solvent, and the solution is added a radical initiator. After three freeze-vacuum cycle operations, the mixture is reacted under heating overnight. Then, the reaction solution is poured into dry diethyl ether to precipitate, and after several times of dissolution-re-precipitation purification process, the o-nitrobenzyl group-containing copolymer is obtained by vacuum drying. (G. Delaittre, T. Pauloehrl, M. Bastmeyer, C. Barner-Kowollik, Macromolecules 2012, 45, 1792-1802.)

The fourth purpose of the present invention is to provide methods of preparing a photo-coupling synergistic crosslinking hydrogel material. The photo-coupling synergistic crosslinking hydrogel material is prepared by using polymer derivatives modified with o-nitrobenzyl phototriggers as raw materials according to the second purpose of the invention.

The methods for preparing the photo-coupling synergistic crosslinking hydrogel material of the present invention include the steps as follows: the component A—the polymer derivatives modified with o-nitrobenzyl phototriggers in the second purpose of the present invention is dissolved in biocompatible medium to obtain solution A as hydrogel precursor solution. Under illumination, the nitroso generated by o-nitrobenzyl phototriggers in component A has strong reactivity, it can react with itself or react with other reactive groups in component A (such as mercapto, hydroxyl, amine, carboxyl, sulfonate, carbonyl, double bond, etc.) to form a hydrogel.

Further, the methods for preparing the photo-coupling synergistic crosslinking hydrogel material of the present invention include the steps as follows:

The component A—the polymer derivatives modified with o-nitrobenzyl phototriggers in the second purpose of the present invention is dissolved in biocompatible medium to obtain solution A;

The component B is dissolved in biocompatible medium to obtain solution B, and component B is selected from one or more of amine-containing polymer derivatives, double bond-containing polymer derivatives or mercapto-containing polymer derivatives;

The solution A and solution B are homogeneously mixed to obtain hydrogel precursor solution;

Under illumination, the nitroso generated from o-nitrobenzyl phototriggers in component A has strong reactivity; it can react with itself or react with other reactive groups in component A or component B (such as mercapto, hydroxyl, amine, carboxyl, sulfonate, carbonyl, double bond, etc.). In addition, the aldehyde or ketone group produced by the o-nitrobenzyl in component A under illumination can react with primary amine, hydrazine, hydrazide, hydroxylamine group in component B by Schiff base to form a hydrogel.

Further, when component A is polymer derivatives modified with cyclic o-nitrobenzyl sulfide phototriggers represented in Formula A-III, except for the above-mentioned crosslinking mode, the mercapto group additionally released under the illumination by the polymer derivatives modified with cyclic o-nitrobenzyl sulfide phototriggers in Formula A-III can crosslink with the nitroso group produced by itself, or react with double bond group in component B by Michael addition, or crosslink with thiol group by disulfide bond to form a hydrogel. This crosslinking mode of simultaneously producing aldehyde/ketone or nitroso and releasing mercapto group under illumination to produce further crosslinking is a multiple photo-coupling crosslinking mode which has synergistic cross-linking effect, and can be called the photo-coupling synergistic crosslinking.

The polymer derivatives containing amine group include polymer derivatives containing primary amine, hydrazine, hydrazide, hydroxylamine group respectively having the structure of Formulas B-I, Formulas B-II, Formulas B-III, Formulas B-IV.

The polymer derivatives containing double bond include polymer derivatives containing maleimide, vinyl sulfone, acrylate or acrylamide group respectively having the structure of Formulas B-V, Formulas B-VI, Formulas B-VII.

The polymer derivatives containing mercapto group have the structure of Formula B-VIII.

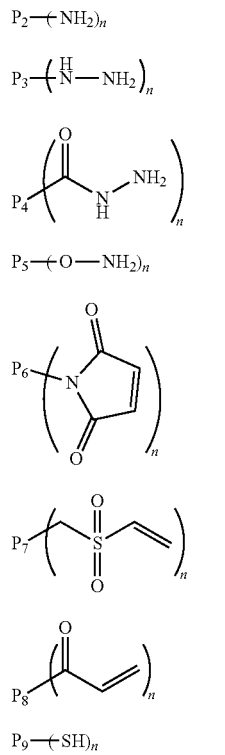

In the above structure of component B, n≥2, $P_2$, $P_3$, $P_4$, $P_5$, $P_6$, $P_7$, $P_8$ and $P_9$ are hydrophilic or water-soluble natural polymers or synthetic polymers.

Among them, the polymer derivatives containing amine group (such as polymer derivatives containing primary amine, hydrazine, hydrazide, hydroxylamine group) as shown in Formula B-I represent hydrophilic or water soluble natural polymer or synthetic polymer containing n amino groups; as shown in Formula B-II represent hydrophilic or water-soluble natural high polymer or synthetic polymer containing n diamine groups; as shown in Formula B-III represent hydrophilic or water-soluble natural high polymer or synthetic polymer containing n hydrazide groups; as shown in Formula B-IV represent hydrophilic or water-soluble natural high polymer or synthetic polymer containing n hydroxylamine groups.

In addition, the polymer derivatives containing primary amine group, hydrazine group, hydrazide group, hydroxylamine group may also be hydrophilic or water-soluble natural high polymer or synthetic polymer containing one or more of the above groups.

Among them, the polymer derivatives containing double bond (such as maleimide, vinyl sulfone, acrylate or acrylamide) as shown in Formula B-V represent hydrophilic or water soluble natural high polymer or synthetic polymer containing n maleimide group; as shown in Formula B-VI represent hydrophilic or water-soluble natural high polymer or synthetic polymer containing n vinylsulfone groups; as shown in Formula B-VII represent hydrophilic or water-soluble natural high polymer or synthetic polymer containing n acrylate or acrylamide groups.

Among them, the polymer derivatives containing mercapto group as shown in Formula B-VIII represent hydrophilic or water-soluble natural high polymer or synthetic polymer containing n mercapto groups.

$P_2$, $P_3$, $P_4$, $P_5$, $P_6$, $P_7$, $P_8$, $P_9$ are defined same as above $P_1$ which is the hydrophilic or water-soluble natural high polymers and their modifications, or hydrophilic or water-soluble synthetic polymers and their modifications.

Hydrophilic or water-soluble natural polymers include natural polysaccharides and their decorations or degradations, proteins and their decorations, modifiers and degradable peptides, etc. The natural polysaccharides include hyaluronic acid, carboxymethyl cellulose, methyl cellulose, hydroxyethyl cellulose, hydroxypropyl cellulose, alginate, dextran, agarose, heparin, chondroitin sulfate, glycol chitosan, propylene glycol chitosan, chitosan lactate, carboxymethyl chitosan or quaternary ammonium salt of chitosan. The protein includes various hydrophilic or water-soluble animal and plant proteins, collagen, serum proteins, silk fibroin proteins and elastin, and the protein degradations include gelatin or polypeptides.

Hydrophilic or water-soluble synthetic polymers include two-arm or multi-arm poly (ethylene glycol), poly (ethylene imine), dendrites, synthetic peptides, polylysine, poly (glutamic acid), poly (acrylic acid), poly (methacrylic acid), polyacrylate, poly (methacrylate), poly (acrylamide), poly (methacrylamide), poly (vinyl alcohol), poly (vinyl pyrrolidone) and their modifiers.

In addition, the polymer derivatives containing amine group, double bond, or mercapto group may be hydrophilic or water-soluble polymer containing one or more different of the above groups, or a mixture of hydrophilic or water soluble polymers containing one or more different of the above groups.

Alternatively, the Formula B-I could be selected from Component B-1 to Component B-9; the Formula B-II could be selected from Component B-10; Formula B-III could be selected from Component B-11 to Component B-13; the Formula B-IV could be selected from Component B-14 to Component B-15; Formula B-V could be selected from Component B-16 to Component B-18; the Formula B-VI could be selected from Component B-19 to Component B-21; Formula B-VII could be selected from Component B-22 to Component B-29; the Formula B-VIII could be selected from Component B-30 to Component B-35:
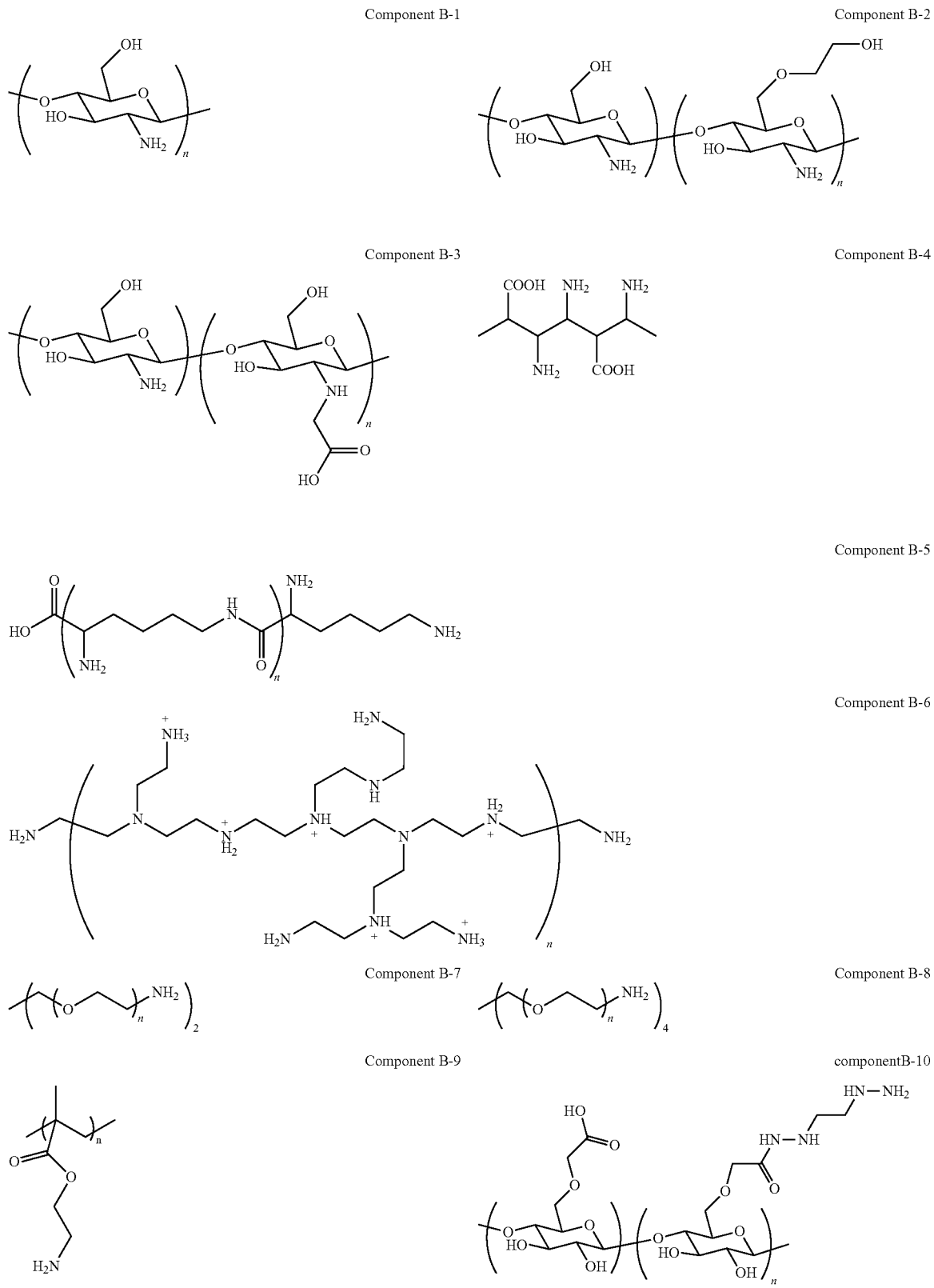

-continued
Component B-11
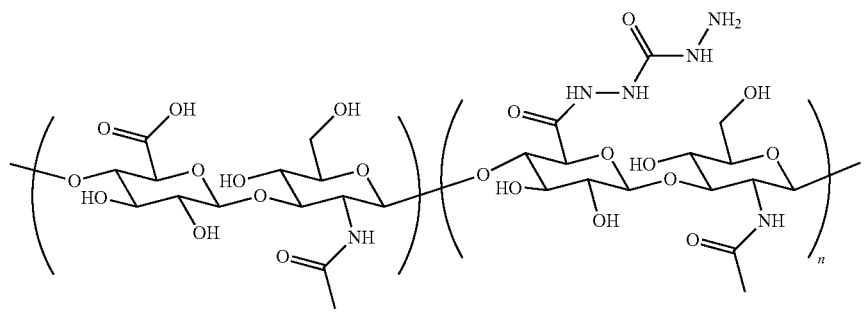
Component B-12
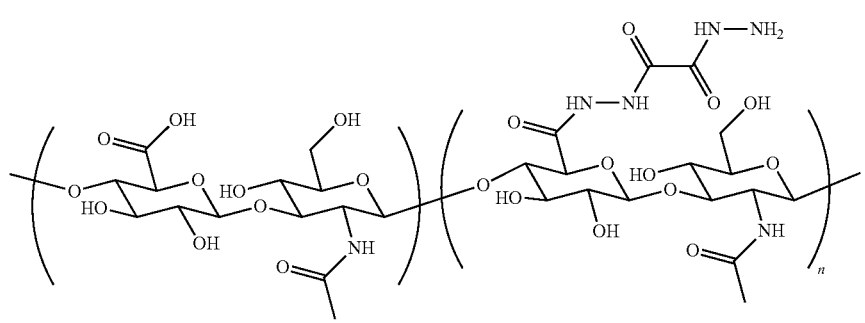
Component B-13
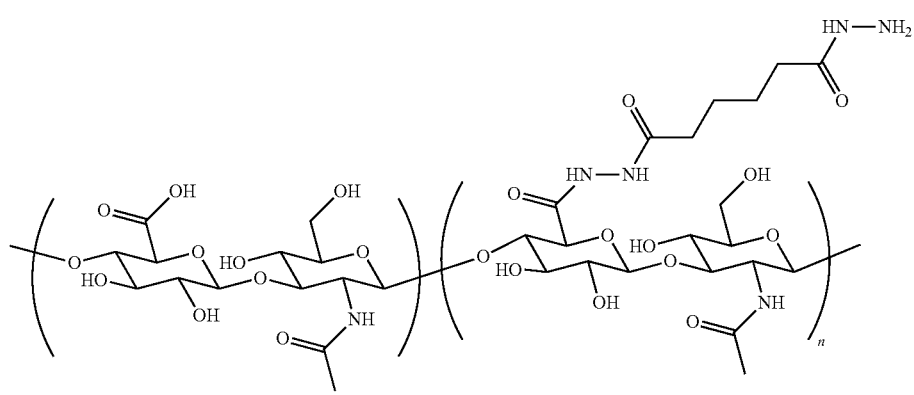
Component B-14
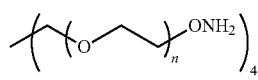
Component B-15
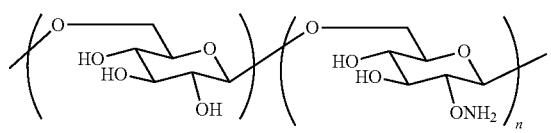
Component B-16
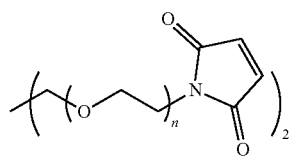
Component B-17
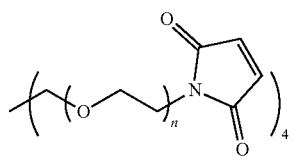
Component B-18
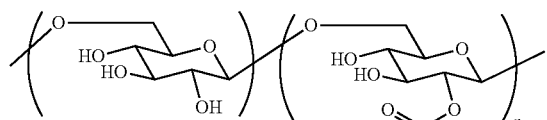
Component B-19
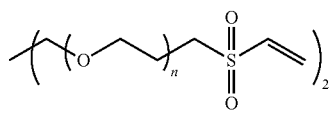
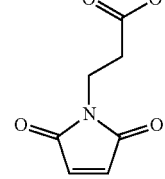

-continued
Component B-20
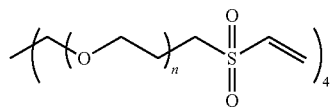
Component B-21
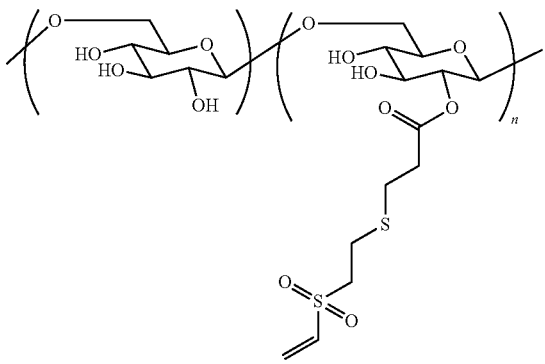
Component B-22
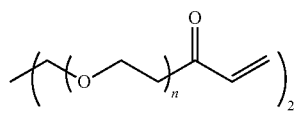
Component B-23
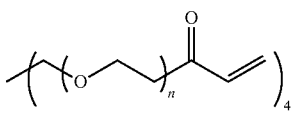
Component B-24
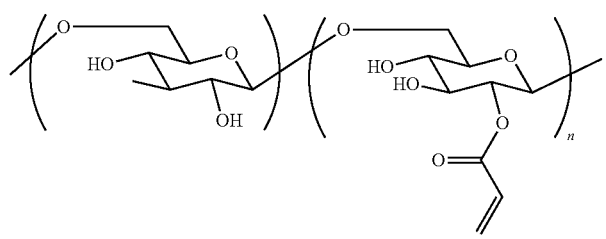
Component B-25
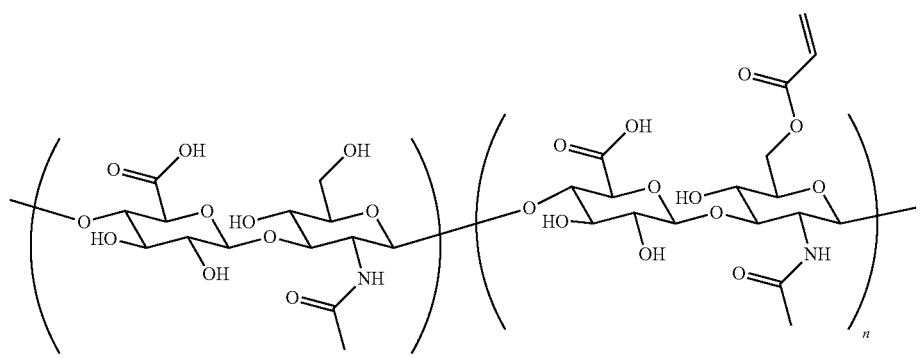
Component B-26
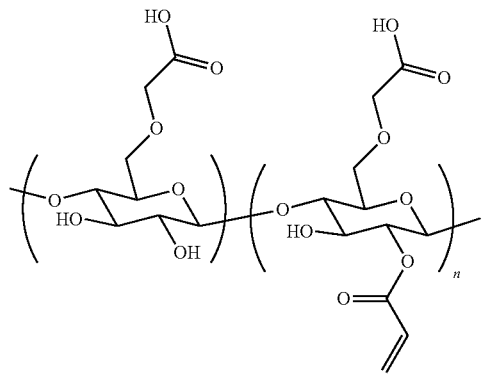
Component B-27
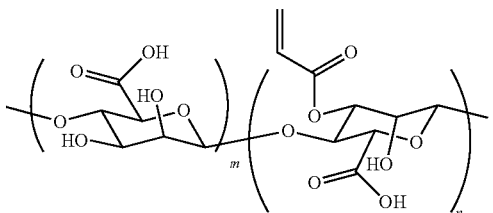

Component B-28
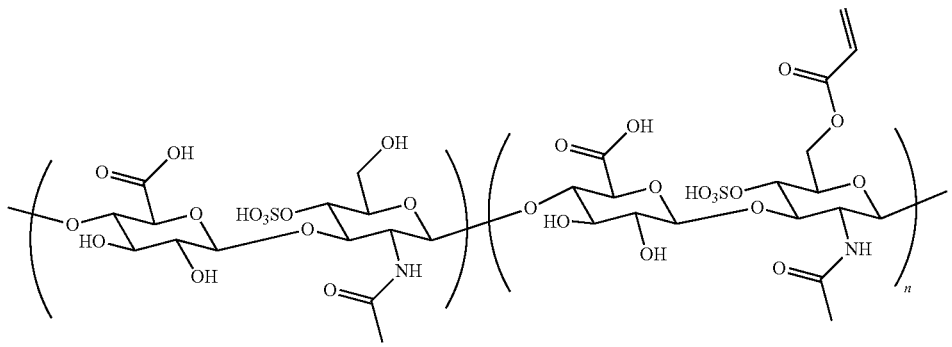
Component B-29
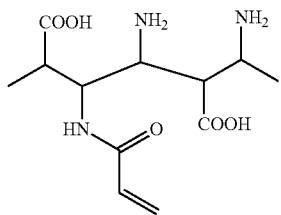
Component B-30
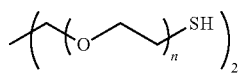
Component B-31
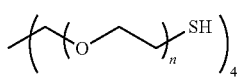
Component B-32
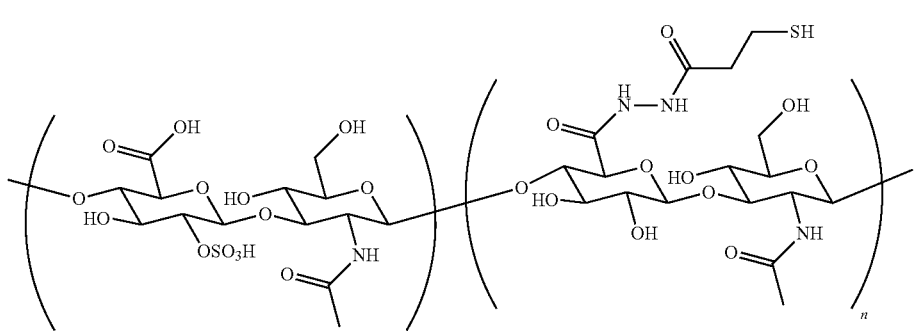
Component B-33
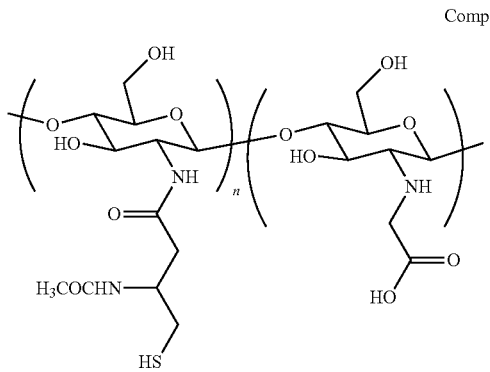
Component B-34
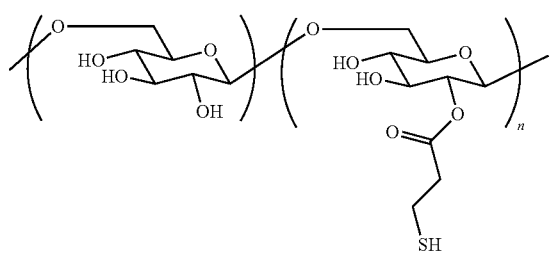

Component B-35

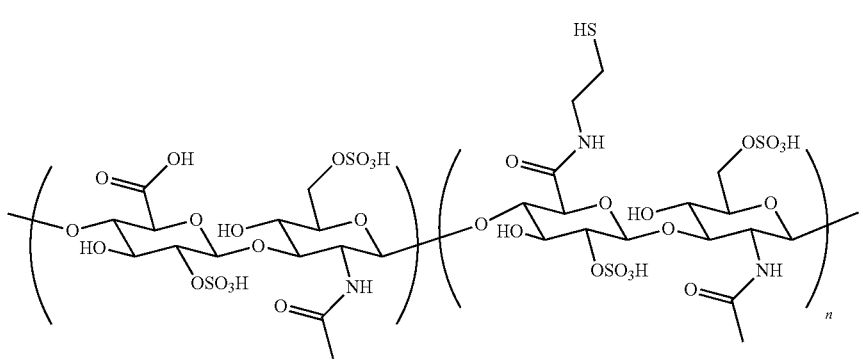

In Component B-1 to Component B-35, n≥2, Component B-1 is chitosan; Component B-2 is ethylene glycol chitosan; Component B-3 is carboxymethyl chitosan; Component B-4 is gelatin; Component B-5 is polylysine; Component B-6 is polyethyleneimine; Component B-7 is bi-arm amine polyglycol; Component B-8 is four-arm amine polyethylene glycol; Component B-9 is amine polymer; Component B-10 is carboxymethyl cellulose modified with diamine; and Component B-11 to Component B-13 is hyaluronic acid modified with hydrazide; Component B-14 is tetra-arm hydroxyamine polyethylene glycol; Component B-15 is glucose modified with hydroxylamine; Component B-16 is a two-arm maleimide polyethylene glycol; Component B-17 is a four-arm maleimide polyethylene glycol; Component B-18 is a maleimide modified glucose; Component B-19 is a two-arm vinyl sulfone polyethylene glycol; Component B-20 is four-arm vinyl sulfone polyethylene glycol; Component B-21 is glucose modified with vinyl sulfone; Component B-22 is two-arm acrylate polyethylene glycol; Component B-23 is a four-arm acrylate polyethylene glycol; Component B-24 is a glucose modified with acrylate; Component B-25 is a hyaluronic acid modified with acrylate; Component B-26 is a carboxymethyl cellulose modified with acrylate; Component B-27 is alginic acid modified with acrylate; Component B-28 is chondroitin sulfate modified with acrylate; Component B-29 is gelatin modified with acrylate; Component B-30 is two-arm thiol polyethylene glycol; Component B-31 is tetrahedyl polyethylene glycol; Component B-32 is hyaluronic acid modified with thiol; Component B-33 is chitosan modified with thiol; Component B-34 is glucose modified with thiol; Component B-35 is heparin modified with thiol.

The invention also provides a process for the preparation of Component B.

In the present invention, the amine-modified water-soluble polymer may be synthetic polyamine polymer and their modifications (such as polyethyleneimine PEI, dendrimer PAMAM, two-arm or multi-arm amine-based polyethylene glycol), or natural amino-containing polysaccharide hydrophilic or water-soluble polymer and their modifications or degradation products (such as ethylene glycol chitosan, propylene glycol chitosan, chitosan lactate, carboxymethyl chitosan, Chitooligosaccharide, etc.); or protein or their modifications or degradation products (such as collagen, serum protein and gelatin, etc.) extracted after being expressed by microorganisms or microorganisms; or hydrophilic or water-soluble polypeptide (such as polylysine, etc.) contains two or more amine groups which synthesized or extracted by microorganisms, or acrylate, methacrylate, acrylamide or acrylamide-based polymers and their modifications. More preferably, it is gelatin or ethylene glycol chitosan.

The polymer derivatives containing hydrazine group, that is, the polymer derivatives modified with hydrazine can be prepared by following: To a solution of water-soluble polymer containing carboxyl group and diamine in distilled water is added condensing agent 1-ethyl-(3-dimethylaminopropyl) carbodiimide hydrochloride (EDC-HCl) and the activator hydroxybenzotriazole (HOBt). Then, the reaction system is stirred at room temperature for 24-48 h. After completion of the reaction, the reaction solution is poured into a dialysis bag and dialyzed against a dilute hydrochloric acid solution for 2-3 d, and then freeze-dried to obtain the polymer derivatives modified with hydrazine.

The water-soluble polymer containing carboxyl group may be carboxyl polyethylene glycol or polysaccharide containing carboxyl group (such as chitosan lactate, carboxymethyl chitosan, hyaluronic acid, alginic acid, or carboxymethyl cellulose, etc.). It is preferably multi-arm carboxy polyethylene glycol or hyaluronic acid, and more preferably hyaluronic acid.

In the above reaction, the molar ratio of the carboxyl group in the water-soluble polymer to the small molecule diamine is preferably 1:0.1-2; the molar ratio of the diamine small molecule to 1-ethyl-(3-dimethylaminopropyl) carbodiimide hydrochloride (EDC-HCl) and the activator hydroxybenzotriazole (HOBt) is preferably 1:2:1.5.

The polymer derivatives containing hydrazide, that is, the polymer derivatives modified with hydrazide can be prepared by following: To a solution of water-soluble polymer containing carboxyl group and dihydrazide in distilled water is added condensing agent 1 ethyl-(3-dimethylaminopropyl) carbodiimide hydrochloride (EDC-HCl) and the activator hydroxybenzotriazole (HOBt). Then reaction system is stirred at room temperature for 24-48 h. After completion of the reaction, the reaction solution is poured into a dialysis bag and dialyzed against a dilute hydrochloric acid solution for 2-3 d, then lyophilized to obtain the polymer derivatives modified with hydrazide.

The water-soluble polymer containing carboxyl group may be carboxyl polyethylene glycol or polysaccharide containing carboxyl group (such as chitosan lactate, carboxymethyl chitosan, hyaluronic acid, alginic acid, or carboxymethyl cellulose, etc.). It is preferably multi-arm carboxyl polyethylene glycol or hyaluronic acid, and more preferably hyaluronic acid.

In the above reaction, the molecule dihydrazide may be any dihydrazide such as carbodihydrazide, oxalic acid dihydrazide, diacylhydrazine malonate, diacylhydrazine succinate, diacylhydrazine glutarate, diacylhydrazine adipate, diacylhydrazine heptanate, etc. It may preferably be carbodihydrazide, oxalic acid dihydrazide, or diacylhydrazine adipate, and more preferably be carbon dihydrazide. The molar ratio of carboxyl group in water-soluble polymer to molecule dihydrazide is optimized as 1:0.1-2. The molar ratio of molecule dihydrazide to 1-ethyl-(3-dimethyl aminopropyl) carbodiimine hydrochloride (EDC-HCl) and the activator hydroxybenzotriazole (HOBt) is optimized as 1:2: 1.5.

The polymer derivatives containing hydroxylamine group, that is, polymer derivatives modified with hydroxylamine can be prepared by following: To a solution of hydroxyl group-containing polymer and N-hydroxyphthalimide in dichloromethane solution is added triphenylphosphine and then slowly added diisopropyl azodicarboxylate, the solution is reacted for 16-24 hours. The system is precipitated in diethyl ether, and the obtained solid is re-dissolved in dichloromethane. Then the above solution is added hydrazine hydrate to react for 1-3 hours and obtains hydroxylamine-modified polymer derivatives.

The above polymer containing hydroxyl group may be polyethylene glycol, polysaccharide (such as glucose or chitosan), and more preferably multi-arm hydroxyl polyethylene glycol.

In the above reaction, the molar ratio of the hydroxyl group in the polymer to N-hydroxyphthalimide, triphenylphosphine, diisopropylazodicarboxylate, hydrazine hydrate is preferably 1:10:10:10:10.

The polymer derivatives containing maleimide group, that is, polymer derivatives modified with maleimide can be prepared by following: To a solution of water-soluble polymer containing hydroxyl group or amino group in water or in dimethyl sulfoxide is dropwise added a certain proportion of N-maleimidopropionic acid, p-toluenesulfonic acid pyridinium salt (DPTS) and dicyclohexylcarbodiimide (DCC) in dimethyl sulfoxide. After completion of the addition, the mixture is reacted at room temperature for 24 hours, and the insoluble matter is filtered off. Then, the filtrate is poured into cold ethanol to precipitate, and washed several times. The obtained crude is dissolved in water, poured into a dialysis bag (MWCO 3500), dialyzed against deionized water for 2-3 d, and lyophilized to obtain the polymer derivatives modified with maleimide.

The above water-soluble polymer containing hydroxyl group or amine group may be polyethylene glycol containing hydroxyl group or amine group or natural polysaccharide or protein/polypeptide, it is preferably multi-arm hydroxyl polyethylene glycol or polyarm amine polyethylene glycol, ethylene glycol, ethylene glycol chitosan, propylene glycol chitosan, carboxymethyl chitosan, chitosan lactate or natural polysaccharide, or polylysine, gelatin, etc., and more preferably glucose, multi-arm hydroxy polyethylene glycol, ethylene glycol chitosan.

The polymer derivatives containing vinyl sulfone group, that is, polymer derivatives modified with vinyl sulfone can be prepared by following: To a solution of water-soluble polymer containing hydroxyl group or amine group in water or dimethyl sulfoxide is dropwise added a certain proportion of carboxylic acid vinyl sulfone, p-toluenesulfonic acid pyridinium salt (DPTS) and dicyclohexyl carbodiimide (DCC) in dimethyl sulfoxide. After completion of the addition, the mixture reaction system is reacted at room temperature for 24 hours, and the insoluble matter is filtered off. The filtrate is poured into cold ethanol to precipitate, and washed several times. The obtained crude product is then dissolved in water, poured into a dialysis bag (MWCO 3500), dialyzed against deionized water for 2-3 d, and then lyophilized to obtain the polymer derivatives modified with vinyl sulfone.

The above water-soluble polymer containing hydroxyl group or amine group may be hydroxyl group or amine group-containing polyethylene glycol or natural polysaccharide or protein/polypeptide, it is preferably multi-arm hydroxyl polyethylene glycol or multi-arm amine polyethylene glycol, ethylene glycol chitosan, propylene glycol chitosan, carboxymethyl chitosan, chitosan lactate or natural polysaccharide, or polylysine, gelatin, etc., and more preferably glucose, multi-arm hydroxyl polyethylene glycol, ethylene glycol chitosan.

The preparation methods of the polymer derivatives modified with the double bond include the following methods:

The first implementable preparation method is: The solution of water-soluble polymer containing hydroxyl group or amine group dissolved in deionized water is added anhydride or methacrylate anhydridec at 0-4° C. and then slowly added 5M NaOH to obtain a mixture. The mixture is stirred for 24 h to obtain a reaction solution. Then, the reaction solution is poured into a dialysis bag, dialyzed against deionized water for 2-3 d, and then freeze-dried to obtain the double bond-modified photosensitive polymer derivative.

The above water-soluble polymer or polymer containing hydroxyl group or amine group may be polyethylene glycol, hydroxyl group or amine group-containing polysaccharide (e.g., hyaluronic acid, alginic acid, carboxymethyl cellulose, carboxymethyl chitosan, dextran, chondroitin sulfate, etc.), protein or polypeptide containing hydroxyl group or amine group (e.g., gelatin, etc.), preferably be hyaluronic acid, gelatin, alginic acid, carboxymethylcellulose, chondroitin sulfate, and more preferably be hyaluronic acid.

The second implementable preparation method is: The solution of water-soluble polymer containing hydroxyl or amine group dissolved in deionized water is added glycidyl acrylate or glycidyl methacrylate at 40° C. and then added 5M NaOH, and the mixture is reacted for 2-3 h. Then the reaction solution is poured into a dialysis bag, dialyzed against deionized water for 2-3 d, and then freeze-dried to obtain the double bond-modified photosensitive polymer derivative.

The above water-soluble polymer or polymer containing hydroxyl group or amine group may be polyethylene glycol, hydroxyl group or amine group-containing polysaccharide (e.g., hyaluronic acid, alginic acid, carboxymethyl cellulose, carboxymethyl chitosan, dextran, chondroitin sulfate, etc.), protein or polypeptide containing hydroxyl group or amine group (e.g., gelatin, etc.), preferably be hyaluronic acid, gelatin or carboxymethyl chitosan, and more preferably be carboxymethyl chitosan.

The third implementable preparation method is: The solution of water-soluble polymer containing hydroxyl or amine groups dissolved in dry dimethyl sulfoxide is added triethylamine and then acryloyl chloride or methacryloyl chloride dissolved in dichloromethane, and the reaction is carried out for 10 hours. Then, the reaction solution is poured into ethyl alcohol to reprecipitate. The crude product obtained by filtration is redissolved in deionized water, dialyzed for 2-3 d, and then freeze-dried to obtain the double-bond modified photopolymer derivative.

The water-soluble polymers or polymers containing hydroxyl or amine group mentioned above may be polyethylene glycol, polysaccharides containing hydroxyl or amine groups (such as: glucan, etc.), preferably be multi-arm polyethylene glycol and glucan, and further preferably be dextran.

The method for preparing polymer derivatives containing mercapto group, that is, polymer derivatives modified with thiol group, is chemical labeling method. It is specifically a chemical reaction between a polymer and a chemical group contained in a thiol-containing derivative, it may be carboxyl group-containing polymer and amine group-containing or hydrazide-containing or hydroxylamine-containing small molecule (with reference of Amy Fu, Kihak Gwon, Julia A. Kornfield, Biomacromolecules. 2015, 16, 497; Tugba Ozdemir, Swati Pradhan-Bhatt, Xinqiao Jia, ACS Biomater. Sci. Eng. 2016, 2, 2217.), or hydroxyl group-containing polymer and carboxyl group-containing or bromine-containing small molecule (with reference of Rayun Choi, Yong-Min Huh, Seungjoo Haam, Langmuir. 2010, 26, 17520.), or amine group-containing polymer and carboxyl group-containing or bromine-containing small molecule (with reference of Hanwei Zhang, Aisha Qadeer, Weiliam Chen, Biomacromolecules. 2011, 12, 1428.), or other labeling methods.

The preparation methods of the thiol-modified polymer derivatives include the following methods:

The first implementable preparation method is as follows. The solution of a water-soluble polymer or a polymer containing a carboxyl group in distilled water is added small molecule containing mercapto group and the active functional group of amine or hydrazide or hydroxylamine, and then added condensing agent 1-ethyl-(3-dimethyl amine propyl) carbodiimine hydrochloride (EDC-HCl) and the activator hydroxybenzotriazole (HOBt), then the mixture is stirred at room temperature for 24-48 h. After the reaction is completed, the reaction solution is added to a dialysis bag and dialyzed against a dilute hydrochloric acid solution for 2-3 d, and then freeze-dried to obtain the o-nitrobenzyl modified photosensitive polymer derivative.

The above water-soluble polymers or polymers containing carboxyl groups can be polyethylene glycol, polysaccharides containing carboxyl groups (such as: hyaluronic acid, carboxymethyl cellulose, alginate, heparin, etc.), preferably be polyethylene glycol, hyaluronic acid, heparin, and further preferably be hyaluronic acid and heparin.

The second implementable preparation method is: The solution of a water-soluble polymer or a polymer containing hydroxyl or amine group dissolved in distilled water is added molecule containing sulphydryl and carboxyl functional group, and then added condensing agent 1-ethyl-(3-dimethyl amine propyl) carbodiimine hydrochloride (EDC-HCl) and the activator 4-(dimethylamine) pyridine. The mixture is stirred at room temperature for 24-48 h. After the reaction is completed, the reaction solution is poured into an insoluble solvent to reprecipitate (for example, the modified polyethylene glycol derivative can be poured into diethyl ether to reprecipitate, the polysaccharide polymer derivative can be poured into ethanol to reprecipitate). The obtained sediment is dissolved in water and dialyzed for 2-3 days in a dialysis bag, and freeze-dried to obtain sulphydryl modified photosensitive polymer derivative.

The water-soluble polymer or polymer containing hydroxyl group may be polyethylene glycol or natural polysaccharide, preferably be multi-arm polyethylene glycol or dextran, and more preferably be dextran. The above mentioned amino-containing water-soluble polymer or polymer may be polyethylene glycol, natural polysaccharide, protein or polypeptide, preferably be poly-arm amine-contained polyethylene glycol, ethylene glycol chitosan, propylene glycol chitosan, carboxymethyl chitosan, chitosan lactates or proteins and peptides, more preferably be carboxymethyl chitosan.

The third implementable preparation method is: The solution of water-soluble polymer containing hydroxyl group or amine group dissolved in distilled water is added small molecule containing mercapto protective group and the active functional group bromine and potassium carbonate as base. And the mixture is stirred at room temperature for 24-48 h. Then the reaction solution is poured into an insoluble solvent to reprecipitate (for example, the modified polyethylene glycol derivative can be poured into diethyl ether to reprecipitate, the polysaccharide polymer derivative can be poured into ethanol to reprecipitate). The obtained sediment is dissolved in water and added DTT for deprotection. After reaction for a period of time, the solution is poured into a dialysis bag to dialyze for 2-3 days and freeze-dried to obtain polymer derivative modified with sulphydryl.

The above water-soluble polymer or polymer containing hydroxyl group may be polyethylene glycol or natural polysaccharide, preferably be multi-arm polyethylene glycol or dextran, and more preferably be dextran. The above water-soluble polymer or polymer containing amino group may be polyethylene glycol or natural polysaccharide or protein and polypeptide, preferably be poly-arm amine-based polyethylene glycol, ethylene glycol chitosan, propylene glycol chitosan, carboxymethyl chitosan, chitosan lactates or proteins and peptides, more preferably be carboxymethyl chitosan.

In the above reaction, the molar ratio of the carboxyl group, the hydroxyl group or the amine group in the water-soluble polymer to the molecule mercapto derivative is preferably 1:0.1-2; the molar ratio of small mercapto molecules modified with amines or hydrazides or hydroxylamines to 1-ethyl-(3-dimethylamine propyl) carbodiimine hydrochloride (EDC-HCl) and the activator hydroxybenzotriazole (HOBt) is optimized to be 1:1.5:1.5; the molar ratio of carboxyl-modified mercapto molecule to 1-ethyl-(3-dimethylamine propyl) carbodiimine hydrochloride (EDC-HCl) and catalyst 4-(dimethylamine) pyridine is optimized to be 1:1.5:1.5, and the molar ratio of bromide mercapto molecule to potassium carbonate is optimized to be 1:2.

In the fourth purpose of the invention, the biocompatible medium is selected from distilled water, physiological saline, buffer, and cell culture medium solutions. Different medium can be selected depending on the application.

In the fourth purpose of the present invention, the total concentration of the polymer in solution A may be 0.1% wt-60% wt, it is preferably 1% wt-10% wt; or the solution A is added to the solution B and then uniformly mixed into the hydrogel precursor solution, the molar ratio of the o-nitrobenzyl group to the amine/double bond/thiol group may be 1:0.02-50, it is preferably 1:0.1-10, the total concentration of the polymer may be 0.1% wt-60% wt, it is preferably from 1% wt-10% wt.

In the fourth purpose of the present invention, that is, the method for preparing hydrogel, the wavelength of the light source is determined according to the absorption wavelength of the o-nitrobenzyl phototriggers, and may be 250-500 nm, it is preferably 300-450 nm, and more preferably is 365, 375, 385, 395, 405 nm.

The technical principle adopted in the preparation method of the hydrogel of the invention is: the aldehyde or ketone group generated by o-nitrobenzyl (including o-nitrobenzyl sulfide, o-nitrobenzylamine, cyclic o-nitrobenzyl, cyclic o-nitrobenzyl sulfide, cyclic o-nitrobenzylamino) phototriggers under illumination can crosslink with primary amine, hydrazine, hydrazide or hydroxylamine group through Schiff base. The produced nitroso group can crosslink by itself and could also crosslink with other reactive groups (such as thiol group, hydroxyl, amine, carboxyl, sulfonate, carbonyl, double bond, etc.) to form a hydrogel. In addition to the above crosslinkings formed from the o-nitrobenzyl sulfide group having an intramolecular cyclic structure, the additionally released thiol group can react with the nitroso group produced from the o-nitrobenzyl sulfide group, or react with a double-bond group via Michael addition, or react with a thiol group to form a crosslinking disulfide bond. This crosslinking mode of simultaneously producing aldehyde/ketone or nitroso groups and releasing thiol groups under illumination to produce further crosslinking is a multiple photo-coupled crosslinking mode which has synergistic cross-linking effect, and can be called a photo-coupled synergistically crosslinking.

The fifth purpose of the present invention is to provide a product prepared by the method of the present invention, that is, hydrogel, or named photo-coupling synergistic crosslinking hydrogel.

The sixth purpose of the present invention is to provide a kit for preparing hydrogel material. It contains component A and instructions for the preparation and application of the hydrogel.

Preferably, in addition to the component A and the instructions for the preparation and application of the hydrogel, the kit provided in the sixth purpose of the present invention further includes the Component B.

The component A is polymer derivatives having o-nitrobenzyl phototriggers, and includes the following materials:
  1. Photosensitive polymer derivatives modified with o-nitrobenzyl sulfide phototriggers have the structure of Formula A-I;
  2. Photosensitive polymer derivatives modified with o-nitrobenzylamine phototriggers have the structure of Formula A-II;
  3. Photosensitive polymer derivatives modified with o-nitrobenzyl phototriggers, o-nitrobenzyl sulfide phototriggers or o-nitrobenzylamine phototriggers have the structure of Formula A-III.

The Component B is selected from one or more of an amine group-containing polymer derivative, a double bond-containing polymer derivative, and a thiol group-containing polymer derivative.

The amine-containing polymer derivative includes a polymer derivative containing a primary amine, hydrazine, hydrazide, or hydroxylamine group. The polymer derivative containing the primary amine group, the polymer derivative containing the hydrazine group, the polymer derivative containing the hydrazide group, and the polymer derivative containing the hydroxylamine group have the structure of Formula B-I, Formula B-II, Formula B-III and Formula B-IV, respectively.

The double bond-containing polymer derivative includes a polymer derivative containing maleimide, vinyl sulfone, acrylate, or acrylamide group. The polymer derivative containing maleimide, vinyl sulfone, acrylate, or acrylamide group have the structure of Formula B-V, Formula B-VI, and Formula B-VII, respectively.

The polymer derivative containing a thiol group has the structure of Formula B-VIII.

Further, the kit of the present invention may further comprise biocompatible medium such as distilled water, physiological saline, buffer and cell culture medium.

Further, the application of the hydrogel in the introduction of the kit of the present invention includes closure of the wound after surgery, leakage of tissue fluid leakage, hemostatic material, tissue engineering scaffold material, bio-ink of 3D printing, and as a cell, protein or a drug carrier.

The seventh purpose of the invention is to provide the application of a product prepared by the preparation method of photo-coupled synergistically crosslinked hydrogel material.

The invention provides the use of the above-mentioned photo-coupled synergistically crosslinked hydrogel to prepare postoperative wound closure-skin repair material or medicament.

The invention also provides the above-mentioned photo-coupled synergistically crosslinked hydrogel to prepare postoperative wound closure-postoperative anti-adhesion material or medicine.

The invention also provides the use of the above photo-coupled synergistically crosslinked hydrogel to prepare a postoperative wound closure-oral ulcer material or medicament.

The invention also provides the above photo-coupled synergistically crosslinked hydrogel to prepare tissue fluid leakage sealing-enteric leakage sealing material or medicine.

The invention also provides the use of the above photo-coupled synergistically crosslinked hydrogel to prepare tissue fluid leakage sealing-surgical suture material or medicament.

The invention also provides the use of the above photo-coupled synergistically crosslinked hydrogel to prepare hemostatic material-hepatic hemostatic material or medicament.

The invention also provides the use of the above photo-coupled synergistically crosslinked hydrogel to prepare hemostatic material-bone section hemostatic material or medicament.

The invention also provides the use of the above photo-coupled synergistically crosslinked hydrogel to prepare hemostatic material-arterial hemostatic material or drug.

The invention also provides the use of the above photo-coupled synergistically crosslinked hydrogel to prepare hemostatic material-cardiac hemostatic material or medicament.

The invention also provides the use of the above photo-coupled synergistically crosslinked hydrogel to prepare tissue engineering scaffold material-cartilage repair material or drug.

The invention also provides the use of the above photo-coupled synergistically crosslinked hydrogel to prepare tissue engineering scaffold materials-bone repair materials or drugs.

The invention also provides the use of the above photo-coupled synergistically crosslinked hydrogel to prepare tissue engineering scaffold materials-bone/cartilage composite defect repair materials or drugs.

The invention also provides the use of the above photo-coupled synergistically crosslinked hydrogel in 3D printing (FDM) material-bio-ink.

The invention also provides the use of the above photo-coupled synergistically crosslinked hydrogel in 3D printing (DLP) material-bio-ink.

The invention also provides the use of the above photo-coupled synergistically crosslinked hydrogel as a carrier for preparing cells, proteins and drugs.

The present invention optimizes the properties of hydrogels prepared by non-radical photo-coupling crosslinking. The invention selects a series of o-nitrobenzyl phototriggers having novel structure and their modified polymer derivatives, and the o-nitrobenzyl phototriggers are selected from o-nitrobenzyl sulfide phototriggers, o-nitrobenzylamine phototriggers, cyclic o-nitrobenzyl phototrigger, cyclic o-nitrobenzyl sulfide phototriggers, cyclic o-nitrobenzylamine phototriggers. The basic principle of the present invention is as follows. The aldehyde or ketone group generated from o-nitrobenzyl phototriggers under illumination can crosslink with primary amine, hydrazine, hydrazide or hydroxylamine group through Schiff base. The produced nitroso group can crosslink by itself and could also crosslink with other reactive groups (such as thiol group, hydroxyl, amine, carboxyl, sulfonate, carbonyl, double bond, etc.) to form a hydrogel. In addition to the above crosslinkings, the o-nitrobenzyl sulfide group having an intramolecular cyclic structure can additionally released a thiol group. The thiol group can react with the nitroso group that is also produced from the o-nitrobenzyl sulfide group, or react with a double-bond group via Michael addition, or react with another thiol group to form a crosslinking disulfide bond to form a hydrogel. This crosslinking mode of simultaneously producing aldehyde/ketone or nitroso and releasing thiol group under illumination to produce further crosslinking is a multiple photo-coupled crosslinking mode which has synergistic cross-linking effect, and can be called a photo-coupled synergistically crosslinking.

The invention has the following innovations compared to the prior art:
(1) Excellent mechanical properties. The synergistic crosslinking of various reactive groups generated by light can form an interpenetrating network structure, enhance the mechanical properties of the hydrogel, and make the hydrogel have excellent ductility and strength. At the same time, the mechanical properties of the hydrogel can be controlled by adjusting the material composition and light intensity of the hydrogel;
(2) Strong tissue adhesion. The aldehyde group/keto group and the nitroso group produced by the light can simultaneously bond to the surrounding tissue to enhance the integration of the hydrogel and the tissue;
(3) The fast gelation speed. The gelation time of the hydrogel is greatly shortened due to the synergistic crosslinking of the aldehyde group/keto group and the nitroso group (The gelation time is within 5 s which is much faster than the simple aldehyde-amine based photo-coupling crosslinking for 30 s).
(4) Simple synthesis, flexible components. It can realize single-component gelation and multi-component gelation by selecting materials of different properties according to different application requirements;
(5) The chemical structure, composition and degradability of the gel as well as the strength and thickness are adjustable. The composition and properties of the gel material can be flexibly adjusted according to different applications. Especially in the case of in-situ forming thin gel of the wound surface, it is suitable for postoperative wound closure and repair, and also suitable for tissue fluid leakage and can be used as hemostatic materials. It can be used as tissue engineering scaffold materials and 3D printed bio-ink, and can also provide an in situ carrier for cells, proteins or drugs which is effective for regenerative medicine.

The technology of photo-coupling synergistic crosslinking to construct hydrogel proposed by the invention not only retains the advantages of non-free radical photo-coupling crosslinking technology, such as no radical toxicity, anaerobic inhibition, thin layer gelation, and tissue adhesion, but also improves the mechanical properties, tissue adhesion, and light curing speed of the hydrogel, which is closer to the clinical application requirements, and it is expected to substantially promote the clinical application of the photo-in-situ gel technique.

DESCRIPTION OF DRAWINGS

Note: sNB is o-nitrobenzyl sulfide phototriggers in Component A-2 of the invention; nNB is o-nitrobenzylamine phototriggers in Component A-47 of the invention; cNB is cyclic o-nitrobenzyl phototriggers in Component A-64 of the invention A. Among them, HA-sNB is Component A-2; HA-nNB is Component A-47; HA-cNB is Component A-64.

EXAMPLES

Figure 1:
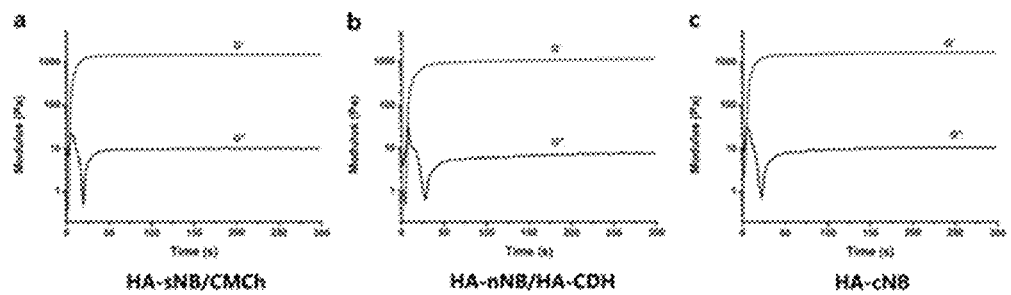
FIG. 1 is a dynamic time sweep rheological diagram of a hydrogel precursor solution (2% HA-sNB/2% CMCh or 2% HA-nNB/2% HA-CDH or 2% HA-cNB) which is illuminated to form a gel.

The following examples describes the present invention in more detail. The present invention is described in connection with the accompanying drawings and examples, but the examples are merely preferred examples of the invention and are not intended to limit the scope of the invention. Any other changes and modifications made by a skilled artisan in the field without departing from the spirit and scope in the invention are still included in the scope of the invention.

Example 1: Synthesis of Component A-1

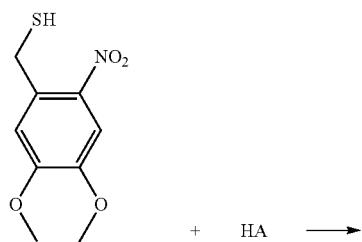

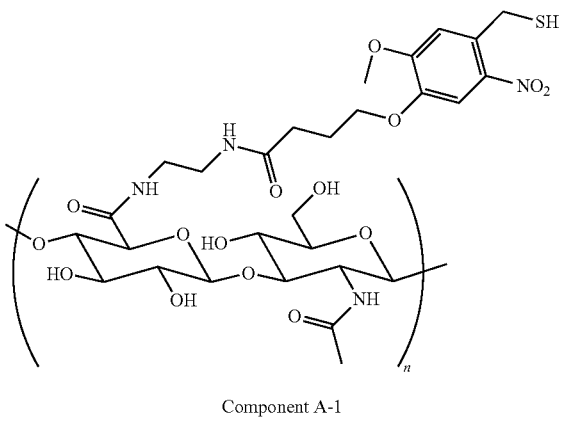

Component A-1

(1) Synthesis of Compound 1: The synthesis was carried out in accordance with the method disclosed in the reference (Kunihiko Morihiro.; Tetsuya Kodama.; Shohei Mori.; Satoshi Obika. Org. Biomol. Chem. 2014, 12, 2468). $^1$H NMR (400 MHz, CDCl$_3$): δ=7.71 (s, 1H), 7.22 (s, 1H), 4.03 (s, 2H), 4.13 (t, J=6.1 Hz, 2H), 3.99 (s, 3H), 3.32 (dd, J=11.6, 5.7 Hz, 2H), 2.82 (t, J=5.9 Hz, 2H), 2.44 (t, J=7.2 Hz, 2H), 2.26-2.17 (m, 2H). MS (ESI): [M+H] 344.1207.

(2) Synthesis of Component A-1: To a solution of hyaluronic acid (2 g, 340 kDa) in 100 mL 0.01 mol/L 2-(N-morpholine) mesylate (MES) buffer solution (pH=5.2) was added Compound 1 (69 mg, 0.2 mmol) dissolved in 10 mL dimethyl sulfoxide (DMSO). 4-(4,6-Dimethoxytriazin-2-yl)-4-methylmorpholine hydrochloride (DMTMM, 0.4 g, 1.5 mmol) dissolved in 3 mL MES buffer was added to the above reaction solution by three times (every 1 h), and the mixture was reacted at 35° C. for 24 h. Then, the reaction solution was poured into a dialysis bag (MWCO 7000), dialyzed against deionized water for 2-3 d, and lyophilized to obtain the photosensitive hyaluronic acid derivative Compound A-1 (1.85 g). According to the nuclear magnetic resonance spectrum, the grafting degree of Compound 1 could be calculated to be about 3.34%.

Example 2: Synthesis of Component A-2

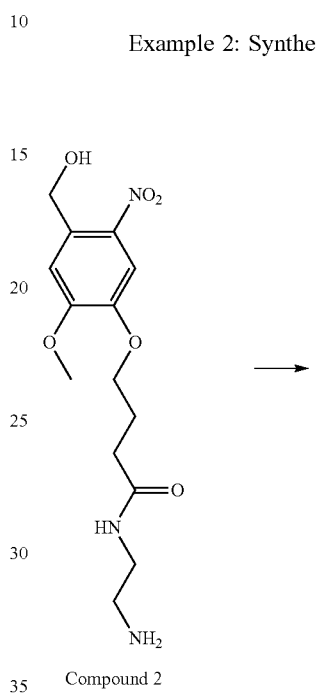

Compound 2

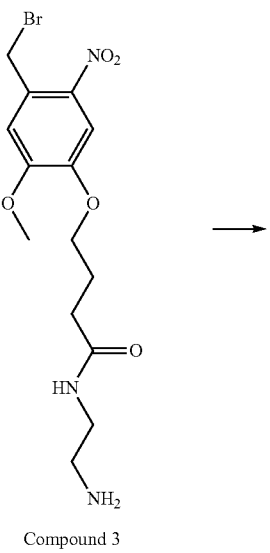

Compound 3

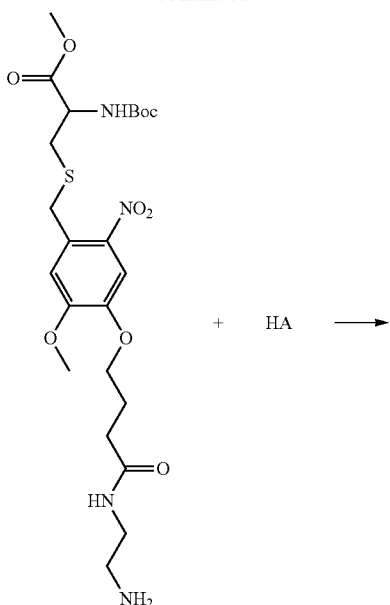

Compound 4

+ HA →

(1) Synthesis of Compound 2: The synthesis was carried out in accordance with the method disclosed in the reference (Yunlong Yang; Jieyuan Zhang; Zhenzhen Liu; Qiuning Lin; Xiaolin Liu; Chunyan Bao; Yang Wang; Linyong Zhu. Adv. Mater. 2016, 28, 2724).

(2) Synthesis of Compound 3: To a solution of Compound 2 (1 g, 3.0 mmol) in tetrahydrofuran (50 ml) was added carbon tetrabromide (CBr$_4$) (2 g, 6.0 mmol) and triphenylphosphine (PPh$_3$) (1.6 g, 6.0 mmol). The solution was stirred for 2 h at room temperature under the protection of Ar$_2$. After completion of the reaction, the reaction was quenched by added water (5 ml), filtered and removed the solvent by rotary evaporation under reduced pressure and extracted with ethyl acetate, then purified by column chromatography (PE:DCM=4:1) to obtain Compound 3 (1.0 g, 84%). $^1$H NMR (400 MHz, CDCl$_3$): δ=7.71 (s, 1H), 7.22 (s, 1H), 4.56 (s, 2H), 4.13 (t, J=6.1 Hz, 2H), 3.99 (s, 3H), 3.32 (dd, J=11.6, 5.7 Hz, 2H), 2.82 (t, J=5.9 Hz, 2H), 2.44 (t, J=7.2 Hz, 2H), 2.26-2.17 (m, 2H). MS (ESI): [M+H] 390.0623.

(3) Synthesis of Compound 4: To a solution of Compound 3 (0.5 g, 1.3 mmol) dissolved in 50 mL acetone was added L-cysteine methyl ester hydrochloride (0.45 g, 2.6 mmol) and sodium hydroxide (0.2 g, 5.2 mmol), the reaction was stirred at room temperature for 2 h under the protection of argon. After completion of the reaction, the solution was added 4 M HCl to adjust the pH=7. The solvent was removed by rotary evaporation under reduced pressure, and the crude was extracted with ethyl acetate and purified by column chromatography (PE:DCM=4:1) to obtain Compound 4 (0.7 g, 88%). $^1$H NMR (400 MHz, CDCl$_3$): δ=7.71 (s, 1H), 7.22 (s, 1H), 4.76 (s, 2H), 4.42 (m, 1H), 4.13 (t, J=6.1 Hz, 2H), 3.99 (s, 3H), 3.95 (s, 3H), 3.43 (d, J=5.6 Hz, 2H), 3.32 (dd, J=11.6, 5.7 Hz, 2H), 2.82 (t, J=5.9 Hz, 2H), 2.44 (t, J=7.2 Hz, 2H), 2.26-2.17 (m, 2H), 1.42 (s, 9H). MS (ESI): [M+H] 545.2219.

(4) Synthesis of Component A-2: To a solution of hyaluronic acid (2 g, 340 kDa) in 100 mL 0.01 mol/L 2-(N-morpholine) mesylate (MES) buffer solution (pH=5.2) was added Compound 4 (109 mg, 0.2 mmol) dissolved in 10 mL dimethyl sulfoxide (DMSO). 4-(4,6-Dimethoxytriazin-2-yl)-4-methylmorpholine hydrochloride (DMTMM, 0.4 g, 1.5 mmol) dissolved in 3 mL MES buffer was added to the above reaction solution by three times (every 1 h), and the mixture was reacted at 35° C. for 24 h. Then, the reaction solution was poured into a dialysis bag (MWCO 7000), dialyzed against deionized water for 2-3 d, and lyophilized to obtain the photosensitive hyaluronic acid derivative Compound A-2 (1.92 g). According to the nuclear magnetic resonance spectrum, the grafting degree of Compound 4 could be calculated to be about 3.32%.

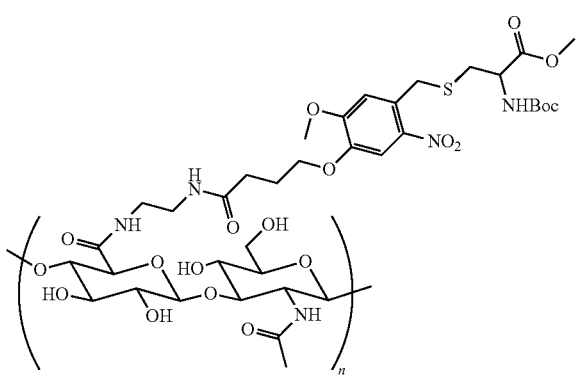

Component A-2

Example 3: Synthesis of Component A-3

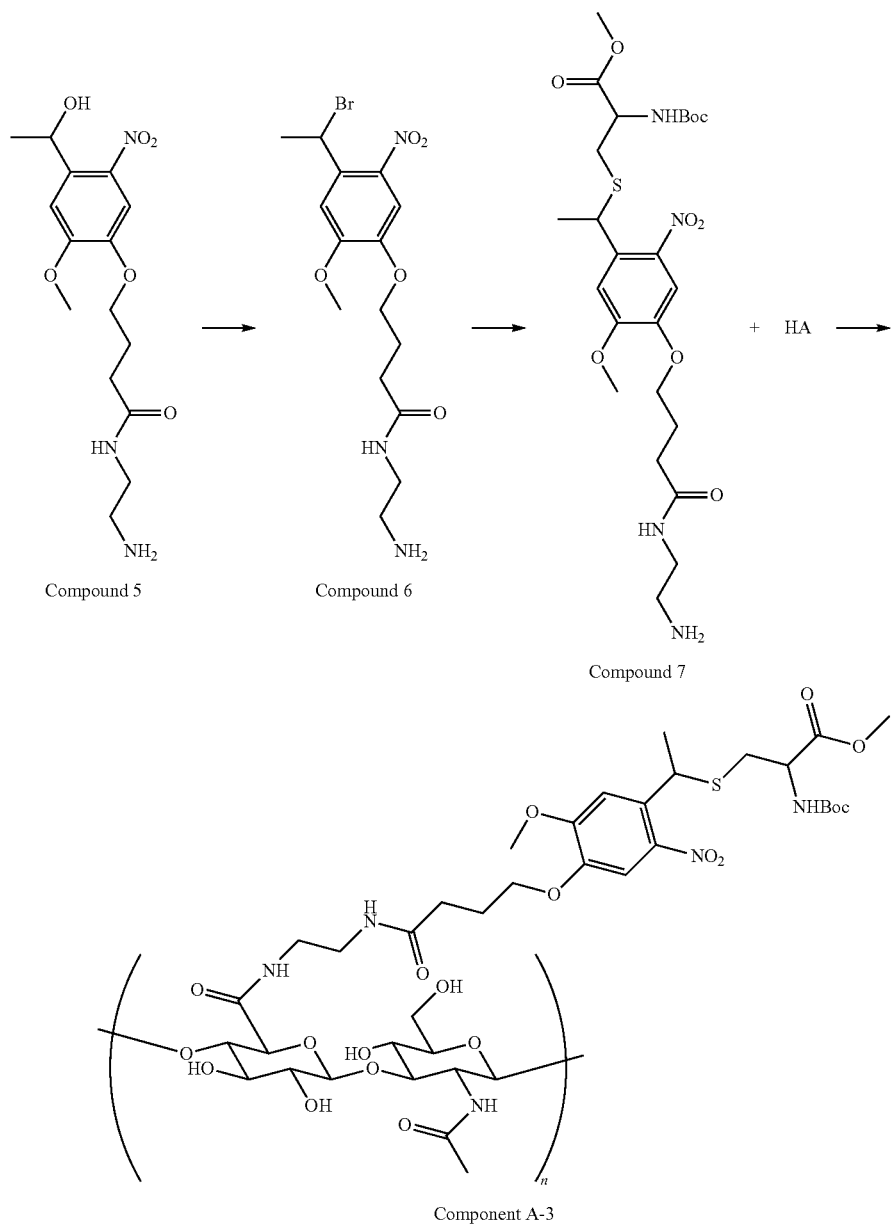

(1) Synthesis of Compound 5. The synthesis was carried out in accordance with the method disclosed in the reference (James F. Cameron.; Jean M. J. Frechet. J. Am. Chem. Soc. 1991, 113, 4303).

(2) Synthesis of Compound 6. Compound 6 was obtained by the method of Example 2 using Compound 5 as raw material, the yield was 73%. $^1$H NMR (400 MHz, CDCl$_3$): δ=7.71 (s, 1H), 7.22 (s, 1H), 4.66 (m, 1H), 4.13 (t, J=6.1 Hz, 2H), 3.99 (s, 3H), 3.32 (dd, J=11.6, 5.7 Hz, 2H), 2.82 (t, J=5.9 Hz, 2H), 2.44 (t, J=7.2 Hz, 2H), 2.26-2.17 (m, 2H), 1.33 (d, J=6.9 Hz, 3H). MS (ESI): [M+H] 404.0863.

(3) Synthesis of Compound 7. Compound 7 was obtained by the method of Example 2 using Compound 6 as raw material, the yield was 70%. $^1$H NMR (400 MHz, CDCl$_3$): δ=7.71 (s, 1H), 7.22 (s, 1H), 4.86 (m, 1H), 4.42 (m, 1H), 4.13 (t, J=6.1 Hz, 2H), 3.99 (s, 3H), 3.95 (s, 3H), 3.43 (d, J=5.6, 2H), 3.32 (dd, J=11.6, 5.7 Hz, 2H), 2.82 (t, J=5.9 Hz, 2H), 2.44 (t, J=7.2 Hz, 2H), 2.26-2.17 (m, 2H), 1.42 (s, 9H), 1.33 (d, J=6.9 Hz, 3H). MS (ESI): [M+H] 559.2402.

(4) Synthesis of Component A-3. To a solution of hyaluronic acid (2 g, 340 kDa) in 100 mL 0.01 mol/L 2-(N-morpholine) mesylate (MES) buffer solution (pH=5.2) was added Compound 7 (112 mg, 0.2 mmol) dissolved in 10 mL dimethyl sulfoxide (DMSO). 4-(4,6-Dimethoxytriazin-2-yl)-4-methylmorpholine hydrochloride (DMTMM, 0.4 g, 1.5 mmol) dissolved in 3 mL MES buffer was added to the above reaction solution by three times (every 1 h), and the mixture was reacted at 35° C. for 24 h. Then, the reaction solution was poured into a dialysis bag (MWCO 7000), dialyzed against deionized water for 2-3 d, and lyophilized to obtain the photosensitive hyaluronic acid derivative Compound A-3 (1.75 g). According to the nuclear magnetic resonance spectrum, the grafting degree of Compound 7 could be calculated to be about 2.34%.

Example 5: Synthesis of Component A-5

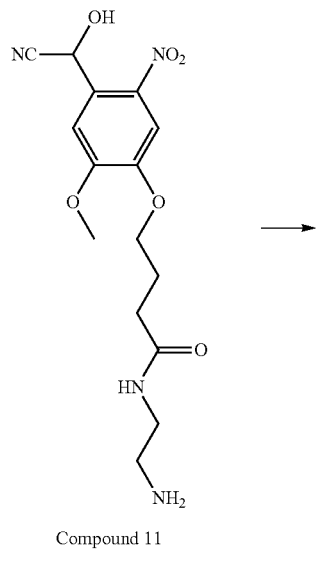

Compound 11

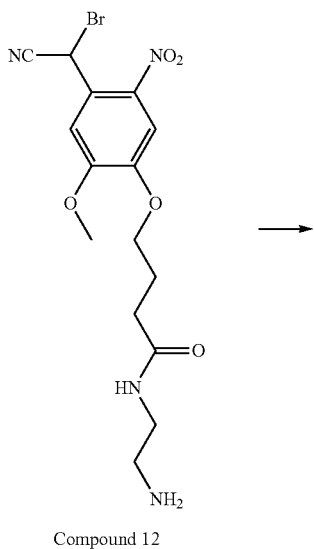

Compound 12

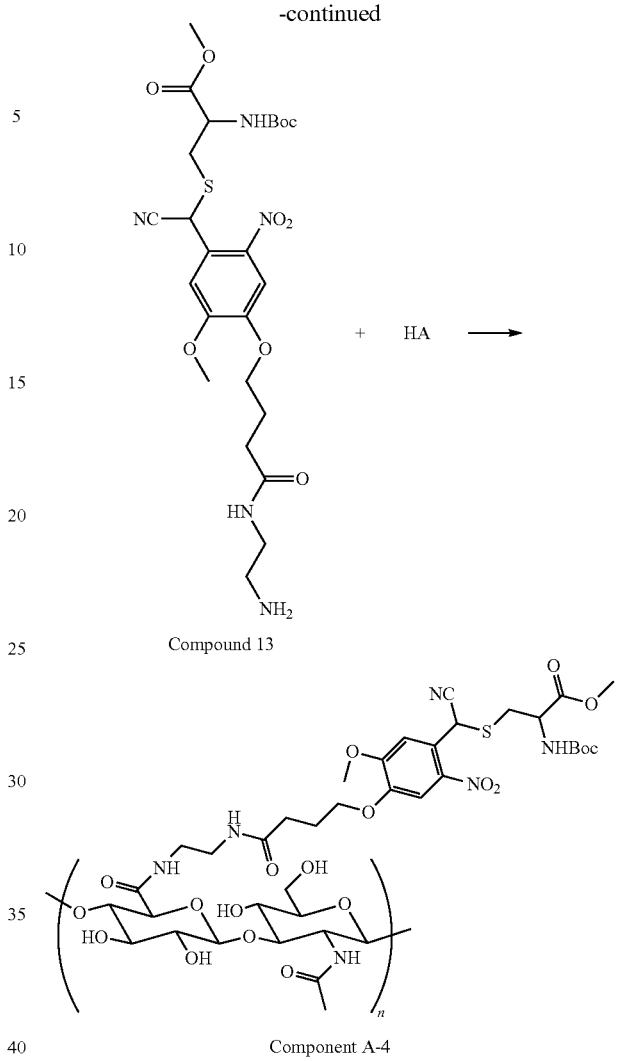

Compound 13

Component A-4

(1) Synthesis of Compound 11: The synthesis was carried out in accordance with the method disclosed in the reference (Isabelle Aujard.; Chouaha Benbrahim.; Ludovic Jullien. Chem. Eur. J. 2006, 12, 6865).

(2) Synthesis of Compound 12: Compound 12 was obtained by the method of Example 2 using Compound 11 as raw material, the yield was 72%. $^1$H NMR (400 MHz, CDCl$_3$): δ=7.71 (s, 1H), 7.22 (s, 1H), 4.66 (s, 1H), 4.13 (t, J=6.1 Hz, 2H), 3.99 (s, 3H), 3.32 (dd, J=11.6, 5.7 Hz, 2H), 2.82 (t, J=5.9 Hz, 2H), 2.44 (t, J=7.2 Hz, 2H), 2.26-2.17 (m, 2H). MS (ESI): [M+H] 415.0646.

(3) Synthesis of Compound 13: Compound 13 was obtained by the method of Example 2 using Compound 12 as raw material, the yield was 77%. $^1$H NMR (400 MHz, CDCl$_3$): δ=7.71 (s, 1H), 7.22 (s, 1H), 4.86 (s, 1H), 4.42 (m, 1H), 4.13 (t, J=6.1 Hz, 2H), 3.99 (s, 3H), 3.95 (s, 3H), 3.43 (d, J=5.6, 2H), 3.32 (dd, J=11.6, 5.7 Hz, 2H), 2.82 (t, J=5.9 Hz, 2H), 2.44 (t, J=7.2 Hz, 2H), 2.26-2.17 (m, 2H), 1.42 (s, 9H). MS (ESI): [M+H] 570.2218.

(4) Synthesis of Component A-5: To a solution of hyaluronic acid (2 g, 340 kDa) in 100 mL 0.01 mol/L 2-(N-morpholine) mesylate (MES) buffer solution (pH=5.2) was added Compound 13 (114 mg, 0.2 mmol) dissolved in 10 mL dimethyl sulfoxide (DMSO). 4-(4,6-Dimethoxytriazin-2-yl)-4-methylmorpholine hydrochloride (DMTMM, 0.4 g, 1.5 mmol) dissolved in 3 mL MES buffer was added to the above reaction solution by three times (every 1 h), and the mixture was reacted at 35° C. for 24 h. Then, the reaction solution was poured into a dialysis bag (MWCO 7000), dialyzed against deionized water for 2-3 d, and lyophilized to obtain the photosensitive hyaluronic acid derivative Compound A-5 (1.82 g). According to the nuclear magnetic resonance spectrum, the grafting degree of Compound 13 could be calculated to be about 3.13%.

Example 6: Synthesis of Component A-6

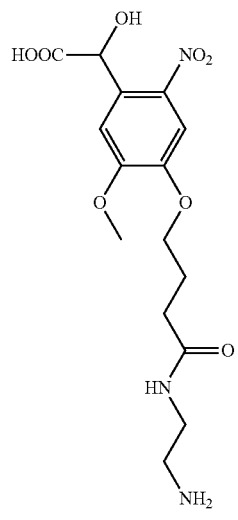

Compound 14

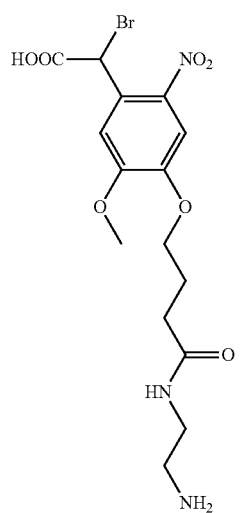

Compound 15

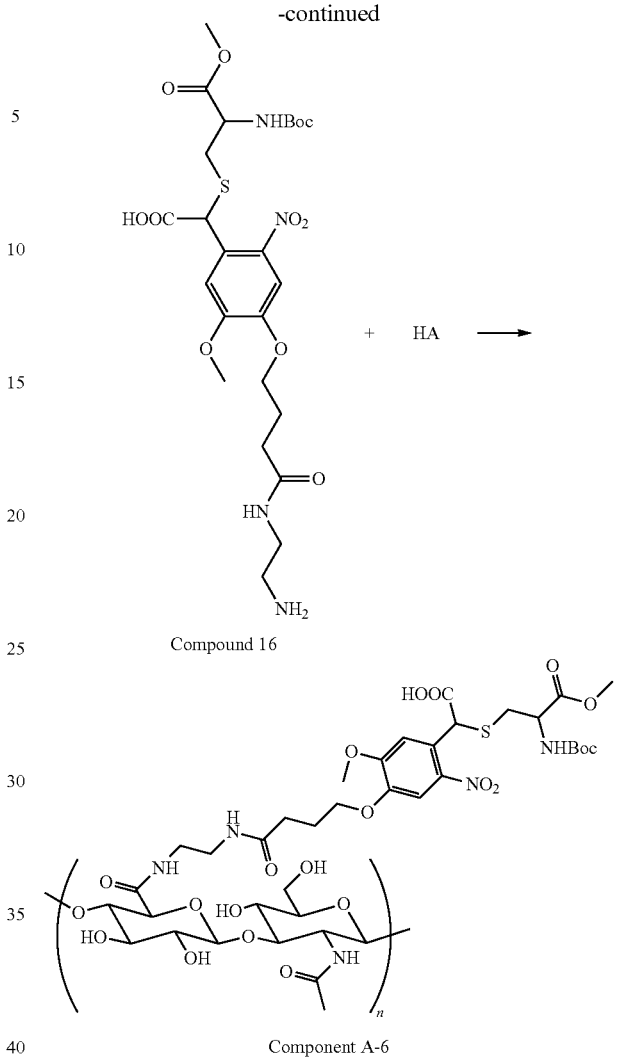

Compound 16

Component A-6

(1) Synthesis of Compound 14: The synthesis was carried out in accordance with the method disclosed in the reference (Alexander G. Russell.; Dario M. Bassani.; John S. Snaith. J. Org. Chem. 2010, 75, 4648).

(2) Synthesis of Compound 15: Compound 15 was obtained by the method of Example 2 using Compound 14 as raw material, the yield was 75%. $^1$H NMR (400 MHz, CDCl$_3$): δ=7.71 (s, 1H), 7.22 (s, 1H), 4.66 (s, 1H), 4.13 (t, J=6.1 Hz, 2H), 3.99 (s, 3H), 3.32 (dd, J=11.6, 5.7 Hz, 2H), 2.82 (t, J=5.9 Hz, 2H), 2.44 (t, J=7.2 Hz, 2H), 2.26-2.17 (m, 2H). MS (ESI): [M+H] 434.0533.

(3) Synthesis of Compound 16: Compound 16 was obtained by the method of Example 2 using Compound 15 as raw material, the yield was 67%. $^1$H NMR (400 MHz, CDCl$_3$): δ=7.71 (s, 1H), 7.22 (s, 1H), 4.86 (s, 1H), 4.42 (m, 1H), 4.13 (t, J=6.1 Hz, 2H), 3.99 (s, 3H), 3.95 (s, 3H), 3.43 (d, J=5.6, 2H), 3.32 (dd, J=11.6, 5.7 Hz, 2H), 2.82 (t, J=5.9 Hz, 2H), 2.44 (t, J=7.2 Hz, 2H), 2.26-2.17 (m, 2H), 1.42 (s, 9H). MS (ESI): [M+H] 589.2125.

(4) Synthesis of Component A-6: To a solution of hyaluronic acid (2 g, 340 kDa) in 100 mL 0.01 mol/L 2-(N-morpholine) mesylate (MES) buffer solution (pH=5.2) was added Compound 16 (112 mg, 0.2 mmol) dissolved in 10 mL dimethyl sulfoxide (DMSO). 4-(4,6-Dimethoxytri-azin-2-yl)-4-methylmorpholine hydrochloride (DMTMM, 0.4 g, 1.5 mmol) dissolved in 3 mL MES buffer was added to the above reaction solution by three times (every 1 h), and the mixture was reacted at 35° C. for 24 h. Then, the reaction solution was poured into a dialysis bag (MWCO 7000), dialyzed against deionized water for 2-3 d, and lyophilized to obtain the photosensitive hyaluronic acid derivative Compound A-6 (1.74 g). According to the nuclear magnetic resonance spectrum, the grafting degree of Compound 16 could be calculated to be about 3.24%.

Example 7: Synthesis of Component A-7

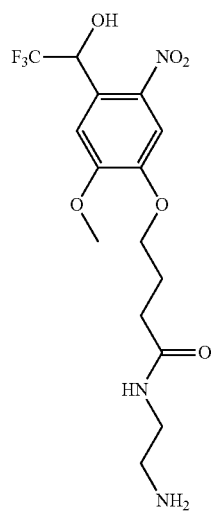

Compound 17

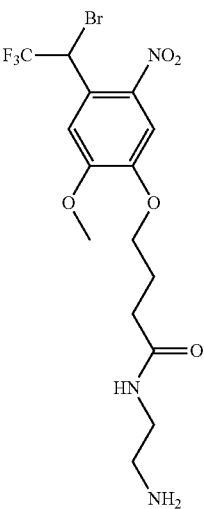

Compound 18

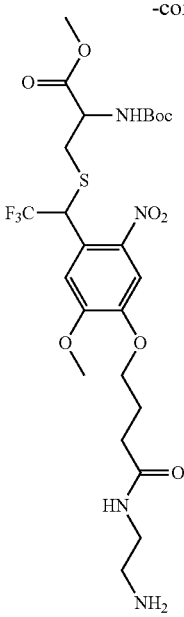

Compound 19

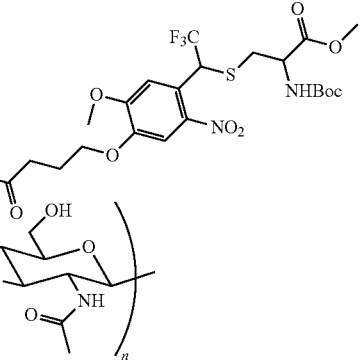

Component A-7

(1) Synthesis of Compound 17: The synthesis was carried out in accordance with the method disclosed in the reference (Alexandre Specht.; Maurice Goeldner. Angew. Chem. Int. Ed. 2004, 43, 2008).

(2) Synthesis of Compound 18: Compound 18 was obtained by the method of Example 2 using Compound 17 as raw material, the yield was 71%. $^1$H NMR (400 MHz, CDCl$_3$): δ=7.71 (s, 1H), 7.22 (s, 1H), 4.66 (s, 1H), 4.13 (t, J=6.1 Hz, 2H), 3.99 (s, 3H), 3.32 (dd, J=11.6, 5.7 Hz, 2H), 2.82 (t, J=5.9 Hz, 2H), 2.44 (t, J=7.2 Hz, 2H), 2.26-2.17 (m, 2H). MS (ESI): [M+H] 458.0523.

(3) Synthesis of Compound 19: Compound 19 was obtained by the method of Example 2 using Compound 18 as raw material, the yield was 78%. $^1$H NMR (400 MHz, CDCl$_3$): δ=7.71 (s, 1H), 7.22 (s, 1H), 4.86 (s, 1H), 4.42 (m, 1H), 4.13 (t, J=6.1 Hz, 2H), 3.99 (s, 3H), 3.95 (s, 3H), 3.43 (d, J=5.6, 2H), 3.32 (dd, J=11.6, 5.7 Hz, 2H), 2.82 (t, J=5.9 Hz, 2H), 2.44 (t, J=7.2 Hz, 2H), 2.26-2.17 (m, 2H), 1.42 (s, 9H). MS (ESI): [M+H] 613.2115.

(4) Synthesis of Component A-7: To a solution of hyaluronic acid (2 g, 340 kDa) in 100 mL 0.01 mol/L 2-(N-morpholine) mesylate (MES) buffer solution (pH=5.2) was added Compound 19 (122 mg, 0.2 mmol) dissolved in 10 mL dimethyl sulfoxide (DMSO). 4-(4,6-Dimethoxytri-azin-2-yl)-4-methylmorpholine hydrochloride (DMTMM, 0.4 g, 1.5 mmol) dissolved in 3 mL MES buffer was added to the above reaction solution by three times (every 1 h), and the mixture was reacted at 35° C. for 24 h. Then, the reaction solution was poured into a dialysis bag (MWCO 7000), dialyzed against deionized water for 2-3 d, and lyophilized to obtain the photosensitive hyaluronic acid derivative Compound A-7 (1.73 g). According to the nuclear magnetic resonance spectrum, the grafting degree of Compound 19 could be calculated to be about 3.08%.

Example 9: Synthesis of Component A-9

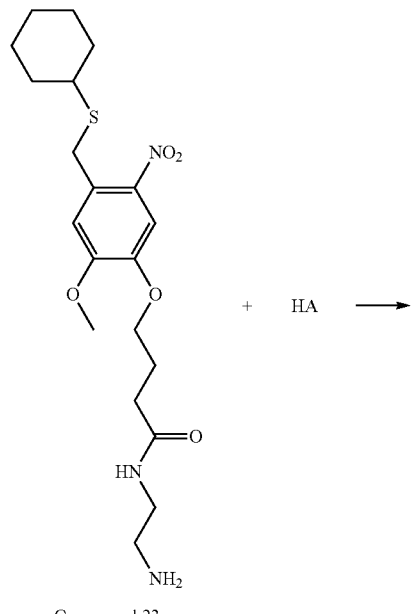

Compound 23

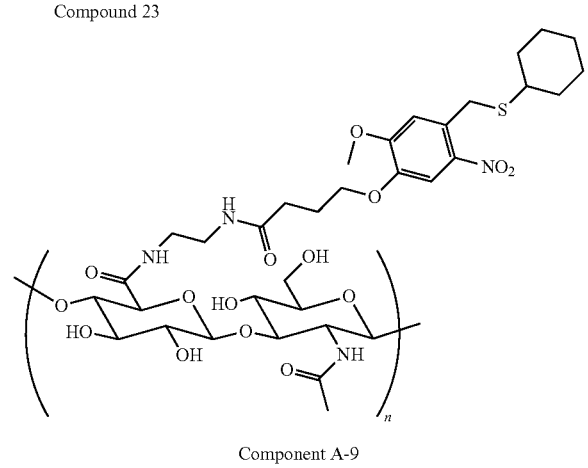

Component A-9

(1) Synthesis of Compound 23: The synthesis was carried out in accordance with the method disclosed in the reference (Pauloehrl, T.; Delaittre, G.; Bruns, M.; MeiBler, M.; Börner, H. G.; Bastmeyer, M.; Barner-Kowollik, C. Angew. Chem. Int. Ed. 2012, 51, 9181). $^1$H NMR (400 MHz, CDCl$_3$): δ=7.71 (s, 1H), 7.22 (s, 1H), 4.76 (s, 2H), 4.13 (t, J=6.1 Hz, 2H), 3.99 (s, 3H), 3.90-3.80 (m, 1H), 3.63-3.52 (m, 1H), 3.32 (dd, J=11.6, 5.7 Hz, 2H), 2.82 (t, J=5.9 Hz, 2H), 2.44 (t, J=7.2 Hz, 2H), 2.26-2.17 (m, 2H), 2.00-1.34 (m, 6H). MS (ESI): [M+H] 428.1831.

(2) Synthesis of Component A-9: To a solution of hyaluronic acid (2 g, 340 kDa) in 100 mL 0.01 mol/L 2-(N-morpholine) mesylate (MES) buffer solution (pH=5.2) was added Compound 23 (85 mg, 0.2 mmol) dissolved in 10 mL dimethyl sulfoxide (DMSO). 4-(4,6-Dimethoxytriazin-2-yl)-4-methylmorpholine hydrochloride (DMTMM, 0.4 g, 1.5 mmol) dissolved in 3 mL MES buffer was added to the above reaction solution by three times (every 1 h), and the mixture was reacted at 35° C. for 24 h. Then, the reaction solution was poured into a dialysis bag (MWCO 7000), dialyzed against deionized water for 2-3 d, and lyophilized to obtain the photosensitive hyaluronic acid derivative Compound A-9 (1.89 g). According to the nuclear magnetic resonance spectrum, the grafting degree of Compound 3 could be calculated to be about 3.42%.

Example 10: Synthesis of Component A-10

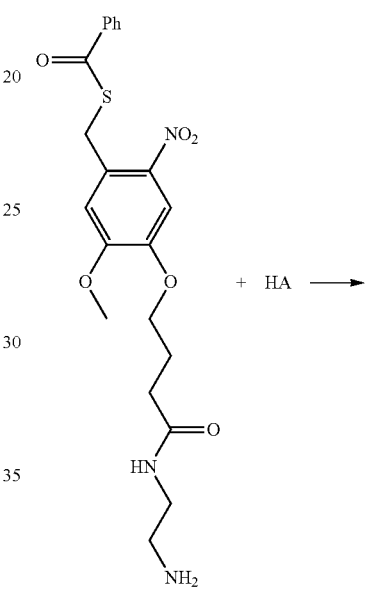

Compound 24

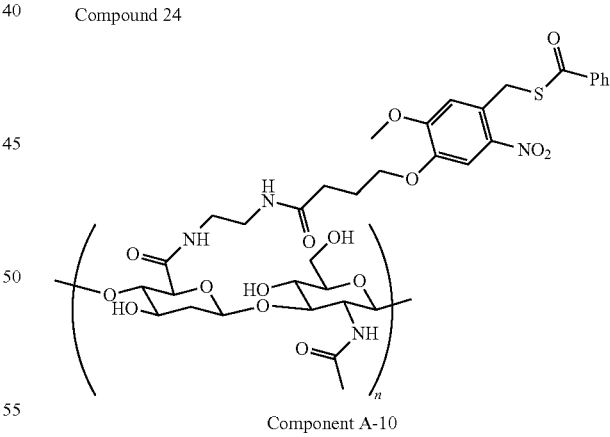

Component A-10

(1) Synthesis of Compound 24: The synthesis was carried out in accordance with the method disclosed in the reference (Patchornik Abraham.; Amit B.; Woodward R. B. J. Am. Chem. Soc. 1970, 92, 6333). $^1$H NMR (400 MHz, CDCl$_3$): δ=8.02-7.23 (m, 5H), 7.71 (s, 1H), 7.22 (s, 1H), 4.76 (s, 2H), 4.13 (t, J=6.1 Hz, 2H), 3.99 (s, 3H), 3.32 (dd, J=11.6, 5.7 Hz, 2H), 2.82 (t, J=5.9 Hz, 2H), 2.44 (t, J=7.2 Hz, 2H), 2.26-2.17 (m, 2H). MS (ESI): [M+H] 448.1561.

(2) Synthesis of Component A-10: To a solution of hyaluronic acid (2 g, 340 kDa) in 100 mL 0.01 mol/L 2-(N-morpholine) mesylate (MES) buffer solution (pH=5.2) was added Compound 24 (89 mg, 0.2 mmol) dissolved in 10 mL dimethyl sulfoxide (DMSO). 4-(4,6-Dimethoxytriazin-2-yl)-4-methylmorpholine hydrochloride (DMTMM, 0.4 g, 1.5 mmol) dissolved in 3 mL MES buffer was added to the above reaction solution by three times (every 1 h), and the mixture was reacted at 35° C. for 24 h. Then, the reaction solution was poured into a dialysis bag (MWCO 7000), dialyzed against deionized water for 2-3 d, and lyophilized to obtain the photosensitive hyaluronic acid derivative Compound A-10 (1.87 g). According to the nuclear magnetic resonance spectrum, the grafting degree of Compound 24 could be calculated to be about 3.21%.

Example 11: Synthesis of Component A-11

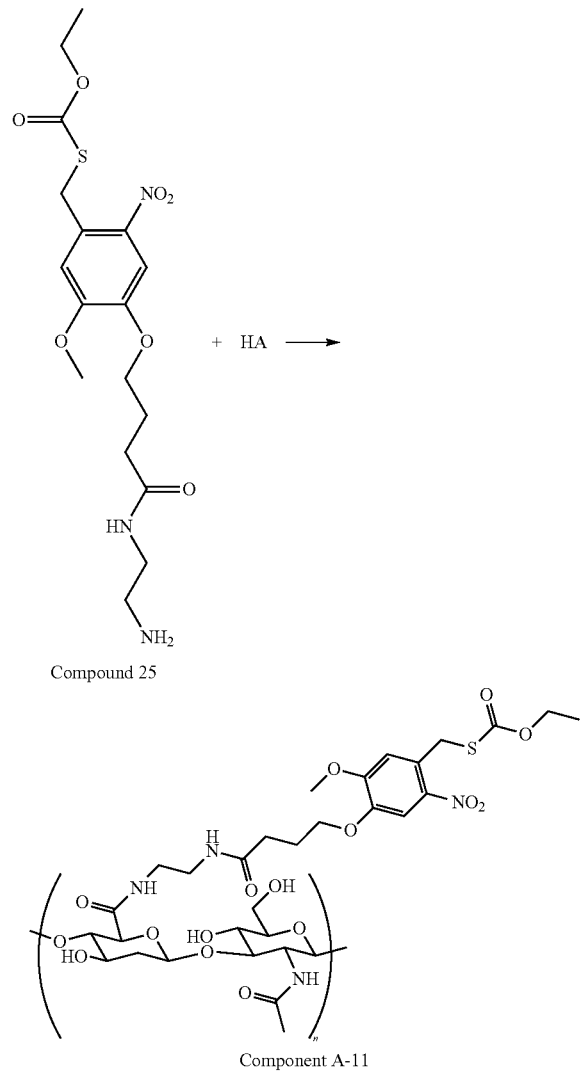

Component A-11

(1) Synthesis of Compound 25: The synthesis was carried out in accordance with the method disclosed in the reference (Patchornik Abraham.; Amit B.; Woodward R. B. J. Am. Chem. Soc. 1970, 92, 6333). $^1$H NMR (400 MHz, CDCl$_3$): δ=7.71 (s, 1H), 7.22 (s, 1H), 4.76 (s, 2H), 4.25 (q, J=6.5 Hz, 2H), 4.13 (t, J=6.1 Hz, 2H), 3.99 (s, 3H), 3.32 (dd, J=11.6, 5.7 Hz, 2H), 2.82 (t, J=5.9 Hz, 2H), 2.44 (t, J=7.2 Hz, 2H), 2.26-2.17 (m, 2H), 1.32 (t, J=6.5 Hz, 3H). MS (ESI): [M+H] 416.1432.

(2) Synthesis of Component A-11: To a solution of hyaluronic acid (2 g, 340 kDa) in 100 mL 0.01 mol/L 2-(N-morpholine) mesylate (MES) buffer solution (pH=5.2) was added Compound 25 (83 mg, 0.2 mmol) dissolved in 10 mL dimethyl sulfoxide (DMSO). 4-(4,6-Dimethoxytriazin-2-yl)-4-methylmorpholine hydrochloride (DMTMM, 0.4 g, 1.5 mmol) dissolved in 3 mL MES buffer was added to the above reaction solution by three times (every 1 h), and the mixture was reacted at 35° C. for 24 h. Then, the reaction solution was poured into a dialysis bag (MWCO 7000), dialyzed against deionized water for 2-3 d, and lyophilized to obtain the photosensitive hyaluronic acid derivative Compound A-11 (1.74 g). According to the nuclear magnetic resonance spectrum, the grafting degree of Compound 25 could be calculated to be about 2.34%.

Example 12: Synthesis of Component A-12

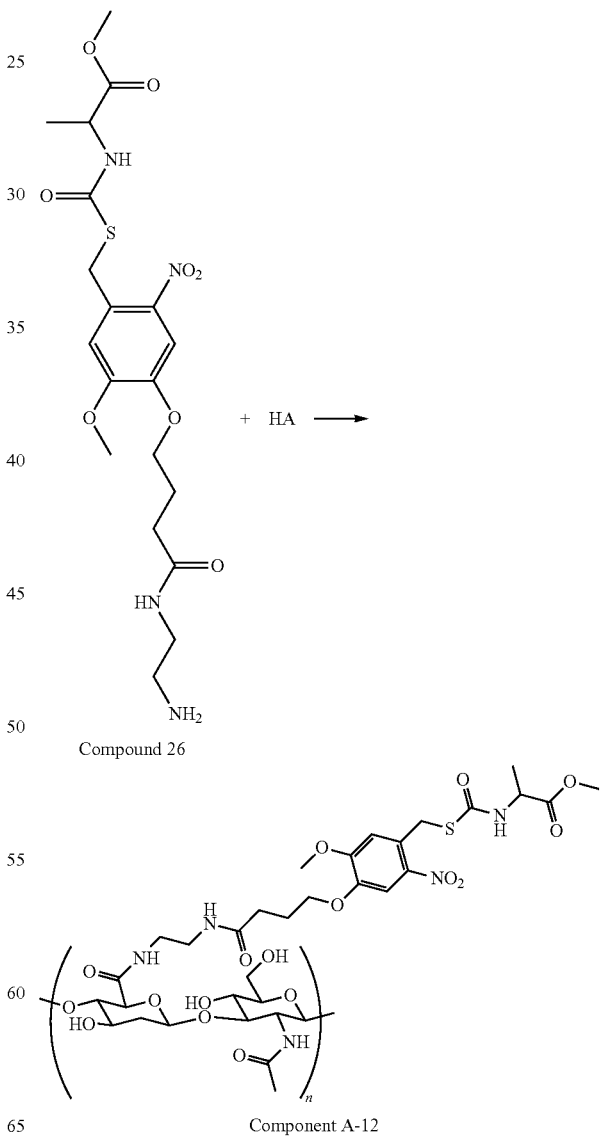

Component A-12

(1) Synthesis of Compound 26: The synthesis was carried out in accordance with the method disclosed in the reference (Kalbag, S. M.; Roeske, R. W. J. Am. Chem. Soc. 1975, 97, 440). $^1$H NMR (400 MHz, CDCl$_3$): δ=7.71 (s, 1H), 7.22 (s, 1H), 4.76 (s, 2H), 4.63 (q, J=6.9 Hz, 1H), 4.13 (t, J=6.1 Hz, 2H), 3.99 (s, 3H), 3.67 (s, 3H), 3.32 (dd, J=11.6, 5.7 Hz, 2H), 2.82 (t, J=5.9 Hz, 2H), 2.44 (t, J=7.2 Hz, 2H), 2.26-2.17 (m, 2H), 1.48 (d, J=6.9 Hz, 3H). MS (ESI): [M+H] 473.1734.

(2) Synthesis of Component A-12: To a solution of hyaluronic acid (2 g, 340 kDa) in 100 mL 0.01 mol/L 2-(N-morpholine) mesylate (MES) buffer solution (pH=5.2) was added Compound 26 (94 mg, 0.2 mmol) dissolved in 10 mL dimethyl sulfoxide (DMSO). 4-(4,6-Dimethoxytriazin-2-yl)-4-methylmorpholine hydrochloride (DMTMM, 0.4 g, 1.5 mmol) dissolved in 3 mL MES buffer was added to the above reaction solution by three times (every 1 h), and the mixture was reacted at 35° C. for 24 h. Then, the reaction solution was poured into a dialysis bag (MWCO 7000), dialyzed against deionized water for 2-3 d, and lyophilized to obtain the photosensitive hyaluronic acid derivative Compound A-12 (1.72 g). According to the nuclear magnetic resonance spectrum, the grafting degree of Compound 26 could be calculated to be about 2.56%.

Example 13: Synthesis of Component A-13

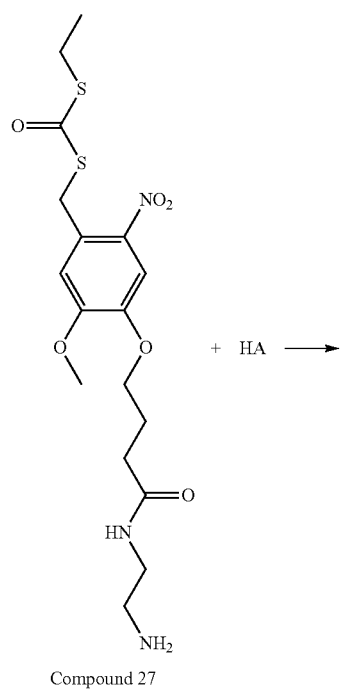

Compound 27

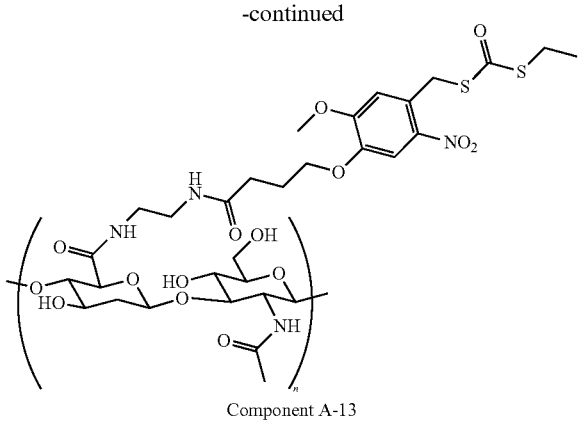

Component A-13

(1) Synthesis of Compound 27: The synthesis was carried out in accordance with the method disclosed in the reference (Patchornik Abraham.; Amit B.; Woodward R. B. J. Am. Chem. Soc. 1970, 92, 6333). $^1$H NMR (400 MHz, CDCl$_3$): δ=7.71 (s, 1H), 7.22 (s, 1H), 4.76 (s, 2H), 4.25 (q, J=6.5 Hz, 2H), 4.13 (t, J=6.1 Hz, 2H), 3.99 (s, 3H), 3.32 (dd, J=11.6, 5.7 Hz, 2H), 2.82 (t, J=5.9 Hz, 2H), 2.44 (t, J=7.2 Hz, 2H), 2.26-2.17 (m, 2H), 1.32 (t, J=6.5 Hz, 3H). MS (ESI): [M+H] 432.1265.

(2) Synthesis of Component A-13: To a solution of hyaluronic acid (2 g, 340 kDa) in 100 mL 0.01 mol/L 2-(N-morpholine) mesylate (MES) buffer solution (pH=5.2) was added Compound 27 (83 mg, 0.2 mmol) dissolved in 10 mL dimethyl sulfoxide (DMSO). 4-(4,6-Dimethoxytriazin-2-yl)-4-methylmorpholine hydrochloride (DMTMM, 0.4 g, 1.5 mmol) dissolved in 3 mL MES buffer was added to the above reaction solution by three times (every 1 h), and the mixture was reacted at 35° C. for 24 h. Then, the reaction solution was poured into a dialysis bag (MWCO 7000), dialyzed against deionized water for 2-3 d, and lyophilized to obtain the photosensitive hyaluronic acid derivative Compound A-13 (1.74 g). According to the nuclear magnetic resonance spectrum, the grafting degree of Compound 27 could be calculated to be about 2.34%.

Example 14: Synthesis of Component A-14

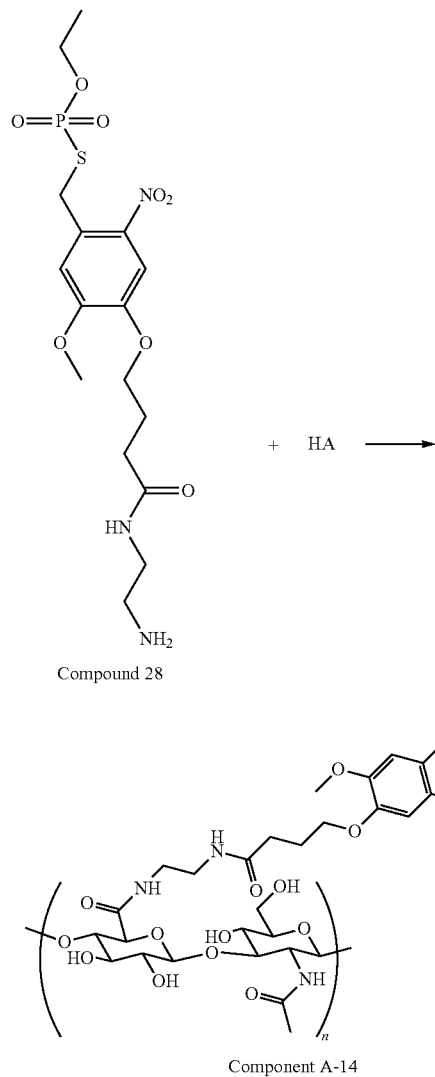

Compound 28

Component A-14

(1) Synthesis of Compound 28: The synthesis was carried out in accordance with the method disclosed in the reference (Engels, J.; Schlaeger, E. J. J. Med. Chem. 1977, 20, 907). $^1$H NMR (400 MHz, CDCl$_3$): δ=7.71 (s, 1H), 7.22 (s, 1H), 4.76 (s, 2H), 4.25 (q, J=6.5 Hz, 2H), 4.13 (t, J=6.1 Hz, 2H), 3.99 (s, 3H), 3.32 (dd, J=11.6, 5.7 Hz, 2H), 2.82 (t, J=5.9 Hz, 2H), 2.44 (t, J=7.2 Hz, 2H), 2.26-2.17 (m, 2H), 1.32 (t, J=6.5 Hz, 3H). MS (ESI): [M+H] 451.1126.

(2) Synthesis of Component A-14: To a solution of hyaluronic acid (2 g, 340 kDa) in 100 mL 0.01 mol/L 2-(N-morpholine) mesylate (MES) buffer solution (pH=5.2) was added Compound 28 (90 mg, 0.2 mmol) dissolved in 10 mL dimethyl sulfoxide (DMSO). 4-(4,6-Dimethoxytriazin-2-yl)-4-methylmorpholine hydrochloride (DMTMM, 0.4 g, 1.5 mmol) dissolved in 3 mL MES buffer was added to the above reaction solution by three times (every 1 h), and the mixture was reacted at 35° C. for 24 h. Then, the reaction solution was poured into a dialysis bag (MWCO 7000), dialyzed against deionized water for 2-3 d, and lyophilized to obtain the photosensitive hyaluronic acid derivative Compound A-14 (1.72 g). According to the nuclear magnetic resonance spectrum, the grafting degree of Compound 28 could be calculated to be about 2.36%.

Example 16: Synthesis of Component A-16

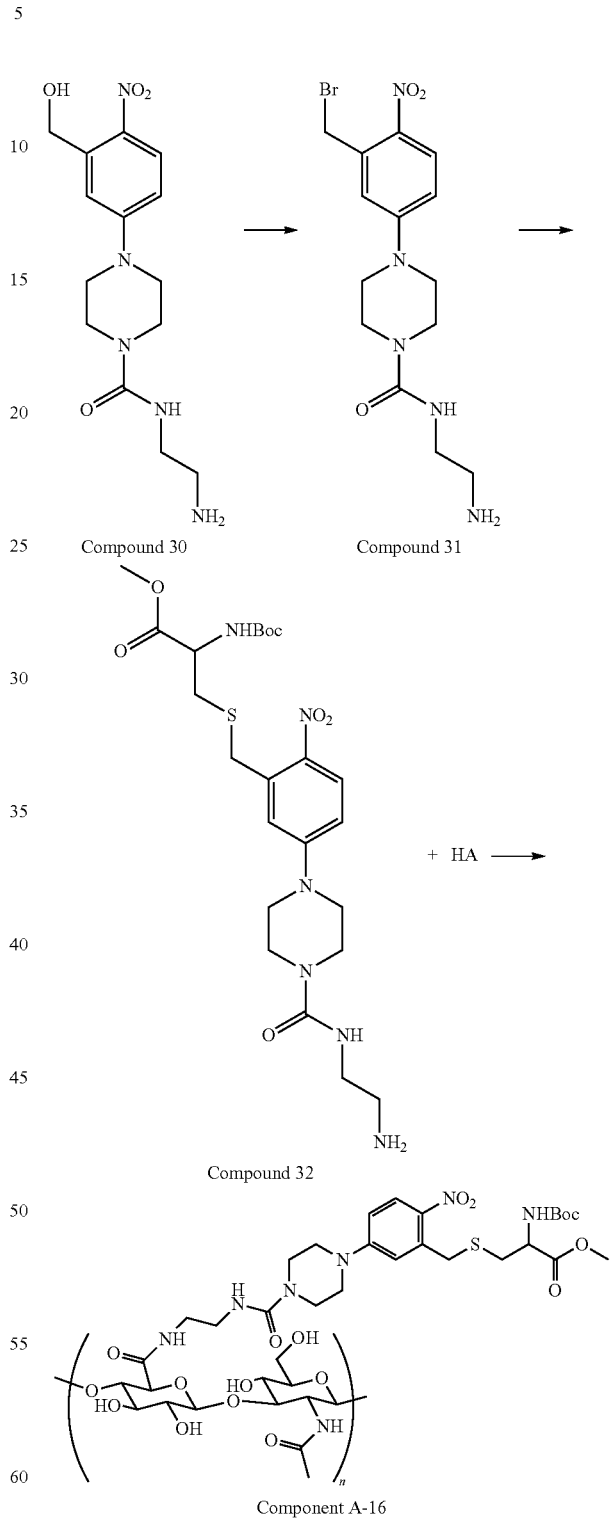

Compound 30     Compound 31

Compound 32

Component A-16

(1) Synthesis of Compound 30: The synthesis was carried out in accordance with the method disclosed in the reference (Emmanuel Riguet.; Christian G. Bochet. Org. Lett. 2007, 26, 5453).

(2) Synthesis of Compound 31: Compound 31 was obtained using Compound 30 as raw material according to the method of Example 2, the yield was 84%. $^1$H NMR (400 MHz, CDCl$_3$): δ=8.05 (d, J=9.54 Hz, 1H), 7.24 (d, J=2.72 Hz, 1H), 6.92 (dd, J=9.54, 2.72 Hz, 1H), 4.56 (s, 2H), 3.56-3.68 (m, 4H), 3.49-3.56 (m, 2H), 3.42-3.49 (m, 2H), 3.32 (t, J=5.9 Hz, 2H), 2.82 (t, J=5.9 Hz, 2H). MS (ESI): [M+H] 386.0824.

(3) Synthesis of Compound 32: Compound 32 was obtained using Compound 31 as raw material according to the method of Example 2, the yield was 78%. $^1$H NMR (400 MHz, CDCl$_3$): δ=8.05 (d, J=9.54 Hz, 1H), 7.24 (d, J=2.72 Hz, 1H), 6.92 (dd, J=9.54, 2.72 Hz, 1H), 4.76 (s, 2H), 4.42 (m, 1H), 3.95 (s, 3H), 3.56-3.68 (m, 4H), 3.49-3.56 (m, 2H), 3.43 (d, J=5.6, 2H), 3.42-3.49 (m, 2H), 3.32 (t, J=5.9 Hz, 2H), 2.82 (t, J=5.9 Hz, 2H), 1.42 (s, 9H). MS (ESI): [M+H] 541.2451.

(4) Synthesis of Component A-16: To a solution of hyaluronic acid (2 g, 340 kDa) in 100 mL 0.01 mol/L 2-(N-morpholine) mesylate (MES) buffer solution (pH=5.2) was added Compound 32 (108 mg, 0.2 mmol) dissolved in 10 mL dimethyl sulfoxide (DMSO). 4-(4,6-Dimethoxytriazin-2-yl)-4-methylmorpholine hydrochloride (DMTMM, 0.4 g, 1.5 mmol) dissolved in 3 mL MES buffer was added to the above reaction solution by three times (every 1 h), and the mixture was reacted at 35° C. for 24 h. Then, the reaction solution was poured into a dialysis bag (MWCO 7000), dialyzed against deionized water for 2-3 d, and lyophilized to obtain the photosensitive hyaluronic acid derivative Compound A-16 (1.83 g). According to the nuclear magnetic resonance spectrum, the grafting degree of Compound 32 could be calculated to be about 3.24%.

Example 17: Synthesis of Component A-17

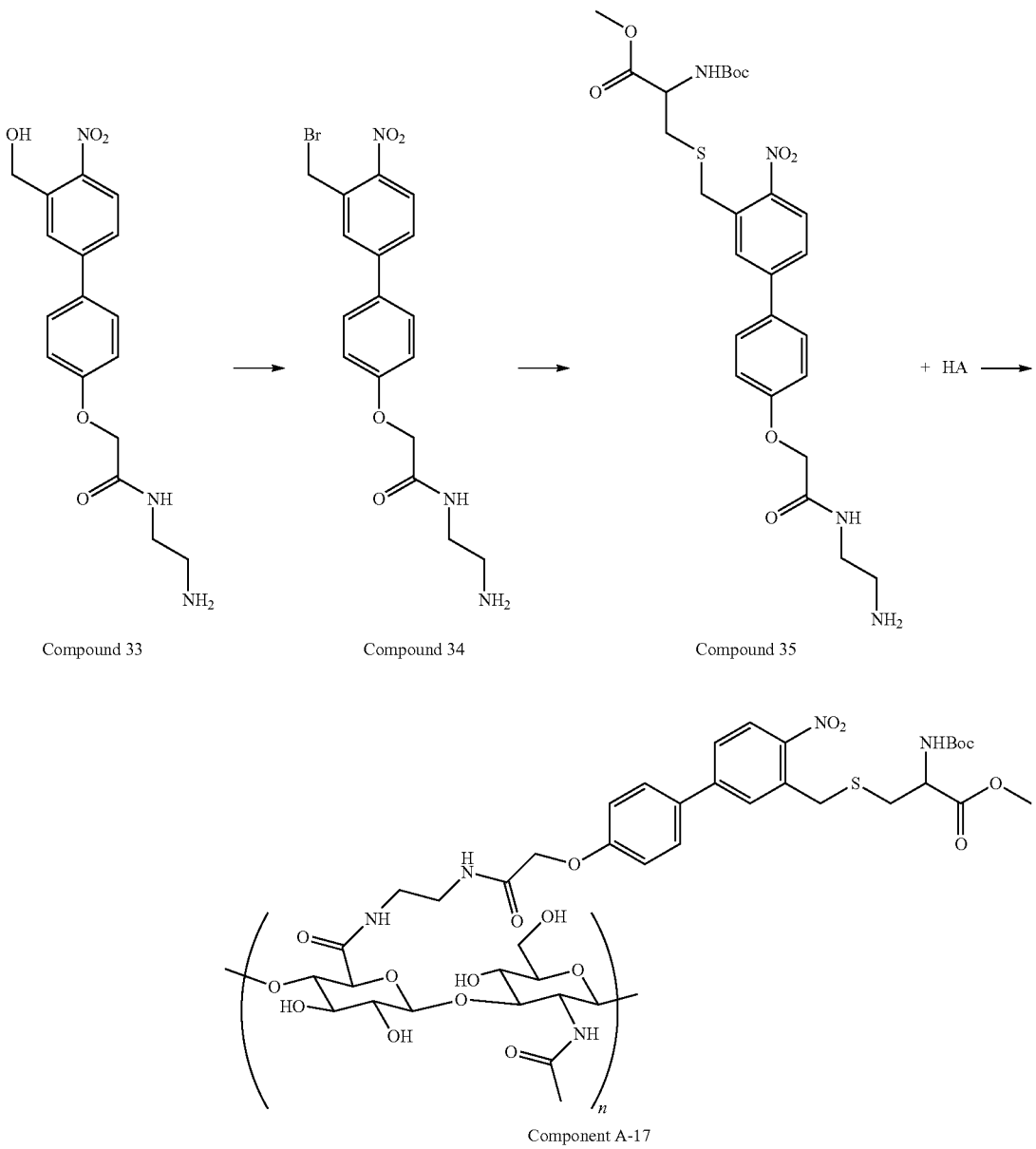

Component A-17

(1) Synthesis of Compound 33: The synthesis was carried out in accordance with the method disclosed in the reference (Isabelle Aujard.; Chouaha Benbrahim.; Ludovic Jullien. Chem. Eur. J. 2006, 12, 6865).

(2) Synthesis of Compound 34: Compound 34 was obtained using Compound 33 as raw material according to the method of Example 2, the yield was 72%. $^1$H NMR (400 MHz, CDCl$_3$): δ=8.05 (d, J=9.54 Hz, 1H), 7.28 (d, J=8.00 Hz, 2H), 7.24 (d, J=2.72 Hz, 1H), 6.92 (dd, J=9.54, 2.72 Hz, 1H), 6.78 (d, 8.00 Hz, 2H), 4.83 (s, 2H), 4.56 (s, 2H), 3.32 (t, J=5.9 Hz, 2H), 2.82 (t, J=5.9 Hz, 2H). MS (ESI): [M+H] 408.0524.

(3) Synthesis of Compound 35: Compound 35 was obtained using Compound 34 as raw material according to the method of Example 2, the yield was 78%. $^1$H NMR (400 MHz, CDCl$_3$): δ=8.05 (d, J=9.54 Hz, 1H), 7.28 (d, J=8.00 Hz, 2H), 7.24 (d, J=2.72 Hz, 1H), 6.92 (dd, J=9.54, 2.72 Hz, 1H), 6.78 (d, 8.00 Hz, 2H), 4.83 (s, 2H), 4.76 (s, 2H), 4.42 (m, 1H), 3.95 (s, 3H), 3.43 (d, J=5.6, 2H), 3.32 (t, J=5.9 Hz, 2H), 2.82 (t, J=5.9 Hz, 2H), 1.42 (s, 9H). MS (ESI): [M+H] 563.2135.

(4) Synthesis of Component A-17: To a solution of hyaluronic acid (2 g, 340 kDa) in 100 mL 0.01 mol/L 2-(N-morpholine) mesylate (MES) buffer solution (pH=5.2) was added Compound 35 (112 mg, 0.2 mmol) dissolved in 10 mL dimethyl sulfoxide (DMSO). 4-(4,6-Dimethoxytriazin-2-yl)-4-methylmorpholine hydrochloride (DMTMM, 0.4 g, 1.5 mmol) dissolved in 3 mL MES buffer was added to the above reaction solution by three times (every 1 h), and the mixture was reacted at 35° C. for 24 h. Then, the reaction solution was poured into a dialysis bag (MWCO 7000), dialyzed against deionized water for 2-3 d, and lyophilized to obtain the photosensitive hyaluronic acid derivative Compound A-17 (1.84 g). According to the nuclear magnetic resonance spectrum, the grafting degree of Compound 35 could be calculated to be about 3.31%.

Example 20: Synthesis of Component A-20

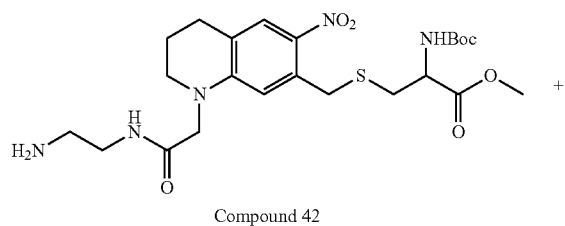

Compound 42

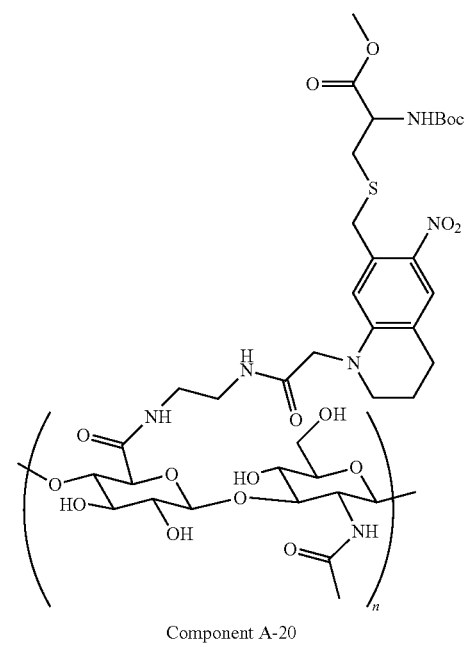

Component A-20

(1) Synthesis of Compound 42: The synthesis was carried out in accordance with the method disclosed in the reference (Emmanuel Riguet.; Christian G. Bochet. Org. Lett. 2007, 26, 5453). $^1$H NMR (400 MHz, CDCl$_3$): δ=7.71 (s, 1H), 7.22 (s, 1H), 4.56 (s, 2H), 4.42 (m, 1H), 4.24 (s, 2H), 3.95 (s, 3H), 3.43 (d, J=5.6, 2H), 3.32 (t, J=5.9 Hz, 2H), 3.27-3.21 (m, 2H), 2.82 (t, J=5.9 Hz, 2H), 2.75 (t, J=6.3 Hz, 2H), 2.00-1.91 (m, 2H), 1.42 (s, 9H). MS (ESI): [M+H] 526.6302.

(2) Synthesis of Component A-20: To a solution of hyaluronic acid (2 g, 340 kDa) in 100 mL 0.01 mol/L 2-(N-morpholine) mesylate (MES) buffer solution (pH=5.2) was added Compound 42 (105 mg, 0.2 mmol) dissolved in 10 mL dimethyl sulfoxide (DMSO). 4-(4,6-Dimethoxytriazin-2-yl)-4-methylmorpholine hydrochloride (DMTMM, 0.4 g, 1.5 mmol) dissolved in 3 mL MES buffer was added to the above reaction solution by three times (every 1 h), and the mixture was reacted at 35° C. for 24 h. Then, the reaction solution was poured into a dialysis bag (MWCO 7000), dialyzed against deionized water for 2-3 d, and lyophilized to obtain the photosensitive hyaluronic acid derivative Compound A-20 (1.82 g). According to the nuclear magnetic resonance spectrum, the grafting degree of Compound 42 could be calculated to be about 3.07%.

Example 21: Synthesis of Component A-21

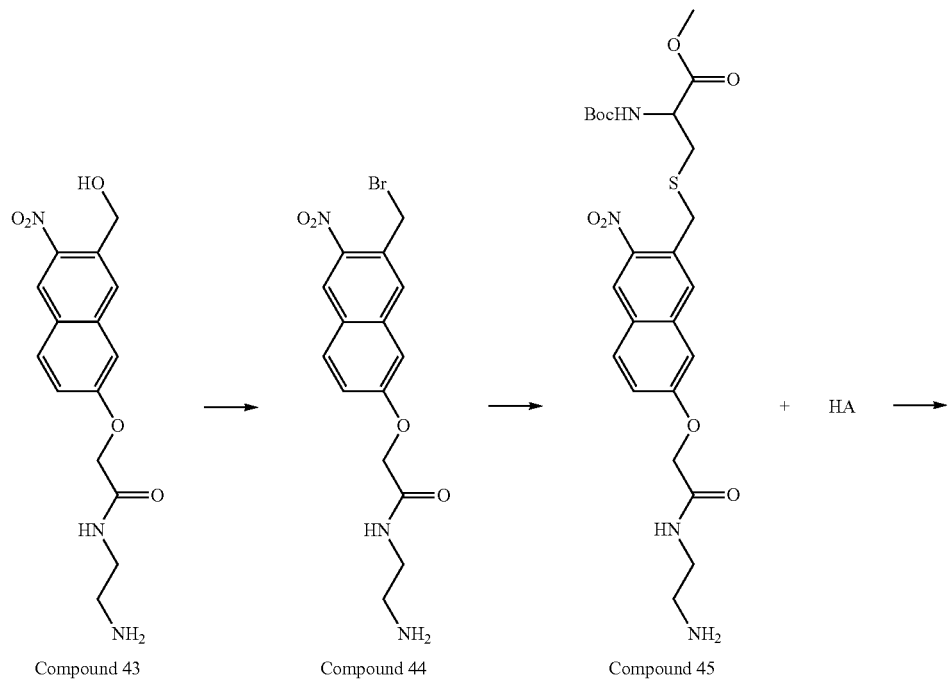

Compound 43    Compound 44    Compound 45

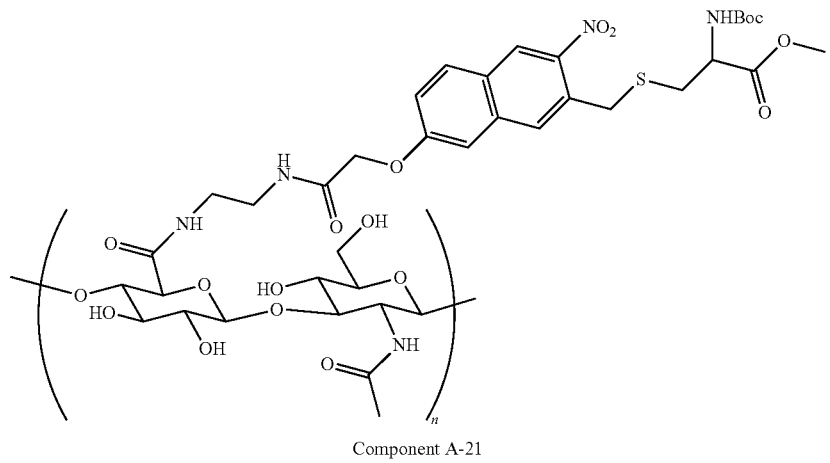

Component A-21

(1) Synthesis of Compound 43. The synthesis was carried out in accordance with the method disclosed in the reference (Singh, A. K.; Khade, P. K. Tetrahedron. 2005, 61, 10007).

(2) Synthesis of Compound 44. Compound 44 was obtained using Compound 43 as raw material according to the method of Example 2, the yield was 73%. $^1$H NMR (400 MHz, CDCl$_3$): δ=8.31-7.12 (m, 5H), 4.83 (s, 2H), 4.56 (s, 2H), 3.32 (t, J=5.9 Hz, 2H), 2.82 (t, J=5.9 Hz, 2H). MS (ESI): [M+H] 382.0319.

(3) Synthesis of Compound 45. Compound 45 was obtained using Compound 44 according to the method of Example 2, the yield was 77%. $^1$H NMR (400 MHz, CDCl$_3$): δ=8.31-7.12 (m, 5H), 4.83 (s, 2H), 4.76 (s, 2H), 4.42 (m, 1H), 3.95 (s, 3H), 3.43 (d, J=5.6, 2H), 3.32 (t, J=5.9 Hz, 2H), 2.82 (t, J=5.9 Hz, 2H), 1.42 (s, 9H). MS (ESI): [M+H] 357.2029.

(4) Synthesis of Component A-21. To a solution of hyaluronic acid (2 g, 340 kDa) in 100 mL 0.01 mol/L 2-(N-morpholine) mesylate (MES) buffer solution (pH=5.2) was added Compound 45 (107 mg, 0.2 mmol) dissolved in 10 mL dimethyl sulfoxide (DMSO). 4-(4,6-Dimethoxytriazin-2-yl)-4-methylmorpholine hydrochloride (DMTMM, 0.4 g, 1.5 mmol) dissolved in 3 mL MES buffer was added to the above reaction solution by three times (every 1 h), and the mixture was reacted at 35° C. for 24 h. Then, the reaction solution was poured into a dialysis bag (MWCO 7000), dialyzed against deionized water for 2-3 d, and lyophilized to obtain the photosensitive hyaluronic acid derivative Compound A-21 (1.76 g). According to the nuclear magnetic resonance spectrum, the grafting degree of Compound 45 could be calculated to be about 3.12%.

Example 22: Synthesis of Component A-22

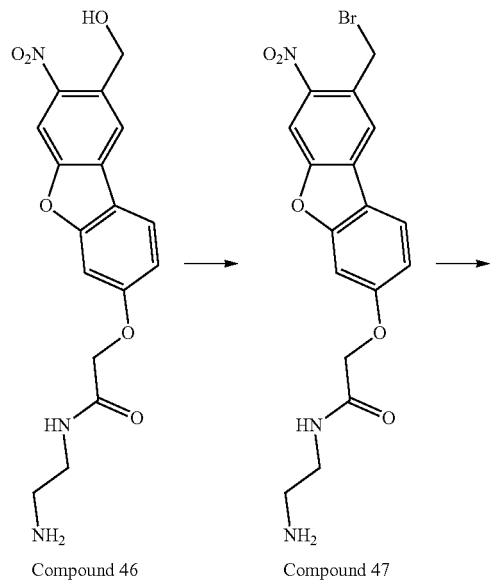

Compound 46 → Compound 47

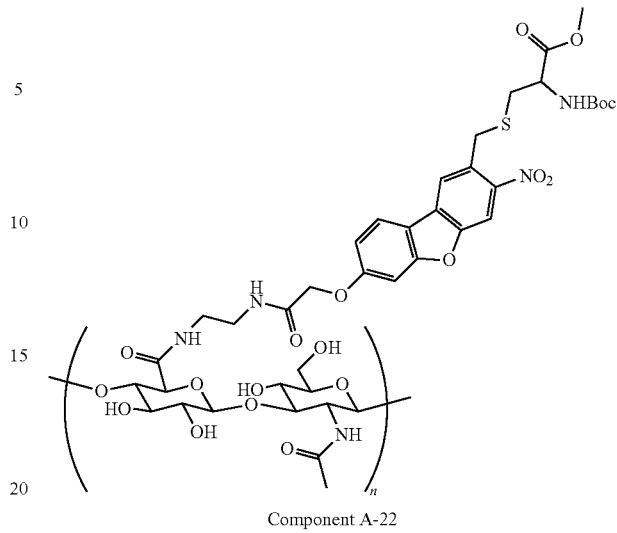

Component A-22

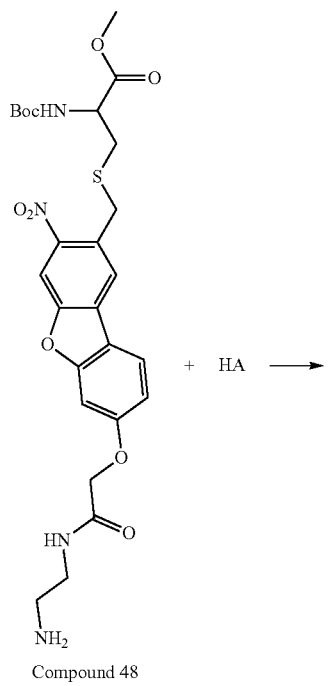

Compound 48 + HA →

(1) Synthesis of Compound 46: The synthesis was carried out in accordance with the method disclosed in the reference (Felix Friedrich.; Mike Heilemann.; Alexander Heckel. Chem. Commun. 2015, 51, 15382).

(2) Synthesis of Compound 47: Compound 47 was obtained using Compound 46 as raw material according to the method of Example 2, the yield was 62%. $^1$H NMR (400 MHz, CDCl$_3$): δ=8.31-7.12 (m, 5H), 4.83 (s, 2H), 4.56 (s, 2H), 3.32 (t, J=5.9 Hz, 2H), 2.82 (t, J=5.9 Hz, 2H). MS (ESI): [M+H] 422.0328.

(3) Synthesis of Compound 48: Compound 48 was obtained using Compound 47 as raw material according to the method of Example 2, the yield was 69%. $^1$H NMR (400 MHz, CDCl$_3$): δ=8.31-7.12 (m, 5H), 4.83 (s, 2H), 4.76 (s, 2H), 4.42 (m, 1H), 3.95 (s, 3H), 3.43 (d, J=5.6, 2H), 3.32 (t, J=5.9 Hz, 2H), 2.82 (t, J=5.9 Hz, 2H), 1.42 (s, 9H). MS (ESI): [M+H] 577.1962.

(4) Synthesis of Component A-22: To a solution of hyaluronic acid (2 g, 340 kDa) in 100 mL 0.01 mol/L 2-(N-morpholine) mesylate (MES) buffer solution (pH=5.2) was added Compound 48 (115 mg, 0.2 mmol) dissolved in 10 mL dimethyl sulfoxide (DMSO). 4-(4,6-Dimethoxytri-azin-2-yl)-4-methylmorpholine hydrochloride (DMTMM, 0.4 g, 1.5 mmol) dissolved in 3 mL MES buffer was added to the above reaction solution by three times (every 1 h), and the mixture was reacted at 35° C. for 24 h. Then, the reaction solution was poured into a dialysis bag (MWCO 7000), dialyzed against deionized water for 2-3 d, and lyophilized to obtain the photosensitive hyaluronic acid derivative Compound A-22 (1.81 g). According to the nuclear magnetic resonance spectrum, the grafting degree of Compound 48 could be calculated to be about 2.41%.

Example 23: Synthesis of Component A-23

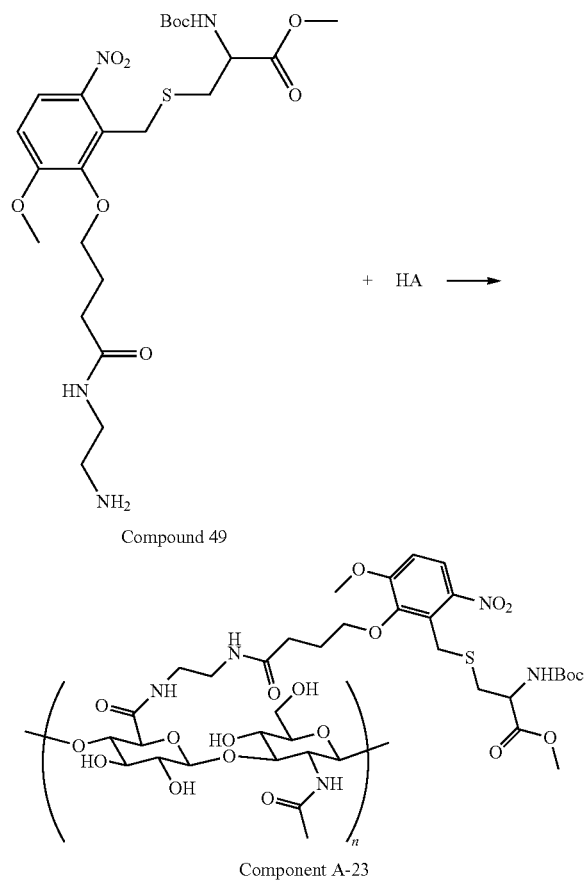

Compound 49

Component A-23

(1) Synthesis of Compound 49: The synthesis was carried out in accordance with the method disclosed in the reference (Grazyna Groszek.; Agnieszka Nowak-Krol.; Barbara Filipek. Eur. J. Med. Chem. 2009, 44, 5103). $^1$H NMR (400 MHz, CDCl$_3$): δ=8.04 (s, 1H), 7.42 (s, 1H), 4.76 (s, 2H), 4.42 (m, 1H), 4.13 (t, J=6.1 Hz, 2H), 3.99 (s, 3H), 3.95 (s, 3H), 3.43 (d, J=5.6, 2H), 3.32 (dd, J=11.6, 5.7 Hz, 2H), 2.82 (t, J=5.9 Hz, 2H), 2.44 (t, J=7.2 Hz, 2H), 2.26-2.17 (m, 2H), 1.42 (s, 9H). MS (ESI): [M+H] 545.2234.

(2) Synthesis of Component A-23: To a solution of hyaluronic acid (2 g, 340 kDa) in 100 mL 0.01 mol/L 2-(N-morpholine) mesylate (MES) buffer solution (pH=5.2) was added Compound 49 (109 mg, 0.2 mmol) dissolved in 10 mL dimethyl sulfoxide (DMSO). 4-(4,6-Dimethoxytriazin-2-yl)-4-methylmorpholine hydrochloride (DMTMM, 0.4 g, 1.5 mmol) dissolved in 3 mL MES buffer was added to the above reaction solution by three times (every 1 h), and the mixture was reacted at 35° C. for 24 h. Then, the reaction solution was poured into a dialysis bag (MWCO 7000), dialyzed against deionized water for 2-3 d, and lyophilized to obtain the photosensitive hyaluronic acid derivative Compound A-23 (1.92 g). According to the nuclear magnetic resonance spectrum, the grafting degree of Compound 49 could be calculated to be about 3.14%.

Example 24: Synthesis of Component A-24

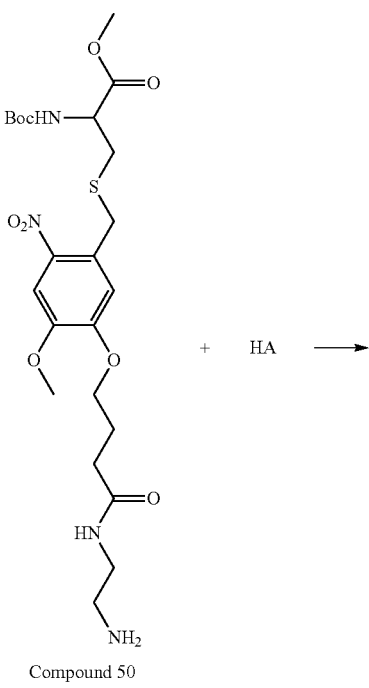

Compound 50

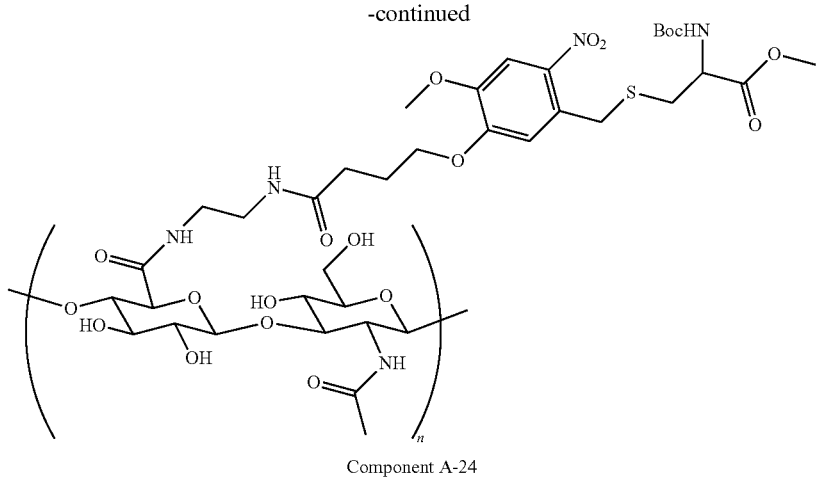

Component A-24

(1) Synthesis of Compound 50: The synthesis was carried out in accordance with the method disclosed in the reference (Thomas F. Greene.; Shu Wang.; Mary J. Meegan. J. Med. Chem. 2016, 59, 90). $^1$H NMR (400 MHz, CDCl$_3$): δ=7.95 (s, 1H), 7.12 (s, 1H), 4.76 (s, 2H), 4.42 (m, 1H), 4.13 (t, J=6.1 Hz, 2H), 3.99 (s, 3H), 3.95 (s, 3H), 3.43 (d, J=5.6, 2H), 3.32 (dd, J=11.6, 5.7 Hz, 2H), 2.82 (t, J=5.9 Hz, 2H), 2.44 (t, J=7.2 Hz, 2H), 2.26-2.17 (m, 2H), 1.42 (s, 9H). MS (ESI): [M+H] 545.2262.

(2) Synthesis of Component A-24: To a solution of hyaluronic acid (2 g, 340 kDa) in 100 mL 0.01 mol/L 2-(N-morpholine) mesylate (MES) buffer solution (pH=5.2) was added Compound 50 (109 mg, 0.2 mmol) dissolved in 10 mL dimethyl sulfoxide (DMSO). 4-(4,6-Dimethoxytri-azin-2-yl)-4-methylmorpholine hydrochloride (DMTMM, 0.4 g, 1.5 mmol) dissolved in 3 mL MES buffer was added to the above reaction solution by three times (every 1 h), and the mixture was reacted at 35° C. for 24 h. Then, the reaction solution was poured into a dialysis bag (MWCO 7000), dialyzed against deionized water for 2-3 d, and lyophilized to obtain the photosensitive hyaluronic acid derivative Compound A-24 (1.88 g). According to the nuclear magnetic resonance spectrum, the grafting degree of Compound 50 could be calculated to be about 3.45%.

Example 25: Synthesis of Component A-25

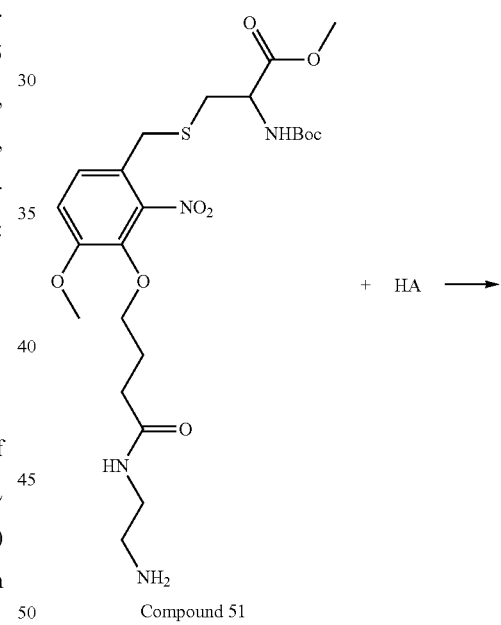

Compound 51

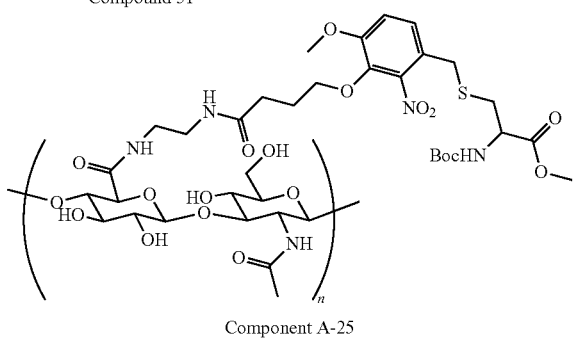

Component A-25

(1) Synthesis of Compound 51: The synthesis was carried out in accordance with the method disclosed in the reference (Yu-Shan.; Mohane Selvaraj Coumar.; Hsing-Pang Hsieh. J.

Med. Chem. 2009, 52, 4941). $^1$H NMR (400 MHz, CDCl$_3$): δ=7.64 (s, 1H), 7.02 (s, 1H), 4.76 (s, 2H), 4.42 (m, 1H), 4.13 (t, J=6.1 Hz, 2H), 3.99 (s, 3H), 3.95 (s, 3H), 3.43 (d, J=5.6, 2H), 3.32 (dd, J=11.6, 5.7 Hz, 2H), 2.82 (t, J=5.9 Hz, 2H), 2.44 (t, J=7.2 Hz, 2H), 2.26-2.17 (m, 2H), 1.42 (s, 9H). MS (ESI): [M+H] 545.2231.

(2) Synthesis of Component A-25: To a solution of hyaluronic acid (2 g, 340 kDa) in 100 mL 0.01 mol/L 2-(N-morpholine) mesylate (MES) buffer solution (pH=5.2) was added Compound 51 (109 mg, 0.2 mmol) dissolved in 10 mL dimethyl sulfoxide (DMSO). 4-(4,6-Dimethoxytri-azin-2-yl)-4-methylmorpholine hydrochloride (DMTMM, 0.4 g, 1.5 mmol) dissolved in 3 mL MES buffer was added to the above reaction solution by three times (every 1 h), and the mixture was reacted at 35° C. for 24 h. Then, the reaction solution was poured into a dialysis bag (MWCO 7000), dialyzed against deionized water for 2-3 d, and lyophilized to obtain the photosensitive hyaluronic acid derivative Compound A-25 (1.85 g). According to the nuclear magnetic resonance spectrum, the grafting degree of Compound 51 could be calculated to be about 3.32%.

Example 26: Synthesis of Component A-26

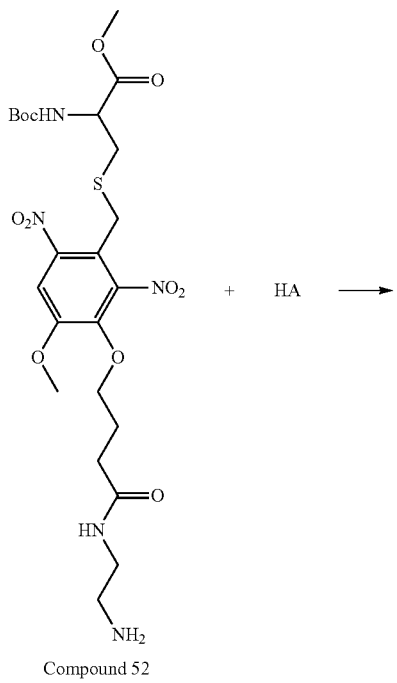

Compound 52

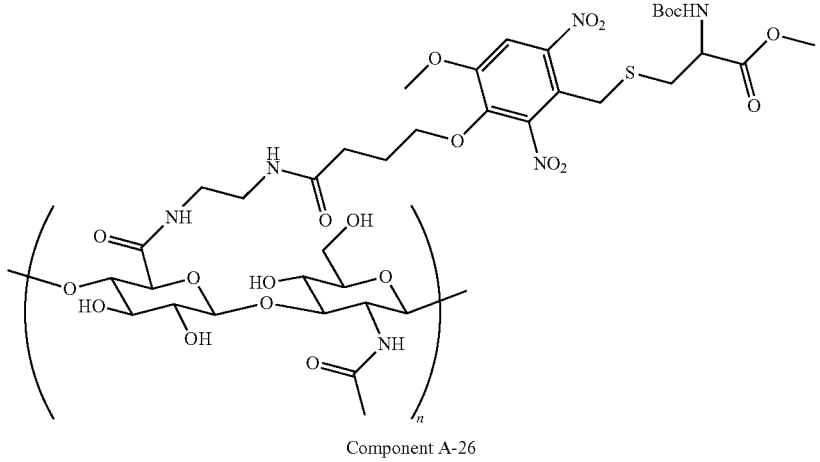

Component A-26

(1) Synthesis of Compound 52: The synthesis was carried out in accordance with the method disclosed in the reference (Sarit S. Agasti.; Apiwat Chompoosor.; Vincent M. Rotello. J. Am. Chem. Soc. 2009, 131, 5728). $^1$H NMR (400 MHz, CDCl$_3$): δ=7.91 (s, 1H), 4.76 (s, 2H), 4.42 (m, 1H), 4.13 (t, J=6.1 Hz, 2H), 3.99 (s, 3H), 3.95 (s, 3H), 3.43 (d, J=5.6, 2H), 3.32 (dd, J=11.6, 5.7 Hz, 2H), 2.82 (t, J=5.9 Hz, 2H), 2.44 (t, J=7.2 Hz, 2H), 2.26-2.17 (m, 2H), 1.42 (s, 9H). MS (ESI): [M+H] 590.2124.

(2) Synthesis of Component A-26: To a solution of hyaluronic acid (2 g, 340 kDa) in 100 mL 0.01 mol/L 2-(N-morpholine) mesylate (MES) buffer solution (pH=5.2) was added Compound 52 (118 mg, 0.2 mmol) dissolved in 10 mL dimethyl sulfoxide (DMSO). 4-(4,6-Dimethoxytriazin-2-yl)-4-methylmorpholine hydrochloride (DMTMM, 0.4 g, 1.5 mmol) dissolved in 3 mL MES buffer was added to the above reaction solution by three times (every 1 h), and the mixture was reacted at 35° C. for 24 h. Then, the reaction solution was poured into a dialysis bag (MWCO 7000), dialyzed against deionized water for 2-3 d, and lyophilized to obtain the photosensitive hyaluronic acid derivative Compound A-26 (1.87 g). According to the nuclear magnetic resonance spectrum, the grafting degree of Compound 52 could be calculated to be about 3.29%.

Example 28: Synthesis of Component A-28

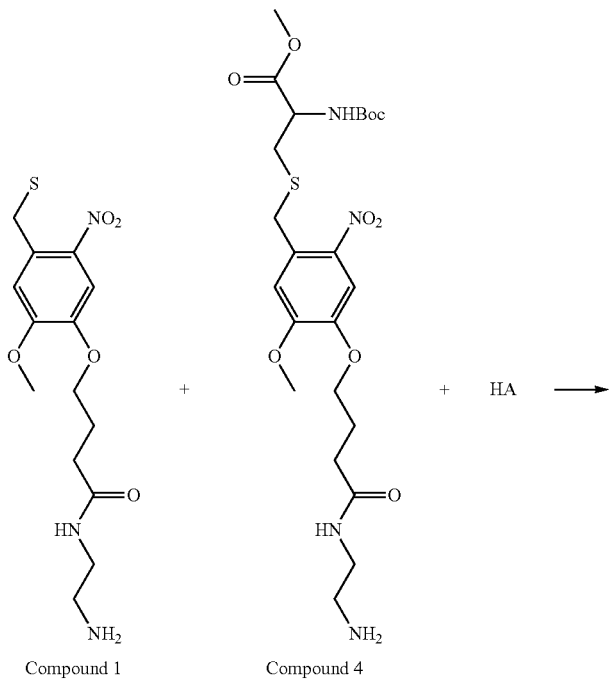

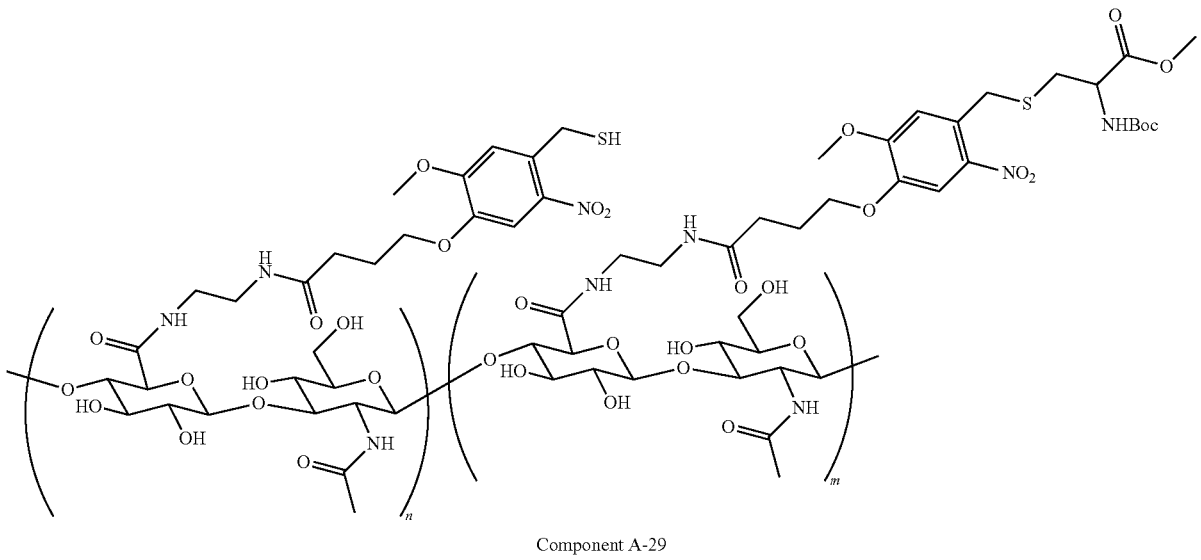

Component A-29

Synthesis of Component A-28: To a solution of hyaluronic acid sodium (2 g, 340 kDa) in 100 mL 0.01 M 2-(N-morpholine) mesylate (MES) buffer solution (pH=5.2) was added the mixture of NB mixture (Compound 1/Compound 4) (60 mg, 1:1) dissolved in 10 mL dimethyl sulfoxide (DMSO). Then, DMTMM (0.4 g, 1.5 mmol) dissolved in 3 mL water was added into the above solution three times with an interval of 1 h, and the mixture was stirred for 24 hours in the dark 35° C. Then, the reaction solution was poured into a dialysis bag (MWCO 7000), dialyzed against deionized water for 2-3 d, and lyophilized to obtain a photosensitive hyaluronic acid derivative Compound A-28 (1.89 g). According to the nuclear magnetic resonance spectrum, the grafting degree of the NB mixture (Compound 1/Compound 4) can be calculated to be about 3.41%.

Example 29: Synthesis of Component A-29

(1) Synthesis of Compound 54: Compound 54 was prepared by the method of Example 2 by conventional chemical means. $^1$H NMR (400 MHz, CDCl$_3$): δ=7.71 (s, 1H), 7.22 (s, 1H), 4.76 (s, 2H), 4.42 (m, 1H), 3.99 (s, 3H), 3.95 (s, 3H), 3.43 (d, J=5.6, 2H), 3.32 (t, J=5.7 Hz, 2H), 2.82 (t, J=5.9 Hz, 2H), 2.55 (t, J=6.1 Hz, 2H), 2.44 (t, J=7.2 Hz, 2H), 2.26-2.17 (m, 2H), 1.42 (s, 9H). MS (ESI): [M+H] 529.2342.

(2) Synthesis of Component A-29: To a solution of hyaluronic acid (2 g, 340 kDa) in 100 mL 0.01 mol/L 2-(N-morpholine) mesylate (MES) buffer solution (pH=5.2) was added Compound 54 (108 mg, 0.2 mmol) dissolved in 10 mL dimethyl sulfoxide (DMSO). 4-(4,6-Dimethoxytriazin-2-yl)-4-methylmorpholine hydrochloride (DMTMM, 0.4 g, 1.5 mmol) dissolved in 3 mL MES buffer was added to the above reaction solution by three times (every 1 h), and the mixture was reacted at 35° C. for 24 h. Then, the reaction solution was poured into a dialysis bag (MWCO 7000), dialyzed against deionized water for 2-3 d, and lyophilized to obtain the photosensitive hyaluronic acid derivative Compound A-29 (1.85 g). According to the nuclear magnetic resonance spectrum, the grafting degree of Compound 54 could be calculated to be about 3.09%.

Example 30: Synthesis of Component A-30

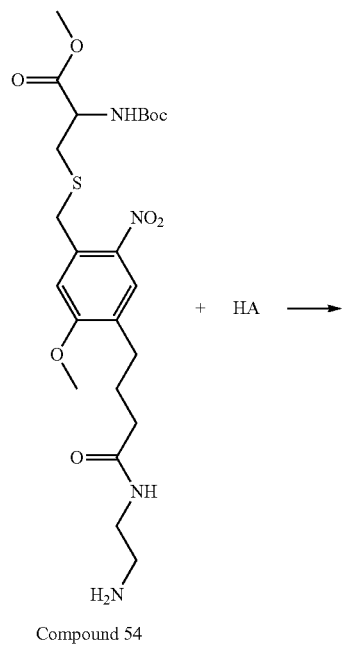

Compound 54

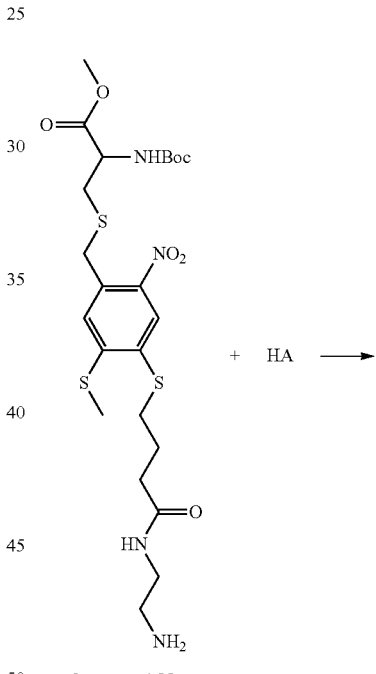

Compound 55

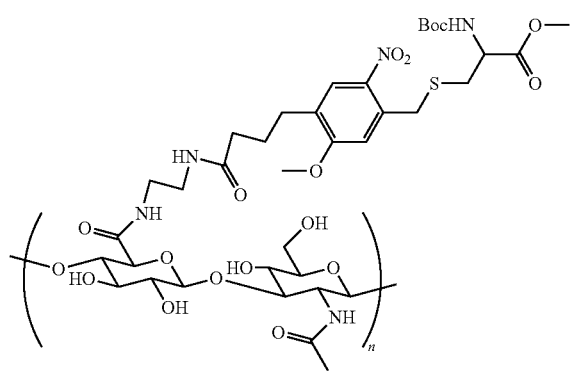

Component A-29

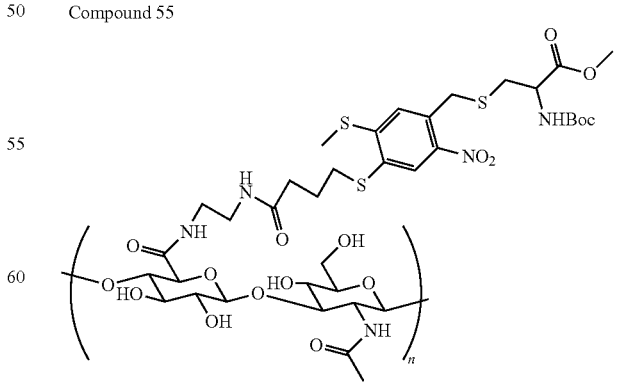

Component A-30

(1) Synthesis of Compound 55: Compound 55 was prepared by the method of Example 2 by conventional chemical means. $^1$H NMR (400 MHz, CDCl$_3$): δ=7.71 (s, 1H), 7.22 (s, 1H), 4.76 (s, 2H), 4.42 (m, 1H), 4.03 (t, J=6.1 Hz, 2H), 3.99 (s, 3H), 3.95 (s, 3H), 3.43 (d, J=5.6, 2H), 3.32 (dd, J=11.6, 5.7 Hz, 2H), 2.82 (t, J=5.9 Hz, 2H), 2.44 (t, J=7.2 Hz, 2H), 2.26-2.17 (m, 2H), 1.42 (s, 9H). MS (ESI): [M+H] 577.1852.

(2) Synthesis of Component A-30: To a solution of hyaluronic acid (2 g, 340 kDa) in 100 mL 0.01 mol/L 2-(N-morpholine) mesylate (MES) buffer solution (pH=5.2) was added Compound 55 (112 mg, 0.2 mmol) dissolved in 10 mL dimethyl sulfoxide (DMSO). 4-(4,6-Dimethoxytriazin-2-yl)-4-methylmorpholine hydrochloride (DMTMM, 0.4 g, 1.5 mmol) dissolved in 3 mL MES buffer was added to the above reaction solution by three times (every 1 h), and the mixture was reacted at 35° C. for 24 h. Then, the reaction solution was poured into a dialysis bag (MWCO 7000), dialyzed against deionized water for 2-3 d, and lyophilized to obtain the photosensitive hyaluronic acid derivative Compound A-30 (1.83 g). According to the nuclear magnetic resonance spectrum, the grafting degree of Compound 55 could be calculated to be about 3.21%.

Example 31: Synthesis of Component A-31

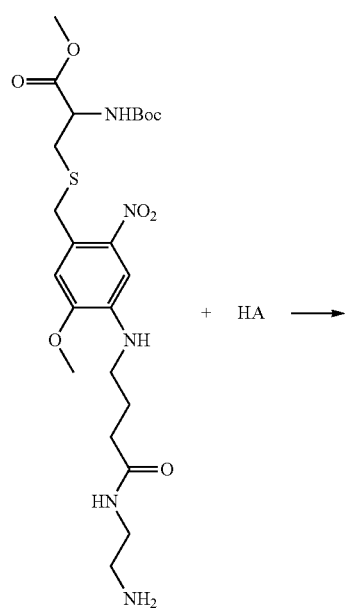

Compound 56

+ HA ⟶

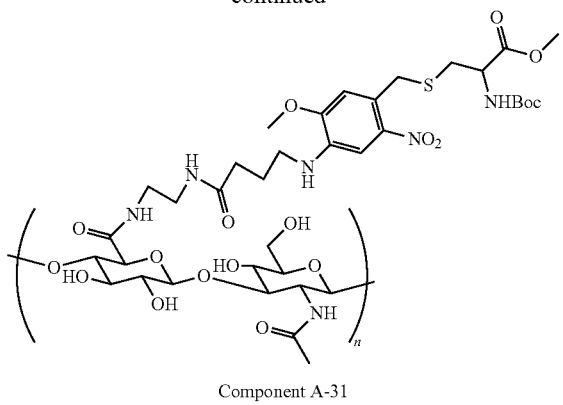

Component A-31

(1) Synthesis of Compound 56: Compound 56 was prepared using the method of Example 2 by conventional chemical means. $^1$H NMR (400 MHz, CDCl$_3$): δ=7.71 (s, 1H), 7.22 (s, 1H), 4.76 (s, 2H), 4.42 (m, 1H), 3.99 (s, 3H), 3.95 (s, 3H), 3.43 (d, J=5.6, 2H), 3.45 (t, J=6.1 Hz, 2H), 3.32 (dd, J=11.6, 5.7 Hz, 2H), 2.82 (t, J=5.9 Hz, 2H), 2.44 (t, J=7.2 Hz, 2H), 2.26-2.17 (m, 2H), 1.42 (s, 9H). MS (ESI): [M+H] 544.2463.

(2) Synthesis of Component A-31: To a solution of hyaluronic acid (2 g, 340 kDa) in 100 mL 0.01 mol/L 2-(N-morpholine) mesylate (MES) buffer solution (pH=5.2) was added Compound 56 (109 mg, 0.2 mmol) dissolved in 10 mL dimethyl sulfoxide (DMSO). 4-(4,6-Dimethoxytriazin-2-yl)-4-methylmorpholine hydrochloride (DMTMM, 0.4 g, 1.5 mmol) dissolved in 3 mL MES buffer was added to the above reaction solution by three times (every 1 h), and the mixture was reacted at 35° C. for 24 h. Then, the reaction solution was poured into a dialysis bag (MWCO 7000), dialyzed against deionized water for 2-3 d, and lyophilized to obtain the photosensitive hyaluronic acid derivative Compound A-31 (1.78 g). According to the nuclear magnetic resonance spectrum, the grafting degree of Compound 56 could be calculated to be about 2.95%.

Example 32: Synthesis of Component A-32

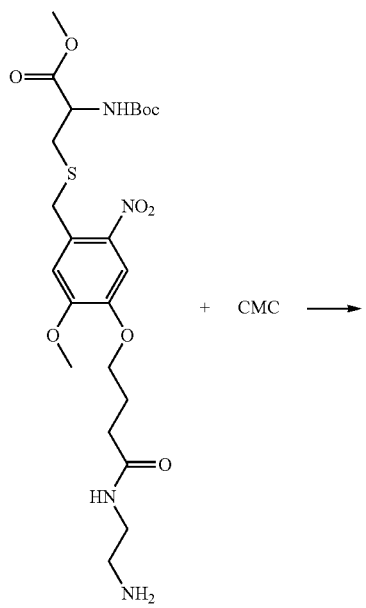

Compound 4

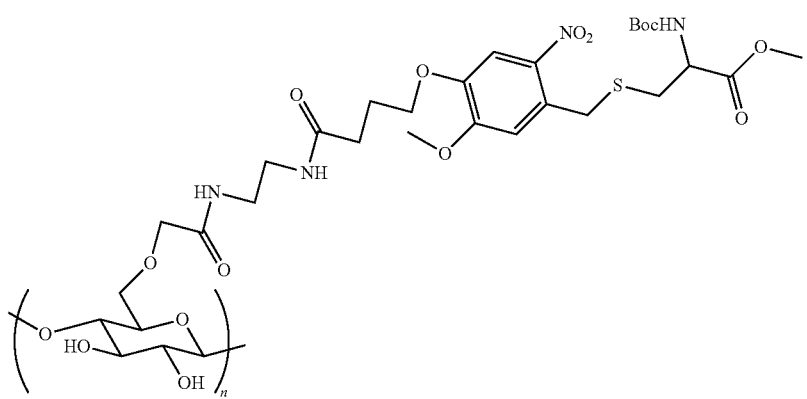

Component A-32

Synthesis of Component A-32: To a solution of carboxymethyl cellulose (2 g, 90 kDa) in 100 mL 0.01M 2-(N-morpholine) mesylate (MES) buffer solution (pH=5.2) was added Compound 4 (109 mg, 0.2 mmol) dissolved in 10 mL dimethyl sulfoxide (DMSO). Then, DMTMM (0.4 g, 1.5 mmol) dissolved in 3 mL water was added into the above solution three times with an interval of 1 h, and the mixture was stirred for 24 hours in the dark 35° C. Then, the reaction solution was poured into a dialysis bag (MWCO 7000), dialyzed against deionized water for 2-3 d, and lyophilized to obtain a photosensitive carboxymethylcellulose derivative Compound A-32 (1.74 g). According to the nuclear magnetic resonance spectrum, the grafting degree of Compound 4 can be calculated to be about 2.34%.

Example 33: Synthesis of Component A-33

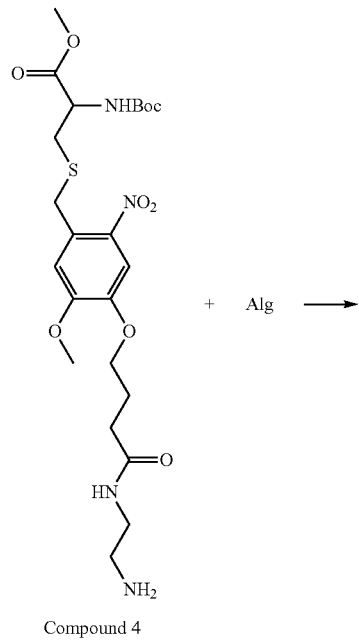

Compound 4

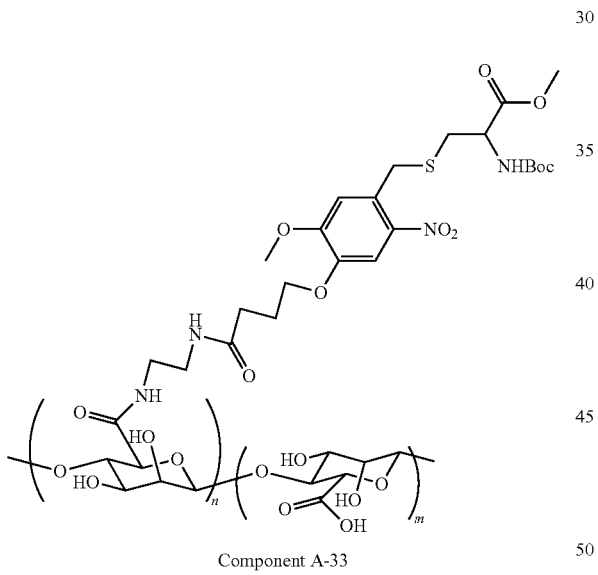

Component A-33

Synthesis of Component A-33: To a solution of alginic acid (2 g) in 100 mL 0.01M 2-(N-morpholine) mesylate (MES) buffer solution (pH=5.2) was added Compound 4 (109 mg, 0.2 mmol) dissolved in 10 mL dimethyl sulfoxide (DMSO). Then, DMTMM (0.4 g, 1.5 mmol) dissolved in 3 mL water was added into the above solution three times with an interval of 1 h, and the mixture was stirred for 24 hours in the dark 35° C. Then, the reaction solution was poured into a dialysis bag (MWCO 7000), dialyzed against deionized water for 2-3 d, and lyophilized to obtain a photosensitive alginic acid derivative Compound A-33 (1.76 g). According to the nuclear magnetic resonance spectrum, the grafting degree of Compound 4 can be calculated to be about 2.18%.

Example 34: Synthesis of Component A-34

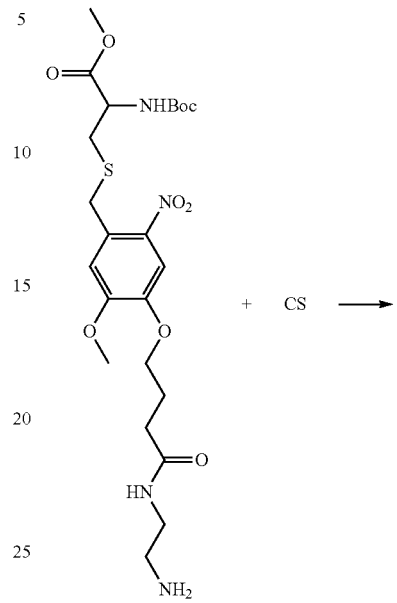

Compound 4

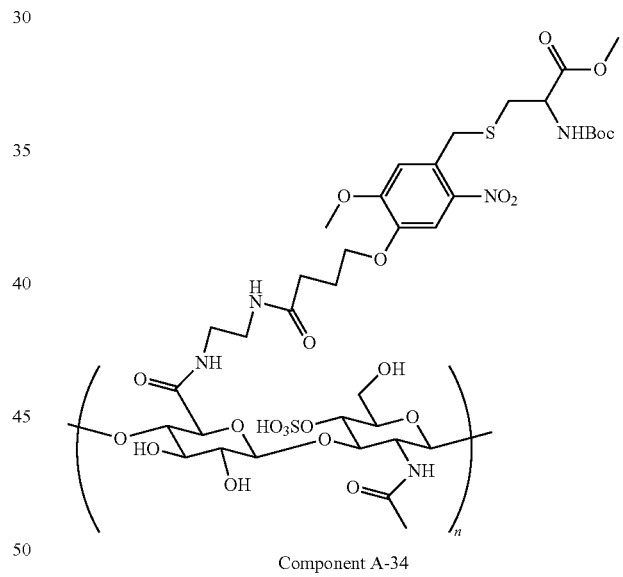

Component A-34

Synthesis of Component A-34: To a solution of chondroitin sulfate (2 g) in 100 mL 0.01M 2-(N-morpholine) mesylate (MES) buffer solution (pH=5.2) was added Compound 4 (109 mg, 0.2 mmol) dissolved in 10 mL dimethyl sulfoxide (DMSO). Then, DMTMM (0.4 g, 1.5 mmol) dissolved in 3 mL water was added into the above solution three times with an interval of 1 h, and the mixture was stirred for 24 hours in the dark 35° C. Then, the reaction solution was poured into a dialysis bag (MWCO 7000), dialyzed against deionized water for 2-3 d, and lyophilized to obtain a photosensitive chondroitin sulfate derivative Compound A-34 (1.72 g). According to the nuclear magnetic resonance spectrum, the grafting degree of Compound 4 can be calculated to be about 3.03%.

Example 35: Synthesis of Component A-35

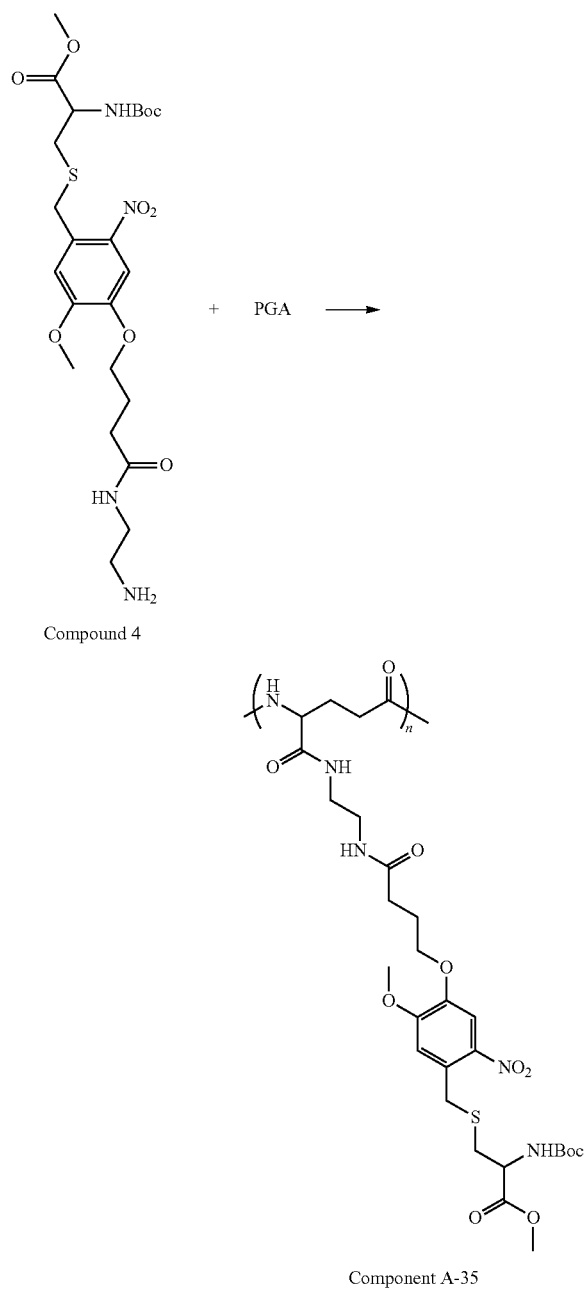

Compound 4

Component A-35

Synthesis of Component A-35: To a solution of polyglutamic acid (PGA, 1 g) in 50 mL distilled water was added hydroxybenzotriazole (HOBt, 0.3 g, 2.3 mmol). Then Compound 4 (0.5 g, 0.9 mmol) and 1-ethyl-(3-dimethylaminopropyl) carbodiimine hydrochloride (EDC-HCl, 0.5 g, 2.6 mmol) dissolved in methanol were added to the above solution, and the mixture was stirred at room temperature for 48 h. The solution was firstly dialyzed with dilute hydrochloric acid solution containing sodium chloride (pH=3.5) for 1 d, and then dialyzed against pure water for 1 d, then freeze-dried to obtain photosensitive polyglutamic acid derivative Compound A-35 (0.85 g). According to its nuclear magnetic resonance spectrum, the grafting degree of Compound 4 can be calculated to be about 18.6%.

Example 36: Synthesis of Component A-36

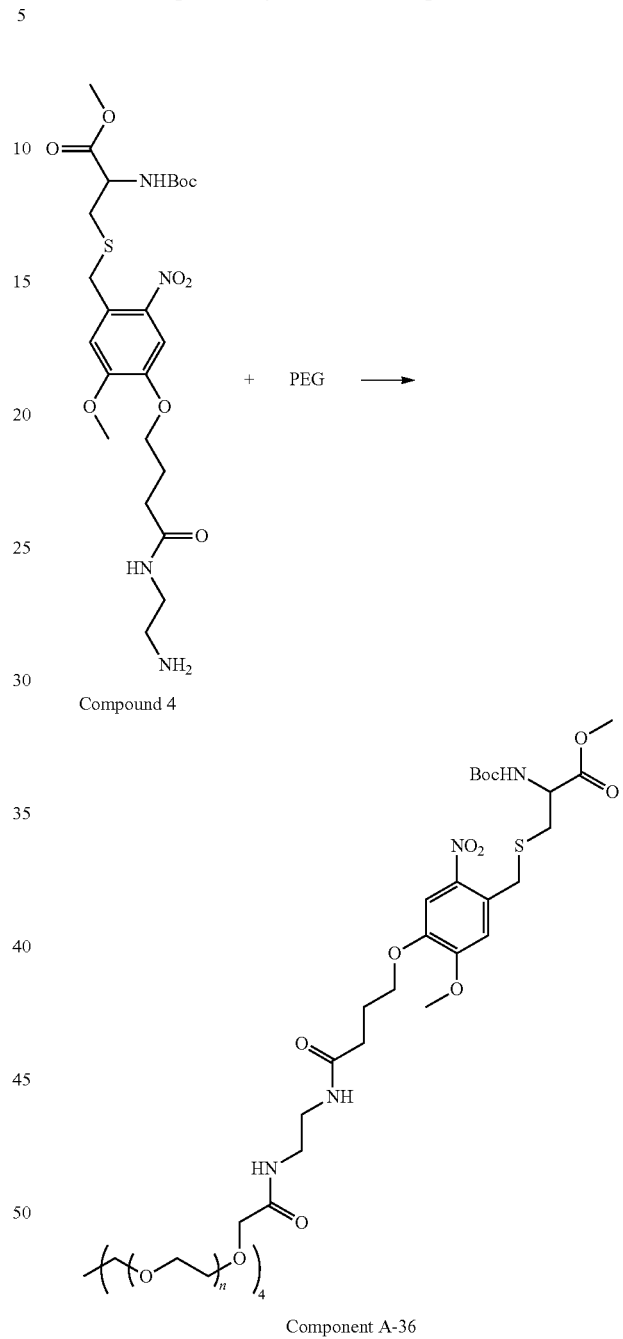

Compound 4

Component A-36

Synthesis of Component A-36: To a solution of four-arm polyglycol carboxylic acid derivative 4-PEG-COOH (0.5 g, 10 kDa) dissolved in 20 mL dry dimethyl sulfoxide (DMSO) was added Compound 4 (218 mg, 0.4 mmol) dissolved in 5 mL dimethyl sulfoxide (DMSO). And, 0.2 ml triethylamine TEA and benzotriazol-1-yl-oxytripyrrolidinylphosphonium (PyBop, 210 mg, 0.4 mmol) were added into the above solution. The mixture was reacted at room temperature for 24 h. Then, it was reprecipitated in diethyl ether, and the crude product was re-dissolved in water and poured into a dialysis bag (MWCO 3500) to dialyze against deionized water for 2-3 d. The photosensitive polyethylene glycol derivative Compound A-36 (0.45 g) was obtained by freeze-drying. According to the nuclear magnetic resonance spectrum, the grafting degree of Compound 4 can be calculated to be about 98%.

Example 37: Synthesis of Component A-37

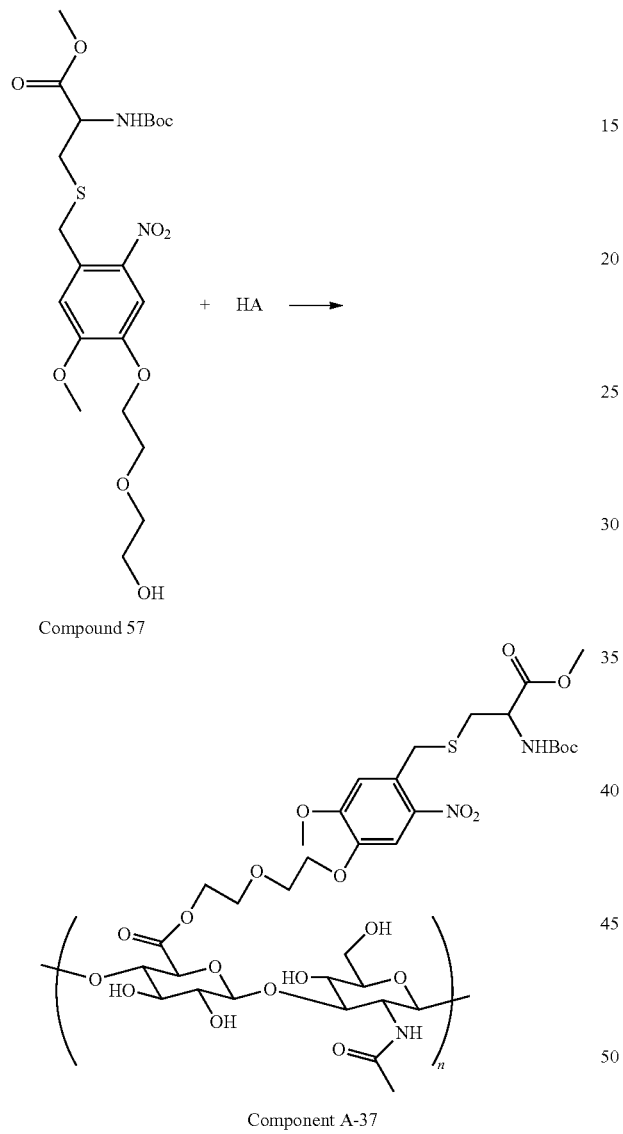

Compound 57

Component A-37

(1) Synthesis of Compound 57: Compound 57 was prepared in accordance with the method of Example 2 by conventional chemical means. $^1$H NMR (400 MHz, CDCl$_3$): δ=7.71 (s, 1H), 7.22 (s, 1H), 4.76 (s, 2H), 4.42 (m, 1H), 4.13 (t, J=6.1 Hz, 2H), 3.99 (s, 3H), 3.95 (s, 3H), 3.79 (t, J=6.1 Hz, 2H), 3.70 (t, J=7.2 Hz, 2H), 3.56 (t, J=7.2 Hz, 2H), 3.43 (d, J=5.6 2H), 1.42 (s, 9H). MS (ESI): [M+H] 505.1842.

(2) Synthesis of Component A-37: Dissolving hyaluronic acid (1 g, 340 KDa) in 50 mL distilled water completely to obtain a solution; to the solution was added hydroxybenzotriazole (HOBt, 0.3 g, 2.3 mmol), followed by adding Compound 57 (0.5 g, 1.0 mmol) in methy alcohol and 1-ethyl-(3-dimethyl amine propyl) carbodiimine hydrochloride (EDC-HCl, 0.5 g, 2.6 mmol) to obtain a mixture; the mixture was stirred for reaction at room temperature for 48 h to obtain a reaction solution; the reaction solution was added to a dialysis bag and dialyzed against a dilute hydrochloric acid solution containing sodium chloride (pH=3.5) for 1 d and then distilled water for 1 d, and then freeze-dried to obtain the photosensitive hyaluronic acid deriviate Component A-37 (0.84 g). According to the nuclear magnetic resonance spectrum, the grafting degree of Compound 57 can be calculated to be about 11.2%.

Example 38: Synthesis of Component A-38

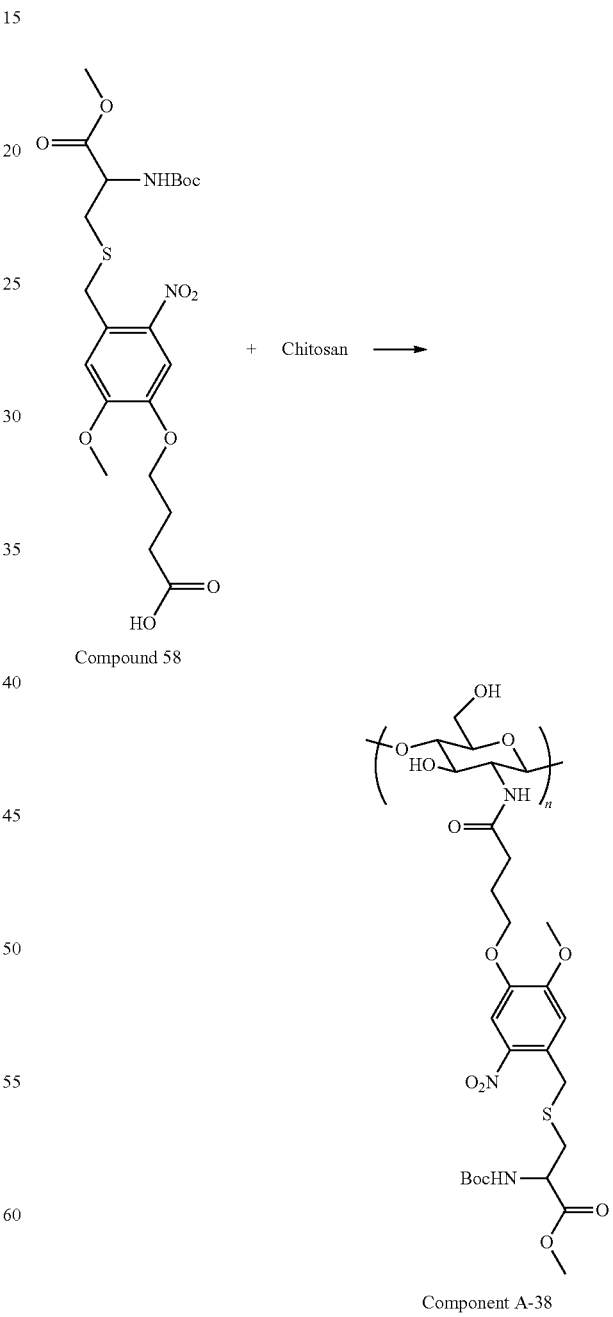

Compound 58

Component A-38

(1) Synthesis of Compound 58: Compound 58 was prepared in accordance with the method of Example 2 by conventional chemical means. $^1$H NMR (400 MHz, CDCl$_3$): δ=7.71 (s, 1H), 7.22 (s, 1H), 4.76 (s, 2H), 4.42 (m, 1H), 4.13 (t, J=6.1 Hz, 2H), 3.99 (s, 3H), 3.95 (s, 3H), 3.43 (d, J=5.6, 2H), 2.44 (t, J=7.2 Hz, 2H), 2.26-2.17 (m, 2H), 1.42 (s, 9H). MS (ESI): [M+H] 503.1732.

(2) Synthesis of Component A-38: dissolving chitosan (1 g) in 75 mL isopropanol to obtain a suspension solution; the suspension solution was sequentially added Compound 58 (0.2 g, 0.40 mmol), EDC-HCl (0.76 g, 3.96 mmol), and NHS (0.46 g, 4.0 mmol), and then stirring for reaction at room temperature for 48 h; after completion of the reaction, the reaction solution was added to a dialysis bag and dialyzed against dilute a hydrochloric acid solution containing sodium chloride (pH=3.5) for 1 d, and dialyzed against distilled water for 1 d, then freeze-dried to obtain the photosensitive chitosan deriviate Component A-38 (0.89 g). According to the nuclear magnetic resonance spectrum, the grafting degree of the Compound 58 can be calculated to be about 12.5%.

Example 39: Synthesis of Component A-39

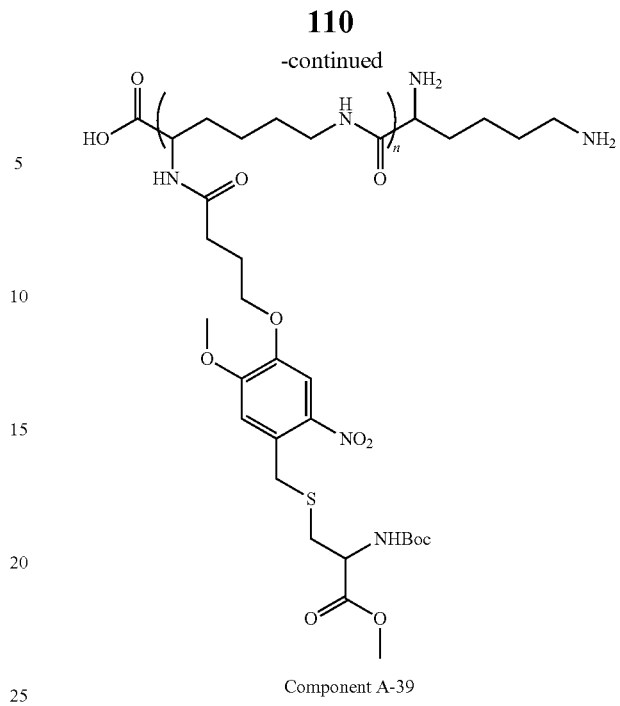

Component A-39

Synthesis of Component A-39: dissolving polylysine (PLL, 1 g) in 50 mL water to obtain a solution; the solution was sequentially added Compound 58 (0.2 g, 0.40 mmol), EDC-HCl (0.76 g, 3.96 mmol), and NHS (0.46 g, 4.0 mmol), and stirring for reaction at room temperature for 48 h; after completion of the reaction, the reaction solution was added to a dialysis bag and dialyzed against dilute hydrochloric acid solution containing sodium chloride (pH=3.5) for 1 d, and dialyzed against distilled water for 1 d, then freeze-dried to obtain photosensitive polylysine deriviate Component A-39 (0.82 g). According to the nuclear magnetic resonance spectrum, the grafting degree of the Compound 58 can be calculated to be about 12.6%.

Example 40: Synthesis of Component A-40

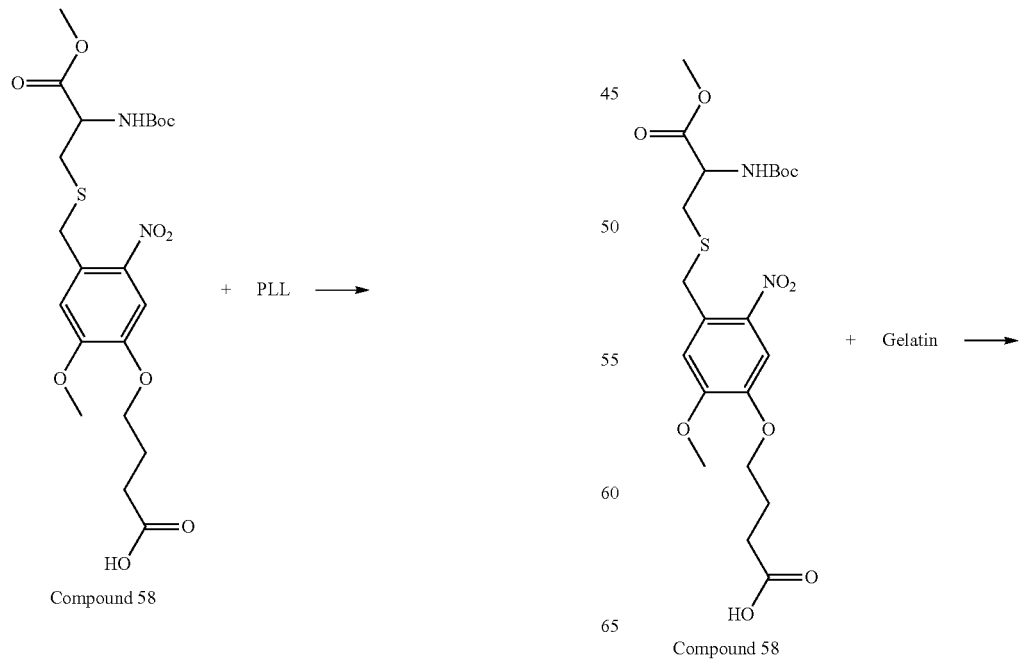

Compound 58

-continued

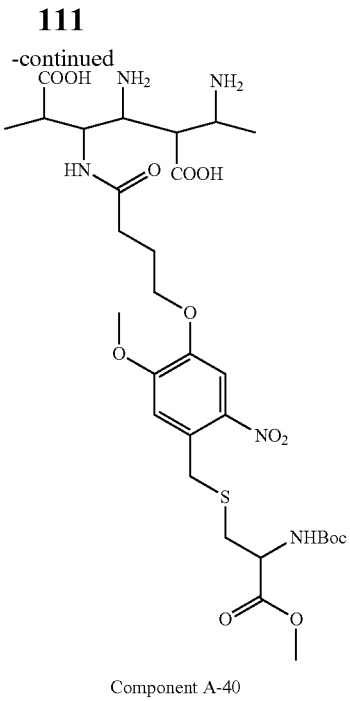

Component A-40

Synthesis of Component A-40: completely dissolving gelatin (1 g) in distilled water (50 ml) to obtain a solution; the solution was added Compound 58 (0.2 g, 0.40 mmol), EDC-HCl (0.76 g, 3.96 mmol) and NHS (0.46 g, 4.0 mmol) to obtain a mixture; stirring the mixture for reaction for 48 h at room temperature; after completion of the reaction, the reaction solution was added to a dialysis bag and dialyzed against a dilute hydrochloric acid solution containing sodium chloride (pH=3.5) for 1 d, and dialyzed against distilled water for 1 d, then freeze-dried to obtain the photosensitive gelatin deriviate Component A-40 (0.87 g). According to the nuclear magnetic resonance spectrum, the grafting degree of the Compound 58 can be calculated to be about 16.3%.

Example 41: Synthesis of Component A-41

-continued

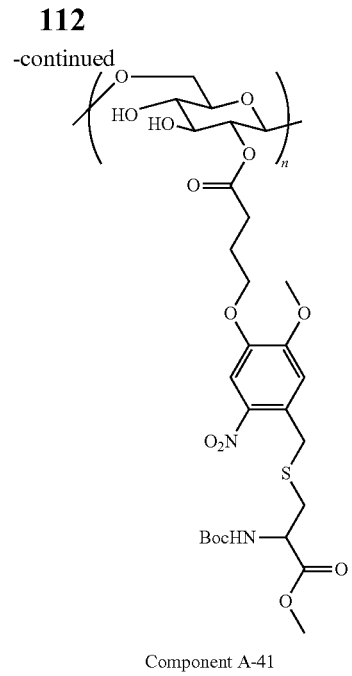

Component A-41

Synthesis of Component A-41: completely dissolving dextran (1 g) in 50 mL of water to obtain a solution; the solution of was sequentially added Compound 58 (0.23 g, 0.40 mmol), EDC-HCl (0.76 g, 3.96 mmol), and DPTS (0.12 g, 0.48 mmol), and stirring for reaction at room temperature for 48 h; After completion of the reaction, the reaction solution was added to a dialysis bag and dialyzed against a dilute hydrochloric acid solution containing sodium chloride (pH=3.5) for 1 d, and then dialyzed against distilled water for 1 d, then freeze-dried to obtain the photosensitive dextran deriviate Component A-41 (0.89 g). According to the nuclear magnetic resonance spectrum, the grafting degree of the Compound 58 can be calculated to be about 18.4%.

Example 42: Synthesis of Component A-42

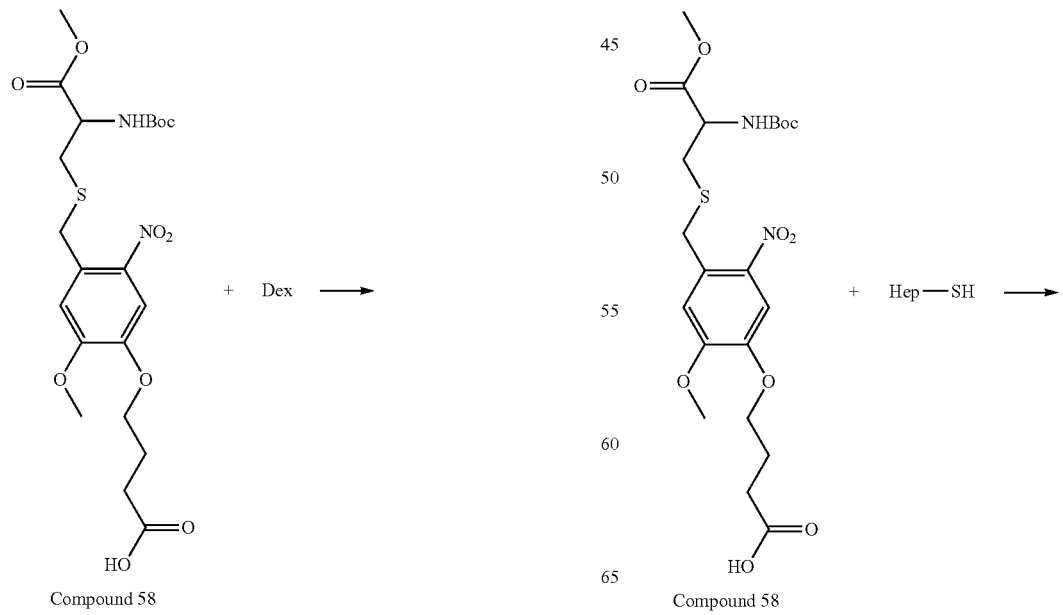

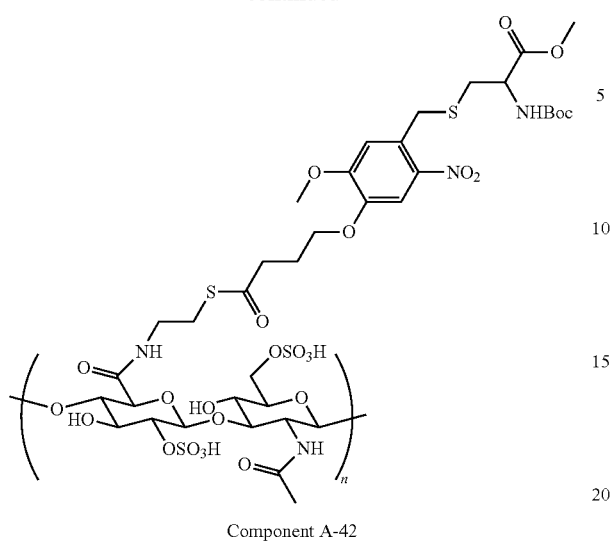

Component A-42

Synthesis of Component A-42: completely dissolving sulphydryl-modified heparin Hep-SH (1 g) in 50 mL distilled water to obtain a solution; the solution of was added hydroxybenzotriazole (HOBt, 0.3 g, 2.3 mmol), followed by adding Compound 58 (0.5 g, 1.0 mmol) and 1-ethyl-(3-dimethyl amino propyl) carbodiimine hydrochloride (EDC-HCl, 0.5 g, 2.6 mmol) dissolved in methanol to react at room temperature for 48 h to obtain a reaction solution; the reaction solution was firstly dialyzed with a dilute hydrochloric acid solution containing sodium chloride (pH=3.5) for 1 d, and then dialyzed against pure water for 1 d, then freeze-dried to obtain the photosensitive heparin derivative Compound A-42 (0.81 g). According to its nuclear magnetic resonance spectrum, the grafting degree of Compound 58 can be calculated to be about 12.5%.

Example 43: Synthesis of Component A-43

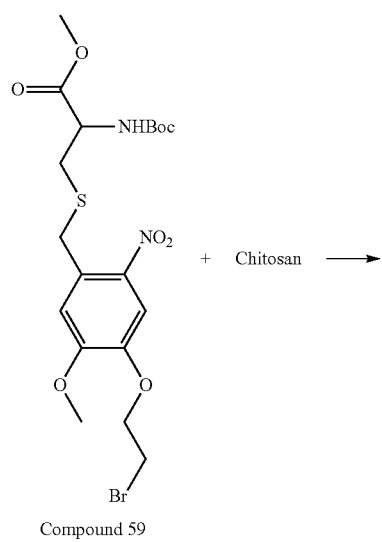

Compound 59

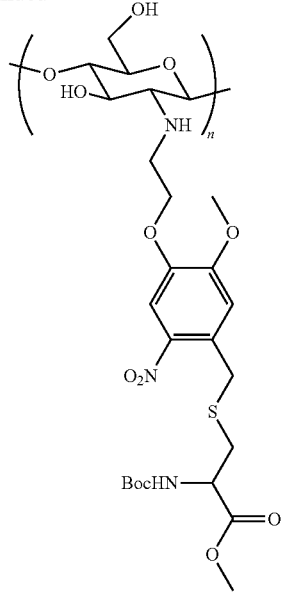

Component A-43

(1) Synthesis of Compound 59: Compound 59 was prepared in accordance with the method of Example 2 by conventional chemical means. $^1$H NMR (400 MHz, CDCl$_3$): δ=7.71 (s, 1H), 7.22 (s, 1H), 4.76 (s, 2H), 4.42 (m, 1H), 4.13 (t, J=6.1 Hz, 2H), 3.99 (s, 3H), 3.95 (s, 3H), 3.43 (d, J=5.6, 2H), 3.04 (t, J=7.2 Hz, 2H), 1.42 (s, 9H). MS (ESI): [M+H] 523.0731.

(2) Synthesis of Component A-43: dissolving chitosan (1 g) in 75 mL isopropanol to obtain a suspension solution; the suspension solution was slowly added 25 mL of NaOH solution (10 mol/L) in five different stages, and continuing to stir for 0.5 h to obtain a mixture. Compound 59 (2 g) was then added to the mixture and reacted at 60° C. for 3 h; After completion of the reaction, the reaction solution was filtered, and the filtrate was dialyzed three times with a methanol/water mixed solvent and twice with methanol, and then freeze-dried to obtain the photosensitive chitosan derivative Compound A-43 (0.9 g). According to its nuclear magnetic resonance spectrum, the grafting degree of the Compound 59 can be calculated to be about 14.5%.

Example 44: Synthesis of Component A-44

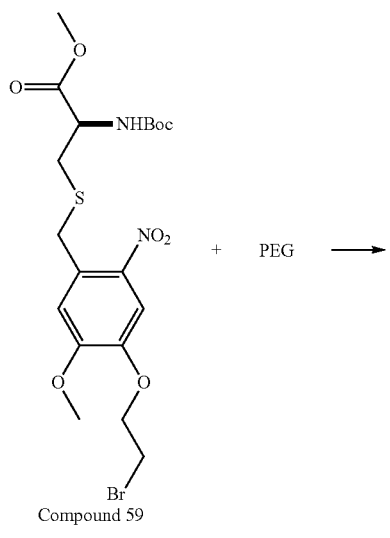
Compound 59

+ PEG →

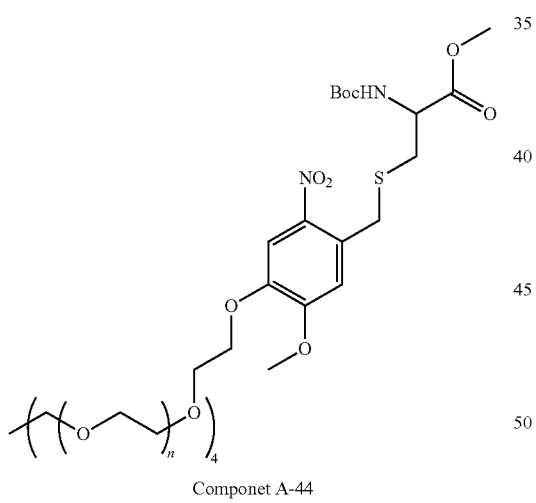
Componet A-44

Synthesis of Component A-44: dissolving PEG-40H (1 g, 0.05 mmol) in anhydrous acetonitrile to obtain a solution; the solution was added $K_2CO_3$ (55.3 mg, 0.4 mmol), stirred for 30 min, and then added Compound 59 (0.20 g, 0.4 mmol), and thereafter continued to react at room temperature for 24 h; after the reaction was completed, most of the solvent was removed, reprecipitated in diethyl ether, and washed several times, the crude was dried to obtain the photosensitive polyethelene glycol derivative Compound A-44 (0.85 g). According to its nuclear magnetic resonance spectrum, the grafting degree of the Compound 59 can be calculated to be about 95%.

Example 45: Synthesis of Component A-45

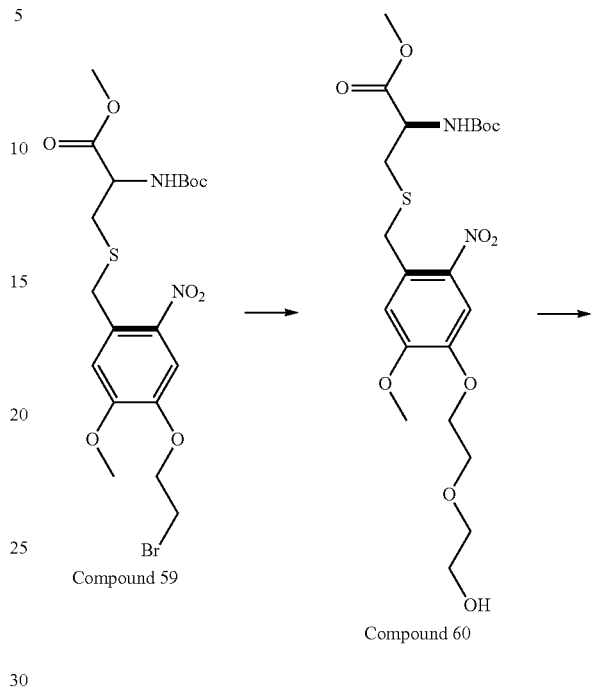
Compound 59        Compound 60

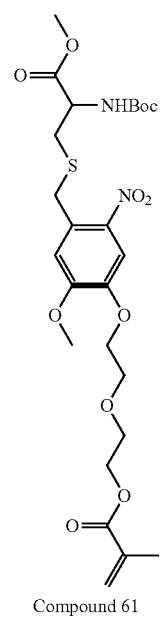
Compound 61

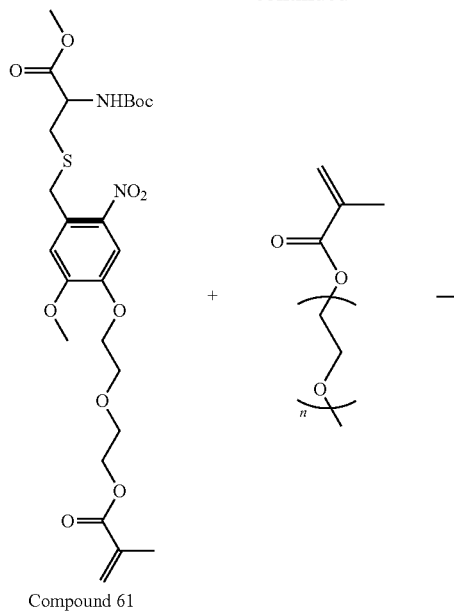

Compound 61

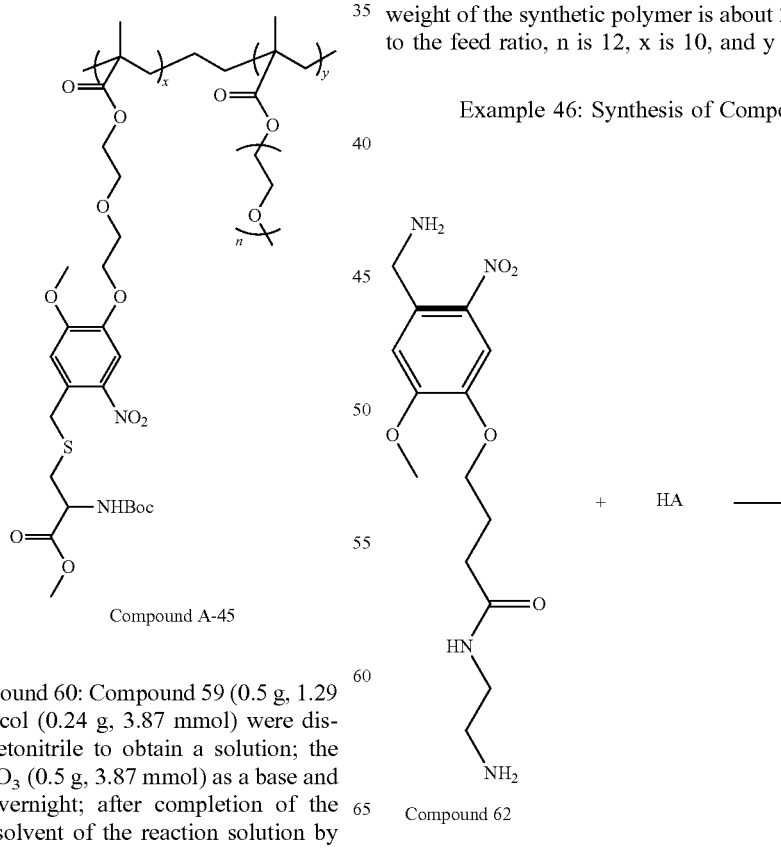

Compound A-45

(1) Synthesis of Compound 60: Compound 59 (0.5 g, 1.29 mmol) and ethylene glycol (0.24 g, 3.87 mmol) were dissolved in anhydrous acetonitrile to obtain a solution; the solution was added $K_2CO_3$ (0.5 g, 3.87 mmol) as a base and refluxed for reaction overnight; after completion of the reaction, removing the solvent of the reaction solution by rotary evaporation under reduced pressure to obtain a solute; purifying the solute by column chromatography to obtain the Compound 60 (0.34 g, 72%).

(2) Synthesis of Compound 61: Compound 60 (0.64 g, 1.72 mmol) and triethylamine (0.34 g, 3.44 mmol) were dissolved in dry dichloromethane to obtain a solution; the solution of was slowly added methacryloyl chloride (0.27 g, 2.58 mmol) under ice bath conditions in dropwise; the reaction was carried out overnight at room temperature after the dropwise addition. After completion of the reaction, the solvent was removed by rotary evaporation under reduced pressure and purified to afford Compound 61 (0.49 g, 65%). $^1$H NMR (400 MHz, $CDCl_3$): δ=7.71 (s, 1H), 7.22 (s, 1H), 6.25 (s, 1H), 5.68 (s, 1H), 4.76 (s, 2H), 4.42 (m, 1H), 4.13 (t, J=6.1 Hz, 2H), 3.99 (s, 3H), 3.95 (s, 3H), 3.79 (t, J=6.1 Hz, 2H), 3.70 (t, J=7.2 Hz, 2H), 3.56 (t, J=7.2 Hz, 2H), 3.43 (d, J=5.6, 2H), 1.87 (s, 3H), 1.42 (s, 9H). MS (ESI): [M+H] 573.2125.

(3) Synthesis of Component A-45: Compound 61 (0.28 g, 0.63 mmol), comonomer PEG-MA (0.882 g, 2.52 mmol) and the initiator azobisisobutyronitrile (11 mg) were added into the Shrek tube and dissolved by anhydrous THF. After repeated freeze-vacuum cycle operation, the reaction system was reacted at 75° C. for 24 h. After the reaction was completed, the reaction solution was poured into cold diethyl ether and reprecipitated several times. The collected precipitate was dried and dissolved in anhydrous DMSO, and the solution was added p-toluenesulfonic acid to remove dihydropyran protecting group to obtain the photosensitive polyethelene glycol derivative Compound A-45 (0.86 g). According to its nuclear magnetic resonance spectrum, it can be calculated that the content of the Compound 61 in the copolymer is about 15.3%. According to GPC, the molecular weight of the synthetic polymer is about 25 kDa. According to the feed ratio, n is 12, x is 10, and y is 40.

Example 46: Synthesis of Component A-46

Compound 62

-continued

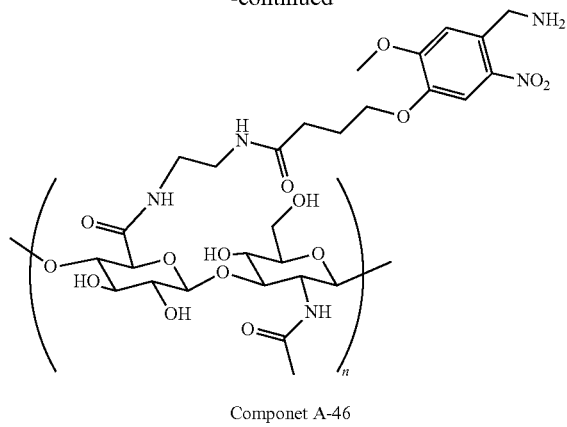

Componet A-46

(1) Synthesis of Compound 62: The synthesis was carried out in accordance with the method disclosed in the reference (Takahiro Muraoka.; Honggang Cui.; Samuel I. Stupp. J. Am. Chem. Soc. 2008, 130, 2946). $^1$H NMR (400 MHz, CDCl$_3$): δ=7.71 (s, 1H), 7.22 (s, 1H), 4.35 (s, 2H), 4.13 (t, J=6.1 Hz, 2H), 3.99 (s, 3H), 3.32 (dd, J=11.6, 5.7 Hz, 2H), 2.82 (t, J=5.9 Hz, 2H), 2.44 (t, J=7.2 Hz, 2H), 2.26-2.17 (m, 2H). MS (ESI): [M+H] 327.1617.

(2) Synthesis of Component A-46: To a solution of hyaluronic acid sodium (2 g, 340 kDa) in 100 mL 0.01M 2-(N-morpholine) mesylate (MES) buffer solution (pH=5.2) was added Compound 62 (65 mg, 0.2 mmol) dissolved in 10 mL dimethyl sulfoxide (DMSO). Then, DMTMM (0.4 g, 1.5 mmol) dissolved in 3 mL water was added into the above solution three times with an interval of 1 h, and the mixture was stirred for 24 hours in the dark 35° C. Then, the reaction solution was poured into a dialysis bag (MWCO 7000), dialyzed against deionized water for 2-3 d, and lyophilized to obtain a photosensitive hyaluronic acid derivative Compound A-46 (1.80 g). According to the nuclear magnetic resonance spectrum, the grafting degree of Compound 62 can be calculated to be about 3.26%.

Example 47: Synthesis of Component A-47

(1) Synthesis of Compound 63: The synthesis was carried out in accordance with the method disclosed in the reference (Takahiro Muraoka.; Honggang Cui.; Samuel I. Stupp. J. Am. Chem. Soc. 2008, 130, 2946).

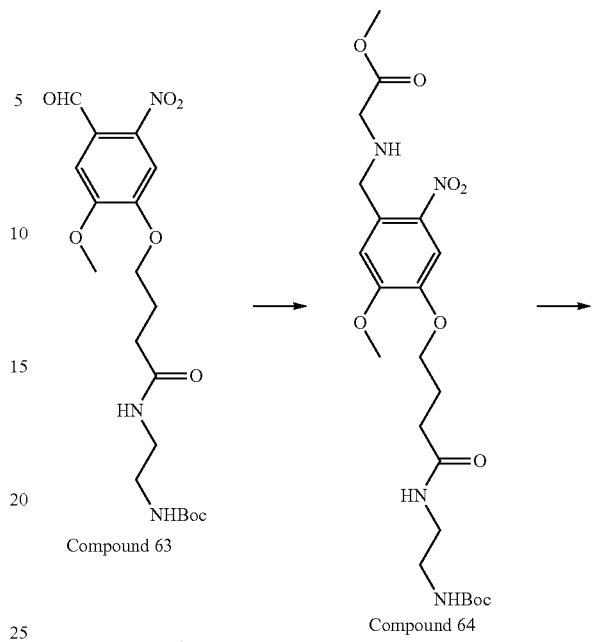

Compound 63

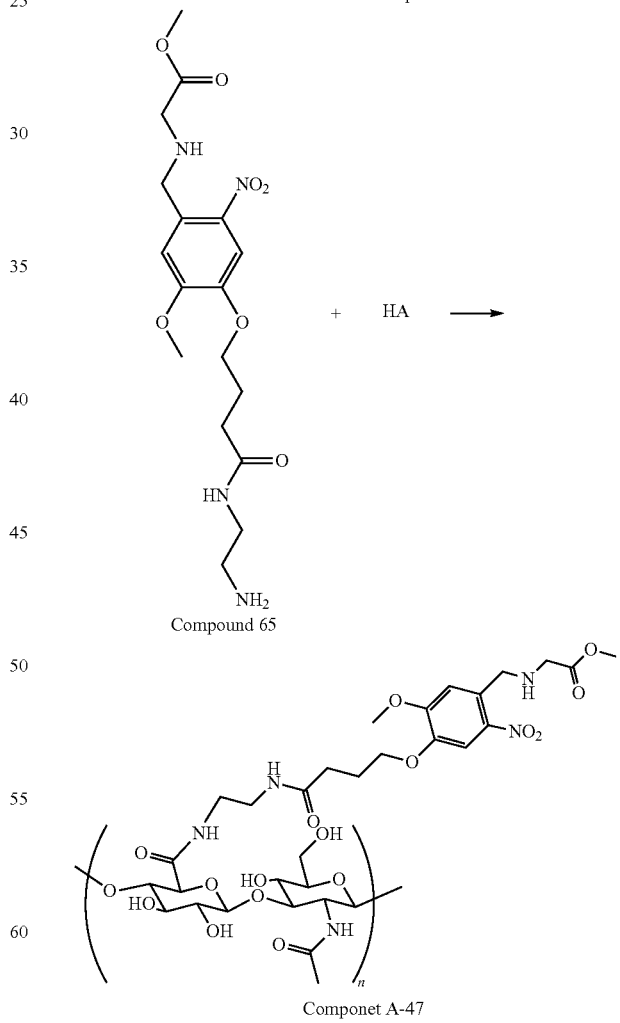

Compound 64

Compound 65

Componet A-47

(2) Synthesis of Compound 64: To a solution of Compound 63 (15.4 g, 36.24 mmol) in methanol (100 ml) was added dropwise methyl aminoacetate (7.0 g, 78.65 mmol) dissolved in methanol (70 ml) and NaOH (2 M, 50 ml). The reaction solution was stirred for 30 min at room temperature, and then NaBH$_4$ (12 g, 317.2 mmol) was slowly added to the above solution at 0° C. After 2 h, the solvent was removed by rotary evaporation under reduced pressure, and then the pH was adjusted to 5 by using 2 M HCl to obtain white solid. The crude product was washed with ether for several times and precipitated by ether to obtain Compound 64 (17.5 g, 97%). $^1$H NMR (400 MHz, CDCl$_3$): δ=7.71 (s, 1H), 7.22 (s, 1H), 4.55 (s, 2H), 4.13 (t, J=6.1 Hz, 2H), 3.99 (s, 3H), 3.95 (s, 3H), 3.74 (s, 2H), 3.32 (dd, J=11.6, 5.7 Hz, 2H), 2.82 (t, J=5.9 Hz, 2H), 2.44 (t, J=7.2 Hz, 2H), 2.26-2.17 (m, 2H), 1.42 (s, 9H). MS (ESI): [M+H] 499.2442.

(3) Synthesis of Compound 65: Compound 64 (15 g, 30 mmol) was dissolved in a mixed solution of dichloromethane/trifluoroacetic acid (3:1), and the mixture was stirred for 30 min at room temperature. The solvent was removed by rotary evaporation under reduced pressure, the obtained crude product was precipitated by ether to obtain Compound 65 (11.4 g, 95%). $^1$H NMR (400 MHz, CDCl$_3$): δ=7.71 (s, 1H), 7.22 (s, 1H), 4.55 (s, 2H), 4.13 (t, J=6.1 Hz, 2H), 3.99 (s, 3H), 3.95 (s, 3H), 3.74 (s, 2H), 3.32 (dd, J=11.6, 5.7 Hz, 2H), 2.82 (t, J=5.9 Hz, 2H), 2.44 (t, J=7.2 Hz, 2H), 2.26-2.17 (m, 2H). MS (ESI): [M+H] 399.1823.

(4) Synthesis of Component A-47: To a solution of hyaluronic acid sodium (2 g, 340 kDa) in 100 mL 0.01M 2-(N-morpholine) mesylate (MES) buffer solution (pH=5.2) was added Compound 65 (80 mg, 0.2 mmol) dissolved in 10 mL dimethyl sulfoxide (DMSO). Then, DMTMM (0.4 g, 1.5 mmol) dissolved in 3 mL water was added into the above solution three times with an interval of 1 h, and the mixture was stirred for 24 hours in the dark 35° C. Then, the reaction solution was poured into a dialysis bag (MWCO 7000), dialyzed against deionized water for 2-3 d, and lyophilized to obtain a photosensitive hyaluronic acid derivative Compound A-47 (1.87 g). According to the nuclear magnetic resonance spectrum, the grafting degree of Compound 65 can be calculated to be about 3.42%.

Example 48: Synthesis of Component A-48

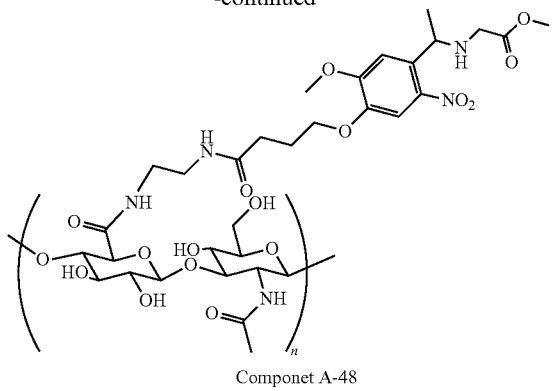

Componet A-48

(1) Synthesis of Compound 66: The synthesis was carried out in accordance with the method disclosed in the reference (James F. Cameron.; Jean M. J. Frechet. J. Am. Chem. Soc. 1991, 113, 4303). $^1$H NMR (400 MHz, CDCl$_3$): δ=7.71 (s, 1H), 7.22 (s, 1H), 4.75 (m, 1H), 4.13 (t, J=6.1 Hz, 2H), 3.99 (s, 3H), 3.95 (s, 3H), 3.74 (s, 2H), 3.32 (dd, J=11.6, 5.7 Hz, 2H), 2.82 (t, J=5.9 Hz, 2H), 2.44 (t, J=7.2 Hz, 2H), 2.26-2.17 (m, 2H), 1.33 (d, J=6.9 Hz, 3H). MS (ESI): [M+H] 413.2041.

(2) Synthesis of Component A-48: To a solution of hyaluronic acid sodium (2 g, 340 kDa) in 100 mL 0.01M 2-(N-morpholine) mesylate (MES) buffer solution (pH=5.2) was added Compound 66 (82 mg, 0.2 mmol) dissolved in 10 mL dimethyl sulfoxide (DMSO). Then, DMTMM (0.4 g, 1.5 mmol) dissolved in 3 mL water was added into the above solution three times with an interval of 1 h, and the mixture was stirred for 24 hours in the dark 35° C. Then, the reaction solution was poured into a dialysis bag (MWCO 7000), dialyzed against deionized water for 2-3 d, and lyophilized to obtain a photosensitive hyaluronic acid derivative Compound A-48 (1.84 g). According to the nuclear magnetic resonance spectrum, the grafting degree of Compound 66 can be calculated to be about 3.21%.

Example 49: Synthesis of Component A-49

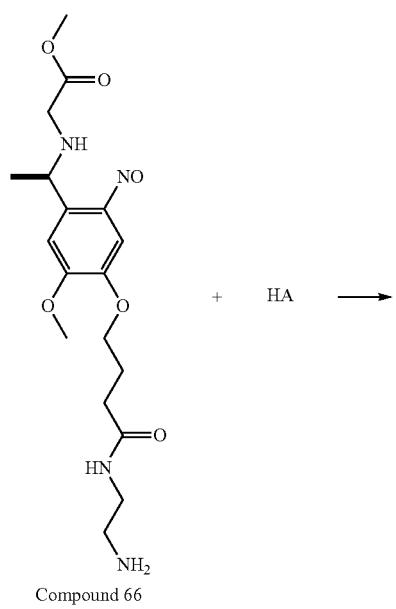

Compound 66

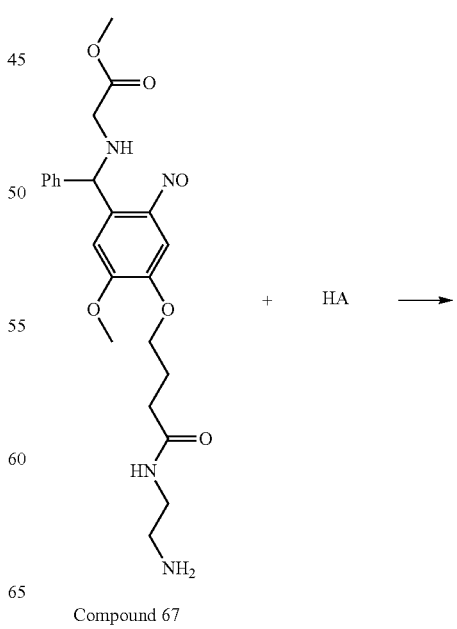

Compound 67

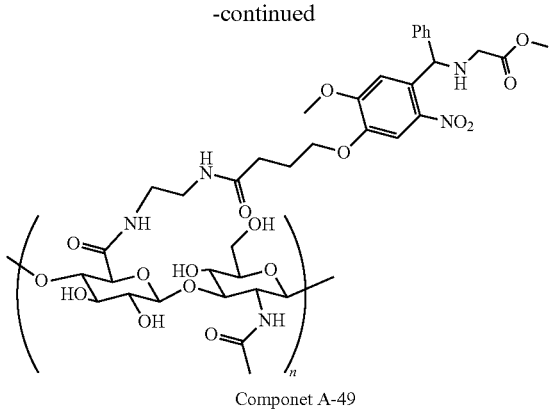

Componet A-49

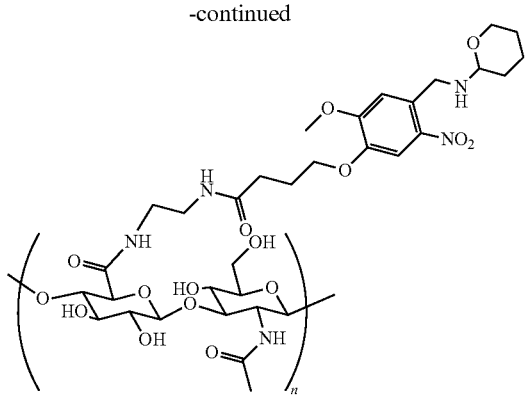

Componet A-50

(1) Synthesis of Compound 67: The synthesis was carried out in accordance with the method disclosed in the reference (Jack E. Baldwin.; Adrian W. McConnaughie.; Sung Bo Shin. Tetrahedron. 1990, 46, 6879). $^1$H NMR (400 MHz, CDCl$_3$): δ=8.02-7.23 (m, 5H), 7.71 (s, 1H), 7.22 (s, 1H), 4.75 (m, 1H), 4.13 (t, J=6.1 Hz, 2H), 3.99 (s, 3H), 3.95 (s, 3H), 3.74 (s, 2H), 3.32 (dd, J=11.6, 5.7 Hz, 2H), 2.82 (t, J=5.9 Hz, 2H), 2.44 (t, J=7.2 Hz, 2H), 2.26-2.17 (m, 2H). MS (ESI): [M+H] 475.2125.

(2) Synthesis of Component A-49: To a solution of hyaluronic acid sodium (2 g, 340 kDa) in 100 mL 0.01M 2-(N-morpholine) mesylate (MES) buffer solution (pH=5.2) was added Compound 67 (95 mg, 0.2 mmol) dissolved in 10 mL dimethyl sulfoxide (DMSO). Then, DMTMM (0.4 g, 1.5 mmol) dissolved in 3 mL water was added into the above solution three times with an interval of 1 h, and the mixture was stirred for 24 hours in the dark 35° C. Then, the reaction solution was poured into a dialysis bag (MWCO 7000), dialyzed against deionized water for 2-3 d, and lyophilized to obtain a photosensitive hyaluronic acid derivative Compound A-49 (1.92 g). According to the nuclear magnetic resonance spectrum, the grafting degree of Compound 67 can be calculated to be about 3.14%.

Example 50: Synthesis of Component A-50

(1) Synthesis of Compound 68: The synthesis was carried out in accordance with the method disclosed in the reference (Pauloehrl, T.; Delaittre, G.; Bruns, M.; Meißler, M.; Börner, H. G.; Bastmeyer, M.; Barner-Kowollik, C. Angew. Chem. Int. Ed. 2012, 51, 9181). $^1$H NMR (400 MHz, CDCl$_3$): δ=7.71 (s, 1H), 7.22 (s, 1H), 4.55 (s, 2H), 4.13 (t, J=6.1 Hz, 2H), 3.99 (s, 3H), 3.90-3.80 (m, 1H), 3.63-3.52 (m, 1H), 3.32 (dd, J=11.6, 5.7 Hz, 2H), 2.82 (t, J=5.9 Hz, 2H), 2.44 (t, J=7.2 Hz, 2H), 2.26-2.17 (m, 2H), 2.00-1.34 (m, 6H). MS (ESI): [M+H] 411.2231.

(2) Synthesis of Component A-50: To a solution of hyaluronic acid sodium (2 g, 340 kDa) in 100 mL 0.01M 2-(N-morpholine) mesylate (MES) buffer solution (pH=5.2) was added Compound 68 (82 mg, 0.2 mmol) dissolved in 10 mL dimethyl sulfoxide (DMSO). Then, DMTMM (0.4 g, 1.5 mmol) dissolved in 3 mL water was added into the above solution three times with an interval of 1 h, and the mixture was stirred for 24 hours in the dark 35° C. Then, the reaction solution was poured into a dialysis bag (MWCO 7000), dialyzed against deionized water for 2-3 d, and lyophilized to obtain a photosensitive hyaluronic acid derivative Compound A-50 (1.88 g). According to the nuclear magnetic resonance spectrum, the grafting degree of Compound 68 can be calculated to be about 3.38%.

Example 51: Synthesis of Component A-51

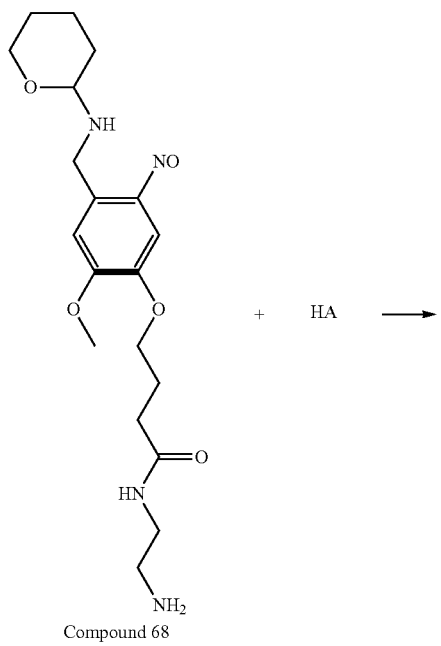

Compound 68

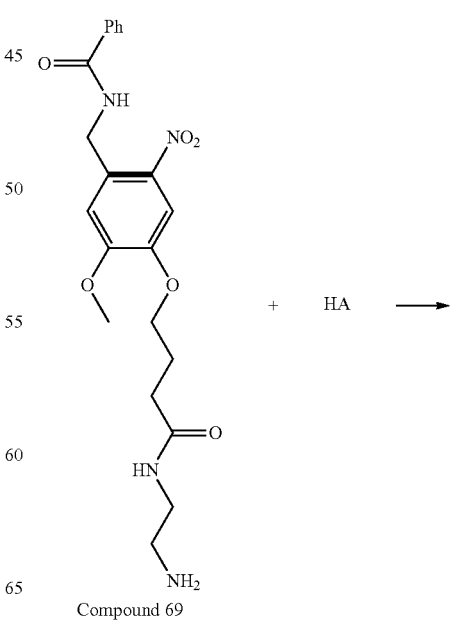

Compound 69

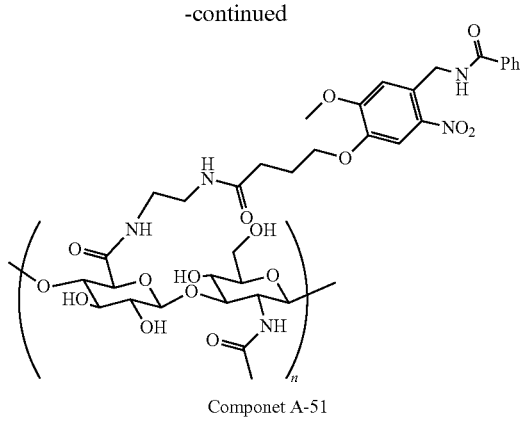

Componet A-51

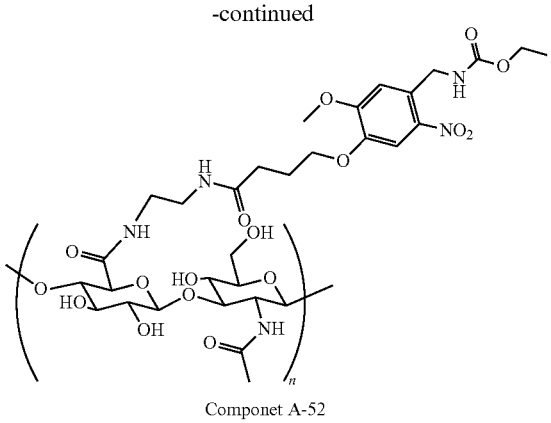

Componet A-52

(1) Synthesis of Compound 69: The synthesis was carried out in accordance with the method disclosed in the reference (Patchornik Abraham.; Amit B.; Woodward R. B. J. Am. Chem. Soc. 1970, 92, 6333). $^1$H NMR (400 MHz, CDCl$_3$): δ=8.02-7.23 (m, 5H), 7.71 (s, 1H), 7.22 (s, 1H), 4.55 (m, 1H), 4.13 (t, J=6.1 Hz, 2H), 3.99 (s, 3H), 3.32 (dd, J=11.6, 5.7 Hz, 2H), 2.82 (t, J=5.9 Hz, 2H), 2.44 (t, J=7.2 Hz, 2H), 2.26-2.17 (m, 2H). MS (ESI): [M+H] 431.1926.

(2) Synthesis of Component A-51: To a solution of hyaluronic acid sodium (2 g, 340 kDa) in 100 mL 0.01M 2-(N-morpholine) mesylate (MES) buffer solution (pH=5.2) was added Compound 69 (86 mg, 0.2 mmol) dissolved in 10 mL dimethyl sulfoxide (DMSO). Then, DMTMM (0.4 g, 1.5 mmol) dissolved in 3 mL water was added into the above solution three times with an interval of 1 h, and the mixture was stirred for 24 hours in the dark 35° C. Then, the reaction solution was poured into a dialysis bag (MWCO 7000), dialyzed against deionized water for 2-3 d, and lyophilized to obtain a photosensitive hyaluronic acid derivative Compound A-51 (1.85 g). According to the nuclear magnetic resonance spectrum, the grafting degree of Compound 67 can be calculated to be about 3.21%.

Example 52: Synthesis of Component A-52

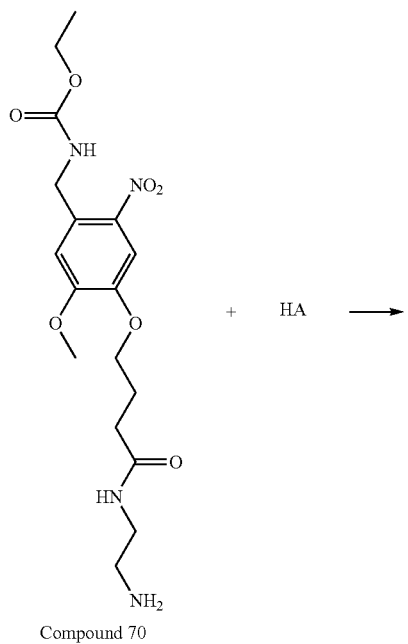

Compound 70

+ HA →

(1) Synthesis of Compound 70: The synthesis was carried out in accordance with the method disclosed in the reference (Patchornik Abraham.; Amit B.; Woodward R. B. J. Am. Chem. Soc. 1970, 92, 6333). $^1$H NMR (400 MHz, CDCl$_3$): δ=7.71 (s, 1H), 7.22 (s, 1H), 4.55 (s, 2H), 4.25 (q, J=6.5 Hz, 2H), 4.13 (t, J=6.1 Hz, 2H), 3.99 (s, 3H), 3.32 (dd, J=11.6, 5.7 Hz, 2H), 2.82 (t, J=5.9 Hz, 2H), 2.44 (t, J=7.2 Hz, 2H), 2.26-2.17 (m, 2H), 1.32 (t, J=6.5 Hz, 3H). MS (ESI): [M+H] 399.1818.

(2) Synthesis of Component A-52: To a solution of hyaluronic acid sodium (2 g, 340 kDa) in 100 mL 0.01M 2-(N-morpholine) mesylate (MES) buffer solution (pH=5.2) was added Compound 70 (80 mg, 0.2 mmol) dissolved in 10 mL dimethyl sulfoxide (DMSO). Then, DMTMM (0.4 g, 1.5 mmol) dissolved in 3 mL water was added into the above solution three times with an interval of 1 h, and the mixture was stirred for 24 hours in the dark 35° C. Then, the reaction solution was poured into a dialysis bag (MWCO 7000), dialyzed against deionized water for 2-3 d, and lyophilized to obtain a photosensitive hyaluronic acid derivative Compound A-52 (1.69 g). According to the nuclear magnetic resonance spectrum, the grafting degree of Compound 70 can be calculated to be about 2.31%.

Example 53: Synthesis of Component A-53

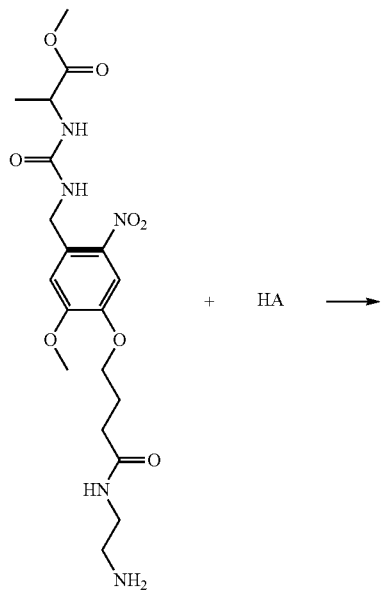

Compound 71

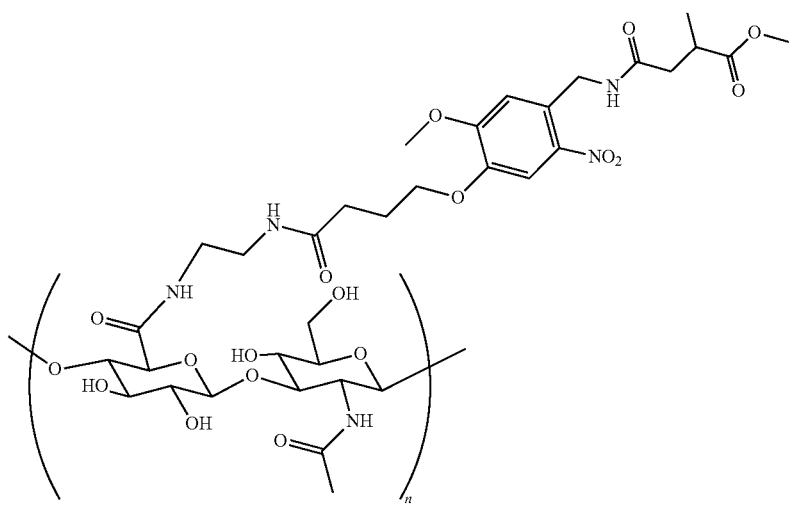

Compound A-53

(1) Synthesis of Compound 71: The synthesis was carried out in accordance with the method disclosed in the reference (Kalbag, S. M.; Roeske, R. W. J. Am. Chem. Soc. 1975, 97, 440). $^1$H NMR (400 MHz, CDCl$_3$): δ=7.71 (s, 1H), 7.22 (s, 1H), 4.55 (s, 2H), 4.63 (q, J=6.9 Hz, 1H), 4.13 (t, J=6.1 Hz, 2H), 3.99 (s, 3H), 3.67 (s, 3H), 3.32 (dd, J=11.6, 5.7 Hz, 2H), 2.82 (t, J=5.9 Hz, 2H), 2.44 (t, J=7.2 Hz, 2H), 2.26-2.17 (m, 2H), 1.48 (d, J=6.9 Hz, 3H). MS (ESI): [M+H] 456.2036.

(2) Synthesis of Component A-53: To a solution of hyaluronic acid sodium (2 g, 340 kDa) in 100 mL 0.01M 2-(N-morpholine) mesylate (MES) buffer solution (pH=5.2) was added Compound 71 (91 mg, 0.2 mmol) dissolved in 10 mL dimethyl sulfoxide (DMSO). Then, DMTMM (0.4 g, 1.5 mmol) dissolved in 3 mL water was added into the above solution three times with an interval of 1 h, and the mixture was stirred for 24 hours in the dark 35° C. Then, the reaction solution was poured into a dialysis bag (MWCO 7000), dialyzed against deionized water for 2-3 d, and lyophilized to obtain a photosensitive hyaluronic acid derivative Compound A-53 (1.82 g). According to the nuclear magnetic resonance spectrum, the grafting degree of Compound 71 can be calculated to be about 3.21%.

Example 56: Synthesis of Component A-56

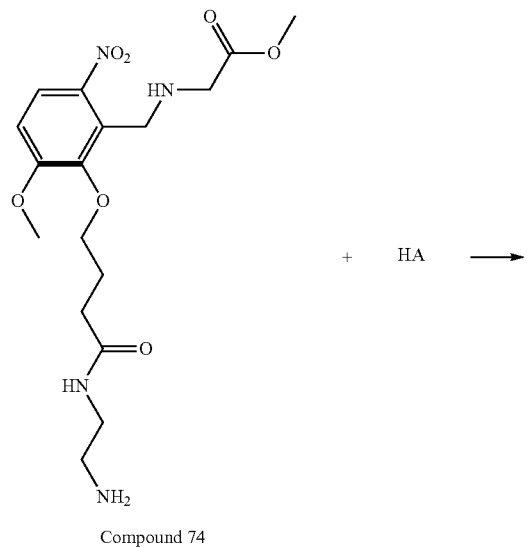

Compound 74

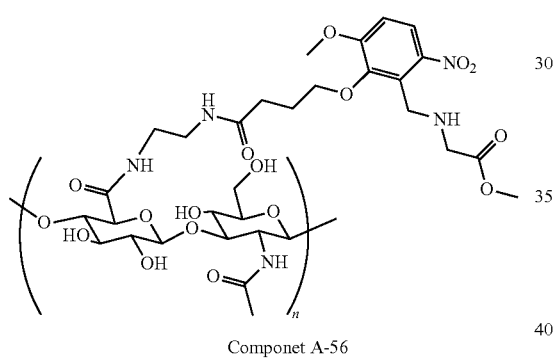

Componet A-56

(1) Synthesis of Compound 74: The synthesis was carried out in accordance with the method disclosed in the reference (Grazyna Groszek.; Agnieszka Nowak-Krol.; Barbara Filipek. Eur. J. Med. Chem. 2009, 44, 5103). $^1$H NMR (400 MHz, CDCl$_3$): δ=8.04 (s, 1H), 7.42 (s, 1H), 4.55 (s, 2H), 4.13 (t, J=6.1 Hz, 2H), 3.99 (s, 3H), 3.95 (s, 3H), 3.74 (s, 2H), 3.32 (dd, J=11.6, 5.7 Hz, 2H), 2.82 (t, J=5.9 Hz, 2H), 2.44 (t, J=7.2 Hz, 2H), 2.26-2.17 (m, 2H). MS (ESI): [M+H] 399.1832.

(2) Synthesis of Component A-56: To a solution of hyaluronic acid sodium (2 g, 340 kDa) in 100 mL 0.01M 2-(N-morpholine) mesylate (MES) buffer solution (pH=5.2) was added Compound 74 (80 mg, 0.2 mmol) dissolved in 10 mL dimethyl sulfoxide (DMSO). Then, DMTMM (0.4 g, 1.5 mmol) dissolved in 3 mL water was added into the above solution three times with an interval of 1 h, and the mixture was stirred for 24 hours in the dark 35° C. Then, the reaction solution was poured into a dialysis bag (MWCO 7000), dialyzed against deionized water for 2-3 d, and lyophilized to obtain a photosensitive hyaluronic acid derivative Compound A-56 (1.86 g). According to the nuclear magnetic resonance spectrum, the grafting degree of Compound 74 can be calculated to be about 3.32%.

Example 57: Synthesis of Component A-57

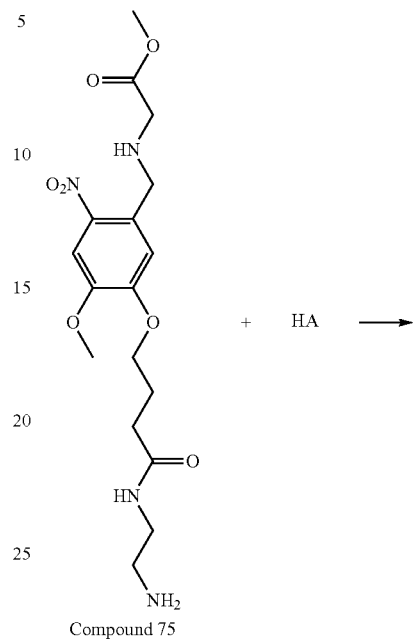

Compound 75

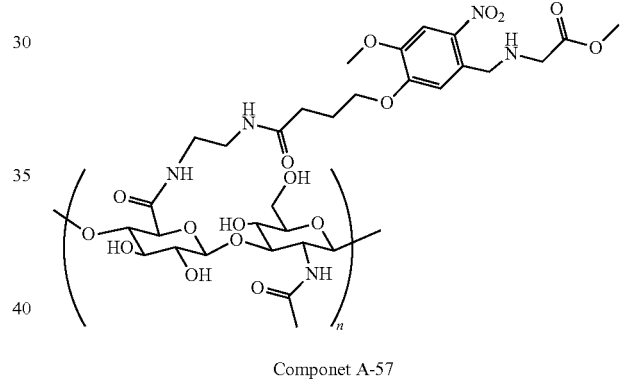

Componet A-57

(1) Synthesis of Compound 75: The synthesis was carried out in accordance with the method disclosed in the reference (Thomas F. Greene.; Shu Wang.; Mary J. Meegan. J. Med. Chem. 2016, 59, 90). $^1$H NMR (400 MHz, CDCl$_3$): δ=7.95 (s, 1H), 7.12 (s, 1H), 4.55 (s, 2H), 4.13 (t, J=6.1 Hz, 2H), 3.99 (s, 3H), 3.95 (s, 3H), 3.74 (s, 2H), 3.32 (dd, J=11.6, 5.7 Hz, 2H), 2.82 (t, J=5.9 Hz, 2H), 2.44 (t, J=7.2 Hz, 2H), 2.26-2.17 (m, 2H). MS (ESI): [M+H] 399.1832.

(2) Synthesis of Component A-57: To a solution of hyaluronic acid sodium (2 g, 340 kDa) in 100 mL 0.01M 2-(N-morpholine) mesylate (MES) buffer solution (pH=5.2) was added Compound 75 (80 mg, 0.2 mmol) dissolved in 10 mL dimethyl sulfoxide (DMSO). Then, DMTMM (0.4 g, 1.5 mmol) dissolved in 3 mL water was added into the above solution three times with an interval of 1 h, and the mixture was stirred for 24 hours in the dark 35° C. Then, the reaction solution was poured into a dialysis bag (MWCO 7000), dialyzed against deionized water for 2-3 d, and lyophilized to obtain a photosensitive hyaluronic acid derivative Compound A-57 (1.89 g). According to the nuclear magnetic resonance spectrum, the grafting degree of Compound 75 can be calculated to be about 3.28%.

Example 58: Synthesis of Component A-58

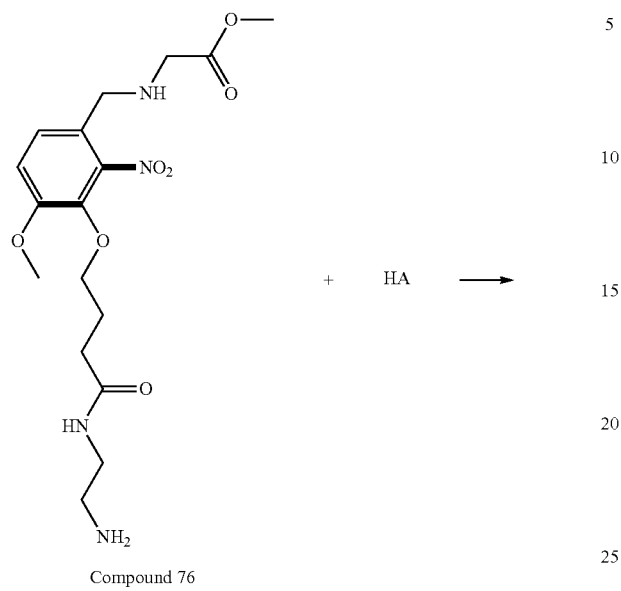

Compound 76

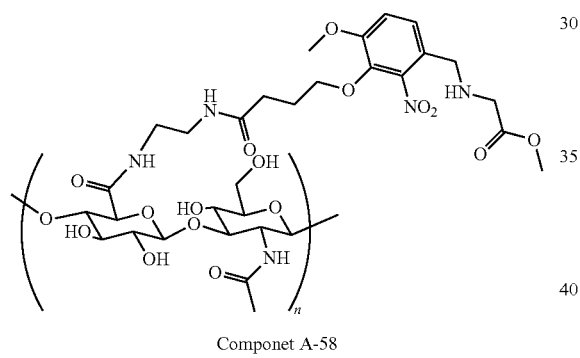

Componet A-58

(1) Synthesis of Compound 76: The synthesis was carried out in accordance with the method disclosed in the reference (Yu-Shan.; Mohane Selvaraj Coumar.; Hsing-Pang Hsieh. J. Med. Chem. 2009, 52, 4941). $^1$H NMR (400 MHz, CDCl$_3$): δ=7.64 (s, 1H), 7.02 (s, 1H), 4.55 (s, 2H), 4.13 (t, J=6.1 Hz, 2H), 3.99 (s, 3H), 3.95 (s, 3H), 3.74 (s, 2H), 3.32 (dd, J=11.6, 5.7 Hz, 2H), 2.82 (t, J=5.9 Hz, 2H), 2.44 (t, J=7.2 Hz, 2H), 2.26-2.17 (m, 2H). MS (ESI): [M+H] 399.1832.

(2) Synthesis of Component A-58: To a solution of hyaluronic acid sodium (2 g, 340 kDa) in 100 mL 0.01M 2-(N-morpholine) mesylate (MES) buffer solution (pH=5.2) was added Compound 76 (80 mg, 0.2 mmol) dissolved in 10 mL dimethyl sulfoxide (DMSO). Then, DMTMM (0.4 g, 1.5 mmol) dissolved in 3 mL water was added into the above solution three times with an interval of 1 h, and the mixture was stirred for 24 hours in the dark 35° C. Then, the reaction solution was poured into a dialysis bag (MWCO 7000), dialyzed against deionized water for 2-3 d, and lyophilized to obtain a photosensitive hyaluronic acid derivative Compound A-58 (1.91 g). According to the nuclear magnetic resonance spectrum, the grafting degree of Compound 76 can be calculated to be about 3.26%.

Example 59: Synthesis of Component A-59

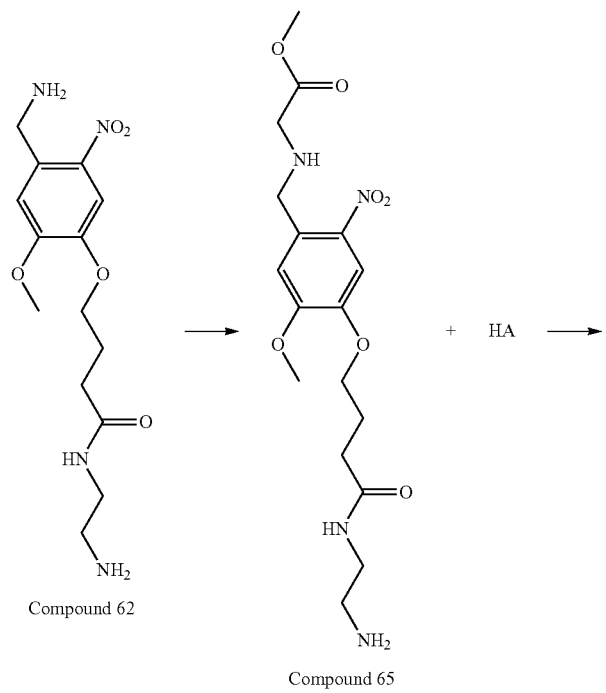

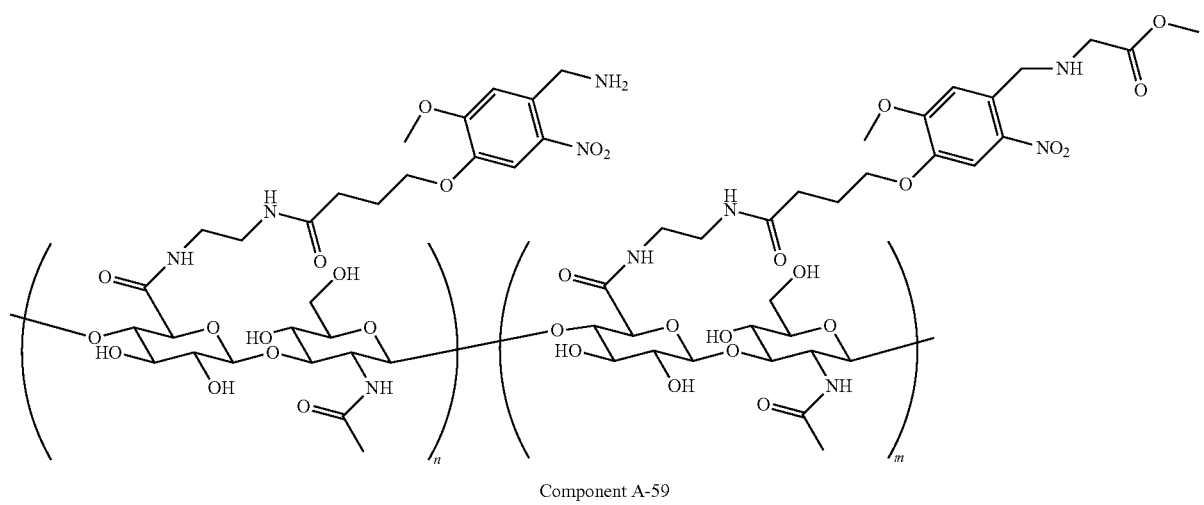

Synthesis of Component A-59: To a solution of hyaluronic acid sodium (2 g, 340 kDa) in 100 mL 0.01M 2-(N-morpholine) mesylate (MES) buffer solution (pH=5.2) was added nNB mixture (Compound 62/Compound 65, 60 mg, 1:1) dissolved in 10 mL dimethyl sulfoxide (DMSO). Then, DMTMM (0.4 g, 1.5 mmol) dissolved in 3 mL water was added into the above solution three times with an interval of 1 h, and the mixture was stirred for 24 hours in the dark 35° C. Then, the reaction solution was poured into a dialysis bag (MWCO 7000), dialyzed against deionized water for 2-3 d, and lyophilized to obtain a photosensitive hyaluronic acid derivative Compound A-59 (1.89 g). According to the nuclear magnetic resonance spectrum, the grafting degree of nNB mixture (Compound 62/Compound 65) can be calculated to be about 3.42%.

Example 60: Synthesis of Component A-60

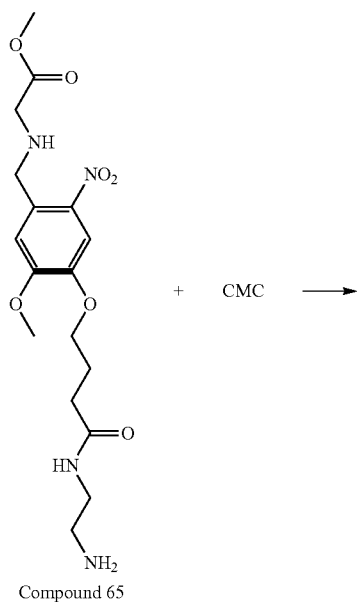

Compound 65

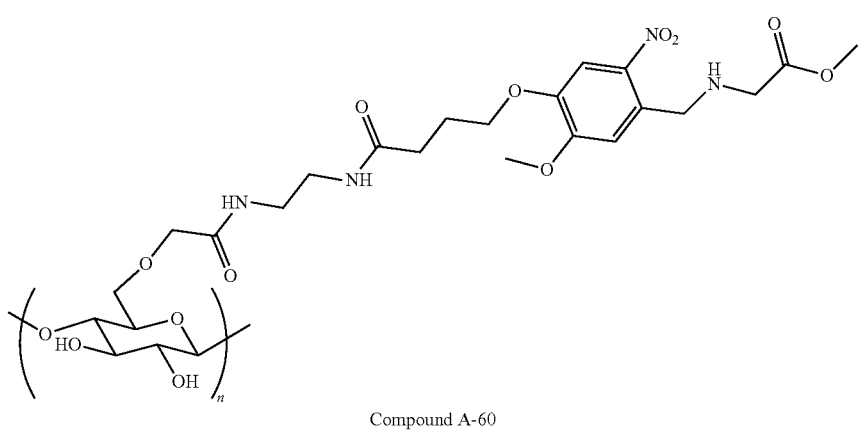

Compound A-60

Synthesis of Component A-60: To a solution of carboxymethyl cellulose (2 g, 340 kDa) in 100 mL 0.01M 2-(N-morpholine) mesylate (MES) buffer solution (pH=5.2) was added Compound 65 (80 mg, 0.2 mmol) dissolved in 10 mL dimethyl sulfoxide (DMSO). Then, DMTMM (0.4 g, 1.5 mmol) dissolved in 3 mL water was added into the above solution three times with an interval of 1 h, and the mixture was stirred for 24 hours in the dark 35° C. Then, the reaction solution was poured into a dialysis bag (MWCO 7000), dialyzed against deionized water for 2-3 d, and lyophilized to obtain a photosensitive hyaluronic acid derivative Compound A-60 (1.72 g). According to the nuclear magnetic resonance spectrum, the grafting degree of Compound 65 is calculated to be about 2.21%.

Example 61: Synthesis of Component A-61

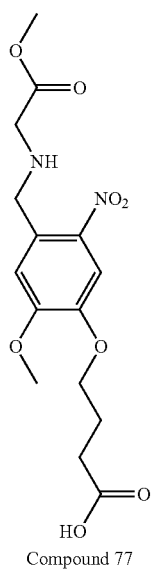

Compound 77

+ Chitosan ⟶

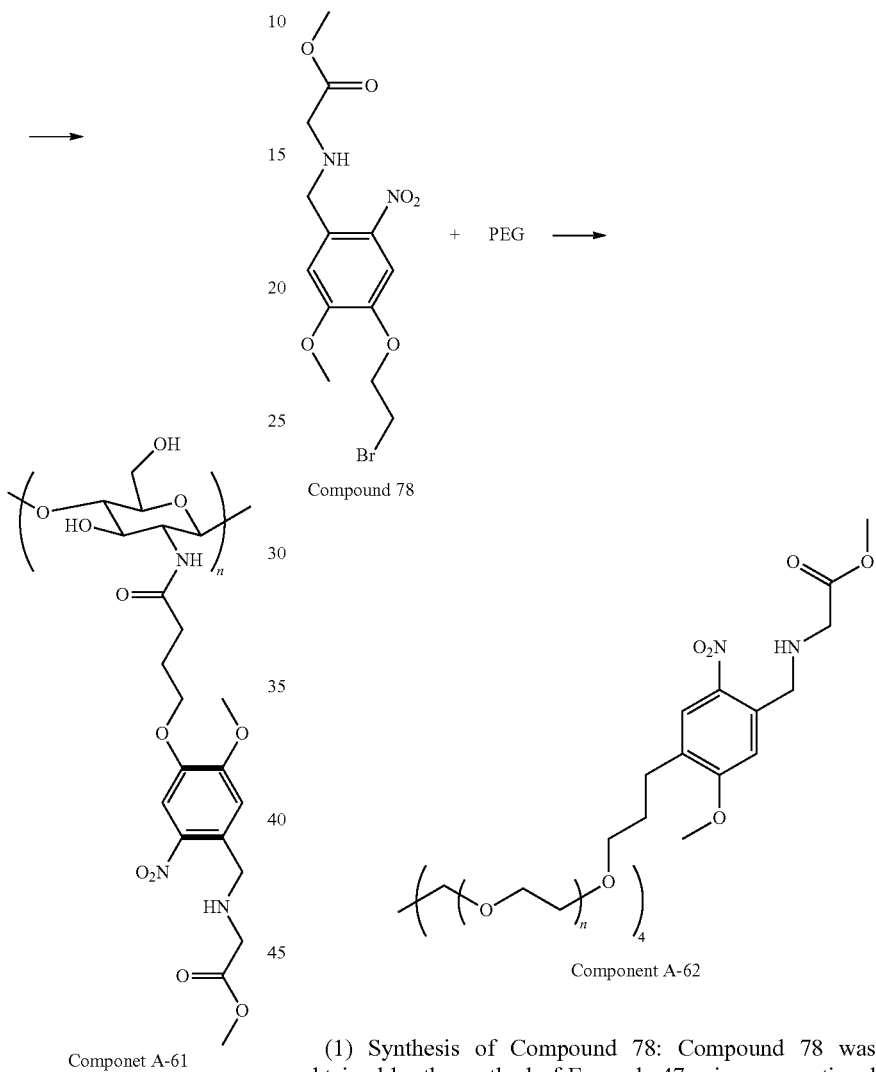

Componet A-61

(1) Synthesis of Compound 77: Compound 77 was obtained by the method of Example 47 using conventional chemical means. $^1$H NMR (400 MHz, CDCl$_3$): δ=7.71 (s, 1H), 7.22 (s, 1H), 4.55 (s, 2H), 4.13 (t, J=6.1 Hz, 2H), 3.99 (s, 3H), 3.95 (s, 3H), 3.74 (s, 2H), 2.44 (t, J=7.2 Hz, 2H), 2.26-2.17 (m, 2H). MS (ESI): [M+H] 357.1342.

(2) Synthesis of Component A-61: To a suspension liquid of chitosan (1 g) in 75 mL isopropanol was sequentially added Compound 77 (0.2 g, 0.54 mmol), EDC-HCl (0.76 g, 3.96 mmol) and NHS (0.46 g, 4.0 mmol), and the reaction was stirred at room temperature for 48 h. After completion of the reaction, the mixture solution was dialyzed with diluted hydrochloric acid solution for 1 d, dialyzed with distilled water for 1 d, and then freeze-dried to obtain photosensitive chitosan derivatives Compound A-61 (0.82 g). According to its nuclear magnetic resonance spectrum, the grafting degree of the Compound 77 can be calculated to be about 11.3%.

Example 62: Synthesis of Component A-62

(1) Synthesis of Compound 78: Compound 78 was obtained by the method of Example 47 using conventional chemical means. $^1$H NMR (400 MHz, CDCl$_3$): δ=7.71 (s, 1H), 7.22 (s, 1H), 4.55 (s, 2H), 4.13 (t, J=6.1 Hz, 2H), 3.99 (s, 3H), 3.95 (s, 3H), 3.74 (s, 2H), 3.04 (t, J=7.2 Hz, 2H). MS (ESI): [M+H] 377.0346.

(2) Synthesis of Component A-62: To a solution of PEG-40H (1 g, 0.05 mmol) in anhydrous acetonitrile was added K$_2$CO$_3$ (55.3 mg, 0.4 mmol) and stirred for 30 min. Then the solution was added Compound 78 (0.15 g, 0.4 mmol) and continued to react at room temperature for 24 h. After the reaction was completed, most of the solvent was removed, the residue was reprecipitated in diethyl ether and washed several times, then dried to obtain the photosensitive polyethelene glycol derivative Compound A-62 (0.93 g). According to its nuclear magnetic resonance spectrum, the grafting degree of the Compound 65 can be calculated to be about 95%.

Example 63: Synthesis of Component A-63

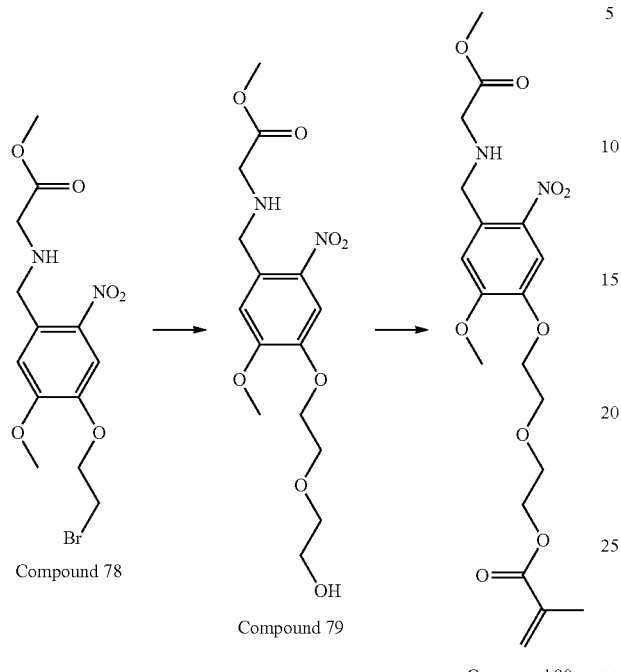

Compound 78

Compound 79

Compound 80

Compound 80

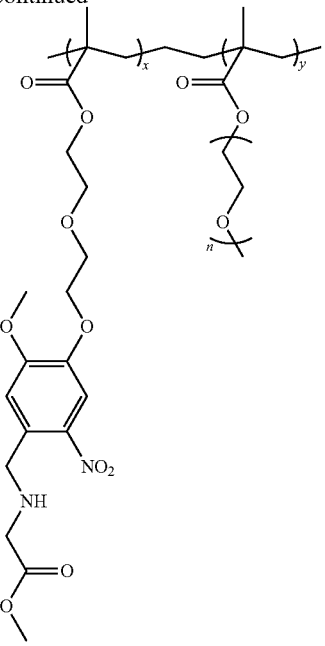

Component A-63

(1) Synthesis of Compound 79: To a solution of Compound 78 (0.5 g, 1.29 mmol) and ethylene glycol (0.24 g, 3.87 mmol) in anhydrous acetonitrile was added $K_2CO_3$ (0.5 g, 3.87 mmol) as a base and refluxed overnight. After completion of the reaction, the solvent was removed by rotary evaporation under reduced pressure and purified by column chromatography to afford Compound 79 (0.34 g, 72%). $^1$H NMR (400 MHz, $CDCl_3$): δ=7.71 (s, 1H), 7.22 (s, 1H), 4.55 (s, 2H), 4.13 (t, J=6.1 Hz, 2H), 3.99 (s, 3H), 3.95 (s, 3H), 3.79 (t, J=6.1 Hz, 2H), 3.74 (s, 2H), 3.70 (t, J=7.2 Hz, 2H), 3.56 (t, J=7.2 Hz, 2H). MS (ESI): [M+H] 359.1462.

(2) Synthesis of Compound 80: To a solution of Compound 79 (0.64 g, 1.72 mmol) and triethylamine (0.34 g, 3.44 mmol) dissolved in dry dichloromethane was slowly dropwise added methacryloyl chloride (0.27 g, 2.58 mmol) under ice bath conditions, and the reaction was carried out overnight at room temperature after the dropwise addition. After completion of the reaction, the solvent was removed by rotary evaporation under reduced pressure and purified to afford Compound 80 (0.49 g, 65%). $^1$H NMR (400 MHz, $CDCl_3$): δ=7.71 (s, 1H), 7.22 (s, 1H), 6.25 (s, 1H), 5.68 (s, 1H), 4.55 (s, 2H), 4.13 (t, J=6.1 Hz, 2H), 3.99 (s, 3H), 3.95 (s, 3H), 3.79 (t, J=6.1 Hz, 2H), 3.74 (s, 2H), 3.70 (t, J=7.2 Hz, 2H), 3.56 (t, J=7.2 Hz, 2H), 1.87 (s, 3H). MS (ESI): [M+H] 427.1725.

(3) Synthesis of Component A-63: Compound 80 (0.28 g, 0.63 mmol), comonomer PEG-MA (0.882 g, 2.52 mmol) and the initiator azobisisobutyronitrile (11 mg) were added into the Shrek tube and dissolved by anhydrous THF. After repeated freeze-vacuum cycle operation, the reaction system was reacted at 75° C. for 24 h. After the reaction was completed, the reaction solution was poured into cold diethyl ether and reprecipitated several times. The collected precipitate was dried and dissolved in anhydrous DMSO, and the solution was added p-toluenesulfonic acid to remove dihydropyran protecting group to obtain the photosensitive polyethelene glycol derivative Compound A-63 (0.85 g). According to its nuclear magnetic resonance spectrum, it can be calculated that the content of the Compound 80 in the copolymer is about 14.6%. According to GPC, the molecular weight of the synthetic polymer is about 25 kDa. According to the feed ratio, n is 12, x is 10, and y is 40.

Example 64: Synthesis of Component A-64
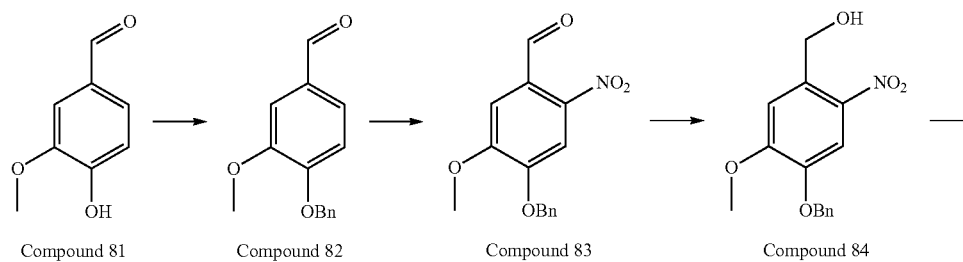
Compound 81, Compound 82, Compound 83, Compound 84
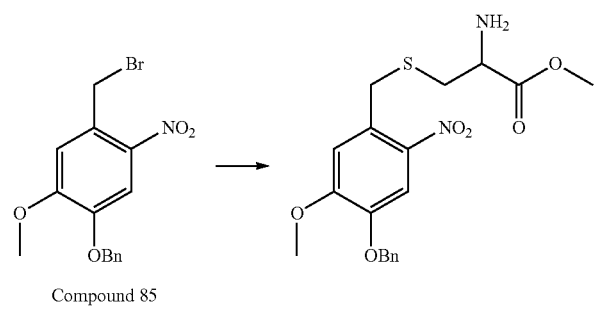
Compound 85
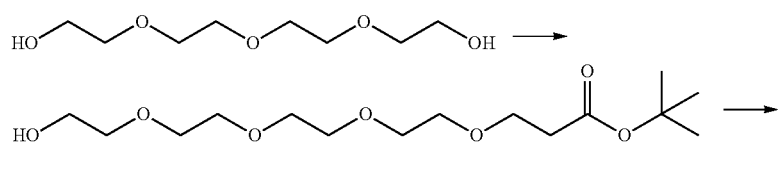
Compound 86
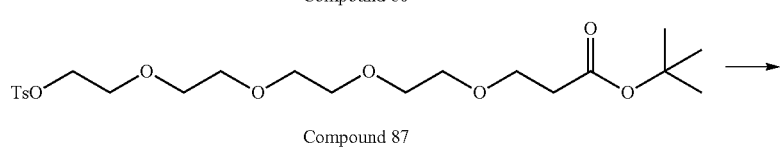
Compound 87
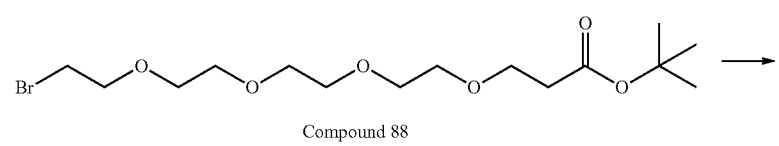
Compound 88
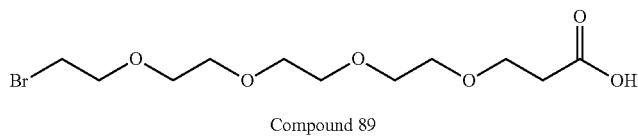
Compound 89
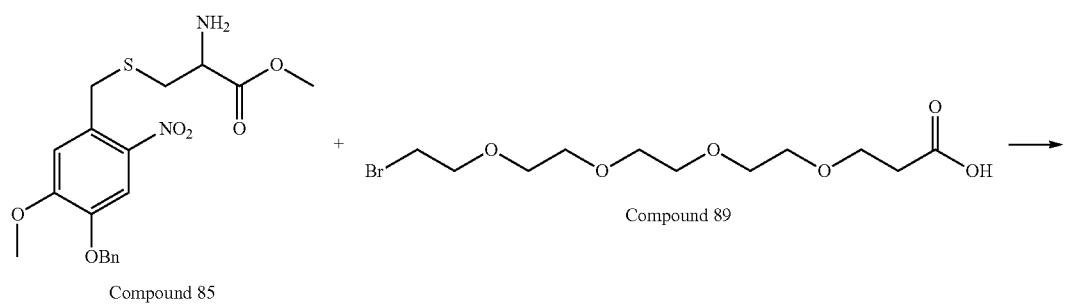
Compound 85 + Compound 89

-continued

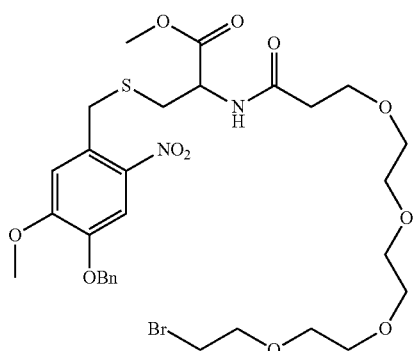

Compound 90

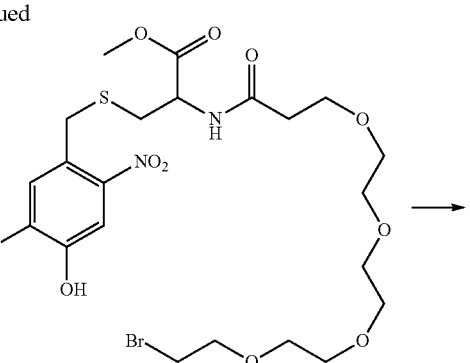

Compound 91

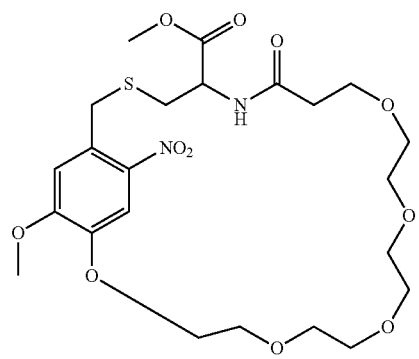

Compound 92

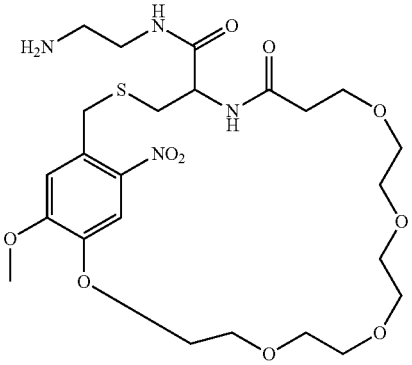

Compound 93

(1) Synthesis of Compound 81: To a solution of vanillin (25 g, 165 mmol) and potassium carbonate (11.4 g, 83 mmol) in 200 mL acetone was dropwise added benzyl bromide (21.2 g, 181 mmol), and the solution was refluxed at 90° C. for 8 h. Then the reaction was cooled to room temperature, the solvent was removed by rotary evaporation under reduced pressure. The crude was added 100 mL water and extracted three times with ethyl acetate. The combined organic layers were dried over $Na_2SO_4$, filtered and removed the solvent under reduced pressure to give the colorless liquid. It was then recrystallized from 100 mL ethanol to give Compound 81 as white powder (36.2 g, 91%). $^1$H NMR (400 MHz, $CDCl_3$): δ=9.83 (s, 1H), 7.39 (ddd, J=24.2, 20.7, 7.4 Hz, 7H), 6.98 (d, J=8.2 Hz, 1H), 5.24 (s, 2H), 3.94 (d, J=0.9 Hz, 3H). MS (ESI): [M+Na] 265.0824.

(2) Synthesis of Compound 82: To a solution of Compound 81 (10 g, 41.3 mmol) dissolved in 50 mL acetic anhydride was dropwise added 50 mL nitric acid (65%) under ice bath. The mixture was reacted at room temperature for 30 min. After completion of the reaction, the reaction system was slowly poured into 600 mL ice water to precipitate a yellow solid. The crude was crystallised from ethanol to obtain yellow needle-like product as Compound 82 (9.72 g, 82%). $^1$H NMR (400 MHz, $CDCl_3$): δ=10.42 (s, 1H), 7.67 (s, 1H), 7.43-7.39 (m, 3H), 7.37 (d, J=7.0 Hz, 1H), 5.26 (s, 2H), 4.01 (s, 3H). MS (ESI): [M+Na] 310.0689.

(3) Synthesis of Compound 83: To a solution of Compound 82 (9 g, 31.3 mmol) dissolved in 200 mL methanol was slowly added sodium borohydride (2.37 g, 62.6 mmol) under ice bath, and the mixture was carried out for 30 min at room temperature. After completion of the reaction, the system was acidified with 2 mol/L hydrochloric acid to pH 7.0, and methanol was removed by rotary evaporation under reduced pressure. The crude was added 100 mL water and extracted three times with ethyl acetate, and the combined organic phases was dried over $Na_2SO_4$, filtered and removed the solvent by rotary evaporation under reduced pressure to give Compound 83 as yellow solid (9.06 g, 92%). $^1$H NMR (400 MHz, $CDCl_3$): δ=7.77 (s, 1H), 7.49-7.42 (m, 2H), 7.40 (dd, J=8.1, 6.4 Hz, 3H), 7.18 (s, 1H), 5.20 (s, 2H), 4.95 (s, 2H), 4.00 (s, 3H). MS (ESI): [M+Na] 312.0834.

(4) Synthesis of Compound 84: To a solution of Compound 83 (3 g, 10.4 mmol) in 100 mL anhydrous tetrahydrofuran under protection of $Ar_2$ was simultaneously added triphenylphosphine (4.08 g, 15.6 mmol) and carbon tetrabromide (5.16 g, 15.6 mmol) under ice bath, and the reaction was carried out for 2 h at room temperature. After completion of the reaction, 6 mL of water was added to quench the reaction system, and then the tetrahydrofuran was removed by rotary evaporation under reduced pressure. The crude was extracted twice with saturated brine and ethyl acetate, and then extracted three times with water and ethyl acetate. The combined organic phases was dried over $Na_2SO_4$, filtered and removed the solvent by rotary evaporation under reduced pressure, then purified by column chromatography (PE:$CH_2Cl_2$=4:1) to obtain Compound 84 as yellow powder (3.09 g, 85%). $^1$H NMR (400 MHz, $CDCl_3$): δ=7.71 (s, 1H), 7.46-7.41 (m, 2H), 7.40-7.30 (m, 3H), 6.93 (s, 1H), 5.17-5.13 (m, 2H), 4.8-4.79 (m, 2H), 3.95 (s, 3H), 1.42 (s, 9H). MS (ESI): [M+Na] 374.0003.

(5) Synthesis of Compound 85: To a solution of Compound 84 (3 g, 8.5 mmol) in 120 mL acetone under protection of $Ar_2$ was added L-cysteine methyl ester hydrochloride (2.9 g, 17 mmol) and sodium hydroxide (0.85 g, 21.25 mmol), and the mixture was reacted at room temperature for 2 h. After completion of the reaction, the system was acidified with 4 mol/L hydrochloric acid to pH 7.0, and the acetone was removed by rotary evaporation under reduced pressure. The crude was extracted three times with saturated brine and ethyl acetate, and then extracted three times with water and ethyl acetate. The combined organic phases was dried over $Na_2SO_4$, filtered and removed the solvent by rotary evaporation under reduced pressure, then purified by column chromatography ($CH_2Cl_2$: $CH_3OH$=100:3) to obtain Compound 85 as a yellow solid (2.71 g, 78%). $^1$H NMR (400 MHz, $CDCl_3$): δ=7.71 (s, 1H), 7.45 (d, J=7.0 Hz, 2H), 7.39 (t, J=7.2 Hz, 3H), 6.95 (s, 1H), 5.18 (s, 2H), 4.13 (q, J=13.6 Hz, 2H), 3.98 (s, 3H), 3.73 (s, 3H), 3.65 (m, 1H), 2.91 (dd, J=13.7, 4.6 Hz, 1H), 2.75 (dd, J=13.6, 7.5 Hz, 1H). MS (ESI): [M+H] 407.1277.

(6) Synthesis of Compound 86: To a solution of triethylene glycol (22 g, 113.2 mmol) in dry tetrahydrofuran was added sodium metal (40 mg, 1.74 mmol), the mixture was stirred until sodium was completely dissolved. The mixture was added tert-butyl acrylate (8 g, 62.4 mmol) and reacted at room temperature for 20 h. After completion of the reaction, the system was acidified with 1 mol/L hydrochloric acid to pH 7.0, and tetrahydrofuran was removed by rotary evaporation under reduced pressure. The crude was extracted three times with saturated brine and ethyl acetate, and then extracted three times with water and ethyl acetate. The combined organic phases was dried over $Na_2SO_4$, filtered and removed the solvent by rotary evaporation under reduced pressure. Without further purification, Compound 86 (16.0 g, 80%) as a colorless oily liquid was obtained. $^1$H NMR (400 MHz, $CDCl_3$): δ=3.78-3.69 (m, 4H), 3.69-3.54 (m, 14H), 2.52 (dd, J=4.3, 2.1 Hz, 2H), 1.45 (s, 9H). MS (ESI): [M+Na] 345.1872.

(7) Synthesis of Compound 87: To a solution of Compound 86 (10 g, 31.2 mmol) in anhydrous dichloromethane was added anhydrous triethylamine (5.2 mm L, 37.4 mmol) and gradually dropwise added p-methylbenzenesulfonyl chloride (8.9 g, 46.8 mmol) in 40 mL dry dichloromethane under ice bath conditions, and the mixture was reacted at room temperature for 6 h. After completion of the reaction, the system was added 200 mL of water and extracted three times with dichloromethane. The combined organic phases were dried over $Na_2SO_4$, filtered and removed the solvent by rotary evaporation under reduced pressure, then purified by column chromatography ($CH_2Cl_2$:$CH_3OH$=50:1) to obtain Compound 87 (12.6 g, 85%) as a pale yellow oily liquid. $^1$H NMR (400 MHz, $CDCl_3$): δ=7.79-7.74 (m, 2H), 7.32 (d, J=8.5 Hz, 2H), 4.21-3.90 (m, 2H), 3.66 (dd, J=5.7, 2.8 Hz, 4H), 3.62-3.35 (m, 12H), 2.47 (dd, J=8.3, 4.8 Hz, 2H), 2.42 (d, J=3.2 Hz, 3H), 1.42 (d, J=3.4 Hz, 9H). MS (ESI): [M+Na] 499.1964.

(8) Synthesis of Compound 88: Compound 87 (10 g, 21.0 mmol) and lithium bromide (4.8 g, 31.5 mmol) were dissolved in 30 mL of N,N-dimethylformamide and heated to 80° C. to react for 1 h. After completion of the reaction, N,N-dimethylformamide was removed the solvent by rotary evaporation under reduced pressure. The crude was extracted three times with water and dichloromethane. The combined organic phases were dried over $Na_2SO_4$, filtered and removed the solvent by rotary evaporation under reduced pressure, then purified by column chromatography to obtain Compound 88 (7.3 g, 90%) as a pale yellow oily liquid. $^1$H NMR (400 MHz, $CDCl_3$): δ=3.72 (t, J=6.3 Hz, 2H), 3.62 (t, J=6.6 Hz, 2H), 3.58 (dd, J=2.6, 1.5 Hz, 8H), 3.54 (d, J=2.2 Hz, 4H), 3.39 (t, J=6.3 Hz, 2H), 2.42 (t, J=6.6 Hz, 2H), 1.36 (s, 9H). MS (ESI): [M+Na] 409.1005.

(9) Synthesis of Compound 89: To a solution of Compound 88 (5 g, 13.0 mmol) in 30 mL anhydrous dichloromethane was added 10 mL trifluoroacetic acid, and the mixture was reacted at room temperature for 30 min. After completion of the reaction, the solvent was removed by rotary evaporation under reduced pressure. Then the crude was re-dissolved with dichloromethane and ethyl acetate and the solvent was removed by rotary evaporation under reduced pressure to absolutely remove trifluoroacetic acid. Without further purification, Compound 89 (3.9 g, 92%) as a yellow oily liquid was obtained. $^1$H NMR (400 MHz, $CDCl_3$): δ=3.72 (t, J=6.3 Hz, 2H), 3.67 (t, J=6.3 Hz, 2H), 3.58 (dd, J=4.1, 1.7 Hz, 4H), 3.57 (s, 4H), 3.55 (s, 4H), 3.39 (t, J=6.3 Hz, 2H), 2.54 (t, J=6.3 Hz, 2H). MS (ESI): [M+Na] 353.0414.

(10) Synthesis of Compound 90: To a solution of Compound 85 (2.0 g, 4.9 mmol) and Compound 89 (2.0 g, 5.9 mmol) in 40 mL anhydrous dichloromethane was added benzotriazol-1-yl-oxytripyrrolidinyl hexafluorophosphate (5.1 g, 9.8 mmol) and anhydrous triethylamine (1.4 mL, 9.8 mmol), and the mixture was reacted at room temperature for 1 h. After completion of the reaction, the system was extracted three times with dichloromethane and water. The combined organic phases were dried over $Na_2SO_4$, filtered and removed the solvent by rotary evaporation under reduced pressure, then purified by column chromatography ($CH_2Cl_2$:$CH_3OH$=100:3) to obtain Compound 90 (2.2 g, 62%) as a yellow solid. $^1$H NMR (400 MHz, $CDCl_3$): δ=7.71 (s, 1H), 7.45 (d, J=7.0 Hz, 2H), 7.39 (t, J=7.2 Hz, 3H), 6.95 (s, 1H), 5.18 (s, 2H), 4.42 (m, 1H), 4.13 (q, J=13.6 Hz, 2H), 3.98 (s, 3H), 3.73 (s, 3H), 3.68-3.63 (m, 2H), 3.62-3.55 (m, 4H), 3.58-3.53 (m, 12H), 3.37 (t, J=6.3 Hz, 2H), 2.43 (t, J=5.8 Hz, 2H). MS (ESI): [M+Na] 741.1529.

(11) Synthesis of Compound 91: Compound 90 (2 g, 2.8 mmol) was dissolved in 20 mL trifluoroacetic acid and reacted at 45° C. for 8 h. After completion of the reaction, trifluoroacetic acid was removed by rotary evaporation under reduced pressure and extracted three times with dichloromethane and water. The combined organic phases were dried over $Na_2SO_4$, filtered and removed the solvent by rotary evaporation under reduced pressure, then purified by column chromatography ($CH_2Cl_2$: $CH_3OH$=25:1) to obtain Compound 91 (1.4 g, 82%) as a yellow liquid. $^1$H NMR (400 MHz, $CDCl_3$): δ=7.60 (s, 1H), 6.79 (s, 1H), 4.73-4.66 (m, 1H), 3.99 (d, J=12.9 Hz, 2H), 3.97 (s, 3H), 3.73 (s, 3H), 3.70 (d, J=6.3 Hz, 2H), 3.62-3.55 (m, 4H), 3.58-3.53 (m, 12H), 3.37 (t, J=6.3 Hz, 2H), 2.43 (t, J=5.8 Hz, 2H). MS (ESI): [M+Na] 651.1026.

(12) Synthesis of Compound 92: To a solution of Compound 91 (0.5 g, 0.8 mmol) in 400 mL acetone was added potassium carbonate (0.2 g, 1.6 mmol), and the mixture was refluxed at 75° C. for 4 h. After completion of the reaction, the system was filtrated to remove insoluble matter and removed solvent by rotary evaporation under reduced pressure. Then, the crude was purified by column chromatography ($CH_2Cl_2$:$CH_3OH$=25:1) to obtain Compound 92 (0.27 g, 61%) as a yellow solid. $^1$H NMR (400 MHz, DMSO): δ=7.71 (s, 1H), 7.17 (s, 1H), 4.76 (s, 2H), 4.42 (m, 1H), 3.97 (s, 3H), 3.73 (s, 3H), 3.72 (d, J=6.3 Hz, 2H), 3.62-3.55 (m, 4H), 3.52-3.39 (m, 14H), 2.49-2.35 (m, 2H). MS (ESI): [M+Na] 569.1782.

(13) Synthesis of Compound 93: Compound 92 (0.2 g, 3.7 mmol) was dissolve in 20 mL anhydrous ethylenediamine and reacted at room temperature for 6 h. After completion of the reaction, the ethylenediamine was removed by rotary evaporation under reduced pressure. The crude was purified by column chromatography ($CH_2Cl_2$: $CH_3OH$: triethylamine=100:8:0.5) to obtain Compound 93 (0.19 g, 89%) as a yellow powder. $^1$H NMR (400 MHz, DMSO): δ=7.71 (s, 1H), 7.17 (s, 1H), 4.76 (s, 2H), 4.42 (m, 1H), 3.97 (s, 3H), 3.72 (d, J=6.3 Hz, 2H), 3.62-3.55 (m, 2H), 3.52-3.39 (m, 16H), 2.86 (d, J=7.6 Hz, 2H), 2.76 (d, J=7.6 Hz, 2H), 2.49-2.35 (m, 2H). MS (ESI): [M+Na] 597.2211.

Example 65: Synthesis of Component A-65

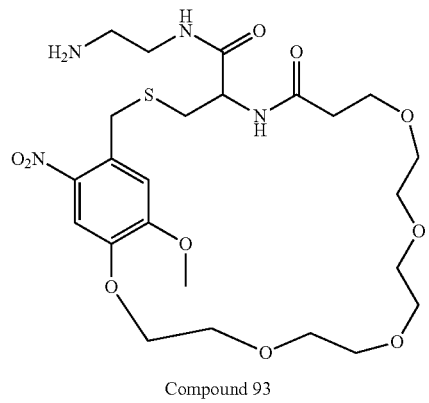

Compound 93

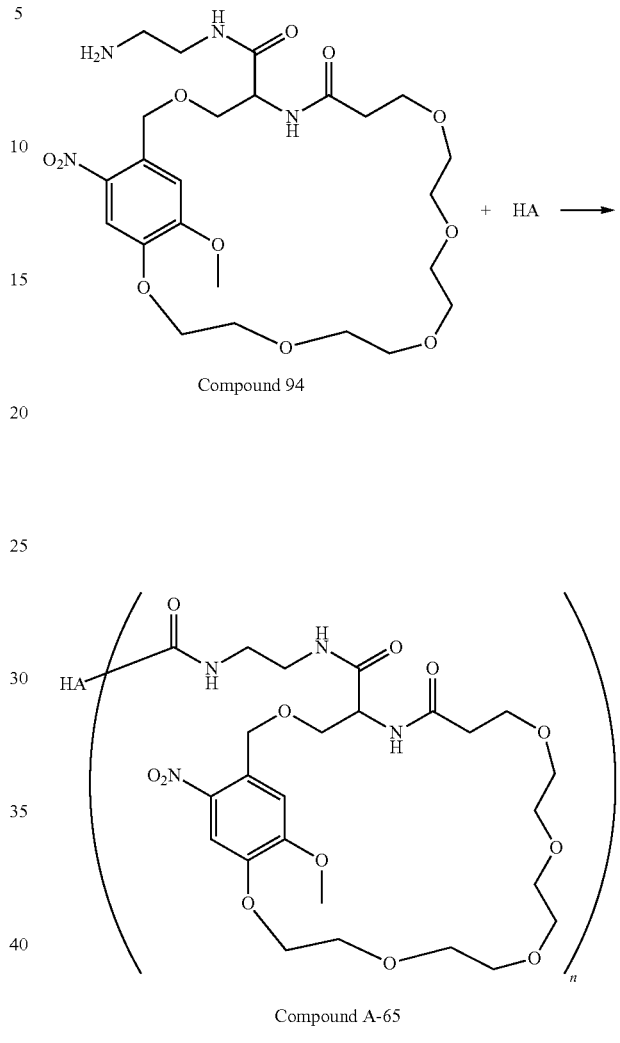

Compound 94

Component A-64

Compound A-65

(14) Synthesis of Component A-64: To a solution of hyaluronic acid sodium (2 g, 340 kDa) in 100 mL 0.01M 2-(N-morpholine) mesylate (MES) buffer solution (pH=5.2) was added Compound 93 (115 mg, 0.2 mmol) in 10 mL dimethyl sulfoxide (DMSO). Then, DMTMM (0.4 g, 1.5 mmol) dissolved in 3 mL water was added into the above solution three times with an interval of 1 h, and the mixture was stirred for 24 hours in the dark 35° C. Then, the reaction solution was poured into a dialysis bag (MWCO 7000), dialyzed against deionized water for 2-3 d, and lyophilized to obtain a photosensitive hyaluronic acid derivative Compound A-64 (1.87 g). According to the nuclear magnetic resonance spectrum, the grafting degree of Compound 93 can be calculated to be about 3.49%.

(1) Synthesis of Compound 94: Compound 94 was prepared by the method of Example 64 by a conventional chemical means. ¹H NMR (400 MHz, DMSO): δ=7.71 (s, 1H), 7.17 (s, 1H), 4.96 (s, 2H), 4.42 (m, 1H), 3.97 (s, 3H), 3.72 (d, J=6.3 Hz, 2H), 3.62-3.55 (m, 2H), 3.52-3.39 (m, 16H), 2.86 (d, J=7.6 Hz, 2H), 2.76 (d, J=7.6 Hz, 2H), 2.49-2.35 (m, 2H). MS (ESI): [M+Na] 559.2642.

(2) Synthesis of Component A-65: To a solution of hyaluronic acid sodium (2 g, 340 kDa) in 100 mL 0.01M 2-(N-morpholine) mesylate (MES) buffer solution (pH=5.2) was added Compound 94 (111 mg, 0.2 mmol) in 10 mL dimethyl sulfoxide (DMSO). Then, DMTMM (0.4 g, 1.5 mmol) dissolved in 3 mL water was added into the above solution three times with an interval of 1 h, and the mixture was stirred for 24 hours in the dark 35° C. Then, the reaction solution was poured into a dialysis bag (MWCO 7000), dialyzed against deionized water for 2-3 d, and lyophilized to obtain a photosensitive hyaluronic acid derivative Compound A-65 (1.82 g). According to the nuclear magnetic resonance spectrum, the grafting degree of Compound 94 can be calculated to be about 3.15%.

Example 66: Synthesis of Component A-66

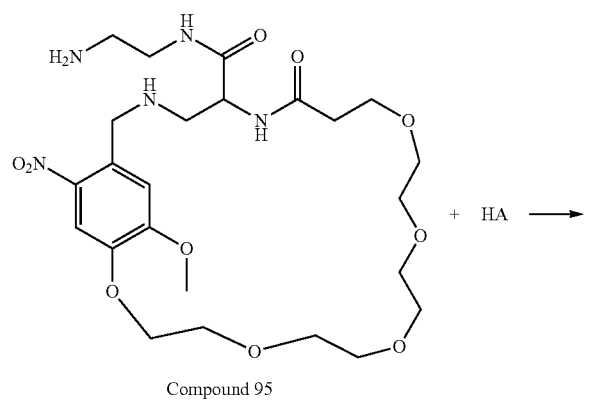

Compound 95

Example 67: Synthesis of Component A-67

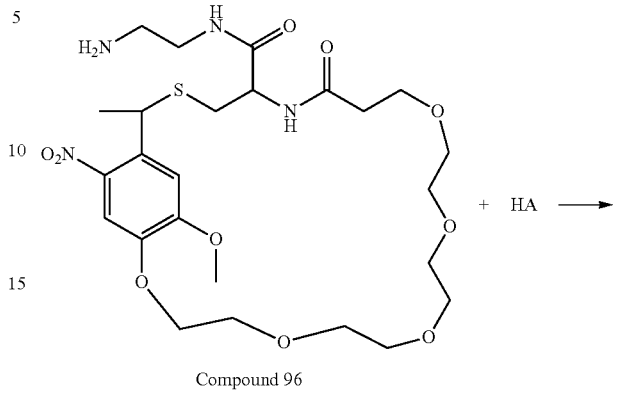

Compound 96

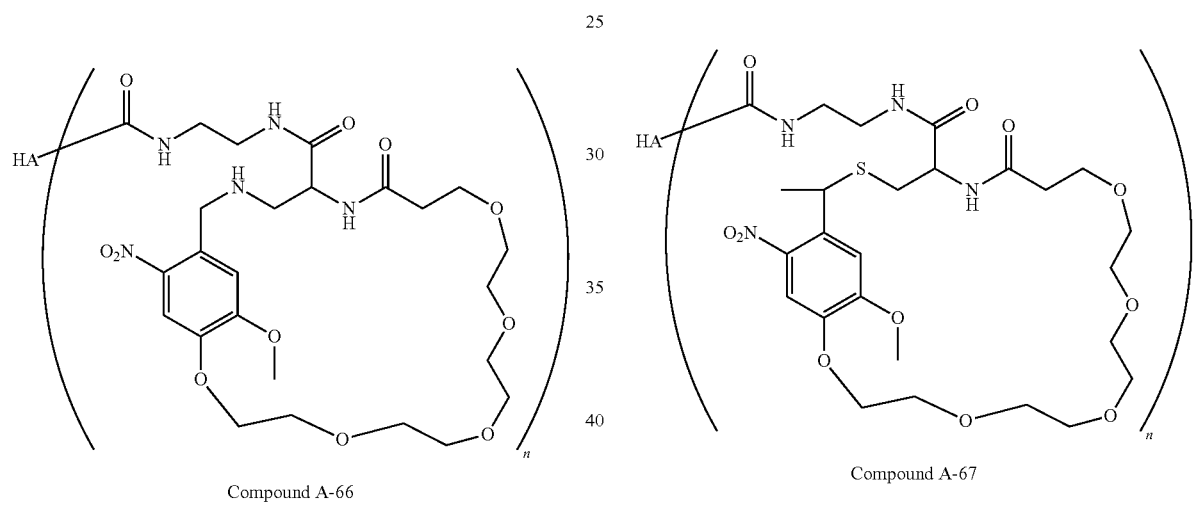

Compound A-66

Compound A-67

(1) Synthesis of Compound 95: Compound 95 was prepared by the method of Example 64 by a conventional chemical means. $^1$H NMR (400 MHz, DMSO): δ=7.71 (s, 1H), 7.17 (s, 1H), 4.26 (s, 2H), 4.42 (m, 1H), 3.97 (s, 3H), 3.42 (d, J=6.3 Hz, 2H), 3.62-3.55 (m, 2H), 3.52-3.39 (m, 16H), 2.86 (d, J=7.6 Hz, 2H), 2.76 (d, J=7.6 Hz, 2H), 2.49-2.35 (m, 2H). MS (ESI): [M+Na] 558.2725.

(2) Synthesis of Component A-66: To a solution of hyaluronic acid sodium (2 g, 340 kDa) in 100 mL 0.01M 2-(N-morpholine) mesylate (MES) buffer solution (pH=5.2) was added Compound 95 (111 mg, 0.2 mmol) in 10 mL dimethyl sulfoxide (DMSO). Then, DMTMM (0.4 g, 1.5 mmol) dissolved in 3 mL water was added into the above solution three times with an interval of 1 h, and the mixture was stirred for 24 hours in the dark 35° C. Then, the reaction solution was poured into a dialysis bag (MWCO 7000), dialyzed against deionized water for 2-3 d, and lyophilized to obtain a photosensitive hyaluronic acid derivative Compound A-66 (1.87 g). According to the nuclear magnetic resonance spectrum, the grafting degree of Compound 95 can be calculated to be about 3.27%.

(1) Synthesis of Compound 96: Compound 96 was prepared by the method of Example 64 by a conventional chemical means. $^1$H NMR (400 MHz, DMSO): δ=7.71 (s, 1H), 7.17 (s, 1H), 5.16 (m, 1H), 4.42 (m, 1H), 3.97 (s, 3H), 3.72 (d, J=6.3 Hz, 2H), 3.62-3.55 (m, 2H), 3.52-3.39 (m, 16H), 2.86 (d, J=7.6 Hz, 2H), 2.76 (d, J=7.6 Hz, 2H), 2.49-2.35 (m, 2H), 1.33 (d, J=6.9 Hz, 3H). MS (ESI): [M+Na] 589.2517.

(2) Synthesis of Component A-67: To a solution of hyaluronic acid sodium (2 g, 340 kDa) in 100 mL 0.01M 2-(N-morpholine) mesylate (MES) buffer solution (pH=5.2) was added Compound 96 (118 mg, 0.2 mmol) in 10 mL dimethyl sulfoxide (DMSO). Then, DMTMM (0.4 g, 1.5 mmol) dissolved in 3 mL water was added into the above solution three times with an interval of 1 h, and the mixture was stirred for 24 hours in the dark 35° C. Then, the reaction solution was poured into a dialysis bag (MWCO 7000), dialyzed against deionized water for 2-3 d, and lyophilized to obtain a photosensitive hyaluronic acid derivative Compound A-67 (1.73 g). According to the nuclear magnetic resonance spectrum, the grafting degree of Compound 96 can be calculated to be about 3.14%.

Example 68: Synthesis of Component A-68

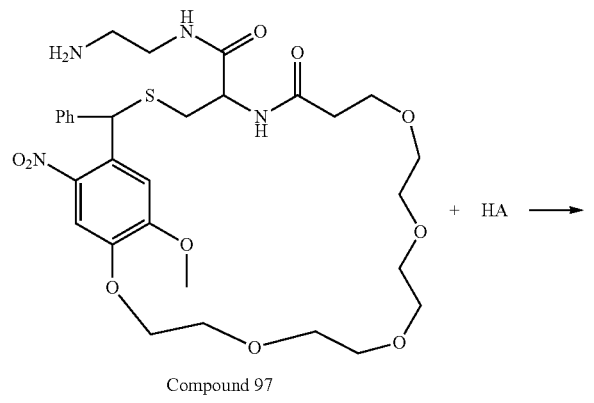

Compound 97

Example 69: Synthesis of Component A-69

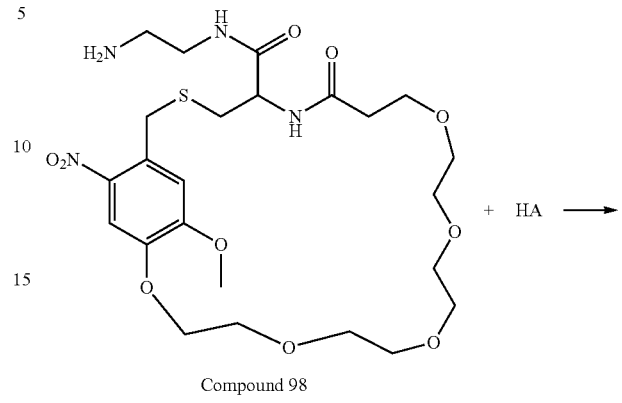

Compound 98

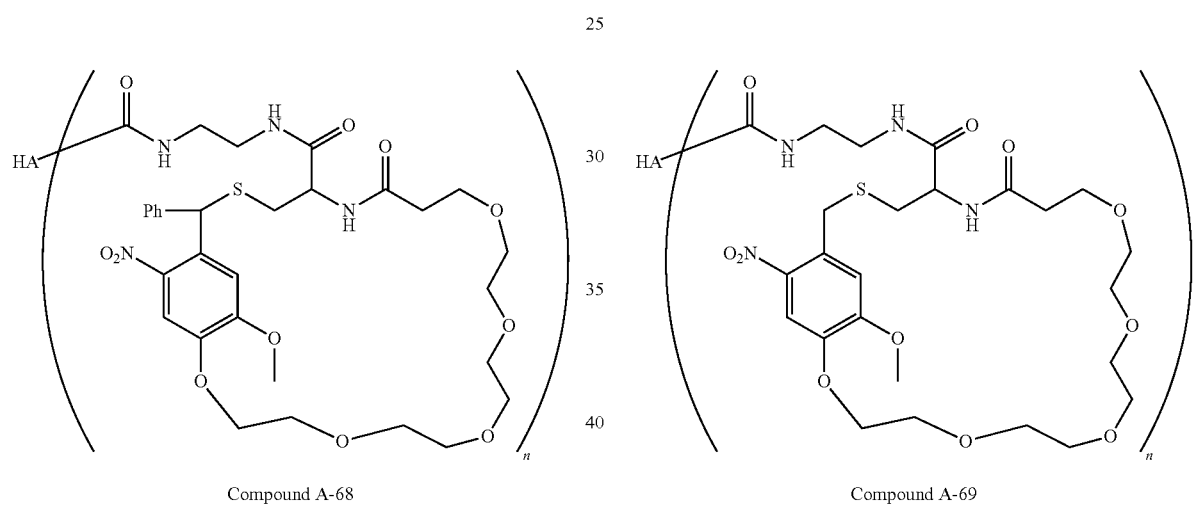

Compound A-68        Compound A-69

(1) Synthesis of Compound 97: Compound 97 was prepared by the method of Example 64 by a conventional chemical means. $^1$H NMR (400 MHz, DMSO): δ=8.02-7.23 (m, 5H), 7.71 (s, 1H), 7.17 (s, 1H), 5.34 (m, 1H), 4.42 (m, 1H), 3.97 (s, 3H), 3.72 (d, J=6.3 Hz, 2H), 3.62-3.55 (m, 2H), 3.52-3.39 (m, 16H), 2.86 (d, J=7.6 Hz, 2H), 2.76 (d, J=7.6 Hz, 2H), 2.49-2.35 (m, 2H). MS (ESI): [M+Na] 651.2761.

(2) Synthesis of Component A-68: To a solution of hyaluronic acid sodium (2 g, 340 kDa) in 100 mL 0.01M 2-(N-morpholine) mesylate (MES) buffer solution (pH=5.2) was added Compound 97 (118 mg, 0.2 mmol) in 10 mL dimethyl sulfoxide (DMSO). Then, DMTMM (0.4 g, 1.5 mmol) dissolved in 3 mL water was added into the above solution three times with an interval of 1 h, and the mixture was stirred for 24 hours in the dark 35° C. Then, the reaction solution was poured into a dialysis bag (MWCO 7000), dialyzed against deionized water for 2-3 d, and lyophilized to obtain a photosensitive hyaluronic acid derivative Compound A-68 (1.78 g). According to the nuclear magnetic resonance spectrum, the grafting degree of Compound 97 can be calculated to be about 3.09%.

(1) Synthesis of Compound 98: Compound 98 was prepared by the method of Example 64 by a conventional chemical means. $^1$H NMR (400 MHz, DMSO): δ=7.71 (s, 1H), 7.17 (s, 1H), 5.82 (m, 1H), 4.76 (s, 2H), 3.97 (s, 3H), 3.62-3.55 (m, 2H), 3.52-3.39 (m, 16H), 2.86 (d, J=7.6 Hz, 2H), 2.76 (d, J=7.6 Hz, 2H), 2.49-2.35 (m, 2H). MS (ESI): [M+Na] 589.2143.

(2) Synthesis of Component A-69: To a solution of hyaluronic acid sodium (2 g, 340 kDa) in 100 mL 0.01M 2-(N-morpholine) mesylate (MES) buffer solution (pH=5.2) was added Compound 98 (118 mg, 0.2 mmol) in 10 mL dimethyl sulfoxide (DMSO). Then, DMTMM (0.4 g, 1.5 mmol) dissolved in 3 mL water was added into the above solution three times with an interval of 1 h, and the mixture was stirred for 24 hours in the dark 35° C. Then, the reaction solution was poured into a dialysis bag (MWCO 7000), dialyzed against deionized water for 2-3 d, and lyophilized to obtain a photosensitive hyaluronic acid derivative Compound A-69 (1.73 g). According to the nuclear magnetic resonance spectrum, the grafting degree of Compound 98 can be calculated to be about 3.15%.

Example 70: Synthesis of Component A-70

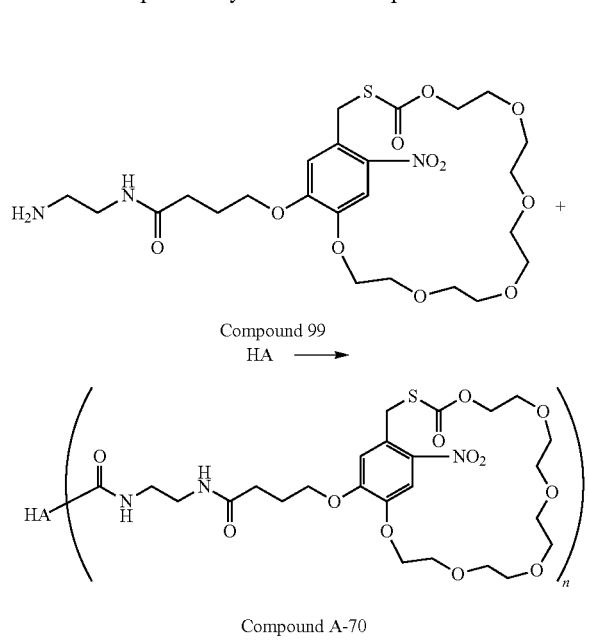

Compound 99

Compound A-70

(1) Synthesis of Compound 99: Compound 99 was prepared by the method of Example 64 by a conventional chemical means. $^1$H NMR (400 MHz, DMSO): δ=7.71 (s, 1H), 7.17 (s, 1H), 4.76 (s, 2H), 4.13 (t, J=7.2 Hz, 2H), 3.62-3.55 (m, 2H), 3.52-3.39 (m, 16H), 2.86 (d, J=7.6 Hz, 2H), 2.76 (d, J=7.6 Hz, 2H), 2.49-2.35 (m, 2H), 2.44 (t, J=7.2 Hz, 2H), 2.26-2.17 (m, 2H). MS (ESI): [M+Na] 575.2332.

(2) Synthesis of Component A-70: To a solution of hyaluronic acid sodium (2 g, 340 kDa) in 100 mL 0.01M 2-(N-morpholine) mesylate (MES) buffer solution (pH=5.2) was added Compound 99 (118 mg, 0.2 mmol) in 10 mL dimethyl sulfoxide (DMSO). Then, DMTMM (0.4 g, 1.5 mmol) dissolved in 3 mL water was added into the above solution three times with an interval of 1 h, and the mixture was stirred for 24 hours in the dark 35° C. Then, the reaction solution was poured into a dialysis bag (MWCO 7000), dialyzed against deionized water for 2-3 d, and lyophilized to obtain a photosensitive hyaluronic acid derivative Compound A-70 (1.84 g). According to the nuclear magnetic resonance spectrum, the grafting degree of Compound 99 can be calculated to be about 2.47%.

Example 71: Synthesis of Component A-71

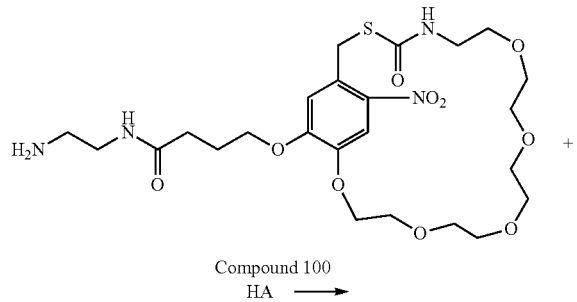

Compound 100

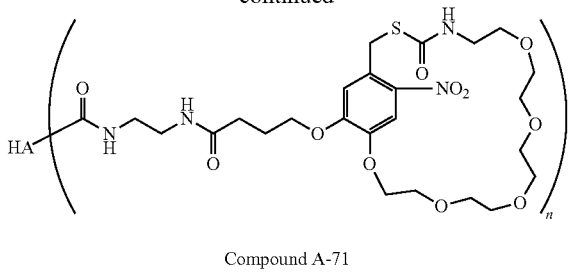

Compound A-71

(1) Synthesis of Compound 100: Compound 100 was prepared by the method of Example 64 by a conventional chemical means. $^1$H NMR (400 MHz, DMSO): δ=7.71 (s, 1H), 7.17 (s, 1H), 4.76 (s, 2H), 4.13 (t, J=7.2 Hz, 2H), 3.62-3.55 (m, 2H), 3.52-3.39 (m, 16H), 2.86 (d, J=7.6 Hz, 2H), 2.76 (d, J=7.6 Hz, 2H), 2.69-2.55 (m, 2H), 2.44 (t, J=7.2 Hz, 2H), 2.26-2.17 (m, 2H). MS (ESI): [M+Na] 576.2242.

(2) Synthesis of Component A-71: To a solution of hyaluronic acid sodium (2 g, 340 kDa) in 100 mL 0.01M 2-(N-morpholine) mesylate (MES) buffer solution (pH=5.2) was added Compound 100 (118 mg, 0.2 mmol) in 10 mL dimethyl sulfoxide (DMSO). Then, DMTMM (0.4 g, 1.5 mmol) dissolved in 3 mL water was added into the above solution three times with an interval of 1 h, and the mixture was stirred for 24 hours in the dark 35° C. Then, the reaction solution was poured into a dialysis bag (MWCO 7000), dialyzed against deionized water for 2-3 d, and lyophilized to obtain a photosensitive hyaluronic acid derivative Compound A-71 (1.75 g). According to the nuclear magnetic resonance spectrum, the grafting degree of Compound 100 can be calculated to be about 3.07%.

Example 74: Synthesis of Component A-74

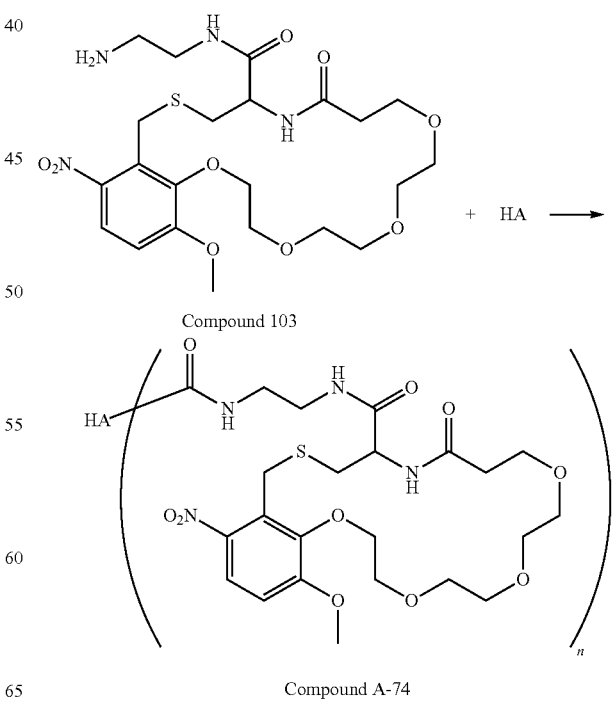

Compound 103

Compound A-74

(1) Synthesis of Compound 103: Compound 103 was prepared by the method of Example 64 by a conventional chemical means. $^1$H NMR (400 MHz, DMSO): δ=8.11 (m, 1H), 7.27 (m, 1H), 4.76 (s, 2H), 4.42 (m, 1H), 3.97 (s, 3H), 3.72 (d, J=6.3 Hz, 2H), 3.62-3.55 (m, 2H), 3.52-3.39 (m, 12H), 2.86 (d, J=7.6 Hz, 2H), 2.76 (d, J=7.6 Hz, 2H), 2.49-2.35 (m, 2H). MS (ESI): [M+Na] 531.2143.

(2) Synthesis of Component A-74: To a solution of hyaluronic acid sodium (2 g, 340 kDa) in 100 mL 0.01M 2-(N-morpholine) mesylate (MES) buffer solution (pH=5.2) was added Compound 103 (118 mg, 0.2 mmol) in 10 mL dimethyl sulfoxide (DMSO). Then, DMTMM (0.4 g, 1.5 mmol) dissolved in 3 mL water was added into the above solution three times with an interval of 1 h, and the mixture was stirred for 24 hours in the dark 35° C. Then, the reaction solution was poured into a dialysis bag (MWCO 7000), dialyzed against deionized water for 2-3 d, and lyophilized to obtain a photosensitive hyaluronic acid derivative Compound A-74 (1.78 g). According to the nuclear magnetic resonance spectrum, the grafting degree of Compound 103 can be calculated to be about 3.31%.

Example 75: Synthesis of Component A-75

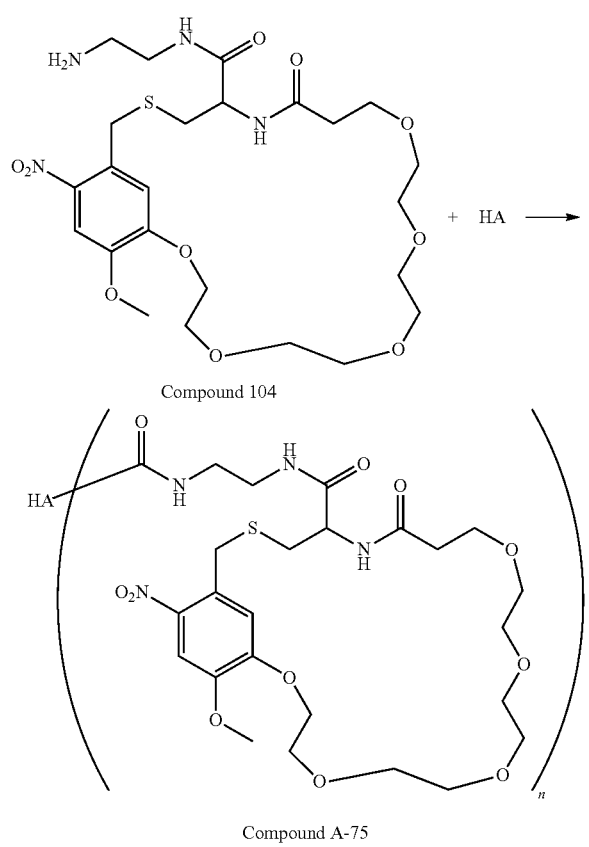

Compound A-75

(1) Synthesis of Compound 104: Compound 104 was prepared by the method of Example 64 by a conventional chemical means. $^1$H NMR (400 MHz, DMSO): δ=7.71 (s, 1H), 7.17 (s, 1H), 4.76 (s, 2H), 4.42 (m, 1H), 3.97 (s, 3H), 3.72 (d, J=6.3 Hz, 2H), 3.62-3.55 (m, 2H), 3.52-3.39 (m, 16H), 2.86 (d, J=7.6 Hz, 2H), 2.76 (d, J=7.6 Hz, 2H), 2.49-2.35 (m, 2H). MS (ESI): [M+Na] 575.2342.

(2) Synthesis of Component A-75: To a solution of hyaluronic acid sodium (2 g, 340 kDa) in 100 mL 0.01M 2-(N-morpholine) mesylate (MES) buffer solution (pH=5.2) was added Compound 104 (118 mg, 0.2 mmol) in 10 mL dimethyl sulfoxide (DMSO). Then, DMTMM (0.4 g, 1.5 mmol) dissolved in 3 mL water was added into the above solution three times with an interval of 1 h, and the mixture was stirred for 24 hours in the dark 35° C. Then, the reaction solution was poured into a dialysis bag (MWCO 7000), dialyzed against deionized water for 2-3 d, and lyophilized to obtain a photosensitive hyaluronic acid derivative too Compound A-75 (1.84 g). According to the nuclear magnetic resonance spectrum, the grafting degree of Compound 104 can be calculated to be about 3.06%.

Example 76: Synthesis of Component A-76

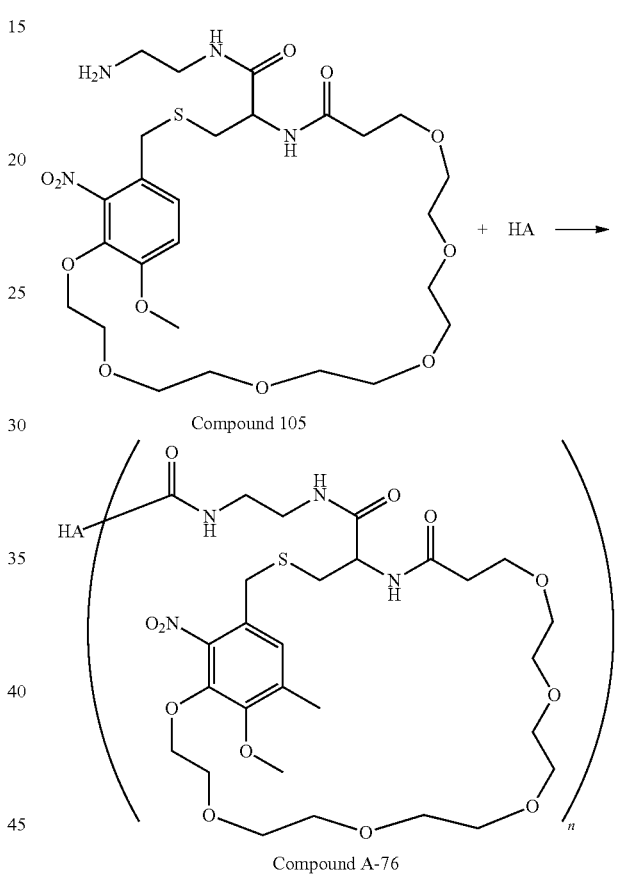

Compound A-76

(1) Synthesis of Compound 105: Compound 105 was prepared by the method of Example 64 by a conventional chemical means. $^1$H NMR (400 MHz, DMSO): δ=7.54 (m, 1H), 7.03 (m, 1H), 4.76 (s, 2H), 4.42 (m, 1H), 3.97 (s, 3H), 3.72 (d, J=6.3 Hz, 2H), 3.62-3.55 (m, 2H), 3.52-3.39 (m, 20H), 2.86 (d, J=7.6 Hz, 2H), 2.76 (d, J=7.6 Hz, 2H), 2.49-2.35 (m, 2H). MS (ESI): [M+Na] 619.2652.

(2) Synthesis of Component A-76: To a solution of hyaluronic acid sodium (2 g, 340 kDa) in 100 mL 0.01M 2-(N-morpholine) mesylate (MES) buffer solution (pH=5.2) was added Compound 105 (118 mg, 0.2 mmol) in 10 mL dimethyl sulfoxide (DMSO). Then, DMTMM (0.4 g, 1.5 mmol) dissolved in 3 mL water was added into the above solution three times with an interval of 1 h, and the mixture was stirred for 24 hours in the dark 35° C. Then, the reaction solution was poured into a dialysis bag (MWCO 7000), dialyzed against deionized water for 2-3 d, and lyophilized to obtain a photosensitive hyaluronic acid derivative Compound A-76 (1.84 g). According to the nuclear magnetic resonance spectrum, the grafting degree of Compound 105 can be calculated to be about 3.16%.

Example 77: Synthesis of Component A-77

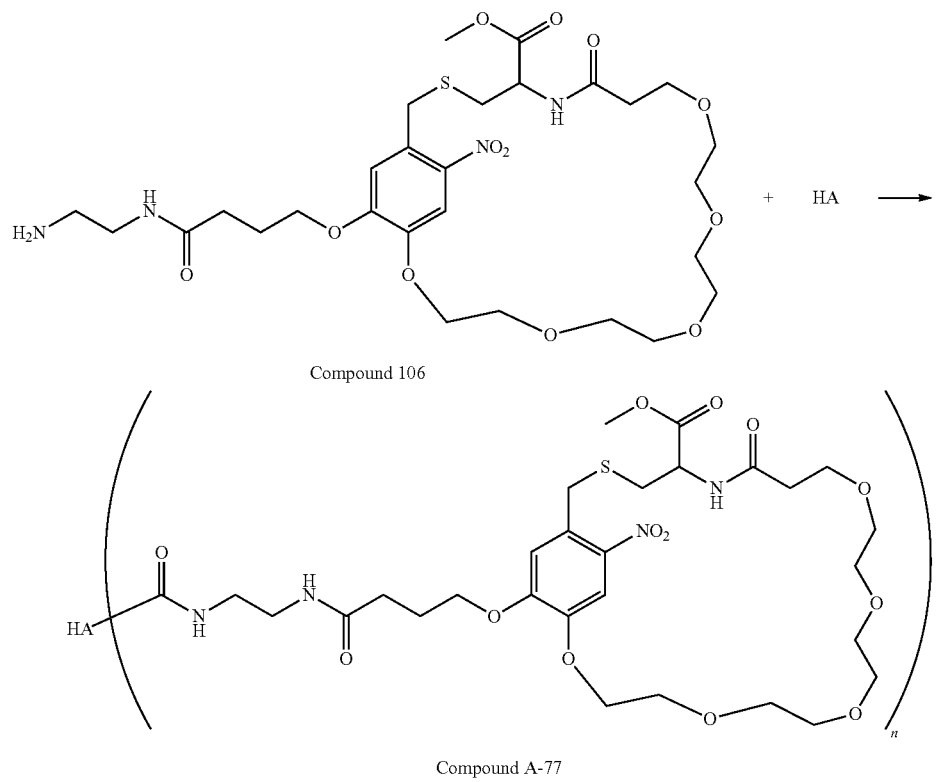

Compound 106

Compound A-77

(1) Synthesis of Compound 106: Compound 106 was prepared by the method of Example 64 by a conventional chemical means. $^1$H NMR (400 MHz, DMSO): δ=7.71 (s, 1H), 7.17 (s, 1H), 4.76 (s, 2H), 4.42 (m, 1H), 4.13 (t, J=7.2 Hz, 2H), 3.73 (s, 3H), 3.72 (d, J=6.3 Hz, 2H), 3.62-3.55 (m, 2H), 3.52-3.39 (m, 16H), 2.86 (d, J=7.6 Hz, 2H), 2.76 (d, J=7.6 Hz, 2H), 2.49-2.35 (m, 2H), 2.44 (t, J=7.2 Hz, 2H), 2.26-2.17 (m, 2H). MS (ESI): [M+Na] 661.2745.

(2) Synthesis of Component A-77: To a solution of hyaluronic acid sodium (2 g, 340 kDa) in 100 mL 0.01M 2-(N-morpholine) mesylate (MES) buffer solution (pH=5.2) was added Compound 105 (118 mg, 0.2 mmol) in 10 mL dimethyl sulfoxide (DMSO). Then, DMTMM (0.4 g, 1.5 mmol) dissolved in 3 mL water was added into the above solution three times with an interval of 1 h, and the mixture was stirred for 24 hours in the dark 35° C. Then, the reaction solution was poured into a dialysis bag (MWCO 7000), dialyzed against deionized water for 2-3 d, and lyophilized to obtain a photosensitive hyaluronic acid derivative Compound A-77 (1.77 g). According to the nuclear magnetic resonance spectrum, the grafting degree of Compound 106 can be calculated to be about 3.21%.

Example 78: Synthesis of Component A-78

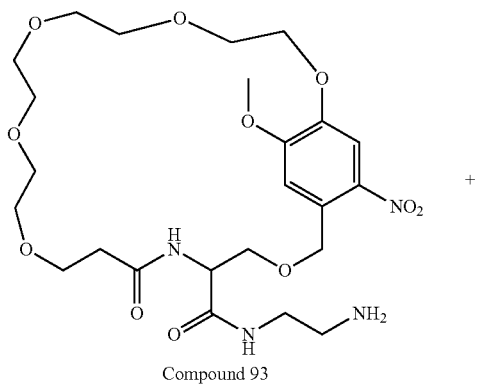

Compound 93

-continued

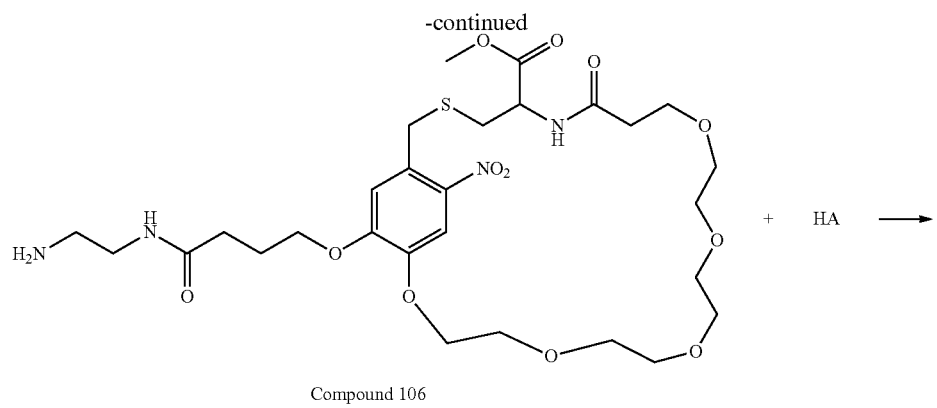

Compound 106

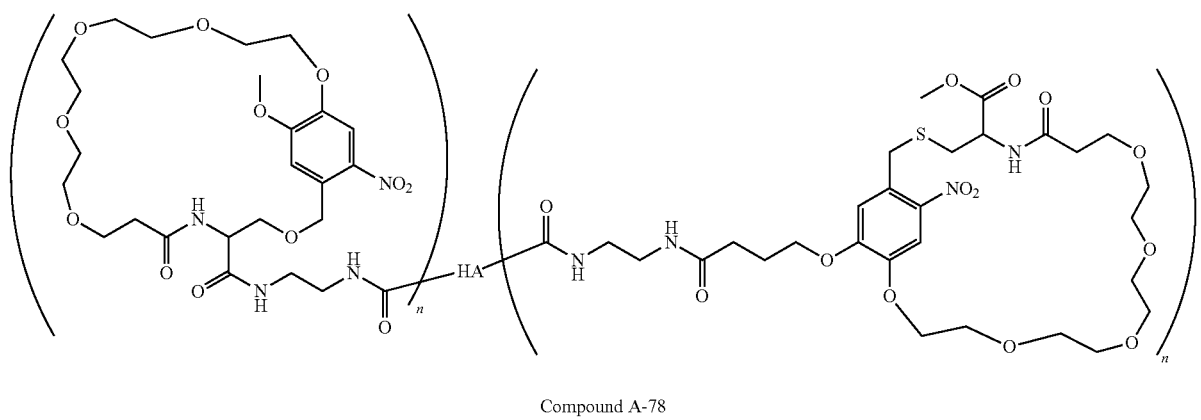

Compound A-78

Synthesis of Component A-78: To a solution of hyaluronic acid sodium (2 g, 340 kDa) in 100 mL 0.01M 2-(N-morpholine) mesylate (MES) buffer solution (pH=5.2) was added cNB mixture (Compound 93/Compound 106, 60 mg, 1:1) in 10 mL dimethyl sulfoxide (DMSO). Then, DMTMM (0.4 g, 1.5 mmol) dissolved in 3 mL water was added into the above solution three times with an interval of 1 h, and the mixture was stirred for 24 hours in the dark 35° C. Then, the reaction solution was poured into a dialysis bag (MWCO 7000), dialyzed against deionized water for 2-3 d, and lyophilized to obtain a photosensitive hyaluronic acid derivative Compound A-78 (1.89 g). According to the nuclear magnetic resonance spectrum, the grafting degree of cNB mixture (Compound 93/Compound 106) can be calculated to be about 3.52%.

Example 79: Synthesis of Component A-79

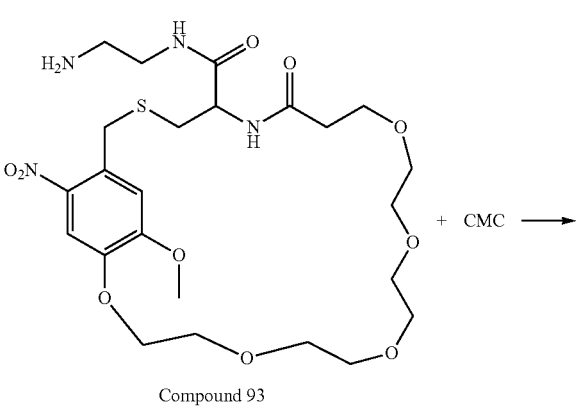

Compound 93

161
-continued

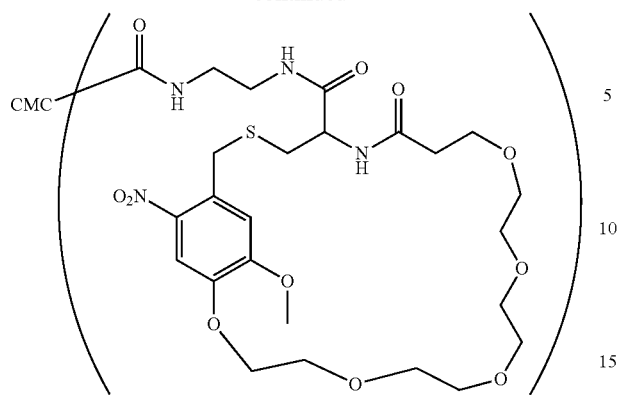

Compound A-79

Synthesis of Component A-79: To a solution of carboxymethyl cellulose (2 g, 340 kDa) in 100 mL 0.01 M 2-(N-morpholine) mesylate (MES) buffer solution (pH=5.2) was added Compound 93 (115 mg, 0.2 mmol) dissolved in 10 mL dimethyl sulfoxide (DMSO). Then, DMTMM (0.4 g, 1.5 mmol) dissolved in 3 mL water was added into the above solution three times with an interval of 1 h, and the mixture was stirred for 24 hours in the dark 35° C. Then, the reaction solution was poured into a dialysis bag (MWCO 7000), dialyzed against deionized water for 2-3 d, and lyophilized to obtain a photosensitive carboxymethyl cellulose derivative Compound A-79 (1.71 g). According to the nuclear magnetic resonance spectrum, the grafting degree of Compound 93 can be calculated to be about 2.41%.

Example 80: Synthesis of Component A-80

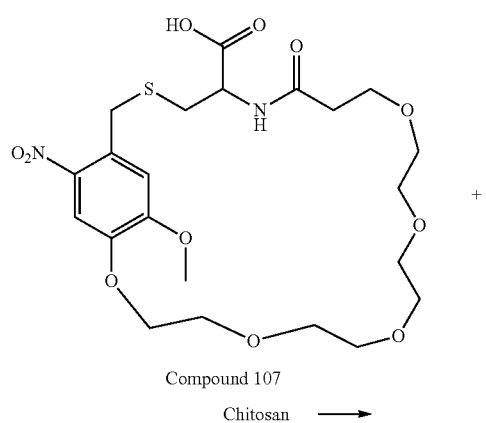

Compound 107

Chitosan ⟶

162
-continued

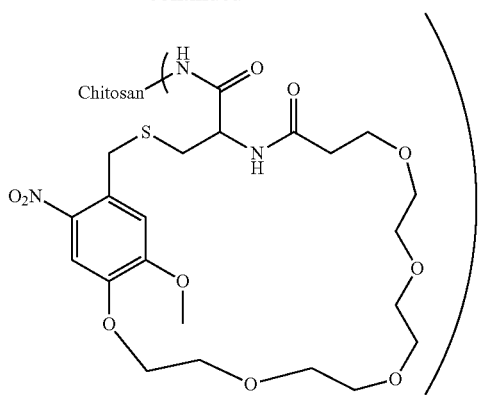

Compound A-80

(1) Synthesis of Compound 107: Compound 107 was prepared by the method of Example 64 by a conventional chemical means. $^1$H NMR (400 MHz, DMSO): δ=7.71 (s, 1H), 7.17 (s, 1H), 4.76 (s, 2H), 4.42 (m, 1H), 3.97 (s, 3H), 3.72 (d, J=6.3 Hz, 2H), 3.62-3.55 (m, 2H), 3.52-3.39 (m, 16H), 2.49-2.35 (m, 2H). MS (ESI): [M+Na] 533.1845.

(2) Synthesis of Component A-80: To a suspension liquid of chitosan (1 g) in 75 mL isopropanol was sequentially added Compound 107 (0.2 g, 0.35 mmol), EDC-HCl (0.76 g, 3.96 mmol) and NHS (0.46 g, 4.0 mmol), and the reaction was stirred at room temperature for 48 h. After completion of the reaction, the mixture solution was dialyzed with diluted hydrochloric acid solution containing sodium chloride (pH=3.5) for 1 d, dialyzed with distilled water for 1 d, and then freeze-dried to obtain photosensitive chitosan derivatives Compound A-80 (0.82 g). According to its nuclear magnetic resonance spectrum, the grafting degree of the Compound 107 can be calculated to be about 12.5%.

Example 81: Synthesis of Component A-81

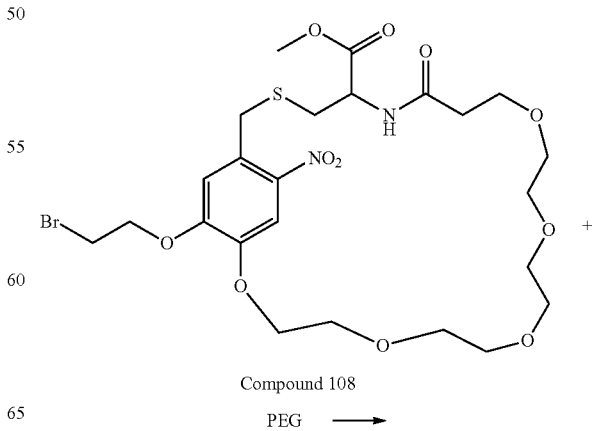

Compound 108

PEG ⟶

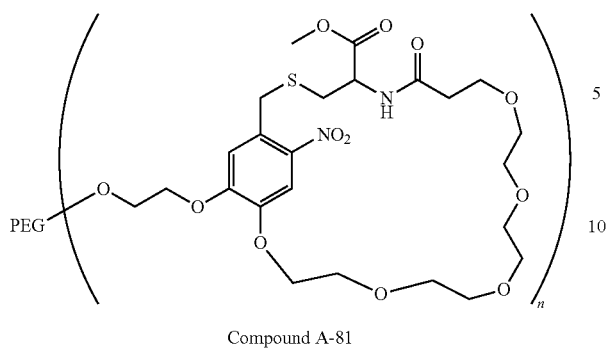

Compound A-81

(1) Synthesis of Compound 108: Compound 108 was prepared by the method of Example 64 by a conventional chemical means. $^1$H NMR (400 MHz, DMSO): δ=7.71 (s, 1H), 7.17 (s, 1H), 4.76 (s, 2H), 4.42 (m, 1H), 4.13 (t, J=6.1 Hz, 2H), 3.93 (s, 3H), 3.72 (d, J=6.3 Hz, 2H), 3.62-3.55 (m, 2H), 3.52-3.39 (m, 16H), 3.04 (t, J=7.2 Hz, 2H), 2.49-2.35 (m, 2H). MS (ESI): [M+Na] 640.1134.

(2) Synthesis of Component A-81: To a solution of PEG-4OH (1 g, 0.05 mmol) in anhydrous acetonitrile was added K$_2$CO$_3$ (55.3 mg, 0.4 mmol) and stirred for 30 min. Then the solution was added Compound 78 (0.15 g, 0.4 mmol) and continued to react at room temperature for 24 h. After the reaction was completed, most of the solvent was removed, reprecipitated in diethyl ether, and washed several times to obtain the photosensitive polyethelene glycol derivative Compound A-81 (0.85 g). According to its nuclear magnetic resonance spectrum, the grafting degree of the Compound 108 can be calculated to be about 95.3%.

Example 82: Synthesis of Component A-82

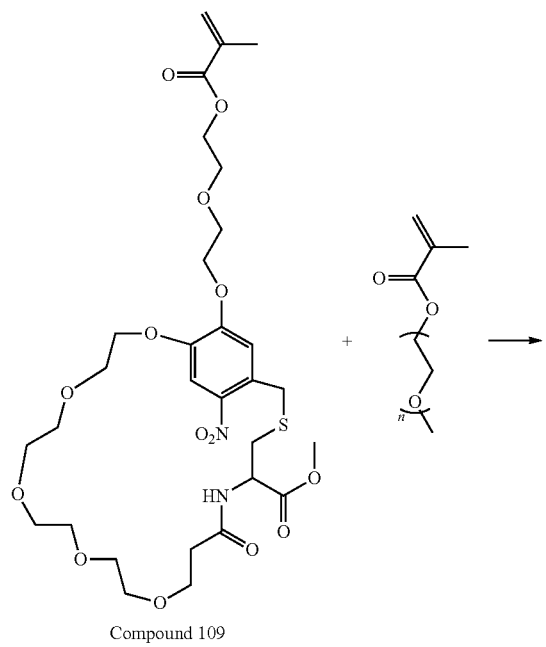

Compound 109

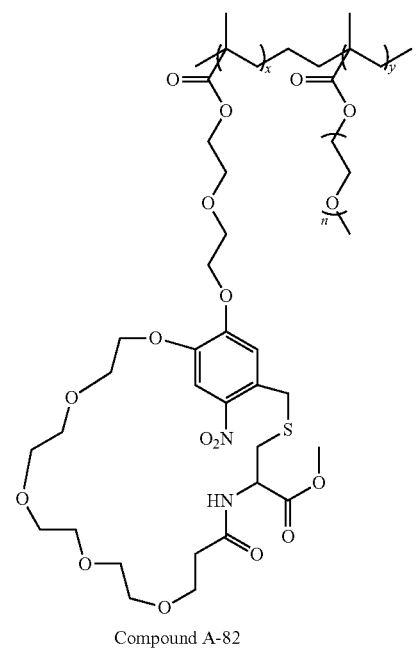

Compound A-82

(1) Synthesis of Compound 109: Compound 109 was prepared by the method of Example 64 by a conventional chemical means. $^1$H NMR (400 MHz, DMSO): δ=7.71 (s, 1H), 7.17 (s, 1H), 6.25 (s, 1H), 5.68 (s, 1H), 4.76 (s, 2H), 4.42 (m, 1H), 4.13 (t, J=6.1 Hz, 2H), 3.93 (s, 3H), 3.79 (t, J=6.1 Hz, 2H), 3.72 (d, J=6.3 Hz, 2H), 3.70 (t, J=7.2 Hz, 2H), 3.62-3.55 (m, 2H), 3.56 (t, J=7.2 Hz, 2H), 3.52-3.39 (m, 16H), 2.49-2.35 (m, 2H), 1.87 (s, 3H). MS (ESI): [M+Na] 689.2523.

(3) Synthesis of Component A-82: Compound 109 (0.28 g, 0.63 mmol), comonomer PEG-MA (0.882 g, 2.52 mmol) and the initiator azobisisobutyronitrile (11 mg) were added into the Shrek tube and dissolved by anhydrous THF. After repeated freeze-vacuum cycle operation, the reaction system was reacted at 75° C. for 24 h. After completion of the reaction, the solution was poured into cold diethyl ether and reprecipitated several times to obtain the photosensitive copolymer derivative Compound A-82 (0.85 g). According to its nuclear magnetic resonance spectrum, it can be calculated that the content of the Compound 109 in the copolymer is about 15.4%. According to GPC, the molecular weight of the synthetic polymer is about 25 kDa. According to the feed ratio, n is 12, x is 10, and y is 40.

Example 83: Synthesis of Component B-10

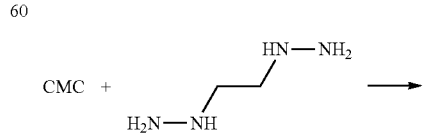

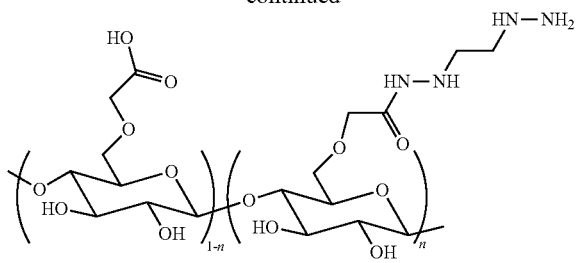

Synthesis of Component B-10: To a solution of carboxymethyl cellulose (CMC, 400 mg) in 50 ml distilled water was added hydroxybenzotriazole (HOBt, 153 mg), diamine (90 mg) and 1-ethyl-(3-dimethylaminopropyl) carbodiimide hydrochloride (EDC-HCl, 90 mg), the reaction was reacted for 48 h at room temperature. Then, the solution was dialyzed against with dilute hydrochloric acid solution containing sodium chloride (pH=3.5) for 1 d, and dialyzed against with pure water for 1 d, then lyophilized to obtain hydrazine-modified carboxymethyl cellulose (410 mg). The grafting degree of the diammonium was tested by the TBNS method to be about 10%.

Example 84: Synthesis of Component B-11

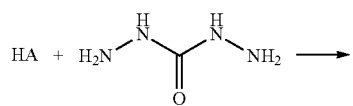

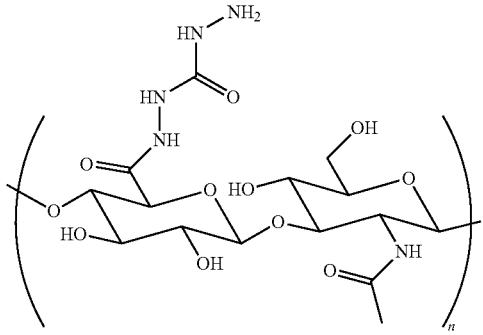

Synthesis of Component B-11: To a solution of hyaluronic acid (HA, 400 mg) in 50 mL distilled water was added hydroxybenzotriazole (HOBt, 153 mg), carbonyl hydrazide (CDH, 90 mg) and 1-ethyl-(3-dimethyl amine propyl) carbodiimine hydrochloride (EDC-HCl, 90 mg), the mixture was stirred at room temperature for 48 h. After completion of the reaction, the reaction solution was added to a dialysis bag and dialyzed against dilute hydrochloric acid solution containing sodium chloride (pH=3.5) for 1 d, and dialyzed against distilled water for 1 d, then freeze-dried to obtain the HA-CDH (410 mg). The grafting degree of hydrazine tested by TBNS method was about 10%.

Example 85: Synthesis of Component B-12

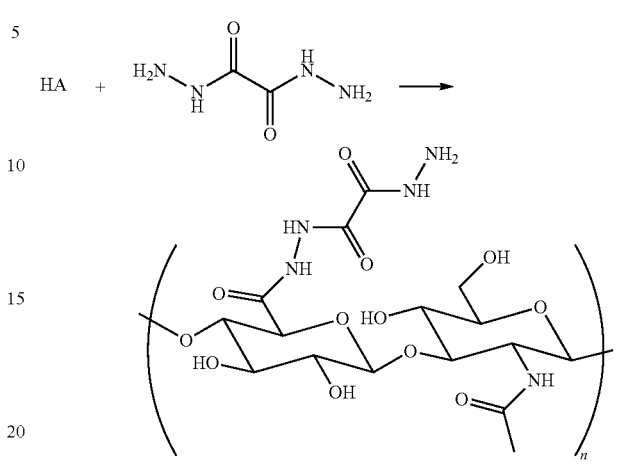

Synthesis of Component B-12: To a solution of hyaluronic acid (HA, 400 mg) in 50 mL distilled water was added hydroxybenzotriazole (HOBt, 153 mg), dihydrazide oxalate (ODH, 90 mg) and 1-ethyl-(3-dimethyl amine propyl) carbodiimine hydrochloride (EDC-HCl, 90 mg), the mixture was stirred at room temperature for 48 h. After completion of the reaction, the reaction solution was added to a dialysis bag and dialyzed against dilute hydrochloric acid solution containing sodium chloride (pH=3.5) for 1 d, and dialyzed against distilled water for 1 d, then freeze-dried to obtain the HA-ODH (410 mg). The grafting degree of hydrazine tested by TBNS method was about 10%.

Example 86: Synthesis of Component B-13

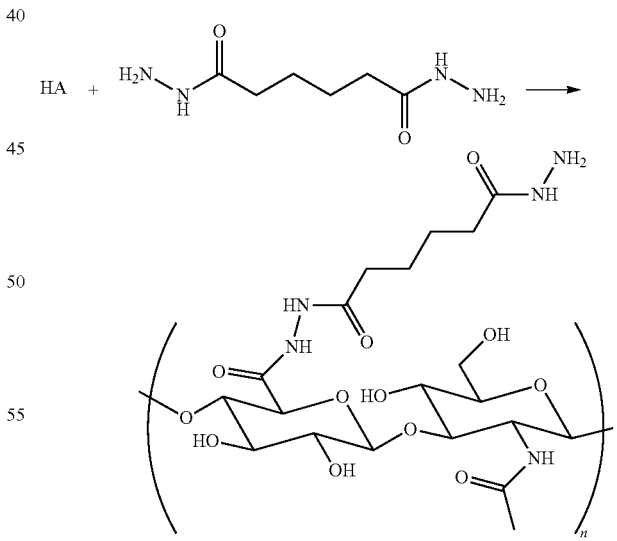

Synthesis of Component B-13: To a solution of hyaluronic acid (HA, 400 mg) in 50 mL distilled water was added hydroxybenzotriazole (HOBt, 153 mg), dihydrazide adipate (ADH, 90 mg) and 1-ethyl-(3-dimethyl amine propyl) carbodiimine hydrochloride (EDC-HCl, 90 mg), the mixture was stirred at room temperature for 48 h. After completion of the reaction, the reaction solution was added to a dialysis bag and dialyzed against dilute hydrochloric acid solution containing sodium chloride (pH=3.5) for 1 d, and dialyzed against distilled water for 1 d, then freeze-dried to obtain HA-ADH (410 mg). The grafting degree of hydrazine tested by TBNS method was about 10%.

Example 87: Synthesis of Component B-14

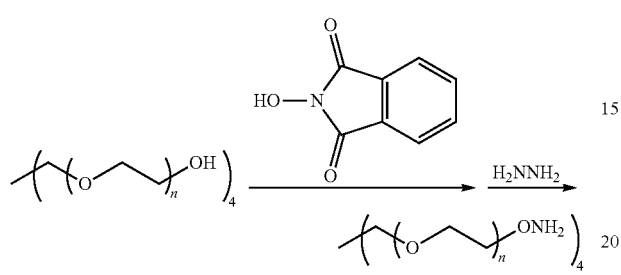

Synthesis of Component B-14: To a solution of PEG-4OH (2 g, 97.3 μmol) and N-hydroxyphthalimide (634.6 mg, 3.89 mmol) in anhydrous dichloromethane was slowly added triphenylphosphine (1.02 g, 3.89 mmol) under ice bath, the mixture was reacted under ice bath for about 30 min. The above solution was slowly added diisopropyl azodicarboxylate (765.9 μL, 3.89 mmol) in dry dichloromethane and reacted at room temperature for 1 d. After completion of the reaction, the system was reprecipitated with diethyl ether. The above precipitate (0.25 g, 11.8 μmol) was re-dissolved in acetonitrile and added hydrazine monohydrate (22.9 μL, 473 μmol), the mixture was stirred for 2 h. The above mixture solution was added dichloromethane and filtered. The solvent was removed by rotary evaporation under reduced pressure to obtain four-arm polyethylene glycol modified with hydroxylamine (PEG-4ONH$_2$).

Example 88: Synthesis of Component B-15

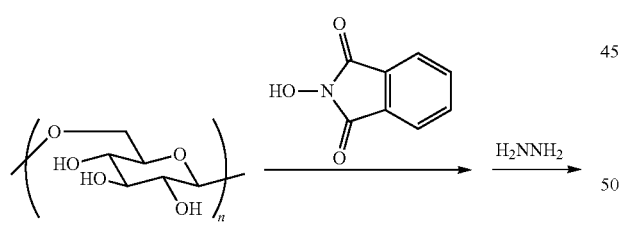

Synthesis of Component B-15: To a solution of dextran (2 g, 97.3 μmol) and N-hydroxyphthalimide (634.6 mg, 3.89 mmol) in anhydrous dichloromethane was slowly added triphenylphosphine (1.02 g, 3.89 mmol) under ice bath, the mixture was reacted under ice bath for about 30 min. The above solution was slowly added diisopropyl azodicarboxylate (765.9 μL, 3.89 mmol) in dry dichloromethane and reacted at room temperature for 1 d. After completion of the reaction, the system was reprecipitated with diethyl ether. The above precipitate (0.25 g, 11.8 μmol) was re-dissolved in acetonitrile and added hydrazine monohydrate (22.9 μL, 473 μmol), the mixture was stirred for 2 h. The above mixture solution was added dichloromethane and filtered. The solvent was removed by rotary evaporation under reduced pressure to obtain dextran modified with hydroxylamine (Dex-ONH$_2$).

Example 89: Synthesis of Component B-18

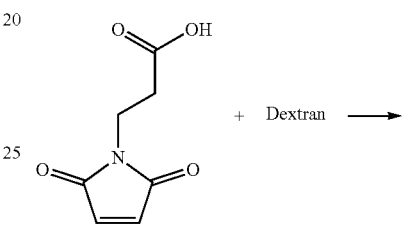

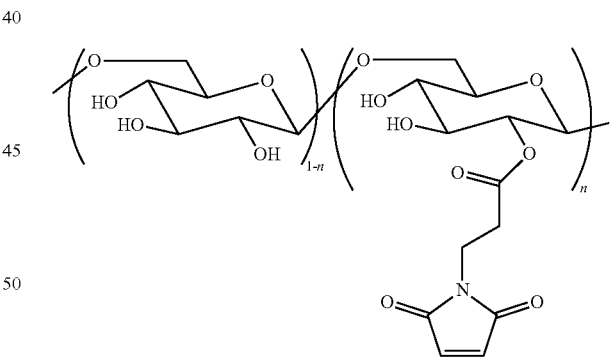

Synthesis of Component B-18: To a solution of N-maleimidopropionic acid (0.4 g, 2.36 mmol), DPTS (0.12 g, 0.37 mmol) and DCC (0.76 g, 3.68 mmol) in 5 ml anhydrous dimethyl sulfoxide was added dropwise dextran (1 g, 6.17 mmol glycoside) dissolved in 5 ml dimethyl sulfoxide, the reaction was reacted for 24 h at room temperature. After completion of the reaction, the system was filtered; the filtrate was poured into cold ethanol to precipitate, and washed several times. Then, the crude product was dissolved in water, poured into a dialysis bag (MWCO 3500), dialyzed against with deionized water for 2-3 d, and lyophilized to obtain dextran-Mal (0.8 g, 80%).

Example 90: Synthesis of Component B-21

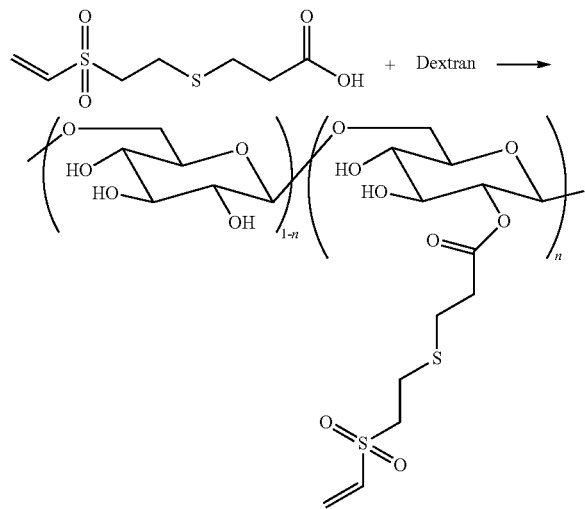

Synthesis of Component B-21: To a solution of carboxylic acid sulfone (0.4 g, 2.36 mmol), DPTS (0.12 g, 0.37 mmol) and DCC (0.76 g, 3.68 mmol) in 5 ml anhydrous dimethyl sulfoxide was dropwise added dextran (1 g, 6.17 mmol glycoside) dissolved in 5 ml dimethyl sulfoxide, the reaction was reacted for 24 h at room temperature. After completion of the reaction, the system was filtered; the filtrate was poured into cold ethanol to precipitate, and washed several times. Then, the crude product was dissolved in water, poured into a dialysis bag (MWCO 3500), dialyzed against with deionized water for 2-3 d, and lyophilized to obtain dextran-VS (0.8 g, 80%).

Example 91: Synthesis of Component B-24

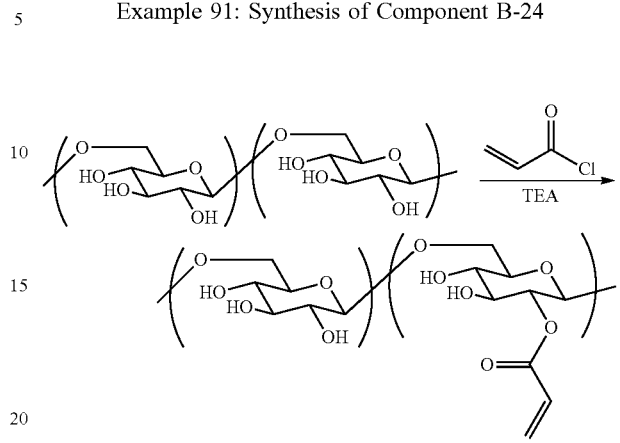

Synthesis of Component B-24: To a solution of dextran (6 g, 70 kDa) in 60 mL anhydrous dimethyl sulfoxide (DMSO) was added 2 mL triethylamine (TEA) and 0.56 mL acryloyl chloride dissolved in 10 mL dichloromethane (DCM), the mixture was reacted for 10 h. After completion of the reaction, the reaction solution was poured into ethanol to reprecipitate. The crude product obtained by filtration was redissolved in deionized water and dialyzed for 2-3 d, and then lyophilized to obtain DexAA (5.8 g). According to the nuclear magnetic resonance spectrum, the content of the double bond can be calculated to be about 10%.

Example 92: Synthesis of Component B-25

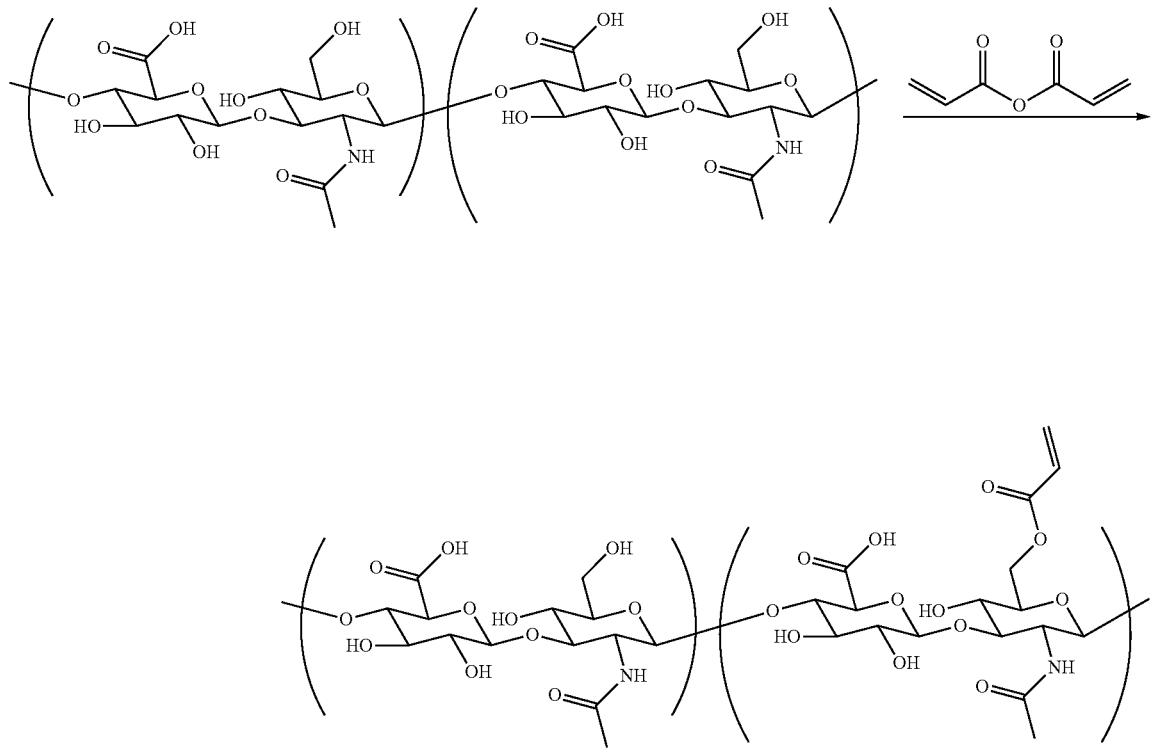

Synthesis of Component B-25: To a solution of hyaluronic acid (1 g, 48 kDa) in 100 mL deionized water was added 4 mL acrylic anhydride at 0-4° C. The solution was slowly added 2 mL 5M NaOH and reacted for 24 h. Then, the reaction solution was poured into a dialysis bag (MWCO 3500), dialyzed against deionized water for 2-3 d, and lyophilized to obtain HA-MA (0.9 g). According to the nuclear magnetic resonance spectrum, the double bond content can be calculated to be about 20%.

Example 93: Synthesis of Component B-26

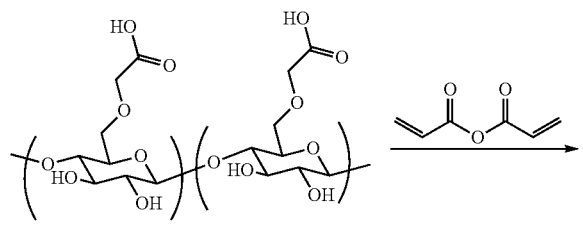

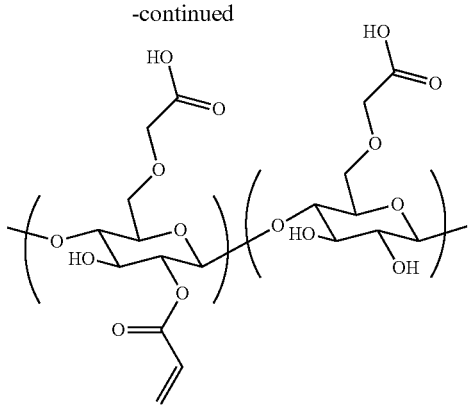

Synthesis of Component B-26: To a solution of carboxymethyl cellulose (1 g, 90 kDa) in 100 mL deionized water was added 4 mL acrylic anhydride at 0-4° C. The solution was slowly added 2 mL 5M NaOH and reacted for 24 h. Then, the reaction solution was poured into a dialysis bag (MWCO 3500), dialyzed against deionized water for 2-3 d, and lyophilized to obtain CMCMA (0.9 g). According to the nuclear magnetic resonance spectrum, the double bond content can be calculated to be about 20%.

Example 94: Synthesis of Component B-27

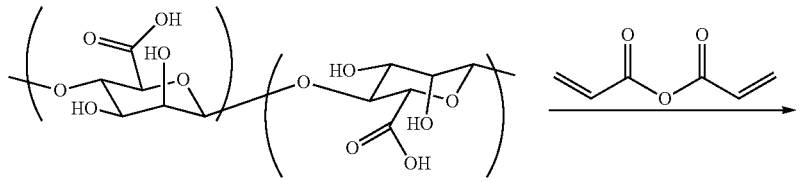

Synthesis of Component B-27: To a solution of alginate (1 g, 48 kDa) in 100 mL deionized water was added 4 mL acrylic anhydride at 0-4° C. The solution was slowly added 2 mL 5M NaOH and reacted for 24 h. Then, the reaction solution was poured into a dialysis bag (MWCO 3500), dialyzed against deionized water for 2-3 d, and lyophilized to obtain AlgMA (0.9 g). According to the nuclear magnetic resonance spectrum, the double bond content can be calculated to be about 20%.

Example 95: Synthesis of Component B-28

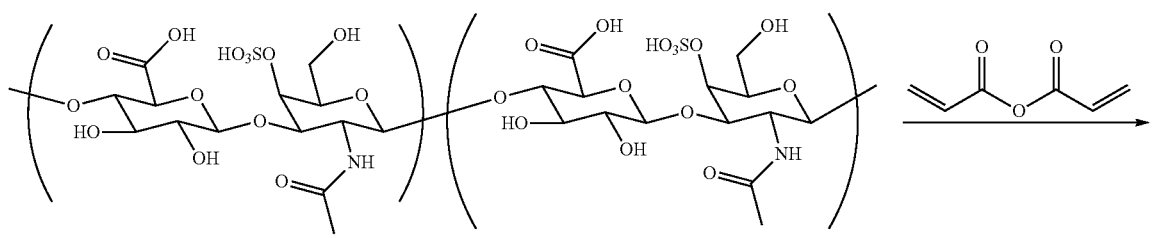

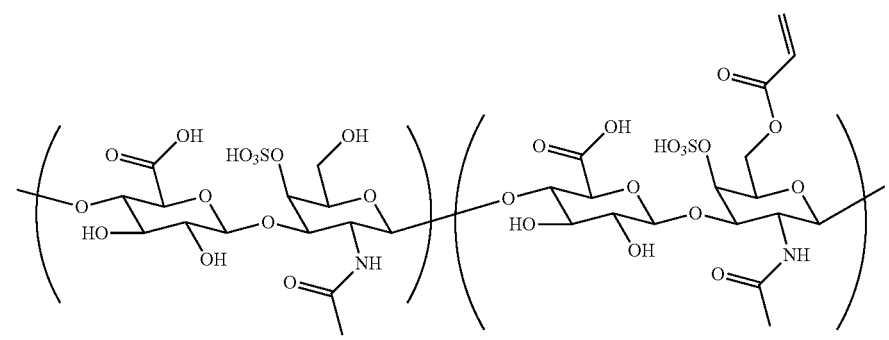

Synthesis of Component B-28: To a solution of chondroitin sulfate (1 g) in 100 mL deionized water was added 4 mL acrylic anhydride at 0-4° C. The solution was slowly added 2 mL 5M NaOH and reacted for 24 h. Then, the reaction solution was poured into a dialysis bag (MWCO 3500), dialyzed against deionized water for 2-3 d, and lyophilized to obtain CSMA (0.9 g). According to the nuclear magnetic resonance spectrum, the double bond content can be calculated to be about 20%.

Example 96: Synthesis of Component B-29

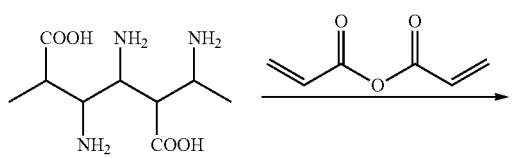

-continued

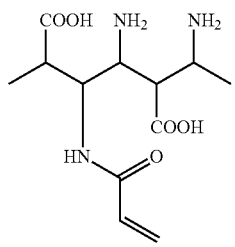

Synthesis of Component B-29: To a solution of gelatin (1 g) in 10 mL D-PBS was added 0.5 mL methacrylic anhydride, and the mixture was reacted for 2-3 h at 50° C. After completion of the reaction, the system was diluted with 40 mL D-PBS. Then, it was poured into a dialysis bag (MWCO 3500), dialyzed against deionized water for 2-3 d, and lyophilized to obtain GelMA (0.9 g). According to the nuclear magnetic resonance spectrum, the content of the double bond can be calculated to be about 20%.

Example 97: Synthesis of Component B-32

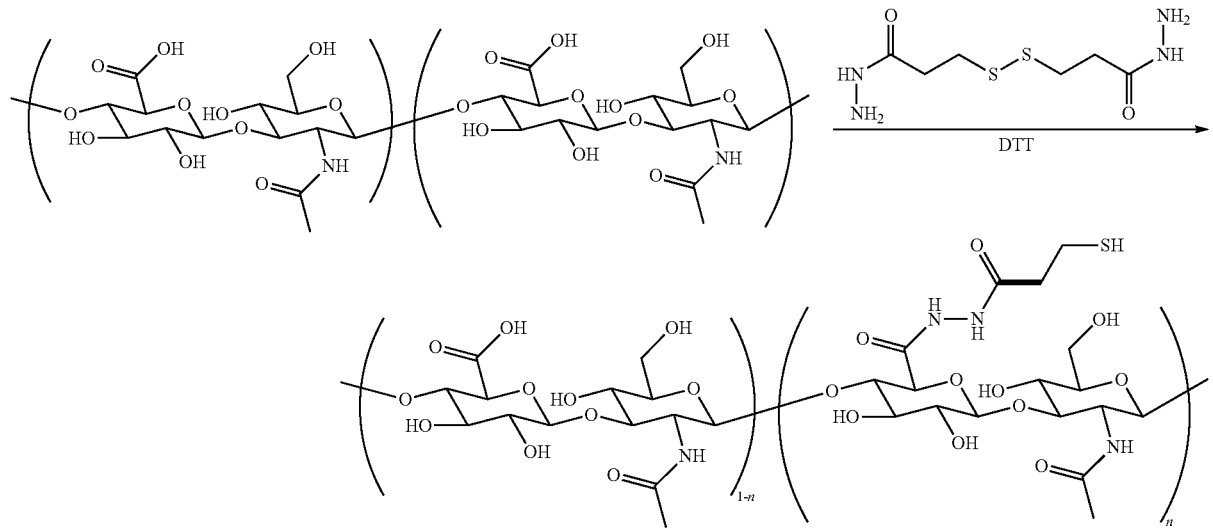

Synthesis of Component B-32: To a solution of hyaluronic acid (0.5 g, 48 kDa) in 50 mL distilled water was added hydroxybenzotriazole (HOBt, 0.2 g), 1-ethyl-(3-dimethylaminopropyl) carbodiimine hydrochloride (EDC-HCl, 0.1 g), 3, 3'-dithiobis (propionide) (DTP, 0.1 g). The mixture was adjusted to pH 4.75 with dilute hydrochloric acid solution and reacted for 24 h. Then, the solution was added DTT and continued to react for 5 h. After completion of the reaction, the solution was poured into a dialysis bag (MWCO 3500), dialyzed against deionized water for 2-3 d, and freeze-dried to obtain HA-SH (0.45 g). According to the nuclear magnetic resonance spectrum, the grafting degree of sulfhydryl group can be calculated to be about 20%.

Example 98: Synthesis of Component B-33

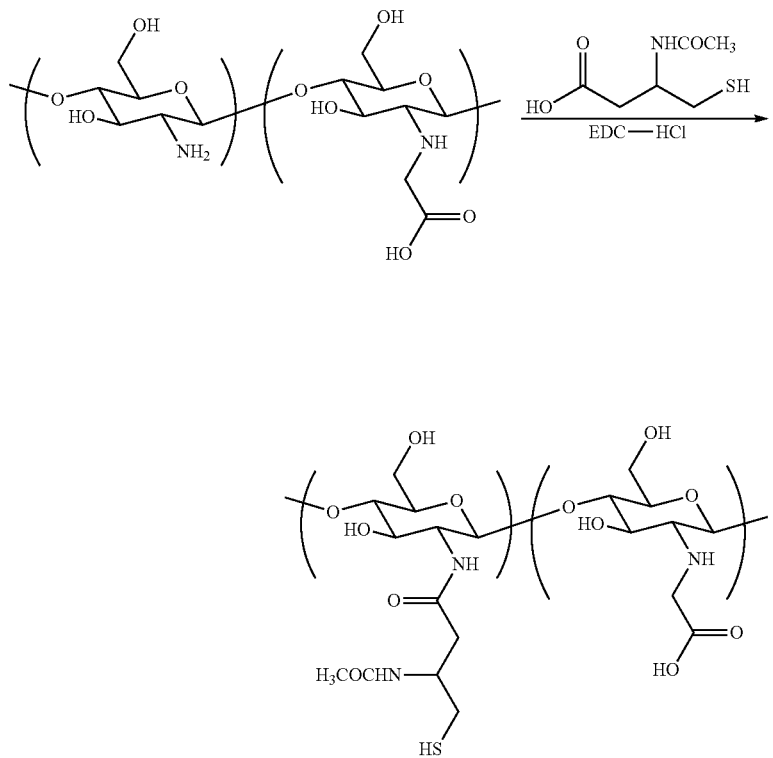

Synthesis of Component B-33: To a solution of carboxymethyl chitosan (1 g) in 100 mL of deionized water was added N-acetylcysteine (1.77 g, 10 mmol) and 1-ethyl-(3-dimethylaminopropyl) carbodiimine hydrochloride (EDC-HCl, 1.91 g, 10 mmol). The mixture was adjusted to pH 5 with hydrochloric acid, and reacted at room temperature for 5 h. Then, the solution was poured into a dialysis bag (MWCO 3500), dialyzed against 5 mM HCl solution for 1 d, and dialyzed against 5 mM HCl/1% NaCl solution for 1 d, then dialyzed against 1 mM HCl solution for 1 d, lyophilized to obtain CMCh-SH (0.9 g). According to the nuclear magnetic resonance spectrum, the grafting degree of sulfhydryl group can be calculated to be about 10%.

Example 99: Synthesis of Component B-34

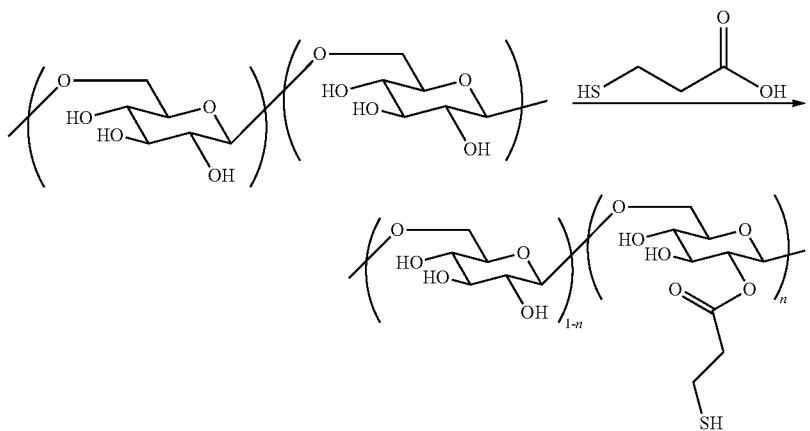

Synthesis of Component B-34: To a solution of dextran (40 kDa, 12 g, 0.3 mmol) in 50 mL DMSO was added 3-mercaptopropionic acid (636.8 mg, 6.0 mmol), 1, 3-dicyclohexyl carbodiimine (910.7 mg, 9.0 mmol) and 4-dimethylaminylpyridine (1099.5 mg, 9.0 mmol), and the solution was reacted at room temperature for 48 h. Then, it was reprecipitated in acetone. The crude product was dissolved in water, poured into a dialysis bag (MWCO 3500), dialyzed against deionized water for 2-3 d, and lyophilized to obtain Dex-SH (11.5 g). According to the nuclear magnetic resonance spectrum, the grafting degree of sulfhydryl group can be calculated to be about 20%.

Example 100: Synthesis of Component B-35

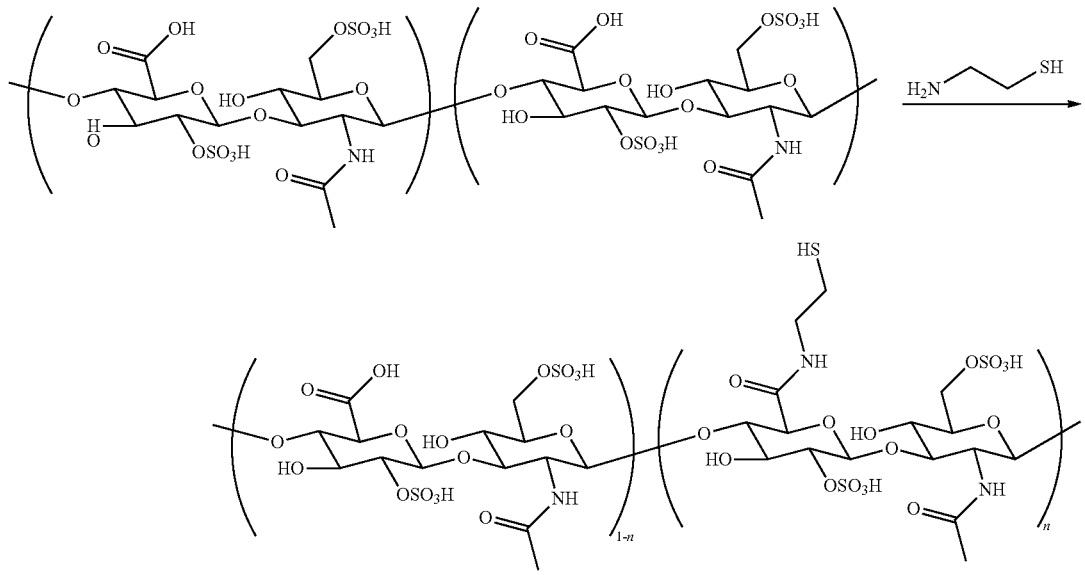

Synthesis of Component B-35: To a solution of heparin (0.5 g, 12 kDa) in 50 mL distilled water was added hydroxybenzotriazole (HOBt, 0.2 g), 1-ethyl-(3-dimethylamine-propyl) carbodiimine hydrochloride (EDC-HCl, 0.1 g) and mercaptoethylamine (0.1 g), the solution was adjusted to pH 5-6 with dilute hydrochloric acid solution and reacted for 24 h. The solution was poured into dialysis bag (MWCO 3500), dialyzed against deionized water for 2-3 d, freeze-dried to obtain Hep-SH (0.45 g). According to the nuclear magnetic resonance spectrum, the grafting degree of sulfhydryl group can be calculated to be about 20%.

Example 101: Preparation of Hydrogel by Photo-Coupling Synergistic Crosslinking Method Different hydrogel precursor solutions were prepared according to the process of the invention at 37° C. as shown in Table 1.

TABLE 1

| | | B | | | | |
|---|---|---|---|---|---|---|
| A | / | Component B-1 | Component B-2 | Component B-3 | Component B ... | Component B-35 |
| | | | | concentration | | |
| Component A-1 | 1-20 wt % | 1-20 wt % | 1-20 wt % | 1-20 wt % | 1-20 wt % | 1-20 wt % |
| Component A-2 | 1-20 wt % | 1-20 wt % | 1-20 wt % | 1-20 wt % | 1-20 wt % | 1-20 wt % |
| Component A-3 | 1-20 wt % | 1-20 wt % | 1-20 wt % | 1-20 wt % | 1-20 wt % | 1-20 wt % |
| Component A ... | 1-20 wt % | 1-20 wt % | 1-20 wt % | 1-20 wt % | 1-20 wt % | 1-20 wt % |
| Component A-82 | 1-20 wt % | 1-20 wt % | 1-20 wt % | 1-20 wt % | 1-20 wt % | 1-20 wt % |

The above different gel solutions are irradiated at 365 or 395 nm (20 mW/cm$^2$) for a certain period of time to obtain hydrogels of different chemical compositions. Different gel materials have different biological effects, and the composition of the gel material can be selected in a targeted manner according to different applications.

Note: Component A . . . is Component A-5~A-81; Component B . . . is Component B-4~B-34.

1-20 wt % in Table 1 is a preferred range of mass concentration of the hydrogel precursor solution.

Example 102: Rheology Test of Photo-Coupled Synergistically Crosslinked Hydrogel Rheology analysis was performed on a 37° C. test platform (φ=20 mm) using a HAAKE MARS rheometer. In this example, the effects of UV light time, light intensity and mass concentration of polymer derivatives on gelation time and storage modulus of hydrogels were investigated. FIG. 1 shows the gelation curve of the prepared hydrogel precursor solution under illumination of Component A-2 (HA-sNB) and Component B-3 (carboxymethyl chitosan CMCh) prepared by Example 2; Component A-47 (HA-nNB) prepared by Example 47 and Component B-11 (hydrazide-modified hyaluronic acid HA-CDH) prepared by Example 84; Component A-64 (HA-cNB) prepared by Example 64 (In the rheological test, G' is the storage modulus, G" is the loss modulus, and when G' exceeds G", it is the gel point.). As shown in FIG. 1, the solution starts to form gel at about 4 s, it is completely gelatinized in about 10 s, and the modulus at the time of complete gel formation can reach 1400 Pa. The hydrogel precursor solution (HA-nNB/HA-CDH) starts to form gel at about 8 s, it is completely gelatinized in about 15 s, and the modulus when fully gelatinized can reach 1200 Pa; The hydrogel precursor solution (HA-cNB) starts to form gel at about 2 s, it is completely gelatinized for about 10 s, and the modulus can reach 1600 Pa when fully gelatinized. Further, the strength of the gel is proportional to the mass concentration of the gel solution, and the greater the mass concentration of the gel is, the greater the strength of the gel is. The gel point and final modulus of hydrogel systems composed of other different materials are also different. The specific data are shown in Table 2.

Further, the strength of the gel is proportional to the mass concentration of the gel solution, and the greater the mass concentration of the gel, the greater the strength of the gel formed. The gel point and gel strength of hydrogel systems composed of other different materials are also different. The specific data are shown in Table 2.

TABLE 2

| Hydrogel material composition (A/B) | Gel point (s) | Gel strength (Pa) |
|---|---|---|
| HA-NB$_0$/CMCh (2% wt:2% wt) | 30 | 200 |
| Component A-2/Component B-3 (2% wt:2% wt) | 4 | 1200 |
| Component A-2/Component B-4 (2% wt:2% wt) | 12 | 550 |
| Component A-2/Component B-10 (2% wt:2% wt) | 11 | 780 |
| Component A-2/Component B-11 (2% wt:2% wt) | 3 | 1500 |
| Component A-2/Component B-14 (2% wt:2% wt) | 8 | 1060 |
| Component A-1/Component B-3 (2% wt:2% wt) | 6 | 1180 |
| Component A-3/Component B-3 (2% wt:2% wt) | 8 | 1070 |
| Component A-9/Component B-3 (2% wt:2% wt) | 5 | 1260 |
| Component A-14/Component B-3 (2% wt:2% wt) | 4 | 1240 |
| Component A-23/Component B-3 (2% wt:2% wt) | 6 | 1180 |
| Component A-28/Component B-3 (2% wt:2% wt) | 3 | 1450 |
| Component A-32/Component B-3 (2% wt:2% wt) | 9 | 1100 |
| Component A-33/Component B-3 (2% wt:2% wt) | 8 | 1150 |
| Component A-34/Component B-3 (2% wt:2% wt) | 12 | 1030 |
| Component A-35/Component B-3 (2% wt:2% wt) | 14 | 870 |
| Component A-36/Component B-3 (2% wt:2% wt) | 13 | 790 |
| Component A-38/Component B-3 (2% wt:2% wt) | 10 | 1030 |
| Component A-39/Component B-3 (2% wt:2% wt) | 12 | 890 |
| Component A-40/Component B-3 (2% wt:2% wt) | 14 | 550 |
| Component A-41/Component B-3 (2% wt:2% wt) | 11 | 670 |
| Component A-42/Component B-3 (2% wt:2% wt) | 9 | 880 |
| Component A-45/Component B-3 (2% wt:2% wt) | 8 | 1130 |
| Component A-47/Component B-11 (2% wt:2% wt) | 8 | 1200 |
| Component A-47/Component B-3 (2% wt:2% wt) | 9 | 1300 |
| Component A-47/Component B-4 (2% wt:2% wt) | 14 | 750 |
| Component A-47/Component B-10 (2% wt:2% wt) | 12 | 980 |
| Component A-47/Component B-14 (2% wt:2% wt) | 11 | 850 |
| Component A-46/Component B-11 (2% wt:2% wt) | 9 | 1080 |
| Component A-48/Component B-11 (2% wt:2% wt) | 9 | 1140 |
| Component A-50/Component B-11 (2% wt:2% wt) | 8 | 1260 |

TABLE 2-continued

| Hydrogel material composition (A/B) | Gel point (s) | Gel strength (Pa) |
|---|---|---|
| Component A-56/Component B-11 (2% wt:2% wt) | 10 | 1190 |
| Component A-59/Component B-11 (2% wt:2% wt) | 6 | 1580 |
| Component A-60/Component B-11 (2% wt:2% wt) | 10 | 1000 |
| Component A-61/Component B-11 (2% wt:2% wt) | 11 | 900 |
| Component A-62 Component B-11 (2% wt:2% wt) | 13 | 860 |
| Component A-63/Component B-11 (2% wt:2% wt) | 2 | 1860 |
| Component A-64/Component B-3 (2% wt:2% wt) | 2 | 1700 |
| Component A-64/Component B-4 (2% wt:2% wt) | 2 | 1680 |
| Component A-64/Component B-10 (2% wt:2% wt) | 2 | 1780 |
| Component A-64/Component B-11 (2% wt:2% wt) | 2 | 1890 |
| Component A-64/Component B-14 (2% wt:2% wt) | 2 | 1670 |
| Component A-64 Component B-17 (2% wt:2% wt) | 2 | 2050 |
| Component A-64/Component B-20 (2% wt:2% wt) | 2 | 1980 |
| Component A-64/Component B-23 (2% wt:2% wt) | 2 | 1800 |
| Component A-64/Component B-32 (2% wt:2% wt) | 2 | 2600 |
| Component A-64 (2% wt) | 2 | 1600 |
| Component A-65 (2% wt) | 2 | 1580 |
| Component A-66 (2% wt) | 2 | 1590 |
| Component A-67 (2% wt) | 2 | 1500 |
| Component A-69 (2% wt) | 2 | 1480 |
| Component A-74 (2% wt) | 2 | 1450 |
| Component A-78 (2% wt) | 2 | 2100 |
| Component A-79 (2% wt) | 2 | 1250 |
| Component A-80 (2% wt) | 2 | 1650 |
| Component A-81 (2% wt) | 2 | 1180 |
| Component A-82 (2% wt) | 2 | 1210 |

Note:
$NB_0$ is o-nitrobenzyl phototriggers used for constructing of hydrogels reported in the literature. (Yunlong Yang; Jieyuan Zhang; Zhenzhen Liu; Qiuning Lin; Xiaolin Liu; Chunyan Bao; Yang Wang; Linyong Zhu. Adv. Mater. 2016, 28, 2724.).
$HA-NB_0$ is hyaluronic acid polymer derivatives modified with $NB_0$.
sNB is o-nitrobenzyl sulfide phototriggers in Component A-2 of the invention;
nNB is cyclic o-nitrobenzylamine phototriggers in Component A-47 of the invention;
cNB is cyclic o-nitrobenzyl phototriggers in Component A-64 of the invention.
Among them, HA-sNB is Component A-2; HA-nNB is Component A-47; HA-cNB is Component A-64.

Example 103: Adhesion Test of Photo-Coupling Synergistic Crosslinking Hydrogel Fresh pig casings were taken and cutted into 3.5 cm×2.5 cm casing pieces, and then fixed to 6.5 cm×2.5 cm tempered glass piece using 502 glue. The above tempered glass piece was taken, and 150 μL of a certain component of the hydrogel precursor solution was applied to one of the connected casing surfaces. Then, another piece of glass was placed over the above piece of glass to completely opposite, and the excess extruded hydrogel precursor solution was wiped off. The casing was irradiated for 5 min using a 395 nm UV LED source (20 mW/cm$^2$) to allow the hydrogel precursor solution to gel in situ between the two casings. After the glue was completed, one end of the glass piece was vertically fixed, and the other end was connected to a container capable of holding water through a string. The metered water was then continuously added to the container until the two pieces of glass were broken. Thereafter, the mass of the water and the container at this time was recorded and converted into gravity, that was, the tensile force F when the glass piece was broken. The tissue adhesion of the hydrogel was calculated using the following formula:

Hydrogel tissue adhesion=$F/A$

Figure 2:
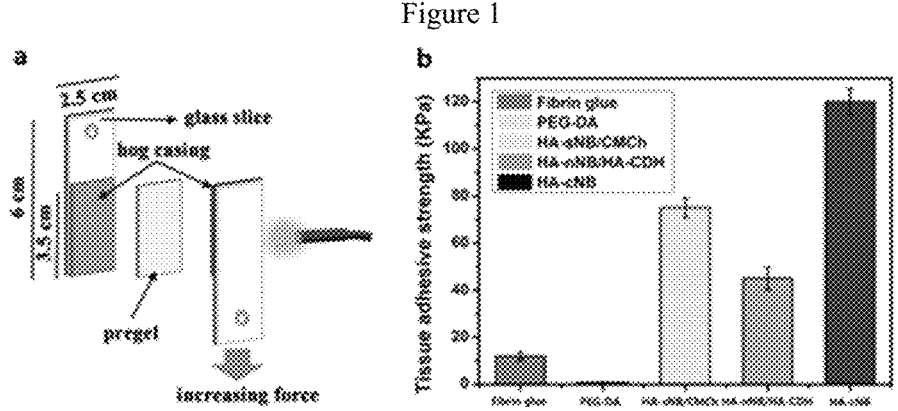
FIG. 2 is an adhesion test graph of the hydrogel (2% HA-sNB/2% CMCh or 2% HA-nNB/2% HA-CDH or 2% HA-cNB).

A is the adhesion area of the casing, and the test device is shown in FIG. 2. The tissue adhesion of hydrogel systems composed of other different materials is also different. The specific data is shown in Table 3.

TABLE 3

| Hydrogel material composition (A/B) | Tissue adhesion (kPa) |
|---|---|
| HA-NB$_0$/CMCh (2% wt:2% wt) | 24 |
| Component A-2/Component B-3 (2% wt:2% wt) | 78 |
| Component A-2/Component B-4 (2% wt:2% wt) | 85 |
| Component A-2/Component B-10 (2% wt:2% wt) | 68 |
| Component A-2/Component B-11 (2% wt:2% wt) | 71 |
| Component A-2/Component B-14 (2% wt:2% wt) | 63 |
| Component A-1/Component B-3 (2% wt:2% wt) | 61 |
| Component A-3/Component B-3 (2% wt:2% wt) | 73 |
| Component A-9/Component B-3 (2% wt:2% wt) | 69 |
| Component A-14/Component B-3 (2% wt:2% wt) | 65 |
| Component A-23/Component B-3 (2% wt:2% wt) | 73 |
| Component A-28/Component B-3 (2% wt:2% wt) | 87 |
| Component A-32/Component B-3 (2% wt:2% wt) | 82 |
| Component A-33/Component B-3 (2% wt:2% wt) | 80 |
| Component A-34/Component B-3 (2% wt:2% wt) | 72 |
| Component A-35/Component B-3 (2% wt:2% wt) | 62 |
| Component A-36/Component B-3 (2% wt:2% wt) | 60 |
| Component A-38/Component B-3 (2% wt:2% wt) | 68 |
| Component A-39/Component B-3 (2% wt:2% wt) | 60 |
| Component A-40/Component B-3 (2% wt:2% wt) | 54 |
| Component A-41/Component B-3 (2% wt:2% wt) | 56 |
| Component A-42/Component B-3 (2% wt:2% wt) | 52 |
| Component A-45/Component B-3 (2% wt:2% wt) | 50 |
| Component A-47/Component B-11 (2% wt:2% wt) | 48 |
| Component A-47/Component B-3 (2% wt:2% wt) | 43 |
| Component A-47/Component B-4 (2% wt:2% wt) | 41 |
| Component A-47/Component B-10 (2% wt:2% wt) | 40 |
| Component A-47/Component B-14 (2% wt:2% wt) | 38 |
| Component A-46/Component B-11 (2% wt:2% wt) | 42 |
| Component A-48/Component B-11 (2% wt:2% wt) | 45 |
| Component A-50/Component B-11 (2% wt:2% wt) | 43 |
| Component A-56/Component B-11 (2% wt:2% wt) | 44 |
| Component A-59/Component B-11 (2% wt:2% wt) | 51 |
| Component A-60/Component B-11 (2% wt:2% wt) | 47 |
| Component A-61/Component B-11 (2% wt:2% wt) | 45 |
| Component A-62 Component B-11 (2% wt:2% wt) | 38 |
| Component A-63/Component B-11 (2% wt:2% wt) | 35 |
| Component A-64/Component B-3 (2% wt:2% wt) | 135 |
| Component A-64/Component B-4 (2% wt:2% wt) | 131 |
| Component A-64/Component B-10 (2% wt:2% wt) | 128 |
| Component A-64/Component B-11 (2% wt:2% wt) | 123 |
| Component A-64/Component B-14 (2% wt:2% wt) | 126 |
| Component A-64Component B-17 (2% wt:2% wt) | 120 |
| Component A-64/Component B-20 (2% wt:2% wt) | 124 |
| Component A-64/Component B-23 (2% wt:2% wt) | 118 |
| Component A-64/Component B-32 (2% wt:2% wt) | 115 |
| Component A-64 (2% wt) | 122 |
| Component A-65 (2% wt) | 121 |
| Component A-66 (2% wt) | 124 |
| Component A-67 (2% wt) | 120 |
| Component A-69 (2% wt) | 119 |
| Component A-74 (2% wt) | 115 |
| Component A-78 (2% wt) | 118 |
| Component A-79 (2% wt) | 116 |
| Component A-80 (2% wt) | 113 |
| Component A-81 (2% wt) | 115 |
| Component A-82 (2% wt) | 114 |

Figure 3:
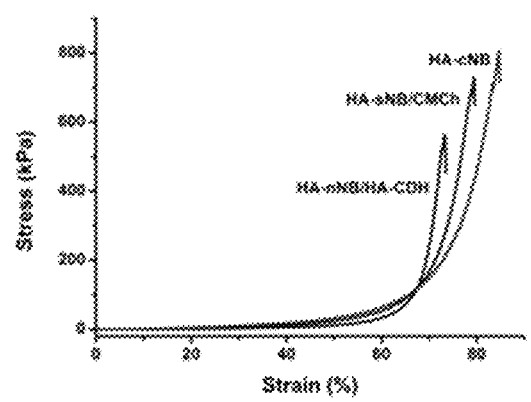
FIG. 3 is a compression test diagram of the hydrogel (2% HA-sNB/2% CMCh or 2% HA-nNB/2% HA-CDH or 2% HA-cNB).

Example 104: Mechanical Properties Test of Photo-Coupling Synergistic Crosslinking Hydrogel The mechanical properties test was performed by GT-TCS-2000 tensile machine (including tensile test and compression test). The tensile test specimen is a dumbbell specimen with a length of 20 mm, a width of 3 mm and a thickness of 2 mm, and the test speed is 5 mm/min. The compression test sample is a cylindrical specimen with a diameter of 10 mm and a height of 3 mm, and the test speed is 1 mm/min. Take the hydrogel compared in Component A-2 (HA-sNB), Component B-3 (carboxymethyl chitosan CMCh) prepared in Example 2; Component A-47 (HA-nNB) prepared in Example 47 and Component B-11 (hydrazide modification hyaluronic acid HA-CDH) prepared in Example 84; Component A-64 (HA-cNB) was prepared in Example 64 as an example to test the tensile and compressive properties of the hydrogel. As shown in FIG. 3, the hydrogel (HA-sNB/CMCh) can be compressed to about 80% with the compression strength of about 700 KPa, and can be stretched to about 120% with the tensile strength of about 75 kPa; the hydrogel (HA-nNB/HA-CDH) can be compressed to about 70% with compression strength of about 450 KPa, and can be stretched to about 90% with tensile strength of about 40 kPa; hydrogel (HA-cNB) can be compressed to about 85%, the compression strength is about 800 kPa, and can be stretched to about 145% with tensile strength of about 90 kPa. The mechanical properties of hydrogel systems composed of other different materials are also different. The specific data are shown in Table 4.

TABLE 4

| Hydrogel material composition (A/B) | compression deformation rate (%) | compression strength (kPa) | Tensile deformation rate (%) | Tensile Strength (kPa) |
|---|---|---|---|---|
| HA-NB$_0$/CMCh (2% wt:2% wt) | 45 | 200 | 55 | 15 |
| Component A-2/Component B-3 (2% wt:2% wt) | 80 | 700 | 120 | 75 |
| Component A-2/Component B-4 (2% wt:2% wt) | 87 | 875 | 145 | 82 |
| Component A-2/Component B-10 (2% wt:2% wt) | 75 | 680 | 112 | 71 |
| Component A-2/Component B-11 (2% wt:2% wt) | 77 | 680 | 116 | 73 |
| Component A-2/Component B-14 (2% wt:2% wt) | 71 | 625 | 105 | 68 |
| Component A-1/Component B-3 (2% wt:2% wt) | 78 | 650 | 112 | 73 |
| Component A-3/Component B-3 (2% wt:2% wt) | 73 | 640 | 107 | 67 |
| Component A-9/Component B-3 (2% wt:2% wt) | 76 | 655 | 113 | 69 |
| Component A-14/Component B-3 (2% wt:2% wt) | 71 | 620 | 112 | 63 |
| Component A-23/Component B-3 (2% wt:2% wt) | 73 | 640 | 104 | 62 |
| Component A-28/Component B-3 (2% wt:2% wt) | 85 | 750 | 127 | 73 |
| Component A-32/Component B-3 (2% wt:2% wt) | 78 | 645 | 112 | 72 |
| Component A-33/Component B-3 (2% wt:2% wt) | 76 | 635 | 108 | 69 |
| Component A-34/Component B-3 (2% wt:2% wt) | 65 | 580 | 102 | 64 |
| Component A-35/Component B-3 (2% wt:2% wt) | 76 | 575 | 104 | 65 |
| Component A-36/Component B-3 (2% wt:2% wt) | 62 | 580 | 100 | 61 |
| Component A-38/Component B-3 (2% wt:2% wt) | 68 | 560 | 103 | 68 |
| Component A-39/Component B-3 (2% wt:2% wt) | 65 | 550 | 108 | 63 |
| Component A-40/Component B-3 (2% wt:2% wt) | 62 | 530 | 105 | 52 |
| Component A-41/Component B-3 (2% wt:2% wt) | 56 | 470 | 89 | 42 |
| Component A-42/Component B-3 (2% wt:2% wt) | 52 | 430 | 82 | 41 |
| Component A-45/Component B-3 (2% wt:2% wt) | 50 | 420 | 81 | 40 |
| Component A-47/Component B-11 (2% wt:2% wt) | 70 | 450 | 90 | 40 |
| Component A-47/Component B-3 (2% wt:2% wt) | 65 | 420 | 82 | 37 |
| Component A-47/Component B-4 (2% wt:2% wt) | 79 | 540 | 105 | 46 |
| Component A-47/Component B-10 (2% wt:2% wt) | 65 | 410 | 87 | 72 |
| Component A-47/Component B-14 (2% wt:2% wt) | 61 | 410 | 82 | 36 |
| Component A-46/Component B-11 (2% wt:2% wt) | 58 | 400 | 83 | 37 |
| Component A-48/Component B-11 (2% wt:2% wt) | 59 | 430 | 85 | 32 |
| Component A-50/Component B-11 (2% wt:2% wt) | 63 | 410 | 81 | 36 |
| Component A-56/Component B-11 (2% wt:2% wt) | 67 | 445 | 84 | 39 |
| Component A-59/Component B-11 (2% wt:2% wt) | 74 | 475 | 95 | 48 |
| Component A-60/Component B-11 (2% wt:2% wt) | 64 | 435 | 81 | 35 |
| Component A-61/Component B-11 (2% wt:2% wt) | 66 | 455 | 85 | 36 |
| Component A-62 Component B-11 (2% wt:2% wt) | 61 | 380 | 78 | 29 |
| Component A-63/Component B-11 (2% wt:2% wt) | 60 | 365 | 76 | 26 |
| Component A-64/Component B-3 (2% wt:2% wt) | 85 | 800 | 145 | 90 |
| Component A-64/Component B-4 (2% wt:2% wt) | 83 | 760 | 134 | 82 |
| Component A-64/Component B-10 (2% wt:2% wt) | 81 | 740 | 130 | 81 |
| Component A-64/Component B-11 (2% wt:2% wt) | 80 | 720 | 136 | 86 |
| Component A-64/Component B-14 (2% wt:2% wt) | 82 | 775 | 132 | 82 |

TABLE 4-continued

| Hydrogel material composition (A/B) | compression deformation rate (%) | compression strength (kPa) | Tensile deformation rate (%) | Tensile Strength (kPa) |
|---|---|---|---|---|
| Component A-64 Component B-17 (2% wt:2% wt) | 78 | 780 | 138 | 80 |
| Component A-64/Component B-20 (2% wt:2% wt) | 76 | 730 | 134 | 76 |
| Component A-64/Component B-23 (2%w t:2% wt) | 74 | 725 | 132 | 72 |
| Component A-64/Component B-32 (2% wt:2% wt) | 71 | 721 | 127 | 70 |
| Component A-64 (2% wt) | 83 | 670 | 124 | 72 |
| Component A-65 (2% wt) | 81 | 620 | 121 | 70 |
| Component A-66 (2% wt) | 78 | 580 | 116 | 67 |
| Component A-67 (2% wt) | 75 | 565 | 113 | 65 |
| Component A-69 (2% wt) | 73 | 555 | 118 | 62 |
| Component A-74 (2% wt) | 71 | 530 | 102 | 63 |
| Component A-78 (2% wt) | 70 | 510 | 105 | 65 |
| Component A-79 (2% wt) | 74 | 505 | 103 | 61 |
| Component A-80 (2% wt) | 71 | 510 | 102 | 66 |
| Component A-81 (2% wt) | 68 | 480 | 98 | 61 |
| Component A-82 (2% wt) | 65 | 450 | 93 | 60 |

Example 105: Biocompatibility Test of Photo-Coupling Synergistic Crosslinking Hydrogel In this experiment, Component A-2 (HA-sNB) and Component B-3 (carboxylmethyl chitosan CMCh) prepared in Example 2, Component A-47 (HA-nNB) prepared in Example 47 and Component B-11 (hydrazide-modified hyaluronic acid HA-CDH) prepared in Example 84, or Component A-64 prepared in Example 64 (HA-cNB) were taken as examples to be evaluated by CCK-8 kit. First, fibroblast HDFs were seeded in a 96-well plate with a cell density of $5 \times 10^3$ cells/well, then added the medium and cultured at 37° C./5% $CO_2$ for 24 h. Each group of test samples diluted in a cell culture medium was added to well plate in which cells were cultured, and cultured for 24 h. Then, the cell fluid in the well was aspirated and added 100 μL of the medium and 10 μL of CCK-8 solution, and the cells were further incubated for 2 h. Finally, the absorbance at 450 nm in each well was measured using a microplate reader. Cell viability is calculated as follows:

Cell Viability (%)=(The average absorbance of the experimental group/the average absorbance of the control group)×100%

Figure 4:
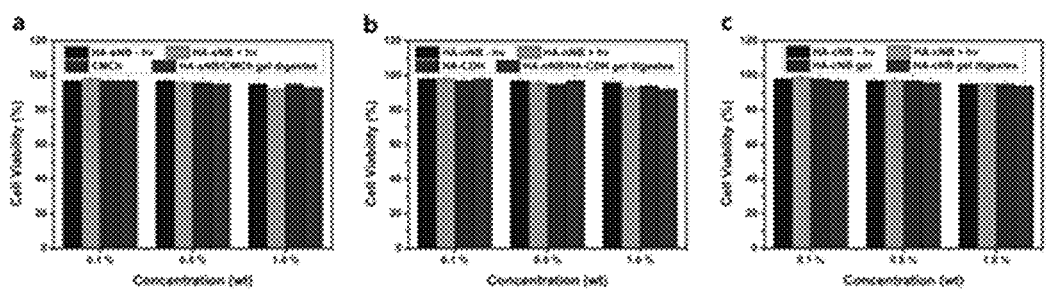
FIG. 4 is a graph of biocompatibility testing of the hydrogel (HA-sNB/CMCh or HA-nNB/HA-CDH or HA-cNB).

As shown in FIG. 4, this Formula of photo-coupling synergistic crosslinking hydrogel has good biocompatibility.

In the in vivo immune inflammatory response test, Component A-2 (HA-sNB) and Component B-3 (carboxylmethyl chitosan CMCh) prepared in Example 2, Component A-47 (HA-nNB) prepared in Example 47 and Component B-11 (hydrazide-modified hyaluronic acid HA-CDH) prepared in Example 84, or Component A-64 prepared in Example 64 (HA-cNB) were taken as examples to be implanted under the skin of the rabbit, and the inflammatory reaction of the hydrogel on the body was analyzed by tissue section staining at different time points.

The biocompatibility of other hydrogel systems compared by different materials is also different. The specific data is shown in Table 5.

TABLE 5

| Hydrogel material composition (A/B) | Survival rate (%) |
|---|---|
| Component A-2/ Component B-3 | 98 |
| Component A-2/ Component B-4 | 95 |
| Component A-2/ Component B-10 | 94 |
| Component A-2/ Component B-11 | 91 |
| Component A-2/ Component B-14 | 93 |
| Component A-1/ Component B-3 | 94 |
| Component A-3/ Component B-3 | 93 |
| Component A-9/ Component B-3 | 95 |
| Component A-14/ Component B-3 | 95 |
| Component A-23/ Component B-3 | 93 |
| Component A-28/ Component B-3 | 97 |
| Component A-32/ Component B-3 | 92 |
| Component A-33/ Component B-3 | 90 |
| Component A-34/ Component B-3 | 92 |
| Component A-35/ Component B-3 | 97 |
| Component A-36/ Component B-3 | 93 |
| Component A-38/ Component B-3 | 98 |
| Component A-39/ Component B-3 | 90 |
| Component A-40/ Component B-3 | 94 |
| Component A-41/ Component B-3 | 96 |
| Component A-42/ Component B-3 | 92 |
| Component A-45/ Component B-3 | 96 |
| Component A-47/ Component B-11 | 98 |
| Component A-47/ Component B-3 | 93 |
| Component A-47/ Component B-4 | 91 |
| Component A-47/ Component B-10 | 94 |
| Component A-47/ Component B-14 | 98 |
| Component A-46/ Component B-11 | 92 |
| Component A-48/ Component B-11 | 95 |
| Component A-50/ Component B-11 | 94 |
| Component A-56/ Component B-11 | 93 |
| Component A-59/ Component B-11 | 96 |
| Component A-60/ Component B-11 | 92 |
| Component A-61/ Component B-11 | 94 |
| Component A-62/ Component B-11 | 96 |
| Component A-63/ Component B-11 | 97 |
| Component A-64/ Component B-3 | 94 |
| Component A-64/ Component B-4 | 98 |

TABLE 5-continued

| Hydrogel material composition (A/B) | Survival rate (%) |
|---|---|
| Component A-64/ Component B-10 | 91 |
| Component A-64/ Component B-11 | 94 |
| Component A-64/ Component B-14 | 98 |
| Component A-64 Component B-17 | 96 |
| Component A-64/ Component B-20 | 94 |
| Component A-64/ Component B-23 | 93 |
| Component A-64/ Component B-32 | 92 |
| Component A-64 | 90 |
| Component A-65 | 95 |
| Component A-66 | 97 |
| Component A-67 | 92 |
| Component A-69 | 98 |
| Component A-74 | 95 |
| Component A-78 | 93 |
| Component A-79 | 94 |
| Component A-80 | 96 |
| Component A-81 | 98 |
| Component A-82 | 92 |

The relationship between component A and component B in the hydrogel materials of the above different components is 2% wt: 0.2% wt. The relationship between component A and component B and component C was 2% wt: 0.2% wt: 2% wt.

Figure 5:
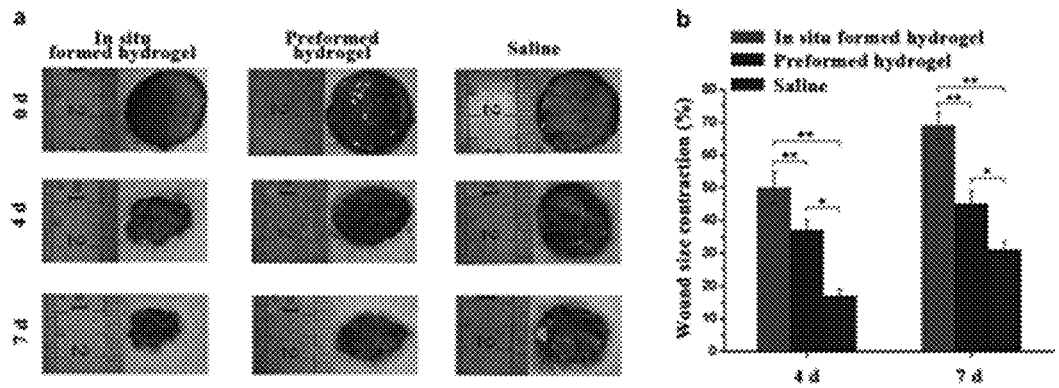
FIG. 5 is a visual representation of the effect of wound closure of the hydrogel (Component A-64).

Example 106: Photo-Coupling Synergistic Crosslinking Hydrogel for Wound Closure-Skin Repair In the experiment, a total skin defect wound with a diameter of 1.8 cm was constructed on the back of SD rats. Then 400 L hydrogel precursor solution (2% Component A-64) was filled into the wound site. Due to the good fluidity of the solution, the wound could be sufficiently filled and infiltrated by the hydrogel precursor solution. Then, under the illumination of 395 nm LED light source, the hydrogel was performed in situ in the skin defect, which closed the wound (as shown in FIG. 5). Then, the repair effects of in-situ hydrogels, preformed hydrogels and saline treatment on the back skin wounds of SD rats were compared within 7 days. The wound healing rate of in-situ hydrogels was significantly faster than the other two groups. The wound shrinkage area was the largest at 7 days, which played a good repairing effect. Preformed hydrogel materials was difficult to adequately fill the wound site. In addition, there is a lack of good organizational integration because of no seamless interface with covalent connections between organizations. And it is difficult for new cells and tissues to quickly enter the hydrogel material, so that the preformed hydrogel cannot fully play the role of the scaffold material. As a result, the repair rates and effects of pre-formed hydrogel were worse than in-situ hydrogels. The wound repair rate without hydrogel filling is the slowest, indicating that the photo-crosslinking hydrogel can promote wound repair as a cell scaffold material to.

Hydrogel systems of different materials (Component A: Component A-1 to Component A-82; Component B: Component B-1 to Component B-35) as photo-coupling synergistic crosslinking hydrogel can also be used for wound closure and skin repair.

Figure 6:
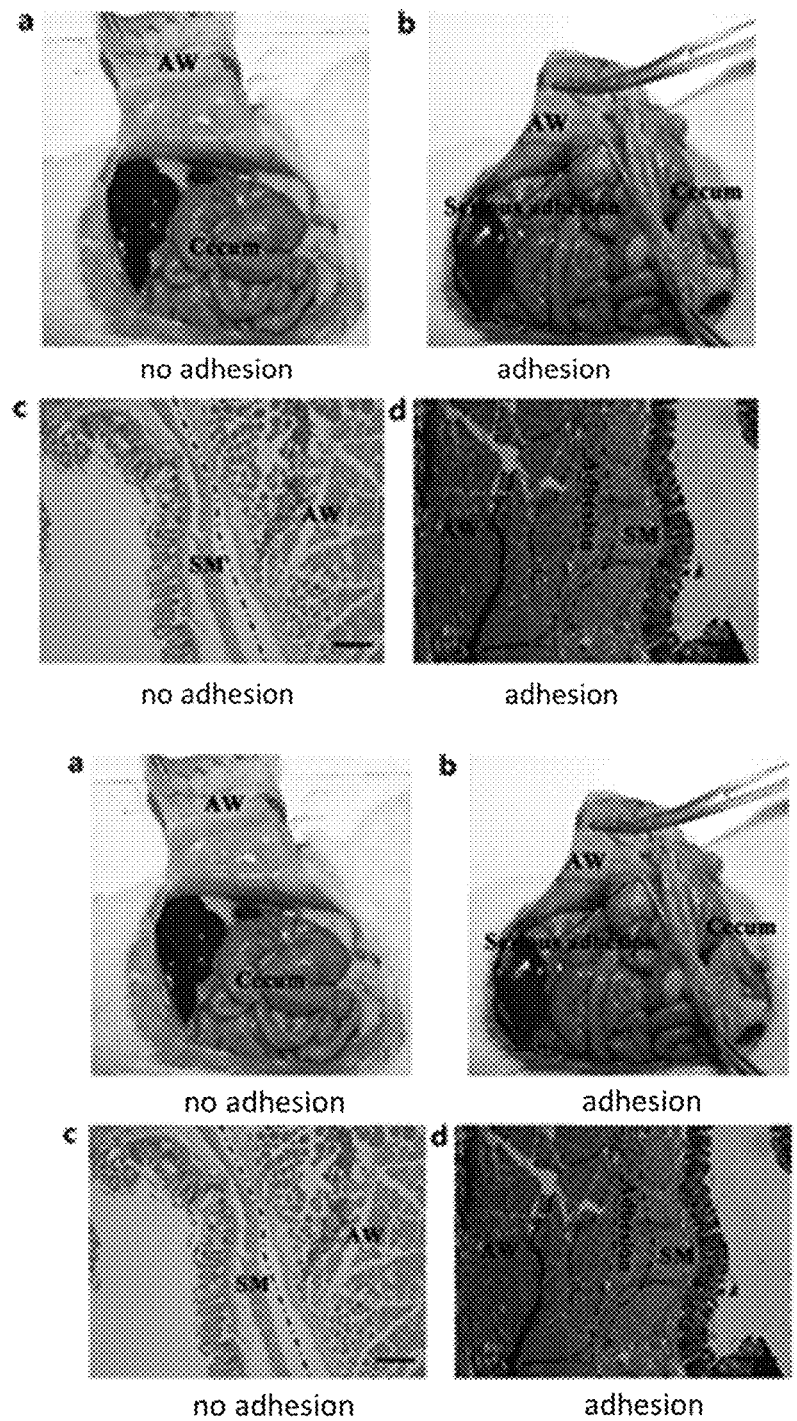
FIG. 6 is an effect view of the hydrogel as postoperative anti-adhesion (Component A-64).

Example 107: Photo-Coupling Synergistic Crosslinking Hydrogel for Wound Closure-Postoperative Anti-Adhesion In the experiment, SD rats were used to construct an adhesion model of abdominal wall-cecum scraping. Because the cecum is the thickest, most accessible, and most abundant intestine in the abdominal cavity, the probability of abdominal adhesion is extremely high when the corresponding abdominal wall is simultaneously damaged and no measures are taken. The structural adhesion model is stable. During the surgery, the hydrogel precursor solution (2% Component A-64) can adequately cover the cecal and abdominal wall wounds, and has sufficient residence time on the vertical tissue surface until it is lightly gelled. After giving 30 s of light, the obtained hydrogel was fixed at the wound site, and the hydrogel was not peeled off from the wound site with a certain force applied by a surgical blade. The above process from the administration of the hydrogel precursor solution to the complete gelation can be completed within 1 min (as shown in FIG. 6). After the surgery, the above SD rats were reared for 14 days in a sterile environment. After 14 days, the abdominal cavity of SD rats was opened again, and the abdominal adhesion was recorded. Among the 10 rats in the hydrogel-treated experimental group, 8 rats did not show any intestinal-abdominal wall and intestinal-intestinal adhesion after 14 days; One rat developed a moderate adhesion between the abdominal wall and the cecum; one rat developed a thin layer of adhesion between the intestine and the intestine. In addition, no residual hydrogel residue was observed in the above 9 SD rats without intestinal-abdominal adhesion, and the wound on the abdominal wall was completely healed. Severe abdominal and cecal adhesions occurred in 10 rats in the control group. Next, histological analysis of the tissue sections of the wound site in the experimental and control groups was performed by H&E staining. The injury of the cecum and abdominal wall was completely restored after 14 days in the SD rats in the experimental group, and the surface layer was re-epithelialized. In 14 days after SD rats in the control group, the smooth muscle of the cecum was completely fused with the muscle tissue of the abdominal wall, and fibroblasts and inflammatory cells were deposited at the adhesion site.

Hydrogel systems of other different materials (Component A: Component A-1 to Component A-82; Component B: Component B-1 to Component B-35) belong to photo-coupling synergistic crosslinking hydrogels, which can also be applied to wound closure-postoperative anti-adhesion.

Example 108: Photo-Coupling Synergistic Crosslinking Hydrogel for Wound Closure-Oral Ulcer In the experiment, an oral ulcer defect wound with a diameter of 1.0 cm was constructed in the oral cavity of SD rats. Then fill the wound site with 200 μL of the hydrogel precursor solution (2% Component A-64). Due to the good fluidity of the solution, the wound can be sufficiently filled and infiltrated by the hydrogel precursor solution. Then, under the illumination of a 395 nm LED light source, a hydrogel was prepared in situ at the oral cavity to achieve closure of the oral wound. Next, the repair effect of the in-situ hydrogel, the pre-formed hydrogel and the SD rat oral wound treated with physiological saline alone was compared in 7 days. The wound healing rate of in-situ hydrogels was significantly faster than the other two groups. The wound shrinkage area was the largest at 7 days, which played a good repairing effect. The pre-formed hydrogel material is difficult to fully fill the wound site; in addition, there is no seamless interface with covalent connections between the tissues, and lack of good tissue integration. It is difficult for new cells and tissues to quickly enter the hydrogel material, so that it can fully play the role of the scaffold material. As a result, pre-formed hydrogel repair rates and effects are worse than in-situ hydrogels. The wound repair rate without hydrogel filling is the slowest, indicating that the photo-crosslinking hydrogel acts as a cell scaffold material to promote oral ulcer repair.

Hydrogel systems of other different materials (Component A: Component A-1 to Component A-82; Component B: Component B-1 to Component B-35) belong to photo-coupling synergistic crosslinking hydrogels and can also be applied to wound closures-oral ulcers.

Example 109: Photo-Coupling Synergistic Crosslinking Hydrogel for Tissue Permeation Sealing-Intestinal Leakage Sealing New Zealand male white rabbits were used and divided into two groups for cecal leakage closure experiments: a: hydrogel treatment (2% Component A-64) group; b: untreated control group. In the experiment, a model of leakage was made in the cecum of the rabbit, and then the hydrogel precursor solution was applied to the wound. After being fully infiltrated, the light was gelled in situ, and the hydrogel adhered firmly to the defect after gelation. No additional fixing is required. Four weeks after the operation, the rabbits in the experiment were sacrificed by intravenous injection of air, and the cecum was extracted to evaluate the effect of the experimental repair. The results showed that there was no leakage of the cecum blocked with hydrogel, and severe leakage occurred in the cecum without hydrogel treatment. After several weeks of repair, the original cecal defect has been repaired by hydrogel treatment. Therefore, the hydrogel can not only effectively block the leakage, but also facilitate the repair of damaged tissue after surgery.

Hydrogel systems composed of other different materials (Component A: Component A-1 to Component A-82; Component B: Component B-1 to Component B-35) belong to photo-coupled synergistically crosslinked hydrogels, and can also be applied to tissue exudate plugging-intestinal leakage plugging.

Example 110: Photo-Coupled Synergistically Crosslinked Hydrogel for Tissue Exudation Plugging-Surgical Suture Male New Zealand white rabbits were used and divided into three groups for surgical suture experiments: a: hydrogel treatment (2% Component A-64) group; b: surgical suture treatment group; c: no control group. In the experiment, a model of wound suture was made in the abdomen of the rabbit. In group a, the hydrogel precursor solution is applied to the wound, and after being fully infiltrated, the light is in situ gelled to achieve the sealing of the wound. Due to the excellent tissue adhesion of the hydrogel, the effect of tissue suturing can be achieved; group b was treated with conventional surgical sutures; group c was treated without treatment. Two weeks after the operation, the rabbits in the experiment were sacrificed by intravenous injection of air, and samples were taken to evaluate the effect of the experimental repair. The results showed that the wound treated with the hydrogel had a better suturing effect, which was almost the same as the surgical suture group, and the wounds that were not treated could not be effectively joined together. After 4 weeks of repair, the original wound defect site was hydrogel treated and the tissue was able to connect together and was significantly repaired. Therefore, the hydrogel can not only effectively suture the wound, but also facilitate the repair of the damaged tissue after surgery.

Hydrogel systems of other different materials (Component A: Component A-1 to Component A-82; Component B: Component B-1 to Component B-35) belong to photo-coupling synergistic crosslinking hydrogel, and can also be applied to tissue exudate plugging-surgical sutures.

Figure 7:
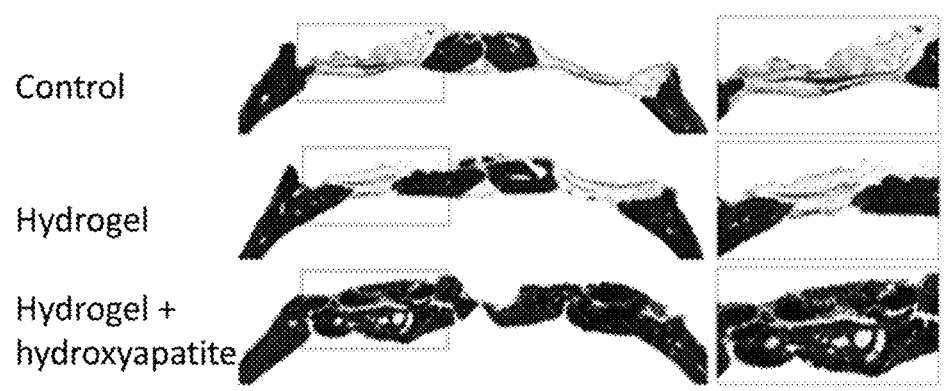
FIG. 7 is an effect view of the hydrogel as bone tissue engineering scaffold material (Component A-64).

Example 111: Photo-Coupling Synergistic Crosslinking Hydrogel for Hemostatic Material-Liver Hemostasis The SD rats were used to evaluate the hemostatic effect of the hydrogel, and the liver hemostasis experiments were divided into three groups: a: gelatin sponge group; b: hydrogel treatment (2% Component A-64) group; c positive control group. The rats were anesthetized by intraperitoneal injection of chloral hydrate (4% aqueous solution). The injection was measured to be 0.9 ml/100 g. After deep anesthesia, the rat's anterior chest was shaved with a shaver and the iodine was disinfected. Then cut approximately 4 cm long incision along the midline of the chest, open the chest and expose the liver. Make an approximately 2 cm incision in the left lobe of the liver. Group a was treated with gelatin sponge to stop bleeding; group b was treated with hydrogel precursor solution at the incision to cover the section, and 395 nm LED light for 2 min to form a gel to stop bleeding; The c group did not do any treatment, so that the liver incision oozing naturally coagulated, and the oozing was sucked by gauze, and the amount of bleeding and the bleeding time were recorded by the weight loss method (as shown in FIG. 7). After the end of the experiment, group a adhered to the cut gelatin sponge and left in the rat for suturing. Group b hydrogels were cross-connected in situ in the incision and the wounds were isolated, the liver was placed back into the chest, and sutured. Group c was directly sutured without treatment. After 14 days, the liver recovery of SD rats was observed. The rats were sacrificed by intraperitoneal injection of excess anesthetic chloral hydrate (4% aqueous solution, 2.7 ml/100 g). The thoracic cavity was opened along the midline of the thoracic cavity, and the liver recovery of the three groups of rats was observed and photographed. At the same time, the liver injury site was sampled, and the specimen was fixed with 4% formalin solution for 2 days. After dehydration treatment, paraffin was embedded and sliced with a microtome. The thickness of the sample was 5 μm. Finally, the specimens were subjected to H&E staining, and photographs were taken with an optical microscope. The experimental results showed that the liver of group b recovered well, the hydrogel was completely degraded, no adhesion occurred, and the liver incision grew new liver tissue. The gelatin sponge in the rats in group a was still not degraded, and the adhesion between the organs and the omentum was severe. Hepatic and omental adhesions were common in group c. H&E staining showed that the liver surface of the experimental group was smooth and round, with abundant blood vessel distribution and clear liver interface. The liver of the adhesion was found by H&E staining, and the liver interface was uneven. The liver and the omentum were stuck together, and there were deposited inflammatory cells at the interface.

Hydrogel systems of other different materials (Component A: Component A-1 to Component A-82; Component B: Component B-1 to Component B-35) belong to photo-coupling synergistic crosslinking hydrogel, and can also be applied to hemostatic materials-liver hemostasis.

Example 112: Photo-Coupling Synergistic Crosslinking Hydrogel Applied to Hemostatic Material-Bone Section Hemostasis Male New Zealand white rabbits were used and divided into three groups for bone section hemostasis experiments: a: hydrogel treatment (2% Component A-64) group; b: bone wax treatment group; c: Control group not treated. In the experiment, a bone section bleeding model was made in the rabbit femur. In group a, the hydrogel precursor solution is applied to the wound, and after being fully infiltrated, the light is in situ gelatinized to achieve effective sealing of the bone section bleeding. Due to the excellent tissue adhesion and photocuring speed of the hydrogel, a timely and effective hemostatic effect can be achieved; Group b is the treatment of bleeding wounds with conventional bone wax; Group c is not treated for bleeding wounds. After 8 weeks of surgery, the rabbits in the experiment were sacrificed by intravenous injection of air, and samples were taken to evaluate the effect of the experimental repair. The results showed that the hydrogel-treated wounds had a better hemostatic effect, which was almost the same as the bone wax group, and the wounds that were not treated had sustained bleeding. After 2 weeks of repair, the original wound hemorrhage site was treated with hydrogel treatment, and the bone wax treated wound was not repaired, mainly because the bone wax did not degrade in the body. Therefore, the hydrogel can not only effectively achieve hemostasis of the bone section, but also facilitate the repair of damaged tissue after surgery.

Hydrogel systems of other different materials (Component A: Component A-1 to Component A-82; Component B: Component B-1 to Component B-35) belong to photo-coupling synergistic crosslinking hydrogel, and can also be applied to hemostasis materials-bone section hemostasis.

Example 113: Photo-Coupling Synergistic Crosslinking Hydrogel for Hemostatic Material-Arterial Hemostasis Male New Zealand white rabbits were used and divided into three groups for arterial hemostasis: a: hydrogel treatment (2% Component A-64) group; b: hemostat treatment group; c: A control group that was not treated. In the experiment, a bleeding model was made in the rabbit femoral artery. In group a, the hydrogel precursor solution is applied to the wound, and after being fully infiltrated, the light is in situ gelatinized to achieve effective sealing of the femoral artery bleeding. Due to the excellent tissue adhesion and photocuring speed of the hydrogel, a timely and effective hemostatic effect can be achieved; group b was treated with conventional hemostatic forceps to treat bleeding wounds; group c was treated without bleeding wounds. Two weeks after the operation, the rabbits in the experiment were sacrificed by intravenous injection of air, and samples were taken to evaluate the effect of the experimental repair. The results show that the wound treated with hydrogel has a better hemostatic effect, which is almost the same as that of the hemostatic forceps, and the wound that is not treated will have a continuous bleeding condition. After 2 weeks of repair, the original wound hemorrhage site was treated with hydrogel and the tissue was repaired. Therefore, the hydrogel can not only effectively achieve femoral artery hemostasis, but also facilitate repair of damaged tissue after surgery.

Hydrogel systems of other different materials (Component A: Component A-1 to Component A-82; Component B: Component B-1 to Component B-35) belong to photo-coupling synergistic crosslinking hydrogel, and can also be applied to hemostatic materials-arterial hemostasis.

Example 114: Photo-Coupling Synergistic Crosslinking Hydrogel for Hemostatic Material-Cardiac Hemostasis New Zealand male white rabbits were used and divided into three groups for cardiac hemostasis experiments: a: hydrogel treatment (2% Component A-64); b: gelatin sponge treatment group; c: control group not treated. In the experiment, a bleeding model was made in the rabbit heart. In group a, the hydrogel precursor solution is applied to the wound, and after being fully infiltrated, the light is in situ gelled to achieve effective sealing of the heart bleeding. Due to the excellent tissue adhesion and photocuring speed of the hydrogel, a timely and effective hemostatic effect can be achieved; Group b is to treat bleeding wounds with a conventional gelatin sponge; Group c is not treated for bleeding wounds. Two weeks after the operation, the rabbits in the experiment were sacrificed by intravenous injection of air, and samples were taken to evaluate the effect of the experimental repair. The results show that the wound treated with hydrogel has a better hemostatic effect, and the hemostatic effect of the gelatin sponge is better than that of the wound without treatment. After 2 weeks of repair, the original wound hemorrhage site was treated with hydrogel and the tissue was repaired significantly, and the repair effect was better than gelatin sponge. Therefore, the hydrogel can not only effectively achieve cardiac hemostasis, but also facilitate repair of damaged tissue after surgery.

Hydrogel systems of other different materials (Component A: Component A-1 to Component A-82; Component B: Component B-1 to Component B-35) belong to photo-coupling synergistic crosslinking hydrogel, and can also be applied to hemostatic materials-cardiac hemostasis.

Example 115: Photo-Coupling Synergistic Crosslinking Hydrogel for Tissue Engineering Scaffold Material-Cartilage Repair Male New Zealand white rabbits were used and divided into three groups for repair of articular cartilage: a: group of hydrogels (2% Component A-64) wrapped with chondrocytes, that is, a group of Gel+ chondrocytes; b: pure hydrogel (2% Component A-64) group, ie Gel group. c: The control group that is not processed, that is, the Control group. In the experiment, the hydrogel precursor solution can fully penetrate and fill the defect of the rabbit articular cartilage, and the glue adheres firmly to the defect after the glue is formed, and no additional fixation is needed. After 12 weeks of surgery, the rabbits in the experiment were sacrificed by intravenous injection of air, and the injured joints were extracted to evaluate the experimental repair effect. Gross photographs of rabbit articular cartilage lesions showed that after 12 weeks, the Gel+ chondrocyte group developed smooth neonatal cartilage tissue at the joint defect and was well integrated with the old cartilage tissue; The cartilage was also repaired in the Gel group, but the contour of the cartilage wound during surgery was also seen; In the Control group, the cartilage tissue was basically not repaired, and the lesion was still obvious. Next, we further evaluated the repair of cartilage in each of the above groups by H&E staining. H&E staining results showed that both the Gel+ chondrocyte group and the Gel group had new tissue formation and integrated well with the old cartilage tissue; however, the thickness of the new tissue of the Gel+ chondrocyte group was better than that of the Gel group, and the surface was flat; In the Control group, it is difficult to find obvious signs of new tissue. In addition, the components of neonatal cartilage were analyzed by Safranin-O and immunohistochemical staining. In the Gel+ chondrocyte group and the Gel group, the neonatal cartilage tissue showed a Safranin-O staining activity, and it was confirmed that the new cartilage tissue contained the glycoprotein component of normal cartilage. At the same time, the neonatal cartilage tissue of the Gel+ chondrocyte group and the Gel group showed staining activity of Formula II collagen, which proved that the cartilage tissue contained a large amount of Formula II collagen. The results of the above-mentioned Safranin-O and immunohistochemical staining demonstrated that the new cartilage tissue was hyaline cartilage when the new photo-crosslinking hydrogel material was used for cartilage repair.

Hydrogel systems of other different materials (Component A: Component A-1 to Component A-82; Component B: Component B-1 to Component B-35) belong to photo-coupled synergistically crosslinked hydrogel and can also be applied to tissue engineering scaffold materials-cartilage repair.

Example 116: Photo-Coupling Synergistic Crosslinking Hydrogel for Tissue Engineering Scaffold Material-Bone Repair SD rats were used for skull repair experiments, and the above SD rats were randomly divided into three groups: a: hydrogel (2% Component A-64)+hydroxyapatite experimental group; b: hydrogel (2% Component A-64) experimental group; c: control group without material treatment. In the experiment, 4% chloral hydrate solution (0.9 mL per gram body weight) was used for abdominal anesthesia and iodine disinfection. Then, the scalp at the skull of the rat is opened using a surgical blade. A complete skull defect model with a diameter of 5 mm was symmetrically fabricated on the left and right sides of the mouse skull using a dental ring drill. In the experimental group, 200 μL of the hydrogel precursor solution was filled into the SD rat skull defect to fully penetrate the wound edge; the 395 nm LED light source (20 mW/cm$^2$) was used to illuminate it for 30 seconds to completely gel. Finally, suture the mouse's scalp with a suture. In the control group, after the SD rat skull defect model was made, the scalp was directly sutured without any other treatment. The above SD rats were kept in a sterile, 37° C. environment for 8 weeks. Then, the repair of the skull of SD rats in each group was evaluated by micro-CT scanning imaging. The results showed that in the control group without any treatment, the skull defect of SD rats was not substantially repaired, and the osteogenesis of the skull defect filled with hydrogel was newly formed, but the amount of new bone tissue was small, most of the defects were not well repaired, and the skull defect filled with hydrogel+hydroxyapatite was basically repaired, and a large amount of new bone tissue was formed at the defect. The histological staining of the skull was then performed by Van Gieson staining. The results showed that both the hydrogel+hydroxyapatite-treated SD rats had intact new bone tissue in the skull defect, while only a small amount of new bone tissue was formed in the skull defect treated with hydrogel. Most of the defects were still found. The bone tissue at the site was still in a defect state, and in the control group, almost no new bone tissue was formed. The tissue staining results further confirmed that the hydrogel coated with hydroxyapatite has a good repair effect on bone defects (as shown in FIG. 7).

Hydrogel systems of different materials (Component A: Component A-1 to Component A-82; Component B: Component B-1 to Component B-35) belong to photo-coupling synergistic crosslinking hydrogel Glue can also be applied to tissue engineering scaffold materials-bone repair.

Figure 8:
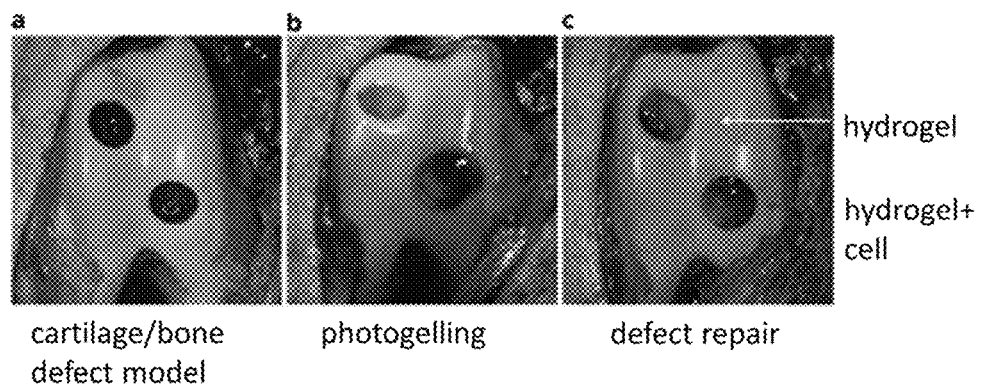
FIG. 8 is an effect view of the hydrogel as bone/cartilage composite defect tissue engineering (Component A-64).

Example 117: Photo-Coupling Synergistic Crosslinking Hydrogel for Tissue Engineering Scaffold Material-Bone/Cartilage Composite Defect Repair Pigs were used as animal models. The cartilage phase material was hydrogel (2% Component A-64)+ chondrocytes. The bone phase material was hydrogel (2% Component A-64)+hydroxyapatite+BMSCs. Repair experiments of joint bone/cartilage complex defects for three groups: a (Gel+ cell group): hydrogel (2% Component A-64) group contains chondrocytes and BMSCs; b (Gel group): simple hydrogel (2% Component A-64) group. In the experiment, the bone phase material is first filled into the bone phase defect, and the gel precursor solution is fully infiltrated. After the light is gelatinized, the hydrogel adheres firmly to the bone defect, and then the cartilage phase material is filled into the cartilage phase defect. At the same time, the hydrogel firmly adheres to the cartilage defect after the light is glued (as shown in FIG. 8). Six months after the operation, the experimental pigs were sacrificed and the injured joints were extracted to evaluate the experimental repair effect. The Gel+ cell group developed smooth neonatal cartilage tissue and bone tissue at the joint defect, and was well integrated with the old cartilage/bone tissue. At the same time, the cartilage tissue and bone tissue were also well integrated; in the Gel group, the middle bone/cartilage tissue is basically not repaired, and the damage is still obvious. Next, the repair of the above groups of cartilage was further evaluated by the method of H&E staining. H&E staining results showed that the Gel+ cell group had new tissue formation and it was well integrated with the old cartilage tissue; however, it was difficult to find obvious signs of new tissue in the Gel group. In addition, the components of neonatal cartilage were analyzed by Safranin-O and immunohistochemical staining. In the Gel+ cell group, the neonatal cartilage tissue exhibited a Safranin-O staining activity, and it was confirmed that the new cartilage tissue contained the glycoprotein Component of normal cartilage. At the same time, the neonatal cartilage tissue of the Gel+ cell group showed the staining activity of type II collagen, which proved that the cartilage tissue contained a large amount of type II collagen. The results of the above Safranin-O and immunohistochemical staining demonstrated that the new cartilage tissue was hyaline cartilage when the new photo-crosslinking hydrogel material was used for cartilage repair. Then, the histological sections of the bone were analyzed by histological staining using Van Gieson staining. The results showed that the bone defect in the Gel+ cell group grew intact new bone tissue, while in the Gel group, only a small amount of new bone tissue was formed in the bone defect, and the bone tissue in most of the defect was still in a defect state. The tissue staining results further confirmed that the cell-added hydrogel has a good repair effect on bone defects.

Hydrogel systems of different materials (Component A: Component A-1 to Component A-82; Component B: Component B-1 to Component B-35) belong to photo-coupling synergistic crosslinking hydrogel can also be applied to tissue engineering scaffold material-bone/cartilage complex defect repair.

Figure 9:
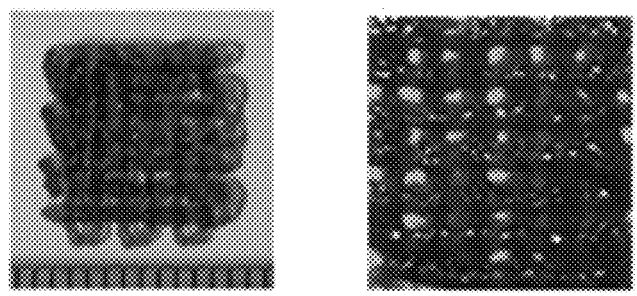
FIG. 9 is an effect view of the hydrogel as bio-ink (Component A-64).

Example 118: Photo-Coupling Synergistic Crosslinking Hydrogel for 3D Printing (FDM) Bio-Ink 3D printing technology is a three-dimensional molding technology that has been rapidly developed in recent years and has been widely used. Currently, 3D printing technology includes fused deposition (FDM), photocuring (SLA), laser sintering (SLS), continuous liquid level. Manufacturing type (CLIP), etc. However, the method suitable for cell printing is mainly FDM. The material with cell printing is mainly hydrogel material. Therefore, the development of 3D printed bio-ink-printable hydrogel materials and improved resolution of hydrogel material printing are fundamental issues in the field. Taking the Component A-64 which was prepared in the Example 64 as an Example, a certain mass concentration of the hydrogel precursor solution is uniformly mixed with the cells, and then placed in a low temperature printing barrel to control the printing temperature at about 25° C., and the viscosity of the bio-ink is adjusted by temperature to obtain the best printing state, and then the appropriate printing pressure and printing speed are determined, and the biological printing of different structures is performed, and the hydrogel is cross-linked by light after printing (or print while lighting) to obtain a cell-structured hydrogel with 3D cell culture (as shown in FIG. 9).

Hydrogel systems of different materials (Component A: Component A-1 to Component A-82; Component B: Component B-1 to Component B-35) belong to photo-coupling synergistic crosslinking hydrogel can also be applied to 3D printing (FDM) bio-ink.

Example 119: Photo-Coupling Synergistic Crosslinking Hydrogel for 3D Printing (DLP) Bio-Ink DLP (Digital Light Processing) 3D printing technology is a new type of photo-curing printing method developed in recent years. Compared with SLA (stereo-curing) printers, DLP has faster printing speed, higher resolution, and the advantages that most printing methods can't match. DLP 3D printing technology had certain application prospects in the fields of dental models and jewelry design. However, the printing inks currently used in the market are limited to photocurable resins, and hydrogels have not received much attention as an emerging bio-ink, mainly because there is no hydrogel material suitable for DLP printing. The photo-coupling synergistic crosslinking hydrogel material proposed by the invention is suitable for 3D printing with its fast photocuring speed and excellent mechanical properties, and it avoids free radicals during printing due to the non-free radical photo-crosslinking principle. The curing problem caused by diffusion makes this type of hydrogel have higher printing accuracy. Taking the Component A-64 which was prepared in Example 64 as an Example, a certain mass concentration of the hydrogel precursor solution is uniformly mixed with the cells, and then charged into the liquid tank. By controlling the intensity of the light source, the exposure time and other parameters to adjust the printing of the bio-ink to obtain the best printing state, a hydrogel with both cells and structure can be obtained, and the 3D cell culture can be studied.

Hydrogel systems of different materials (Component A: Component A-1 to Component A-82; Component B: Component B-1 to Component B-35) belong to photo-coupling synergistic crosslinking hydrogel can also be applied to 3D printing (DLP) bio-ink.

Example 120: Photo-Coupling Synergistic Crosslinking Hydrogel for Drug Wrapping and Release Hydrogel is a crosslinking polymer network that swells in water but does not dissolve. Since the hydrogel is mostly composed of water, it has very good biocompatibility and it is especially suitable for pharmaceuticals and a carrier of a biologically active macromolecule. The drug or biologically active macromolecule encapsulated in the hydrogel material achieves the sustained release of the drug by diffusion of the molecule and degradation of the material. Taking the drug package and release as an Example, the following is a specific Example: taking the Component A-64 which was prepared in the Example 64 as an Example, dissolving it in physiological saline to prepare a hydrogel precursor solution of a certain mass concentration, and added a certain amount of the drug molecule, take 200 µL of the above solution in a circular mold to be a hydrogel under illumination, and then put it into a 24-well cell culture plate, added a certain amount of physiological saline for drug release test, and analyze the drug in the solution by ultraviolet test. The release amount is used to evaluate the release effect of the material on the drug.

Hydrogel systems of different materials (Component A: Component A-1 to Component A-82; Component B: Component B-1 to Component B-35) belong to photo-coupling synergistic crosslinking hydrogel can also be applied to the wrapping and release of drugs.

The above description of the embodiments is intended to facilitate the understanding and application of the invention by those skilled in the field. It will be apparent to those skilled in the field that various modifications may be made to these embodiments and the general principles described herein may be applied to other embodiments without departing from the invention. Therefore, the present invention is not limited to the embodiments described above, and those skilled in the field should be able to make modifications and changes within the scope of the invention without departing from the scope of the invention.

We claim:

1. A cyclic o-nitrobenzyl phototrigger represented by Formula I-2:

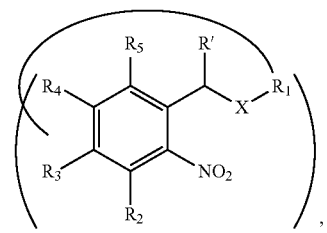

where X is S or NH;

when X=S, the cyclic o-nitrobenzyl phototrigger is a cyclic o-nitrobenzyl sulfide phototrigger, when X=NH, the cyclic o-nitrobenzyl phototrigger is a cyclic o-nitrobenzyl amine phototrigger;

$R_1$ is directly bonded to X, and $R_1$ is directly bonded to one of $R_2$, $R_3$, $R_4$, and $R_5$ to form a cyclic structure;

R' is selected from the group consisting of a hydrogen atom, a halogen atom, a hydroxyl group, a sulfhydryl group, an amine group, a nitro group, a cyano group, an aldehyde group, a ketone group, an ester group, an amide group, a phosphonic acid group, a phosphonate group, a sulfonate group, a sulfone group, a sulfoxide group, an aryl group, a heteroaryl group, an alkyl group, an alkylene group, a modified alkyl group, and a modified alkylene group;

$R_1$ includes one selected from the group consisting of a hydrogen atom, an ether group, an ester group, a carbonate group, urethane group, mercapto formate group, and a phosphate group;

$R_2$, $R_3$, $R_4$, and $R_5$ each independently includes one selected from the group consisting of a hydrogen atom, a halogen atom, a hydroxyl group, a sulfhydryl group, an amine group, a nitro group, a cyano group, an aldehyde group, a ketone group, an ester group, an amide group, a phosphonic acid group, a phosphonate group, a sulfonic acid group, a sulfonate group, a sulfone group, a sulfoxide group, an aryl group, a heteroaryl group, an alkyl group, an alkylene group, a modified alkyl group, and a modified alkylene group;

two or more of $R_2$, $R_3$, $R_4$, and $R_5$ are connected to form a saturated or unsaturated alicyclic ring, alicyclic heterocycle, aromatic ring, or aromatic heterocycle, together with carbon atom(s).

2. The cyclic o-nitrobenzyl phototrigger as in claim 1, wherein the alkyl group is a saturated or unsaturated aliphatic linear or branched alkyl group having 1 to 30 carbon atoms, the alkylene group is a saturated or unsaturated aliphatic linear chain or branched alkylene group with 1-30 carbon atoms, the modified alkyl group contains a carbon atom at least substituted by one selected from the group consisting of a halogen atom, —OH, —SH, —NO$_2$, —CN, —CHO, —COOH, ester, amide, aromatic, arylidene, —CO—, —O—, —S—, —SO—, —SO$_2$—, amino, secondary amine, tertiary amine, quaternary ammonium salt, saturated or unsaturated single or double cyclic alkylene, and bridged aliphatic heterocyclic, the modified alkyl group has 1~30 carbon atoms whose carbon-carbon single bond is replaced optionally and independently by a carbon-carbon double bond or a carbon-carbon triple bond, the modified alkylene group contains a carbon atom at least substituted by one selected from the group consisting of a halogen atom, —OH, —SH, —NO$_2$, —CN, —CHO, —COOH, ester, amide, aromatic, arylidene, —CO—, —O—, —S—, —SO—, —SO$_2$—, amino, secondary amine, tertiary amine, quaternary ammonium salt, saturated or unsaturated single or double cyclic alkylene, and bridged aliphatic heterocyclic, the modified alkylene group has 1~30 carbon atoms whose carbon-carbon single bond is optionally and independently replaced by a carbon-carbon double bond or a carbon-carbon triple bond, the ether group is selected from the following structures:
—(CH$_2$)$_x$CH$_3$, —(CH$_2$CH$_2$O)$_x$CH$_3$, —(CH$_2$)$_x$(CH$_2$CH$_2$O)$_y$CH$_3$, and

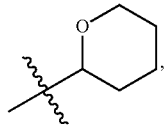

where x and y≥0 and are integers, the ester group is selected from the following structures:
—CO(CH$_2$)$_x$CH$_3$, —CO(CH$_2$CH$_2$O)$_x$CH$_3$, and —CO(CH$_2$)$_x$(CH$_2$CH$_2$O)$_y$CH$_3$, where x and y≥0 and are integers, the carbonate group is selected from the following structures:
—COO(CH$_2$)$_x$CH$_3$, —COO(CH$_2$CH$_2$O)$_x$CH$_3$, and —COO(CH$_2$)$_x$(CH$_2$CH$_2$O)$_y$CH$_3$, where x and y≥0 and are integers, the urethane group is selected from the following structures:
—CONH(CH$_2$CH$_2$O)$_x$CH$_3$, or —CONH(CH$_2$)$_x$(CH$_2$CH$_2$O)$_y$CH$_3$, where x and y≥0 and are integers, the mercapto formate group is selected from the following structures:
—COS(CH$_2$)$_x$CH$_3$, —COS(CH$_2$CH$_2$O)$_x$CH$_3$, and —COS(CH$_2$)$_x$(CH$_2$CH$_2$O)$_y$CH$_3$, where x and y≥0 and are integers, the phosphate group is selected from the following structures:
—POOO(CH$_2$)$_x$CH$_3$, —POOO(CH$_2$CH$_2$O)$_x$CH$_3$, and —POOO(CH$_2$)$_x$(CH$_2$CH$_2$O)$_y$CH$_3$, where x and y≥0 and are integers, the aryl ring is a monocyclic or fused bicyclic ring of 5-10 atoms, the heteroaryl is a monocyclic or fused bicyclic ring containing 5 to 10 atoms, the ring contains at least one hetero atom selected from N, O, S, and Si, the halogen atom is independently selected from F, Cl, Br, and I, the alicyclic ring is a saturated or unsaturated monocyclic or polycyclic alicyclic ring of 3 to 10 atoms, the aliphatic heterocyclic ring is a saturated or unsaturated monocyclic or polycyclic alicyclic ring of 3 to 10 atoms, and the ring contains at least one hetero atom selected from N, O, S, and Si, when the heteroalicyclic ring contains an S atom, the S atom optionally takes the form of —S—, —SO— or —SO$_2$—; H on the alicyclic or alicyclic ring is optionally substituted by a halogen atom, a nitro group, an aryl group, or an alkyl group or a modified alkyl group, the aromatic ring is a monocyclic or fused bicyclic ring of 5-10 atoms, and the aromatic heterocycle is a monocyclic or fused bicyclic ring containing 5 to 10 atoms, the ring contains at least one hetero atom selected from N, O, S, and Si; H on the aromatic ring or the aromatic heterocyclic ring is substituted by a halogen atom, a nitro group, an aryl group, an alkyl group, or a modified alkyl group.

3. The cyclic o-nitrobenzyl phototrigger as in claim 2, wherein the cyclic o-nitrobenzyl phototrigger is selected from the following cyclic structures:

-continued
Compound 93
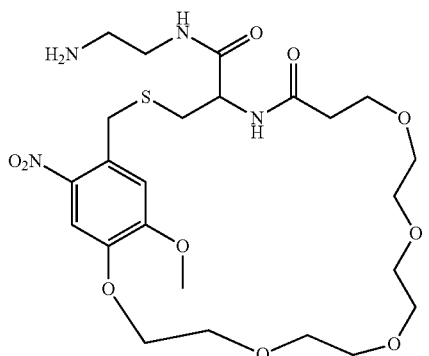
Compound 94
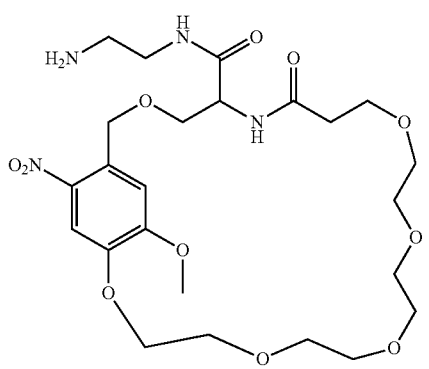
Compound 95
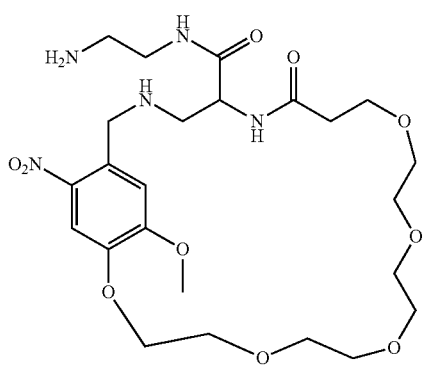
Compound 96
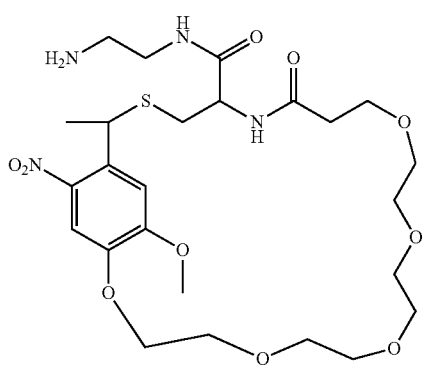
Compound 97
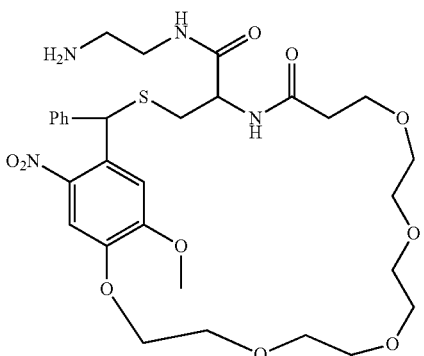
Compound 98
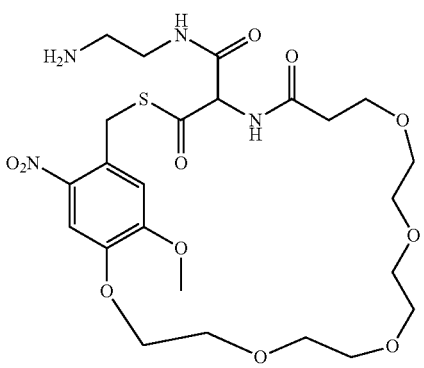
Compound 99
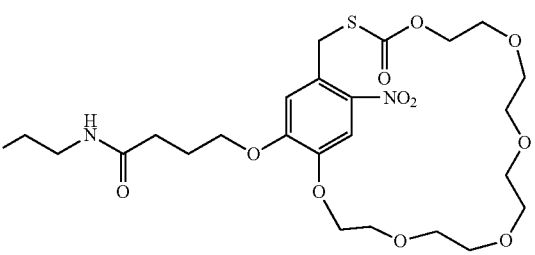
Compound 100
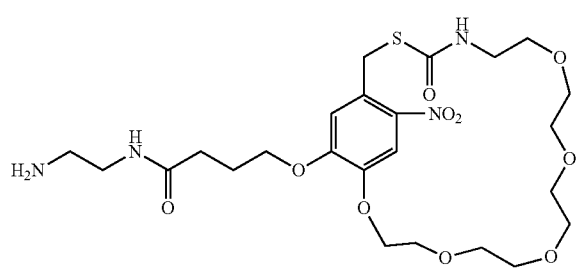

Compound 101
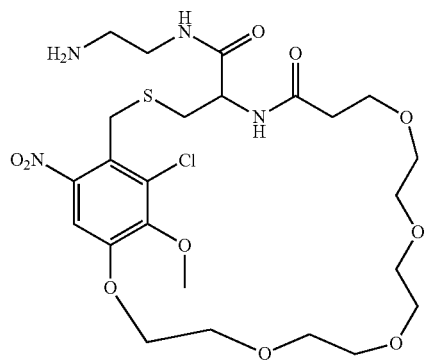
Compound 105
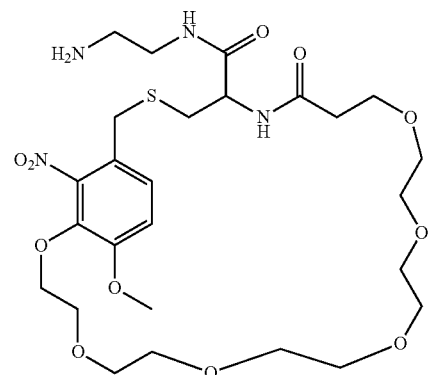
Compound 102
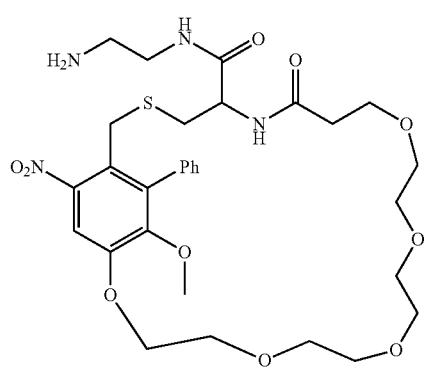
Compound 106
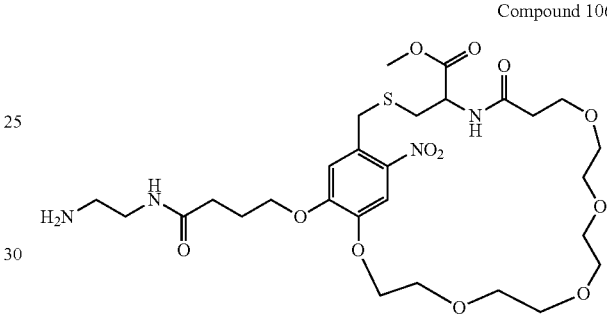
Compound 103
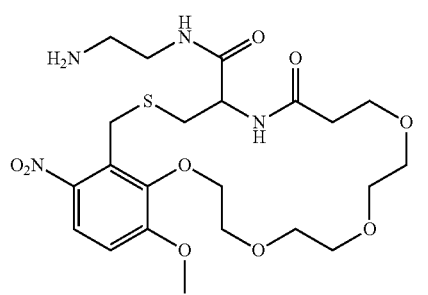
Compound 107
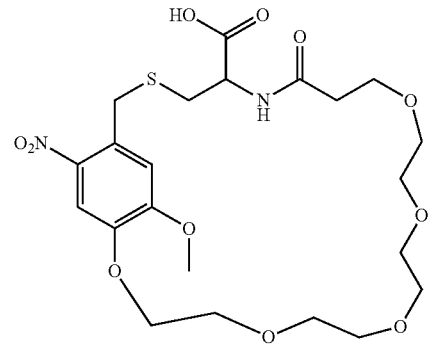
Compound 104
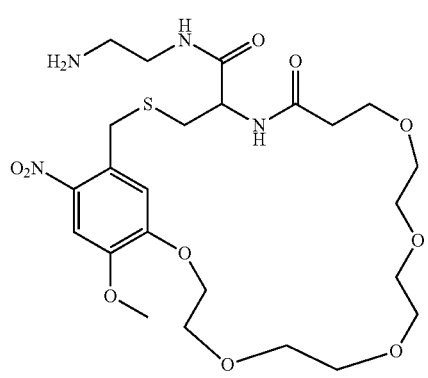
Compound 108
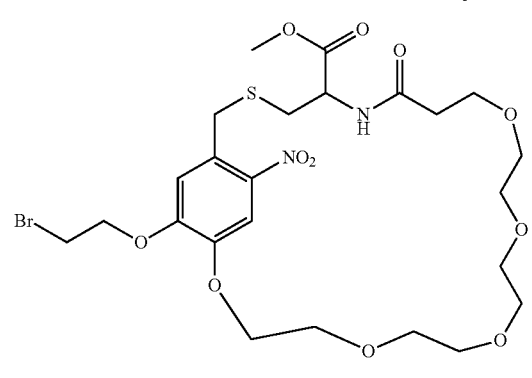

Compound 109

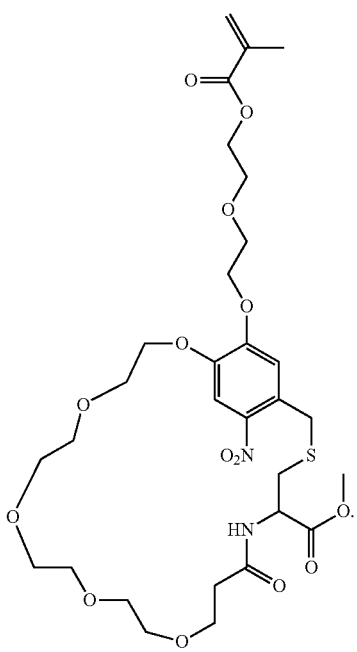

4. A photosensitive polymer derivative having an o-nitrobenzyl phototrigger, wherein
   the o-nitrobenzyl phototrigger is an o-nitrobenzyl sulfide phototrigger, an o-nitrobenzyl amine phototrigger, a cyclic o-nitrobenzyl phototrigger, a cyclic o-nitrobenzyl sulfide phototrigger, or a cyclic o-nitrobenzylamine phototrigger,
   the polymer derivative having the o-nitrobenzyl sulfide phototrigger has the structure of Formula A-I,
   the polymer derivative having the o-nitrobenzyl amine phototrigger has the structure of Formula A-II,
   the polymer derivative having the cyclic o-nitrobenzyl sulfide phototrigger and the polymer derivative having the cyclic o-nitrobenzylamine phototrigger have the structure of Formula A-III, respectively, Formula A-I

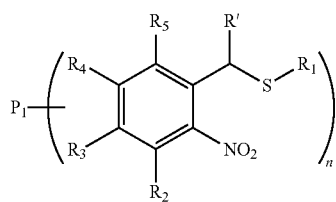

Formula A-II

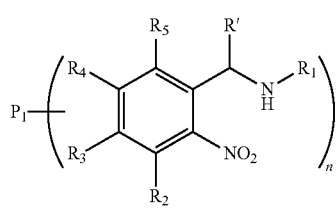

Formula A-III

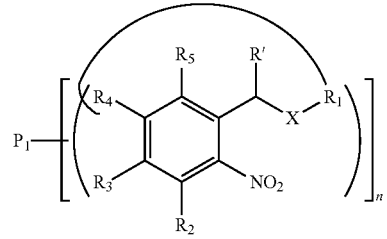

in the Formula A-I, A-II and A-III, R' is selected from the group consisting of a hydrogen atom, a halogen atom, a hydroxyl group, a sulfhydryl group, an amine group, a nitro group, a cyano group, an aldehyde group, a ketone group, an ester group, an amide group, a phosphonic acid group, a phosphonate group, a sulfonic group, a sulfonate group, a sulfone group, a sulfoxide group, an aryl group, an heteroaryl group, an alkyl group, an alkylene group, a modified alkyl group, and a modified alkylene group, in the Formula A-I, A-II and A-III, $R_1$ includes one selected from the group consisting of a hydrogen atom, an ether group, an ester group, a carbonate group, a urethane group, a mercapto formate group, and a phosphate group, in the Formula A-I, A-II and A-III, $R_2$, $R_3$, $R_4$, and $R_5$ each independently includes one selected from the group consisting of a hydrogen atom, a halogen atom, a hydroxyl group, a sulfhydryl group, an amine group, a nitro group, a cyano group, an aldehyde group, a ketone group, an ester group, an amide group, a phosphonic acid group, a phosphonate group, a sulfonic group, a sulfonate group, a sulfone group, a sulfoxide group, an aryl group, an heteroaryl group, an alkyl group, an alkylene group, a modified alkyl group, and a modified alkylene group, in the Formula A-I, A-II, and A-III, $n \geq 2$, in the Formula A-I, A-II, and A-III, $P_1$ includes one or more of hydrophilic or water-soluble natural polymers or synthetic polymers, in the Formula A-III, X is S or NH, $R_1$ is directly bonded to X, and $R_1$ is directly bonded to one of $R_2$, $R_3$, $R_4$, and $R_5$ to form a cyclic structure, in the Formula A-I, A-II, and A-III, two or more of $R_2$, $R_3$, $R_4$, and $R_5$ are connected to form a saturated or unsaturated alicyclic ring, alicyclic heterocycle, aromatic ring, or aromatic heterocycle, together with carbon atom(s).

5. The photosensitive polymer derivative of claim 4, wherein
   the alkyl group is a saturated or unsaturated aliphatic linear or branched alkyl group having 1 to 30 carbon atoms,
   the alkylene group is a saturated or unsaturated aliphatic linear or branched alkylene group having 1 to 30 carbon atoms,
   the modified alkyl group contains a carbon atom at least substituted by one of a halogen atom, —OH, —SH, —$NO_2$, —CN, —CHO, —COOH, ester, amide, aromatic, arylidene, —CO—, —O—, —S—, —SO—, —$SO_2$—, amino, secondary amine, tertiary amine, quaternary ammonium salt, saturated or unsaturated single or double cyclic alkylene, and bridged aliphatic heterocyclic, the modified alkyl group has 1~30 carbon atoms whose carbon-carbon single bond is optionally and independently replaced by a carbon-carbon double bond or a carbon-carbon triple bond, the modified alkylene group contains a carbon atom at least substituted by one of a halogen atom, —OH, —SH, —NO$_2$, —CN, —CHO, —COOH, ester, amide, aromatic, arylidene, —CO—, —O—, —S—, —SO—, —SO$_2$—, amino, secondary amine, tertiary amine, quaternary ammonium salt, saturated or unsaturated single or double cyclic alkylene, bridged aliphatic heterocyclic, the modified alkyl group has 1~30 carbon atoms whose carbon-carbon single bond is optionally and independently replaced by a carbon-carbon double bond or a carbon-carbon triple bond, the ether group is selected from the following structures: —(CH$_2$)$_x$CH$_3$, —(CH$_2$CH$_2$O)$_x$CH$_3$, —(CH$_2$)$_x$(CH$_2$CH$_2$O)$_y$CH$_3$, and

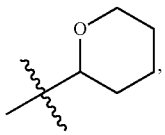

where x and y≥0 and are integers, the ester group is selected from the following structures: —CO(CH$_2$)$_x$CH$_3$, —CO(CH$_2$CH$_2$O)$_x$CH$_3$, and —CO(CH$_2$)$_x$(CH$_2$CH$_2$O)$_y$CH$_3$, where x and y≥0 and are integers, the carbonate group is selected from the following structures: —COO(CH$_2$)$_x$CH$_3$, —COO(CH$_2$CH$_2$O)$_x$CH$_3$, and —COO(CH$_2$)$_x$(CH$_2$CH$_2$O)$_y$CH$_3$, where x and y≥0 and are integers, the urethane group is selected from the following structures: —CONH(CH$_2$CH$_2$O)$_x$CH$_3$, and —CONH(CH$_2$)$_x$(CH$_2$CH$_2$O)$_y$CH$_3$, where x and y≥0 and are integers, the mercapto formate group is selected from the following structures: —COS(CH$_2$)$_x$CH$_3$, —COS(CH$_2$CH$_2$O)$_x$CH$_3$, and —COS(CH$_2$)$_x$(CH$_2$CH$_2$O)$_y$CH$_3$, where x and y≥0 and are integers, the phosphate group is selected from the following structures: —POOO(CH$_2$)$_x$CH$_3$, —POOO(CH$_2$CH$_2$O)$_x$CH$_3$, and —POOO(CH$_2$)$_x$(CH$_2$CH$_2$O)$_y$CH$_3$, wherein x and y≥0 and are integers, the aryl ring is a monocyclic or fused bicyclic ring of 5-10 atoms, the heteroaryl is a monocyclic or fused bicyclic ring containing 5 to 10 atoms, the ring contains at least one hetero atom selected from N, O, S, and Si, the halogen atom is selected from F, Cl, Br, and I, the alicyclic ring is a saturated or unsaturated monocyclic or polycyclic alicyclic ring of 3 to 10 atoms, the heteroalicyclic ring is a saturated or unsaturated monocyclic or polycyclic alicyclic ring of 3 to 10 atoms, and the ring contains at least one hetero atom selected from N, O, S, and Si, when the heteroalicyclic ring contains an S atom, the S atom takes the form of —S—, —SO— or —SO$_2$—, H on the alicyclic or alicylic ring is optionally substituted by a halogen atom, a nitro group, an aryl group or an alkyl group, or a modified alkyl group, the aromatic ring is a monocyclic or fused bicyclic ring of 5-10 atoms, the aromatic heterocycle is a monocyclic or fused bicyclic ring containing 5 to 10 atoms, the ring contains at least one hetero atom selected from N, O, S, and Si, H on the aromatic ring or the aromatic heterocyclic ring is optionally substituted by a halogen atom, a nitro group, an aryl group, an alkyl group, or a modified alkyl group.

6. The photosensitive polymer derivative of claim 4, wherein

P$_1$ of the Formula A-I and Formula A-II is connected to one or more of R$_2$, R$_3$, R$_4$ and R$_5$, or the saturated or unsaturated alicyclic or aliphatic heterocycle ring formed between R$_2$, R$_3$, R$_4$ and R$_5$, or an aromatic ring or an aromatic heterocyclic ring formed between R$_2$, R$_3$, R$_4$ and R$_5$, via a linkage bond;

P$_1$ of the Formula A-III is connected to one or more of R$_2$, R$_3$, R$_4$ and R$_5$, or the saturated or unsaturated alicyclic or aliphatic heterocycle ring formed between R$_2$, R$_3$, R$_4$ and R$_5$, or the aromatic ring or aromatic heterocyclic ring formed between R$_2$, R$_3$, R$_4$ and R$_5$, or the cyclic structure formed by linking R$_1$ to one of R$_2$, R$_3$, R$_4$, and R$_5$, via a linkage bond; and the linkage bond is represented by —O—, —S—, —NH—,-alkyl group-, —COO— and —CONH—.

7. The photosensitive polymer derivative of claim 4, wherein the natural hydrophilic or water-soluble polymer includes at least one selected from a natural polysaccharide, a decoration or degradation of the natural polysaccharide, a protein, and a decoration, modifier, or degradation of the protein, the natural polysaccharide includes hyaluronic acid, carboxymethyl cellulose, methyl cellulose, hydroxyethyl cellulose, hydroxypropyl cellulose, alginate, dextran, agarose, heparin, chondroitin sulfate, glycol chitosan, propylene glycol chitosan, chitosan lactate, carboxymethyl chitosan, or quaternary ammonium salt of chitosan, the protein includes a hydrophilic or water-soluble animal and plant protein, collagen, serum protein, silk fibroin protein and elastin, and the protein degradation include a gelatin or polypeptide, the hydrophilic or water-soluble synthetic polymer includes two-arm or multi-arm poly (ethylene glycol), poly (ethylene imine), dendrites, synthetic peptides, polylysine, poly (glutamic acid), poly (acrylic acid), poly (methacrylic acid), polyacrylate, poly (methacrylate), poly (acrylamide), poly (methacrylamide), poly (vinyl alcohol), or poly (vinyl pyrrolidone).

8. The photosensitive polymer derivative of claim 4, wherein the polymer derivative having the structure of the Formula A-I is selected from the structures of Component A-1 to the Component A-45 as follows:

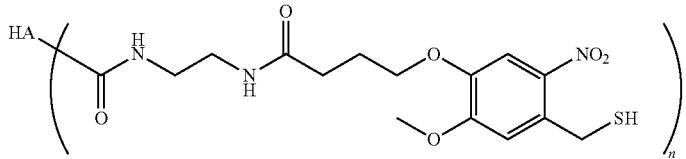
Component A-1
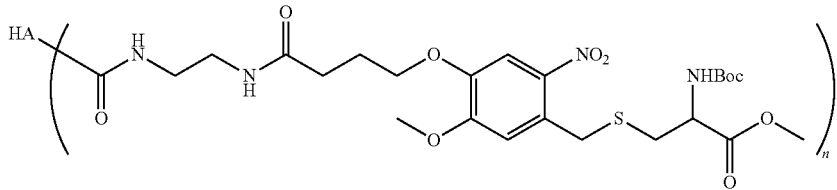
Component A-2
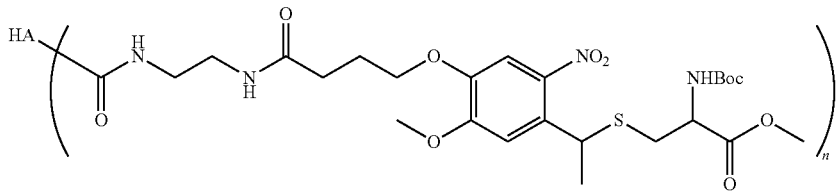
Component A-3
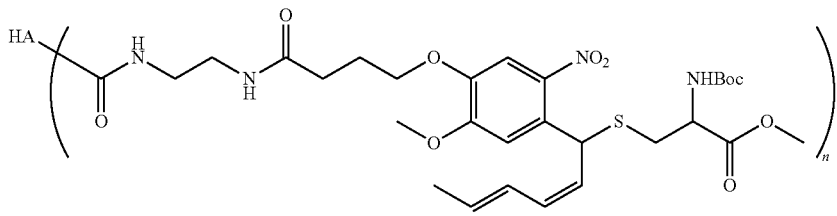
Component A-4
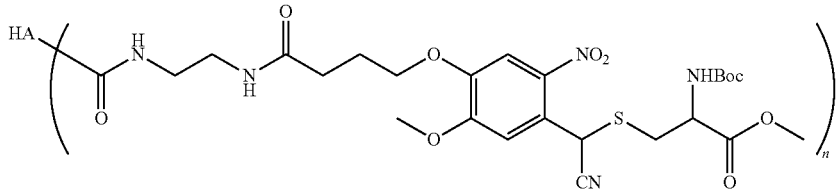
Component A-5
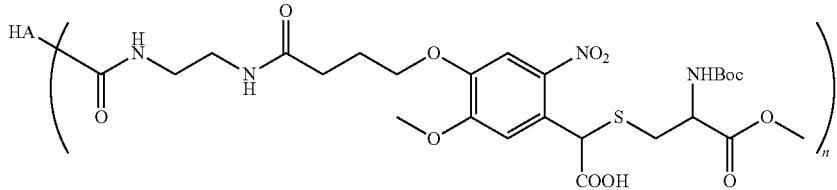
Component A-6
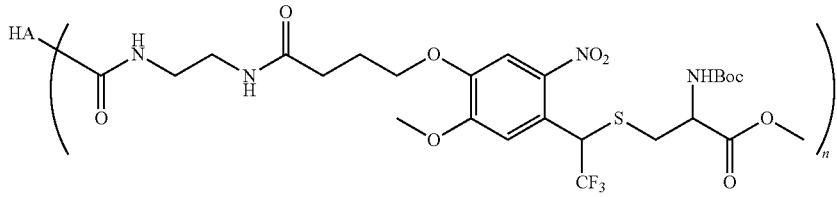
Component A-7

-continued
Component A-8
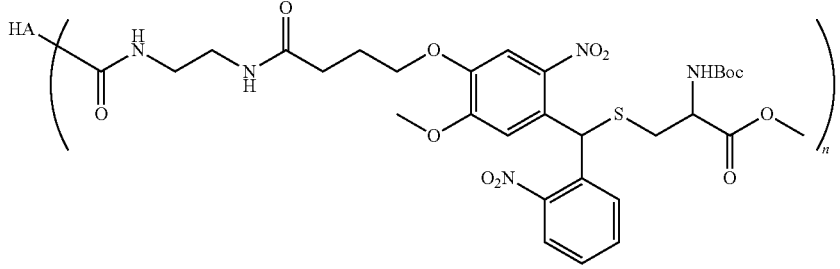
Component A-9
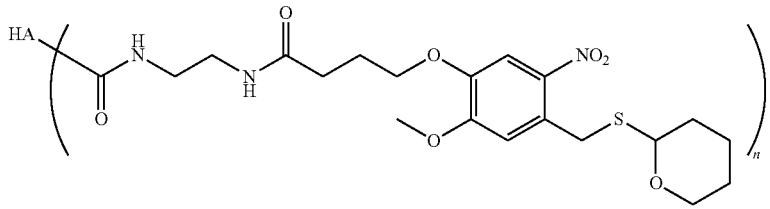
Component A-10
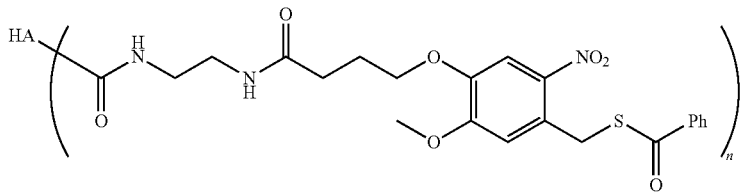
Component A-11
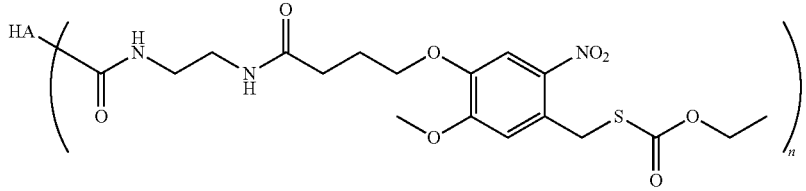
Component A-12
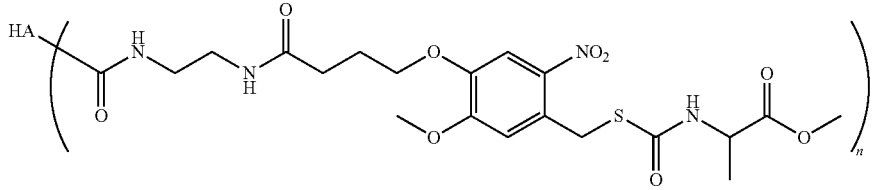
Component A-13
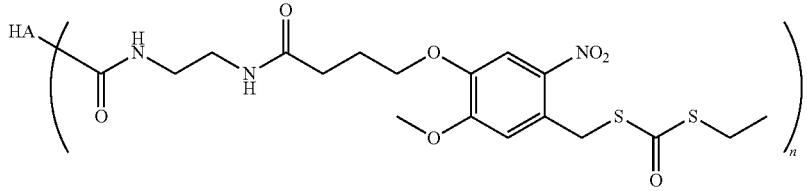
Component A-14
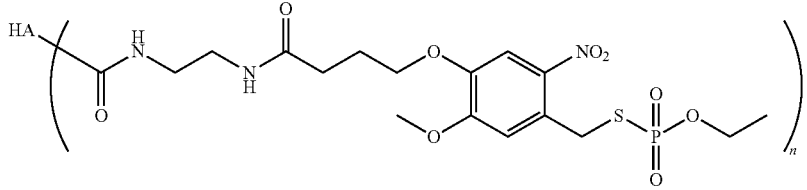

-continued
Component A-15
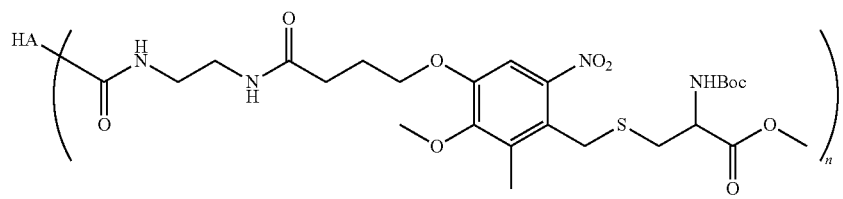
Component A-16
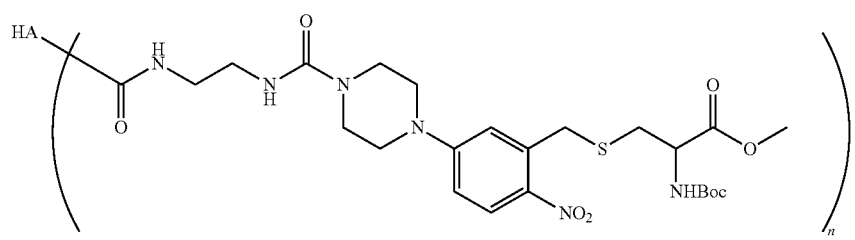
Component A-17
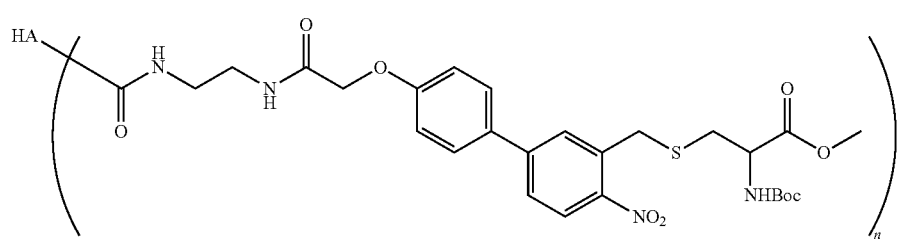
Component A-18
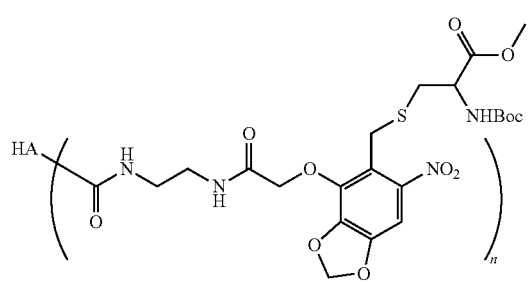
Component A-19
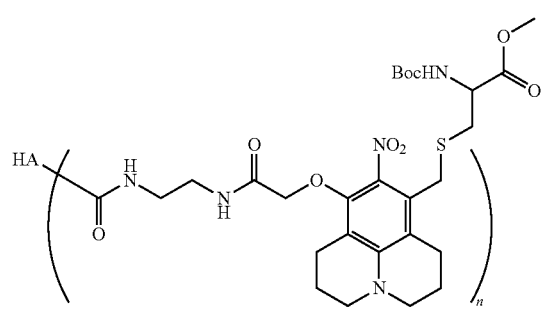
Component A-20
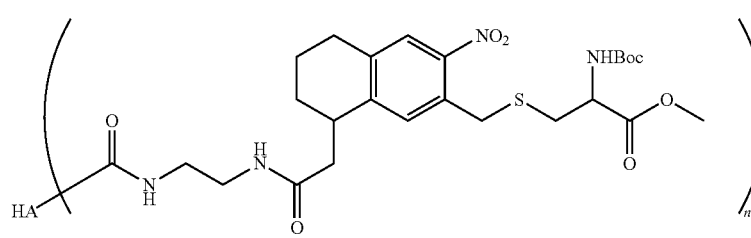
Component A-21
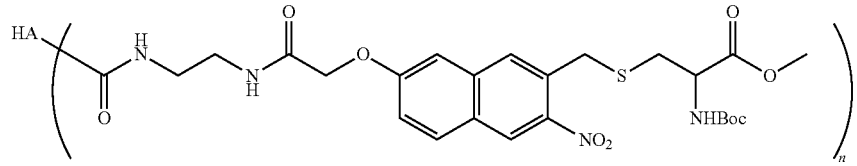
Component A-22
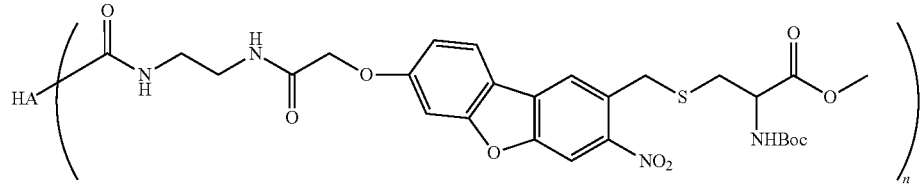

-continued
Component A-23
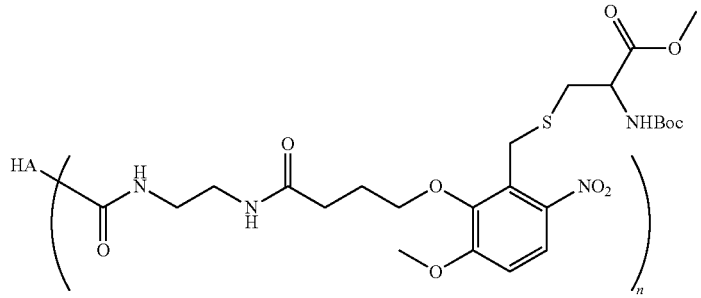
Component A-24
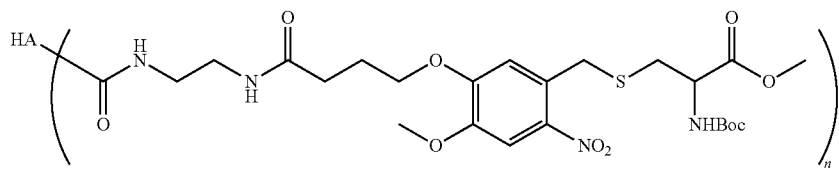
Component A-25
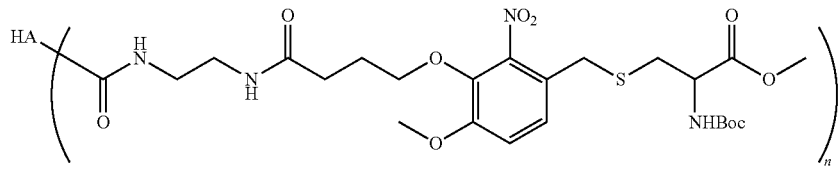
Component A-26
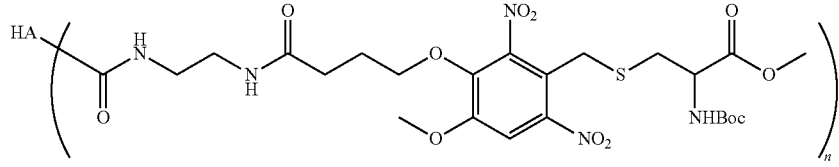
Component A-27
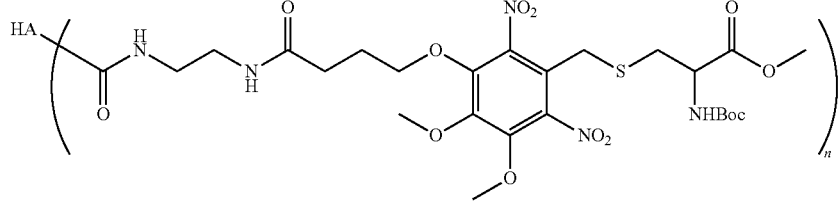
Component A-28
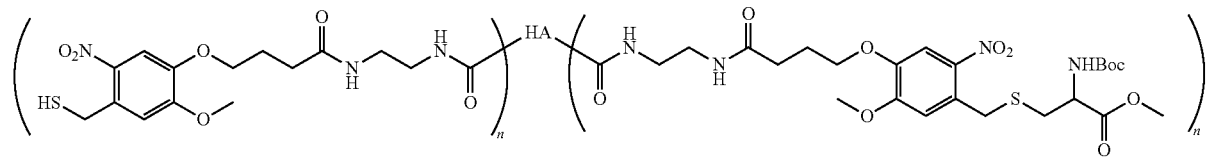
Component A-29
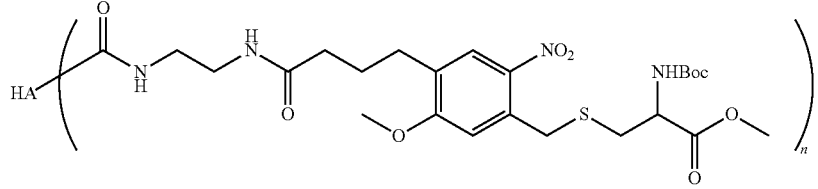

-continued
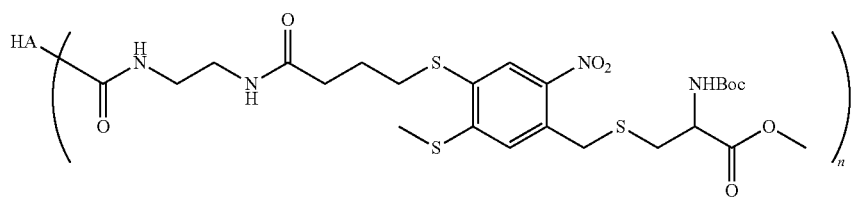
Component A-30
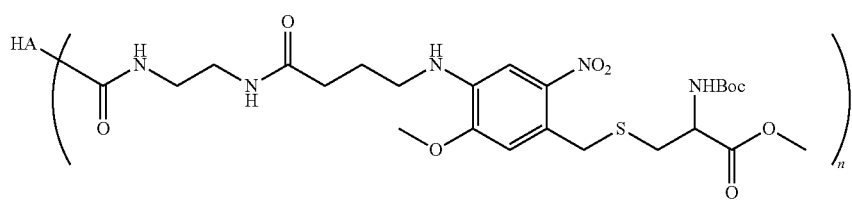
Component A-31
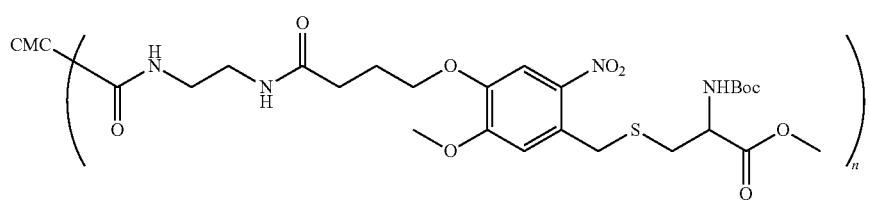
Component A-32
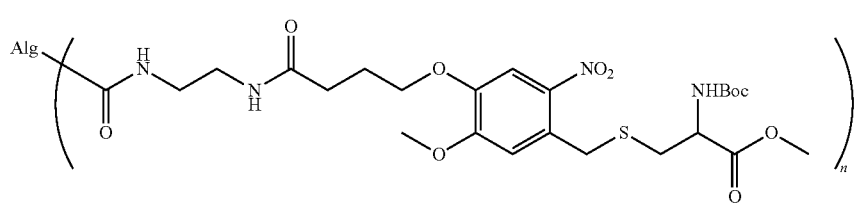
Component A-33
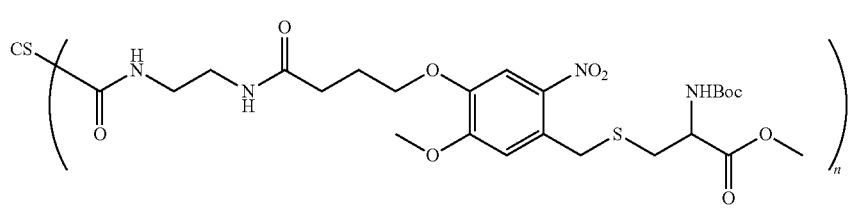
Component A-34
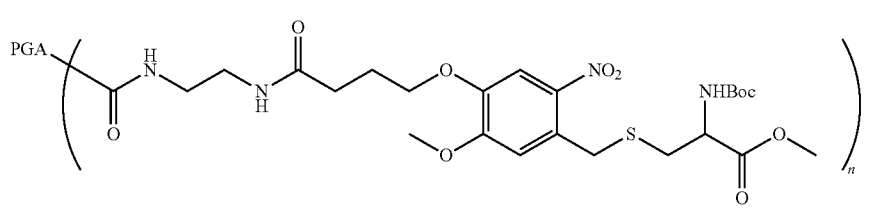
Component A-35
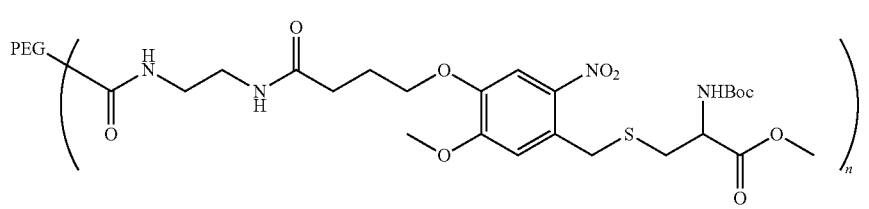
Component A-36
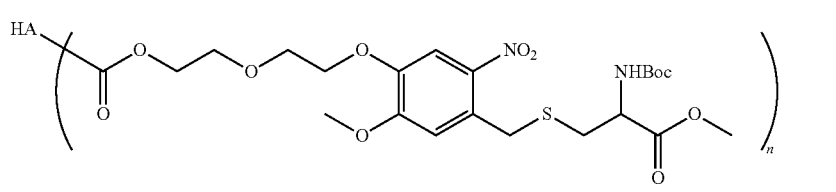
Component A-37

Component A-38
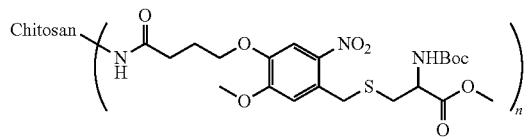
Component A-39
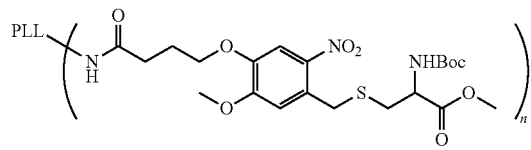
Component A-40
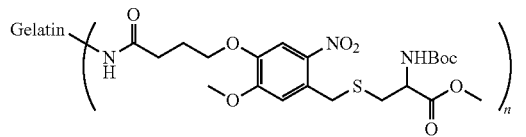
Component A-41
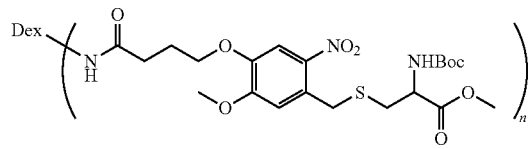
Component A-42
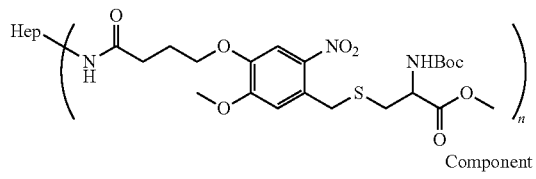
Component A-43
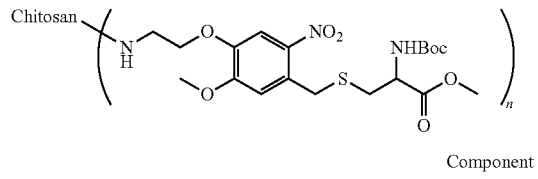
Component A-43
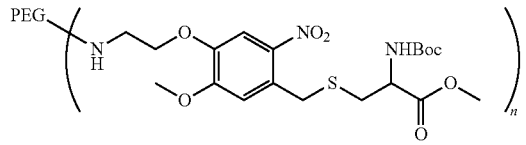
Component A-45
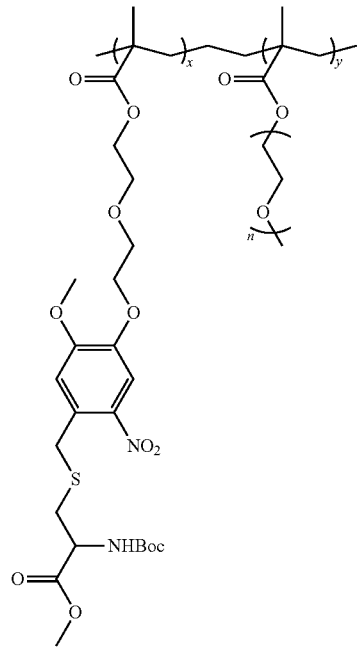
the polymer derivative having the structure of the Formula A-II is selected from the structures of the following Component A-46 to Compound A-63:
Component A-46
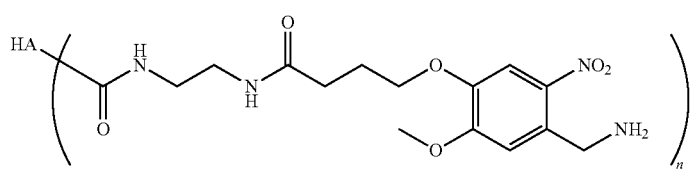

-continued
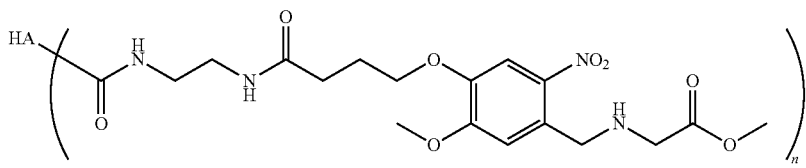
Component A-47
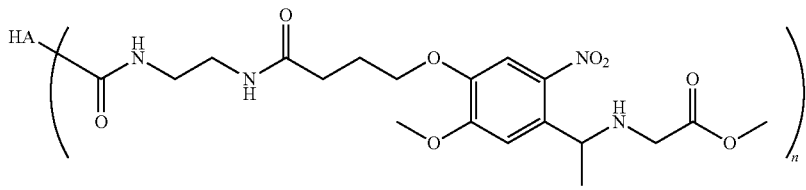
Component A-48
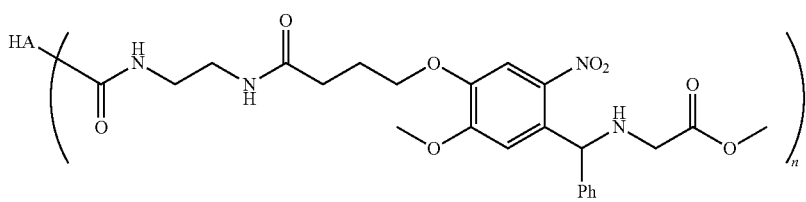
Component A-49
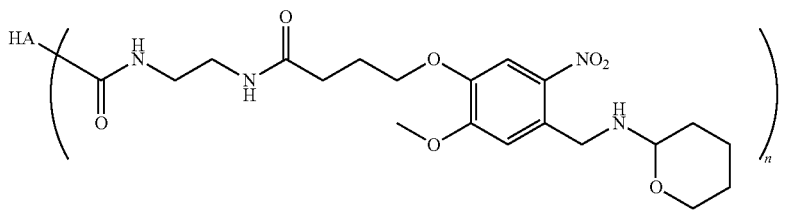
Component A-50
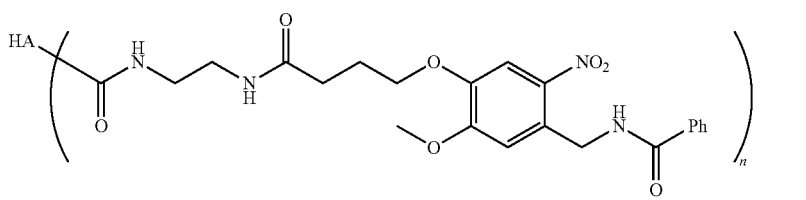
Component A-51
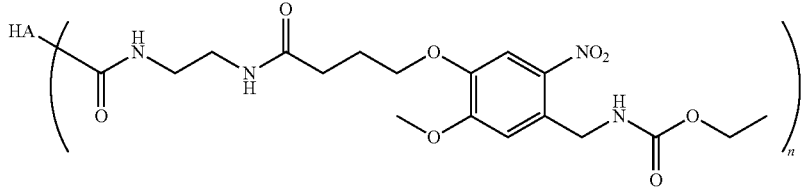
Component A-52
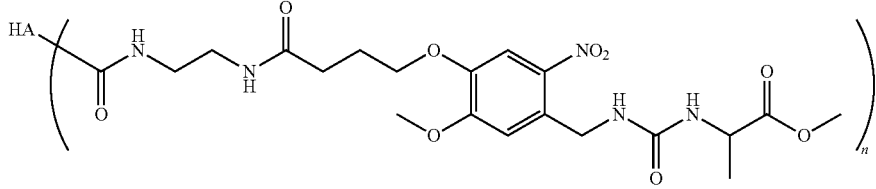
Component A-53
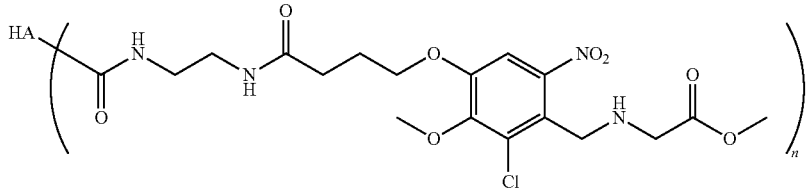
Component A-54

-continued
Component A-55
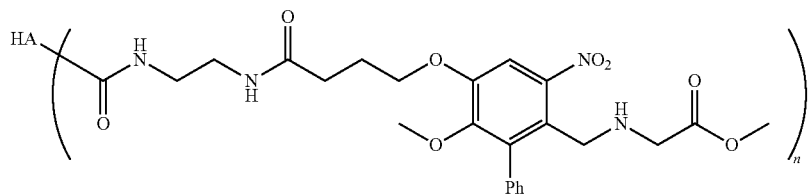
Component A-56
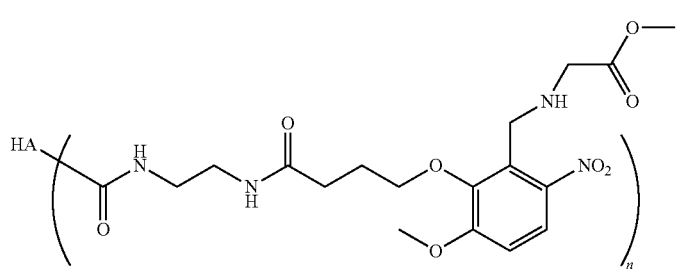
Component A-57
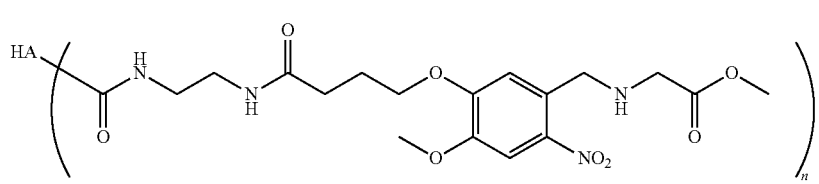
Component A-58
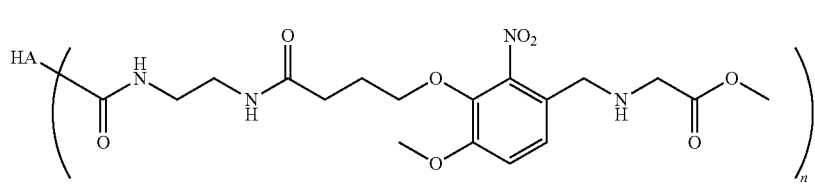
Component A-59
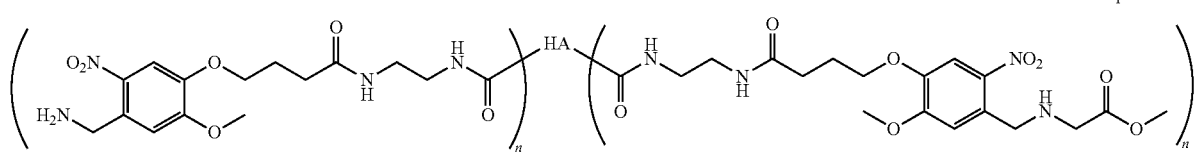
Component A-60
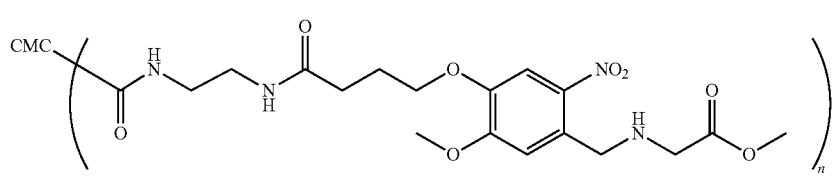
Component A-61
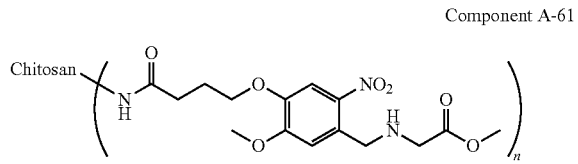
Component A-62
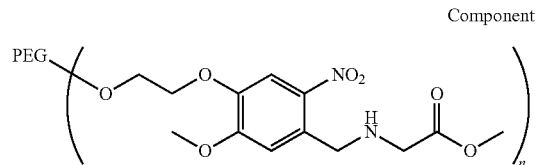

-continued
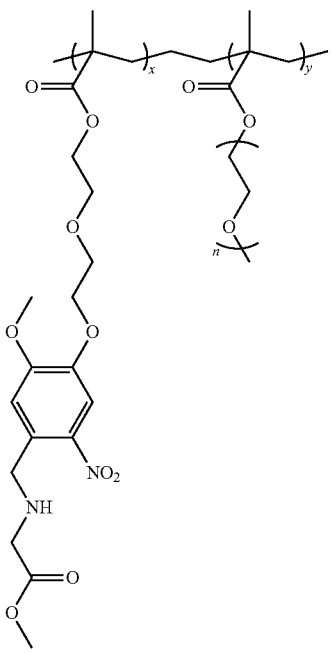
Component A-63
,
the polymer derivative having the structure of the Formula A-III is selected from the following Component A-64 to Compound A-82:
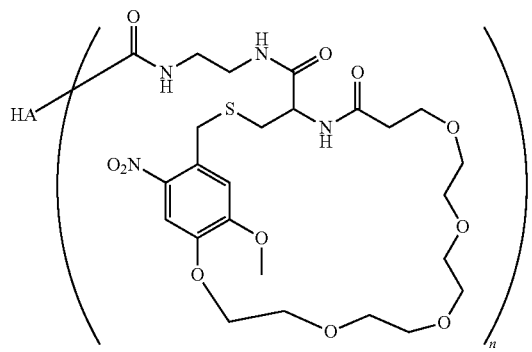
Component A-64
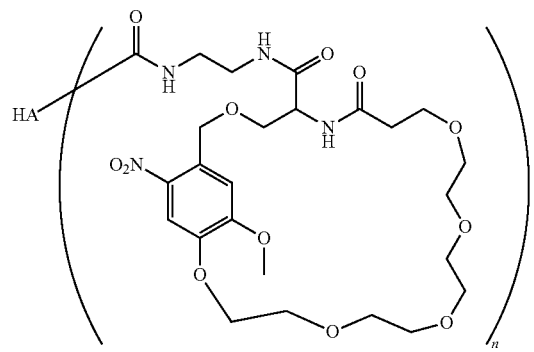
Component A-65
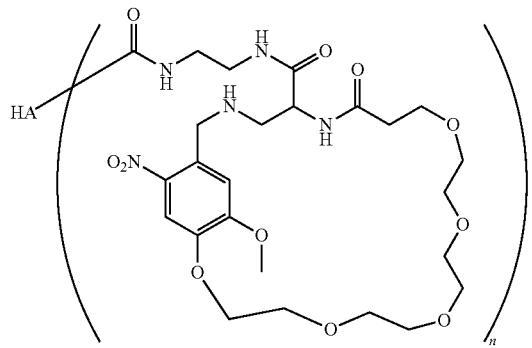
Component A-66
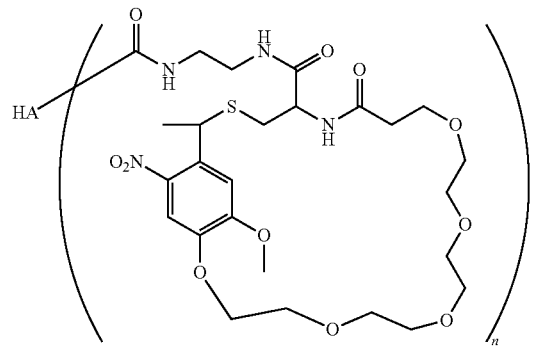
Component A-67

-continued
Component A-68
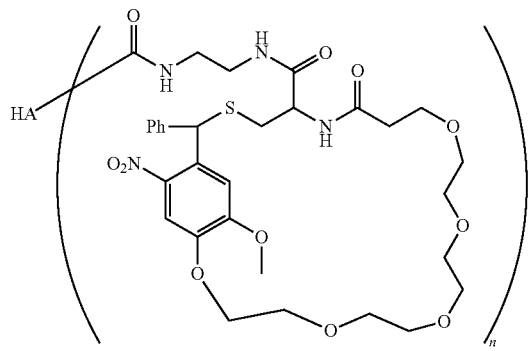
Component A-69
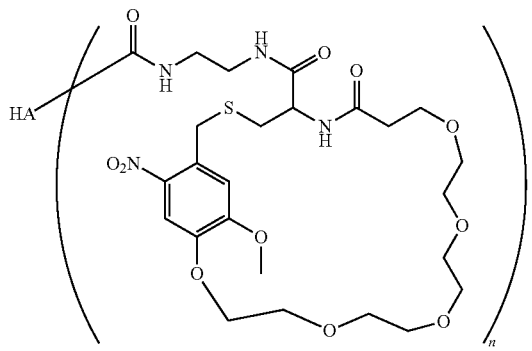
Component A-70
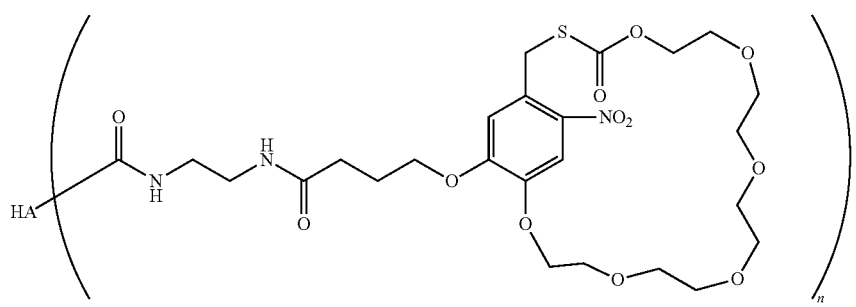
Component A-71
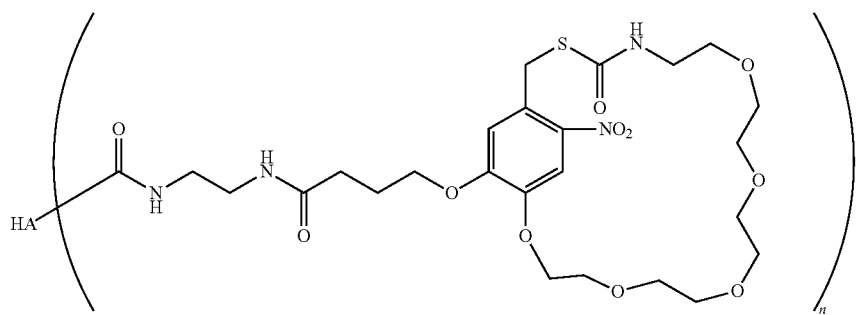
Component A-72
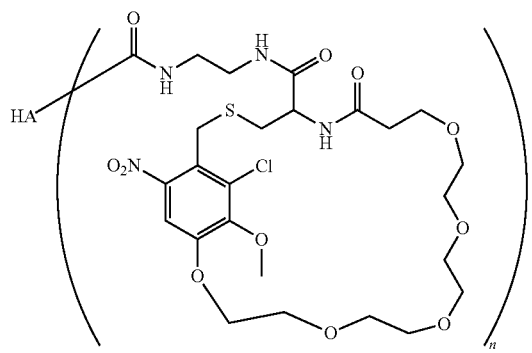
Component A-73
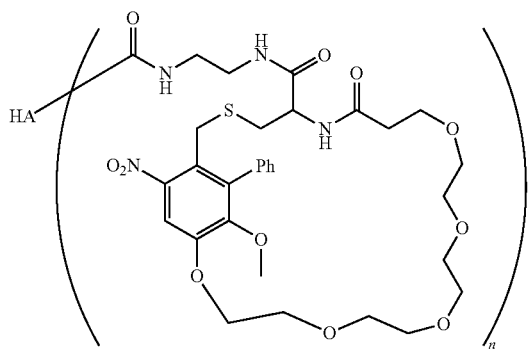

-continued
Component A-74
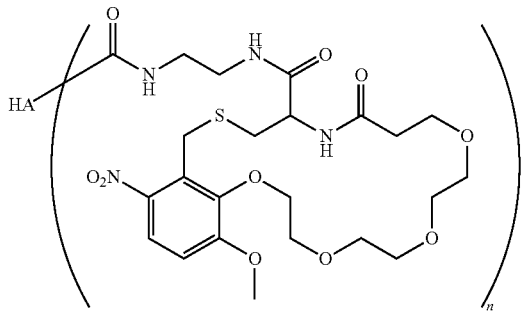
Component A-75
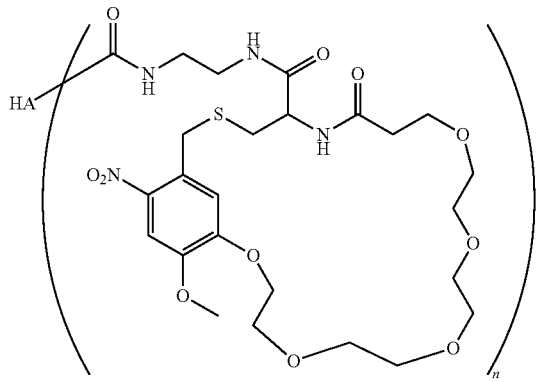
Component A-76
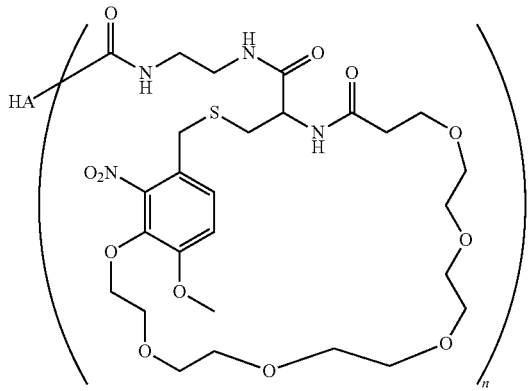
Component A-77
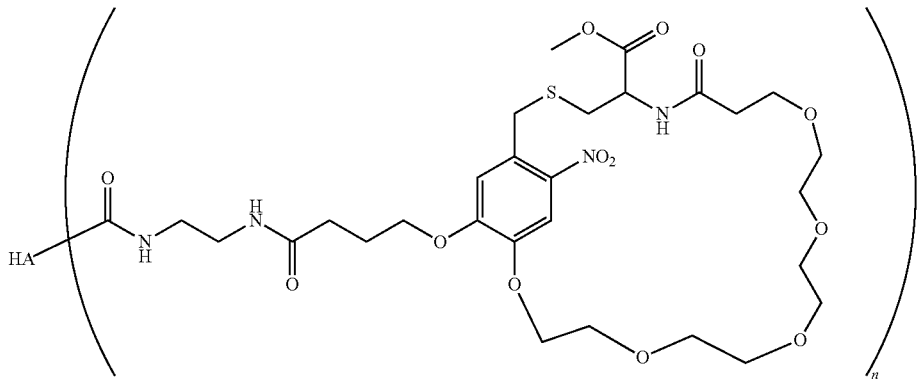
Component A-78
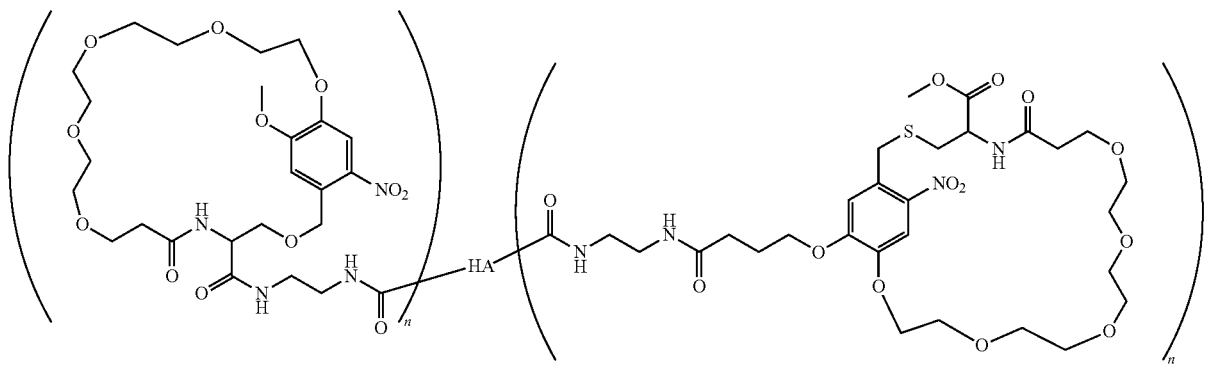

-continued

Component A-79

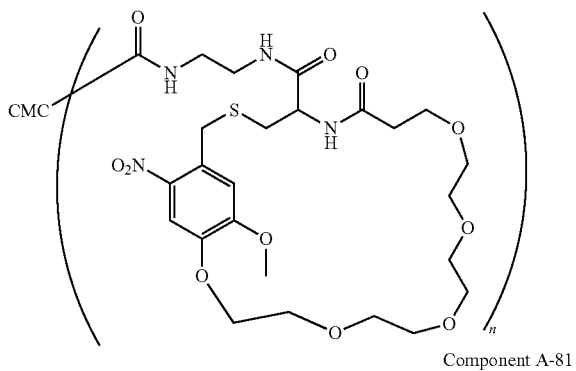

Component A-80

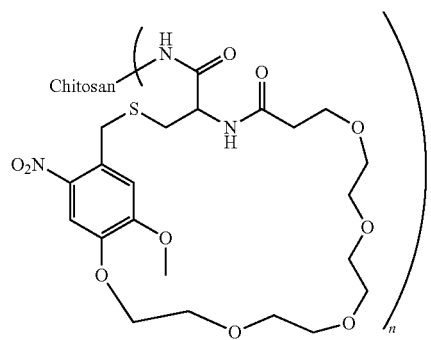

Component A-81

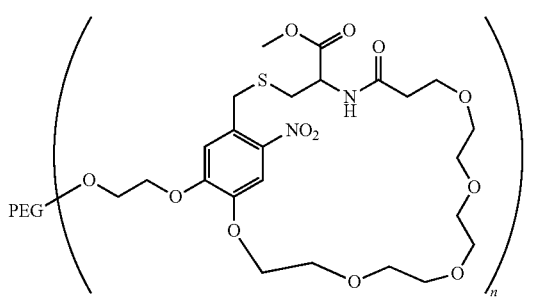

Component A-82

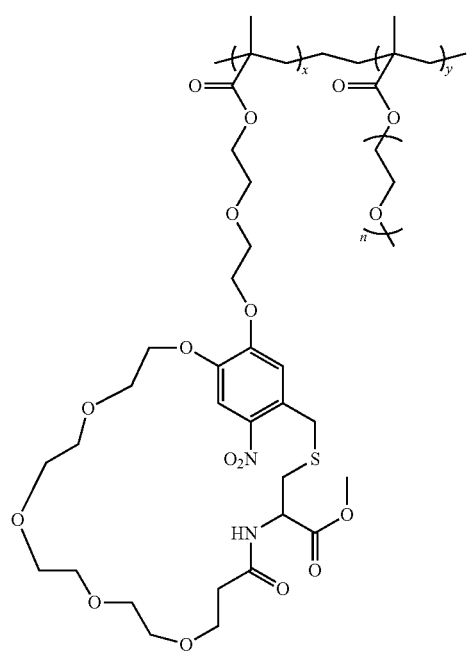

where, in the molecules of Component A-1 to Component A-82, n≥2, HA stands for hyaluronic acid, CMC stands for carboxymethyl cellulose, Alg stands for alginic acid; CS stands for chondroitin sulfate, PGA stands for polyglutamic acid, PEG stands for polyethylene glycol, PLL stands for polylysine, Dex stands for dextran, and Hep stands for heparin.

9. A method of preparing the polymer derivative as in claim 4, wherein
the polymer derivative is produced by a chemical labeling or artificial polymerization method,
the chemical labeling method is realized by a chemical reaction between a polymer and a chemical group in the o-nitrobenzyl phototrigger, and includes the following labeling methods:
a chemical reaction between a polymer containing carboxyl group and an o-nitrobenzyl molecule containing a hydroxyl group, a mercapto group or an amine group;
a chemical reaction between a polymer containing hydroxyl group and an o-nitrobenzyl molecule containing a carboxyl group or a bromine group;
a chemical reaction between a polymer containing amine group and an o-nitrobenzyl molecule containing a carboxyl group or a bromine group,
the artificial polymerization method includes a copolymerization of an o-nitrobenzyl derivative functional monomer with a comonomer, and the artificial polymerization method includes a random radical polymerization method and control radical polymerization method,
the method comprises one of the following:
A: dissolving a water-soluble polymer containing a carboxyl group in distilled water to obtain a solution, adding an o-nitrobenzyl molecule containing a reactive functional group of hydroxyl group or a mercapto group or an amine group to the solution, following by adding a condensing agent of 1-ethyl-(3-dimethyl amine propyl) carbodiimide hydrochloride and an activator of hydroxybenzotriazole to obtain a mixture, stirring the mixture to obtain a reaction solution, transferring the reaction solution a dialysis bag and dialyzing with a diluted hydrochloric acid solution, and then freeze-drying to obtain a polymer derivative having o-nitrobenzyl groups;

B: dissolving a water-soluble polymer containing a carboxyl group in MES (2-(N-morpholine) ethyl sulfonic acid) solution to obtain a solution, adding an o-nitrobenzyl molecule in DMSO to the solution, followed by adding DMTMM (4-(4, 6-dimethoxytriazin-2-yl)-4-methylmorpholine hydrochloride) dissolved in a MES solution to obtain a mixture, stirring the mixture to obtain a reaction solution, transferring the reaction solution to a dialysis bag and dialyzing with distilled water, and then freeze-drying to obtain the polymer derivative having o-nitrobenzyl groups;

C: dissolving a water-soluble polymer containing a hydroxyl group or an amine group in distilled water to obtain a solution, adding an o-nitrobenzyl molecule containing a reactive functional group of carboxyl group to the solution, followed by adding a condensing agent of 1-ethyl-(3-dimethyl amine propyl) carbodiimide hydrochloride and a catalyst of pyridinium p-toluenesulfonate to obtain a mixture, stirring the mixture at room temperature, adding the reaction solution to an insoluble solvent for reprecipitation to obtain a precipitate, redissolving the precipitate in distilled water and dialyzing with distilled water, and then freeze-drying to obtain the polymer derivative having o-nitrobenzyl groups;

D: dissolving a water-soluble polymer containing a hydroxyl group or an amine group in distilled water to obtain a solution, adding an o-nitrobenzyl molecule containing a reactive functional group of bromine group and potassium carbonate as a base to the solution and stirring to obtain a reaction solution, transferring the reaction solution to an insoluble solvent for reprecipitation to obtain a precipitate, redissolving the precipitate in distilled water and dialyzing with distilled water, and then freeze-drying to obtain the polymer derivative having o-nitrobenzyl groups; or E: polymerizing an o-nitrobenzyl polymerizable monomer derivative with one or more polymerizable co-monomers to obtain a synthetic copolymer having o-nitrobenzyl groups, wherein the o-nitrobenzyl polymerizable monomer derivative includes an acrylate compound, a methacrylate compound, an acrylamide compound, or a methacrylamide compound, at least one of the polymerizable co-monomers is water-soluble, and the polymerizableco-monomers include polyethylene glycol methacrylate, polyethylene glycol acrylate, methacrylic acid, acrylic acid, hydroxyethyl acrylate, or acrylamide.

10. A method for preparing a photocoupled synergistically crosslinked hydrogel material comprising:
dissolving component A including the photosensitive polymer derivative having an o-nitrobenzyl phototrigger of claim 4 in a biocompatible medium to obtain a hydrogel precursor solution; and
irradiating the hydrogel precursor solution with a UV light to form a hydrogel,
wherein, under irradiation with the UV light, a nitroso group generated from the o-nitrobenzyl phototrigger in component A has strong reactivity, and crosslinks with itself, or crosslinks with a reactive group in component A to form the hydrogel,
the reactive group includes a mercapto group, a hydroxyl group, an amine group, a carboxyl group, a sulfonic acid group, a carbonyl group, or a double bond,
when the o-nitrobenzyl phototrigger is a cyclic o-nitrobenzyl sulfide phototrigger, a thiol group released from the photosensitive polymer derivative is crosslinkable with the nitroso group.

11. The preparation method as in claim 10, further comprising:
dissolving component B in a biocompatible medium to obtain solution B; and
mixing solution A and solution B homogeneously to obtain the hydrogel precursor solution, wherein
the component B contains one or more of polymer derivatives containing an amine group, double bond group, or a mercapto group.

12. The methods as in claim 11, wherein
the amine group includes a primary amine group, a diamine group, a hydrazide group, or a hydroxylamine group, the one or more polymer derivatives containing the primary amine group, the diamine group, the hydrazide group, or the hydroxylamine group are respectively represented by Formula B-I, Formula B-II, Formula B-III, and Formula B-IV,
the double bond group includes one or more selected from the group consisting of a maleimide group, a vinyl sulfone group, and an acrylate or acrylamide group, the one or more polymer derivatives containing the maleimide group, the vinyl sulfone group, and the acrylate or acrylamide group are represented by Formulas B-V, B-VI and B-VII, respectively,
the one or more polymer derivatives containing the mercapto group have the structure of Formula B-VIII,

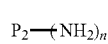

Formula B-I

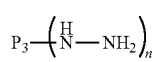

Formula B-II

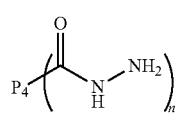

Formula B-III

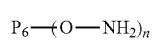

Formula B-IV

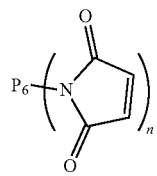

Formula B-V

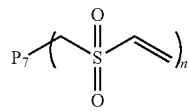

Formula B-VI

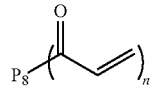

Formula B-VII

P$_9$—(SH)$_n$,

Formula B-VIII where n≥2, $P_2$, $P_3$, $P_4$, $P_5$, $P_6$, $P_7$, $P_8$ and $P_9$ are hydrophilic or water-soluble natural polymers or synthetic polymer,
the hydrophilic or water-soluble natural polymer is a natural polysaccharide, a modifier or degradant of a natural polysaccharide, a protein, or a modifier or degradant of a protein, the natural polysaccharide is selected from the group consisting of: hyaluronic acid, carboxymethyl cellulose, methyl cellulose, hydroxyethyl cellulose, hydroxypropyl cellulose, alginate, dextran, agarose, heparin, chondroitin sulfate, glycol chitosan, propylene glycol chitosan, chitosan lactate, carboxymethyl chitosan, and quaternary ammonium salt of chitosan, the protein is selected from the group consisting of: hydrophilic or water-soluble animal and plant proteins, collagen, serum proteins, silk fibroin proteins and elastin, the degradant of a protein is selected from the group consisting of gelatin and polypeptides, the hydrophilic or water-soluble synthetic polymer is selected from the group consisting of two-arm or multi-arm poly (ethylene glycol), poly (ethylene imine), dendrites, synthetic peptides, polylysine, poly (glutamic acid), poly (acrylic acid), poly (methacrylic acid), polyacrylate, poly (methacrylate), poly (acrylamide), poly (methacrylamide), poly (vinyl alcohol), and poly (vinyl pyrrolidone), the Formula B-I is selected from the structures of the following Component B-1 to Component B-9, the Formula B-II is selected from the structures of Component B-10, the Formula B-III is selected from the following structures of Component B-11 to Component B-13, the Formula B-IV is selected from the following structures of Component B-14 and Component B-15, the Formula B-VI is selected from the structures of the following Component B-16 to Component B-18, the Formula B-VI is selected from the structures of the following Component B-19 to Component B-21, the Formula B-VII is selected from the structures of the following Component B-22 to Component B-29, the Formula B-VIII is selected from the structures of the following Component B-30 to Component B-35, Component B-1

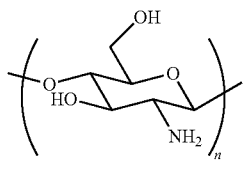

Component B-2

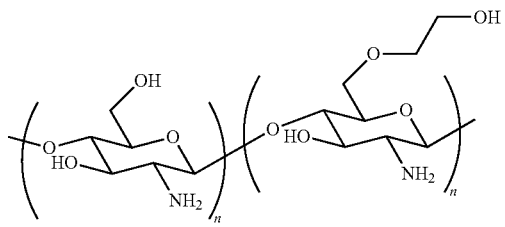

Component B-3

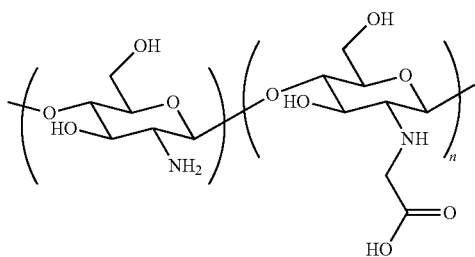

Component B-4

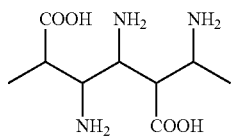

Component B-5

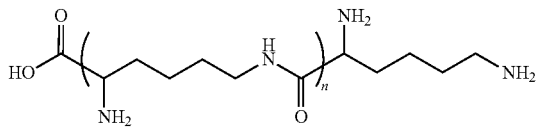

Component B-6

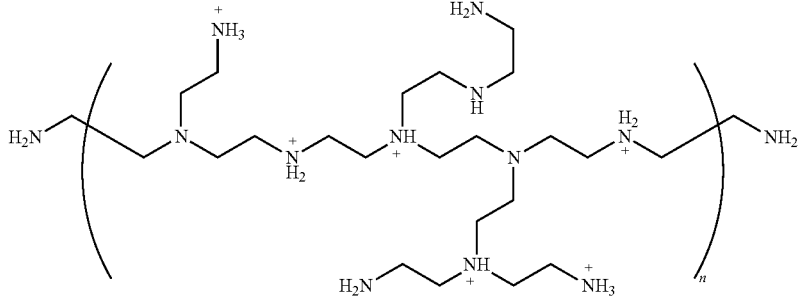

Component B-7

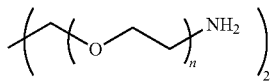

Component B-8

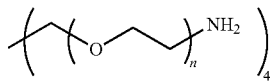

-continued
Component B-9
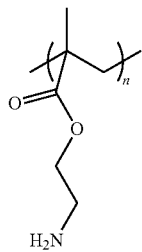
Component B-10
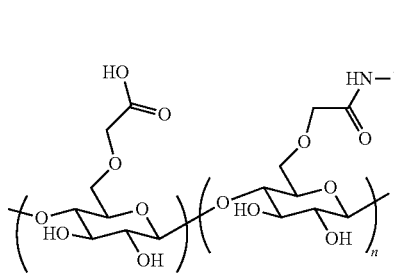
Component B-11
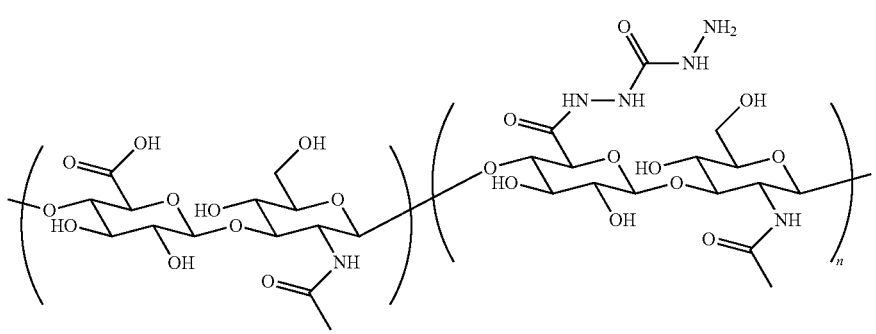
Component B-12
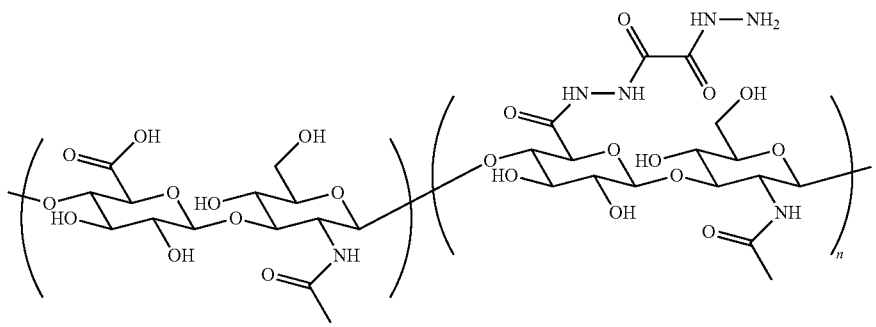
Component B-13
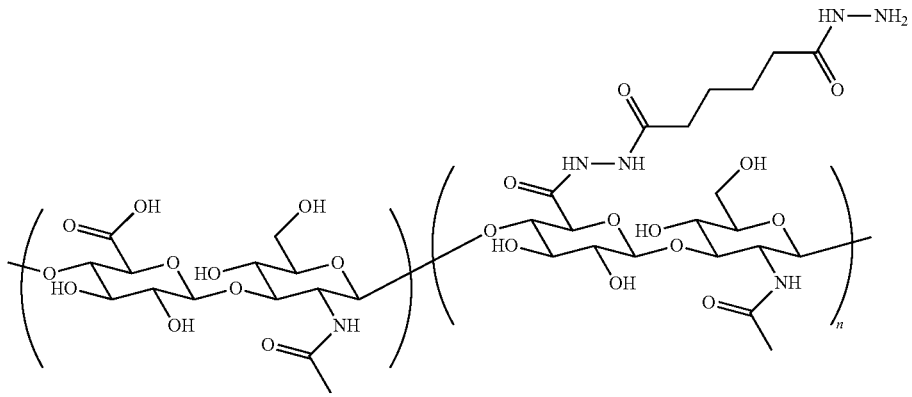
Component B-14
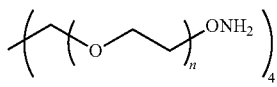
Component B-15
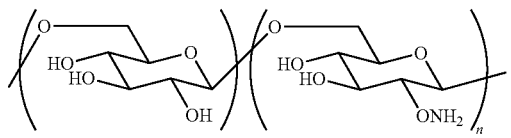

-continued
Component B-16
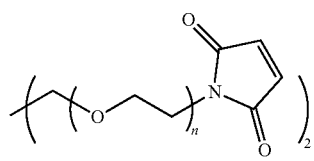
Component B-17
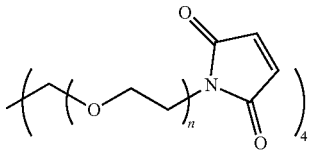
Component B-18
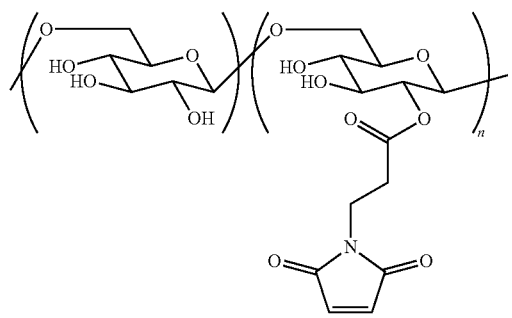
Component B-19
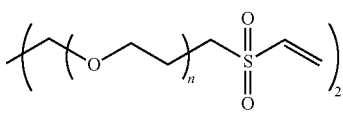
Component B-20
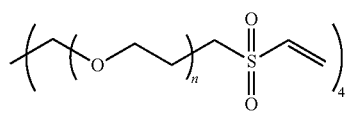
Component B-21
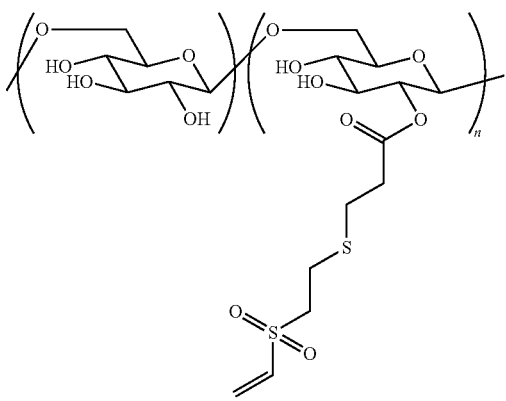
Component B-22
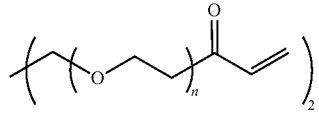
Component B-23
Component B-24
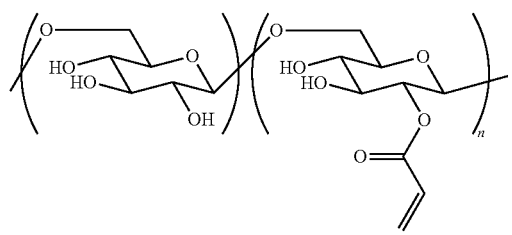
Component B-25
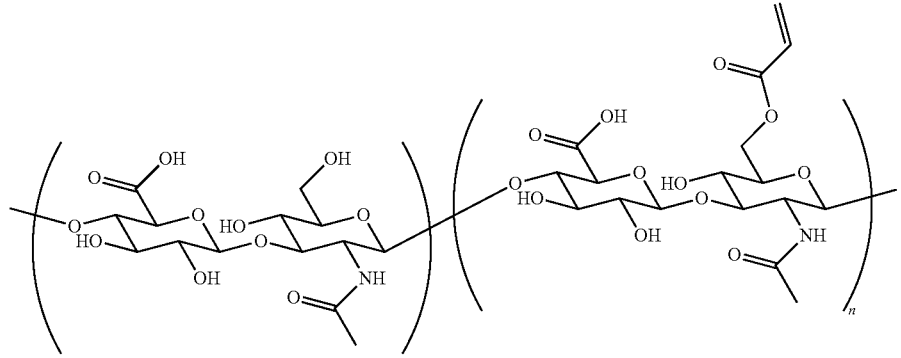

-continued
Component B-26
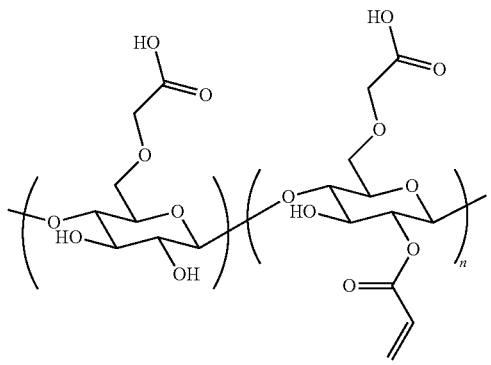
Component B-27
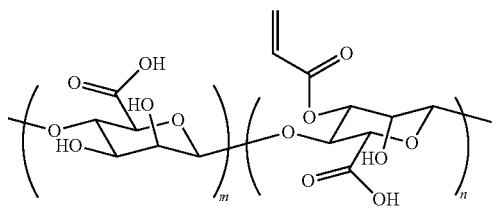
Component B-28
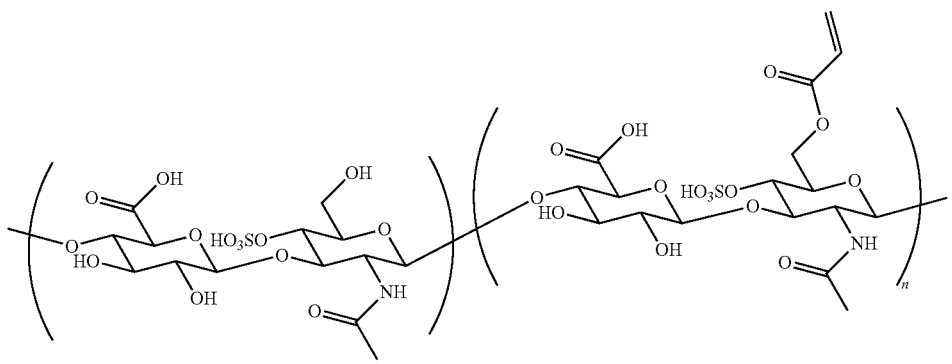
Component B-29
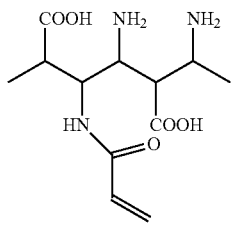
Component B-30
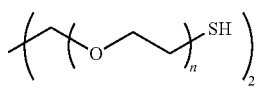
Component B-31
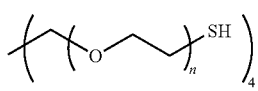
Component B-32
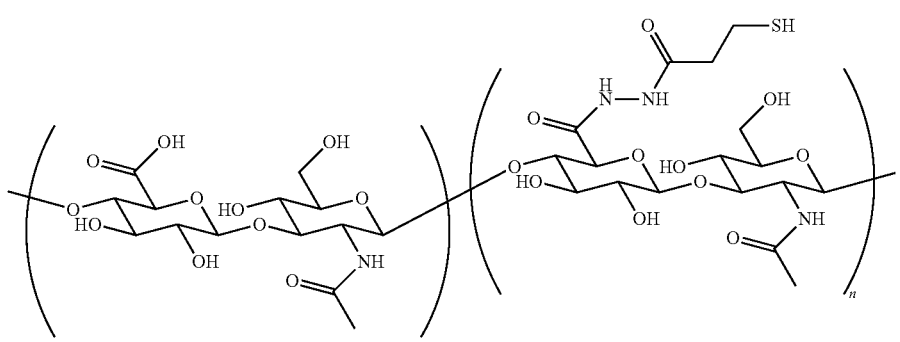

Component B-33

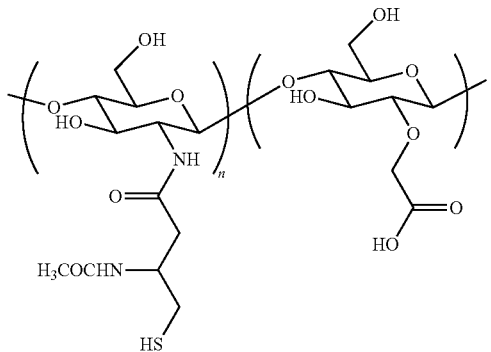

Component B-34

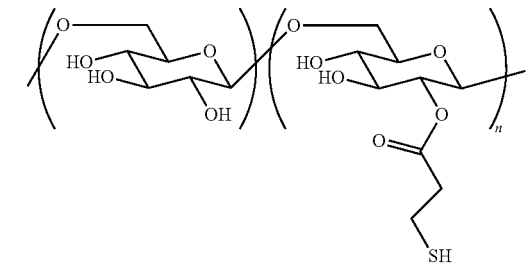

Component B-35

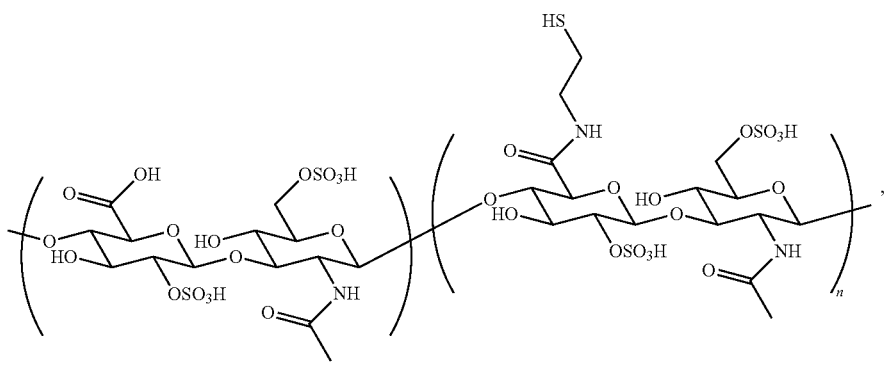

where, in Component B-1 to Component B-35, n≥2.

13. A photo-coupled synergistically crosslinked hydrogel material made by the photo-coupled synergistically crosslinked method of claim 10.

14. The photo-coupled synergistically crosslinked hydrogel material of claim 13, wherein the photo-coupled synergistically crosslinked hydrogel material is:
  a component of a skin repair material or medicine, or
  a component of a postoperative anti-adhesion material or medicine, or
  a component of a postoperative wound closure-oral ulcer material or medicine, or
  a component of an enteric leakage sealant material or medicine, or
  a component of a tissue fluid leakage-surgical suture material or medicine, or
  a component of a liver hemostatic material or medicine, or
  a component of a hemostasis of bone fracture material or medicine, or
  a component of an arterial hemostatic material or medicine, or
  a component of a heart hemostatic material or medicine, or
  a component of a cartilage repair material or medicine, or
  a component of a bone repair material or medicine, or
  a component of a bone/cartilage composite defect repair material or medicine, or
  a component of a bio-ink for 3D, or
  a component of cell, protein, and drug carriers.

15. A kit for preparing a photo-coupled synergistically crosslinked hydrogel material, comprising component A and instructions for preparation and application of the photo-coupled synergistically crosslinked hydrogel,
  the component A includes a polymer derivative having an o-nitrobenzyl phototrigger selected from the group consisting of a polymer derivative having the structure of Formula A-I, a polymer derivative having the structure of Formula A-II, and a polymer derivative having the structure of Formula A-III, Formula A-I

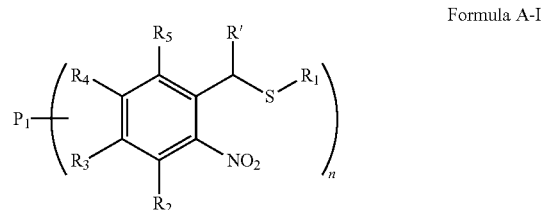

Formula A-II

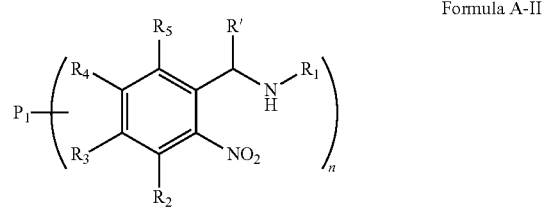

Formula A-III

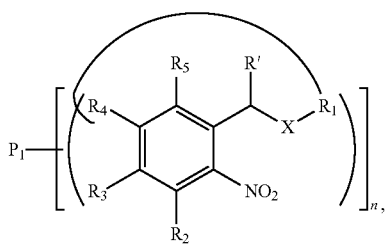

where, in the Formula A-I, A-II, and A-III, R' is selected from the group consisting of a hydrogen atom, a halogen atom, a hydroxyl group, a sulfhydryl group, an amine group, a nitro group, a cyano group, an aldehyde group, a ketone group, an ester group, an amide group, a phosphonic acid group, a phosphonate group, a sulfonic group, a sulfonate group, a sulfone group, a sulfoxide group, an aryl group, a heteroaryl group, an alkyl group, an alkylene group, a modified alkyl group, and a modified alkylene group, in the Formula A-I, A-II and A-III, $R_1$ is selected from the group consisting of a hydrogen atom, an ether group, an ester group, a carbonate group, a urethane group, a mercapto formate group, and a phosphate group, in the Formula A-I, A-II and A-III, $R_2$, $R_3$, $R_4$, and $R_5$ each independently includes one selected from the group consisting of a hydrogen atom, a halogen atom, a hydroxyl group, a sulfhydryl group, an amine group, a nitro group, a cyano group, an aldehyde group, a ketone group, an ester group, an amide group, a phosphonic acid group, a phosphonate group, a sulfonic group, a sulfonate group, a sulfone group, a sulfoxide group, an aryl group, a heteroaryl group, an alkyl group, an alkylene group, a modified alkyl group, and a modified alkylene group, in the Formula A-I, A-II, and A-III, $n \geq 2$, in the Formula A-I, A-II and A-III, $P_1$ includes one or more of hydrophilic or water-soluble natural polymers or synthetic polymers, in the Formula A-III, X is S or NH, $R_1$ is directly bonded to X, and $R_1$ is directly bonded to one of $R_2$, $R_3$, $R_4$, and $R_5$ to form a cyclic structure, in the Formula A-I, A-II, and A-III, two or more of $R_2$, $R_3$, $R_4$, and $R_5$ are connected to form a saturated or unsaturated alicyclic ring, alicyclic heterocycle, aromatic ring, or aromatic heterocycle, together with carbon atom(s).

16. The kit of claim 15, further comprising component B, wherein the component B includes one or more selected from the group consisting of: an amine group-containing polymer derivative, a double bond-containing polymer derivative, and a mercapto group-containing polymer derivative, the amine-containing polymer derivative includes at least one of a polymer derivative containing a primary amine group that has the structure of Formula B-I, polymer derivative containing a hydrazine group and has the structure of Formula B-II, a polymer derivative containing a hydrazide group and has the structure of Formula B-III, or a polymer derivative containing a hydroxylamine group and has the structure of Formula B-IV, the double bond-containing polymer derivative includes at least one of a polymer derivative containing a maleimide group and has the structure of Formula B-V, a polymer derivative containing a vinyl sulfone group and has the structure of Formula B-VI, or an polymer derivative containing a acrylate or acrylamide group and has the structure of Formula B-VII, the mercapto group-containing polymer derivative has the structure of Formula B-VIII, Formula B-I
$$P_2\text{—}(NH_2)_n,$$

Formula B-II
$$P_3\text{—}\left(\overset{H}{N}\text{—}NH_2\right)_n,$$

Formula B-III
$$P_4\left(\underset{}{\overset{O}{\underset{}{\bigwedge}}}\underset{H}{N}\text{—}NH_2\right)_n,$$

Formula B-IV
$$P_6\text{—}(O\text{—}NH_2)_n,$$

Formula B-V $$P_6\left(N\underset{O}{\overset{O}{\bigwedge}}\right)_n,$$

Formula B-VI $$P_7\left(\overset{O}{\underset{O}{\overset{\|}{S}}}\diagup\right)_n,$$

Formula B-VII $$P_8\left(\overset{O}{\bigwedge}\diagup\right)_n,$$

Formula B-VIII
$$P_9\text{—}(SH)_n,$$

where $n \geq 2$, $P_2$, $P_3$, $P_4$, $P_5$, $P_6$, $P_7$, $P_8$, and $P_9$ are hydrophilic or water-soluble natural polymers or synthetic polymers, the hydrophilic or water-soluble natural polymers are selected from the group consisting of natural polysaccharides, modifier or degradant of the natural polysaccharides, proteins, and modifiers or degradants of the proteins, the natural polysaccharides are selected from the group consisting of hyaluronic acid, carboxymethyl cellulose, methyl cellulose, hydroxyethyl cellulose, hydroxypropyl cellulose, alginate, dextran, agarose, heparin, chondroitin sulfate, glycol chitosan, propylene glycol chitosan, chitosan lactate, carboxymethyl chitosan, and quaternary ammonium salt of chitosan, the proteins are selected from the group consisting of hydrophilic or water-soluble animal and plant proteins, collagen, serum proteins, silk fibroin proteins and elastin, and protein degradations including gelatin or polypeptides, the hydrophilic or water-soluble synthetic polymers are two-arm or multi-arm poly (ethylene glycol), poly (ethylene imine), dendrites, synthetic peptides, polylysine, poly (glutamic acid), poly (acrylic acid), poly (methacrylic acid), polyacrylate, poly (methacrylate), poly (acrylamide), poly (methacrylamide), poly (vinyl alcohol), or poly (vinyl pyrrolidone), the Formula B-I is selected from the structures of the following Component B-1 to Component B-9, the Formula B-II is selected from the structures of Component B-10, the Formula B-III is selected from the following structures of Component B-11 to Component B-13, the Formula B-IV is selected from the following structures of Component B-14 and Component B-15, the Formula B-VI is selected from the structures of the following Component B-16 to Component B-18, the Formula B-VI is selected from the structures of the following Component B-19 to Component B-21, the Formula B-VII is selected from the structures of the following Component B-22 to Component B-29, the Formula B-VIII is selected from the structures of the following Component B-30 to Component B-35, Component B-1

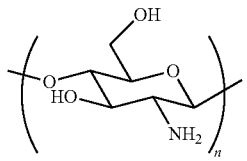

Component B-2

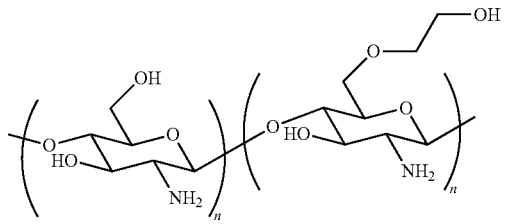

Component B-3

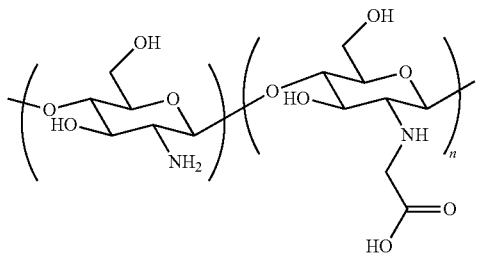

Component B-4

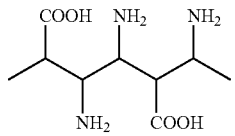

Component B-5

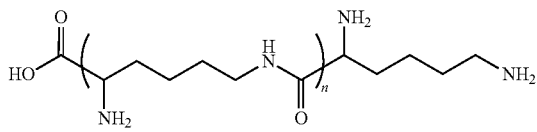

Component B-6

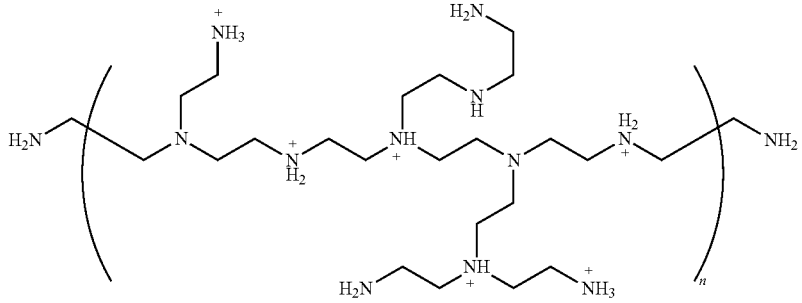

Component B-7

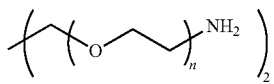

Component B-8

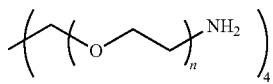

Component B-9

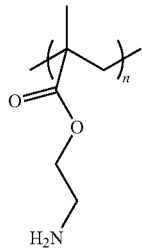

Component B-10

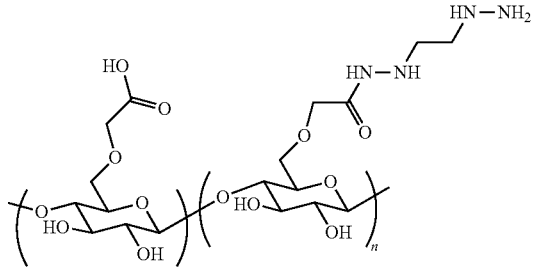

-continued
Component B-11
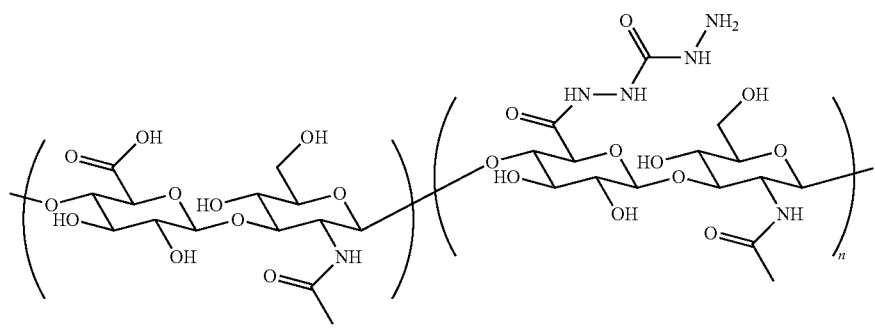
Component B-12
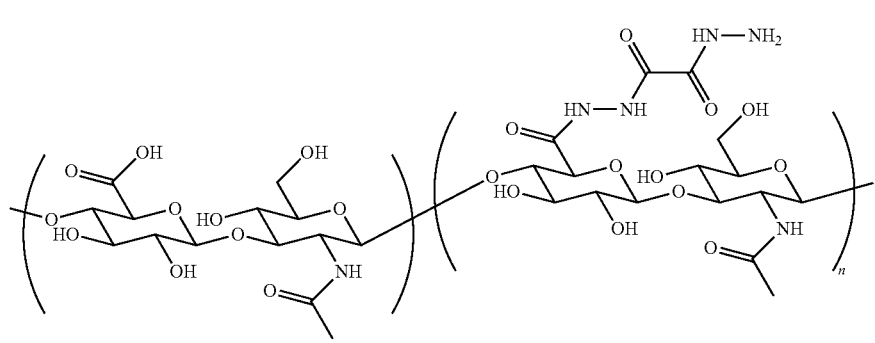
Component B-13
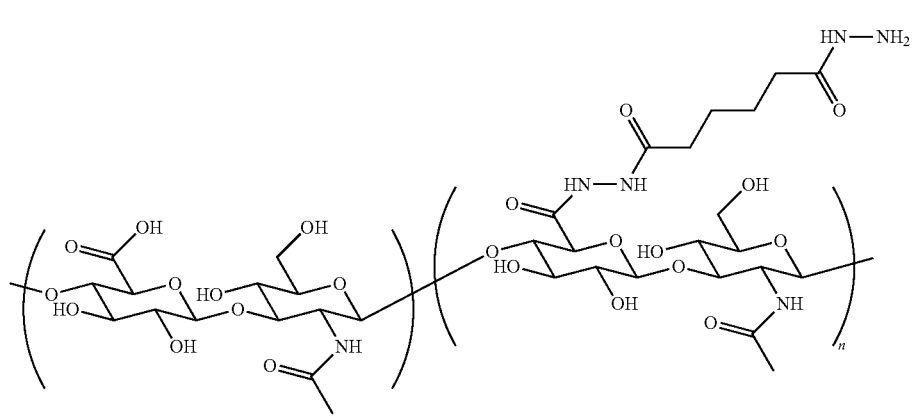
Component B-14
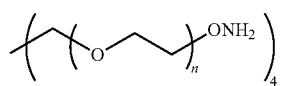
Component B-15
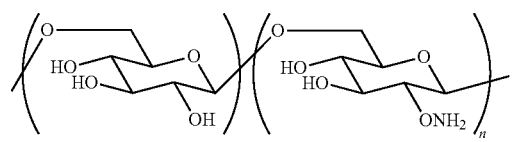
Component B-16
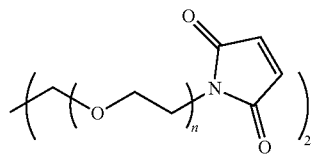
Component B-17
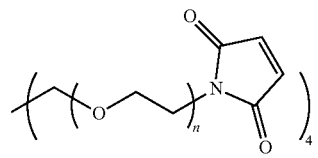

Component B-18
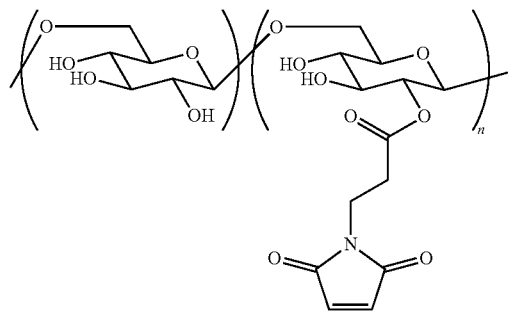
Component B-19
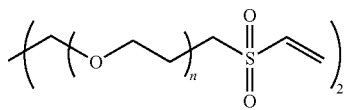
Component B-20
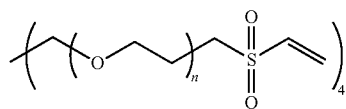
Component B-21
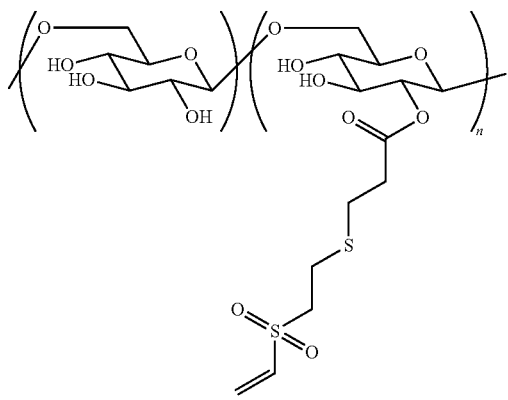
Component B-22
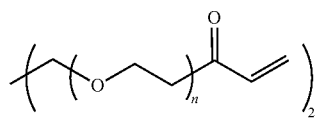
Component B-23
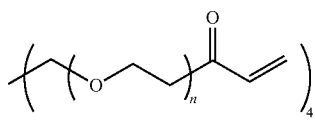
Component B-24
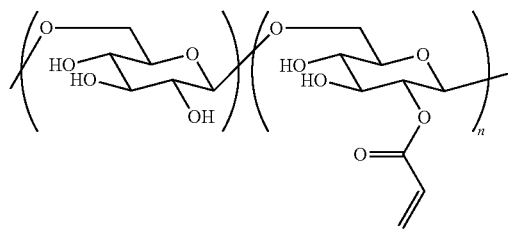
Component B-25
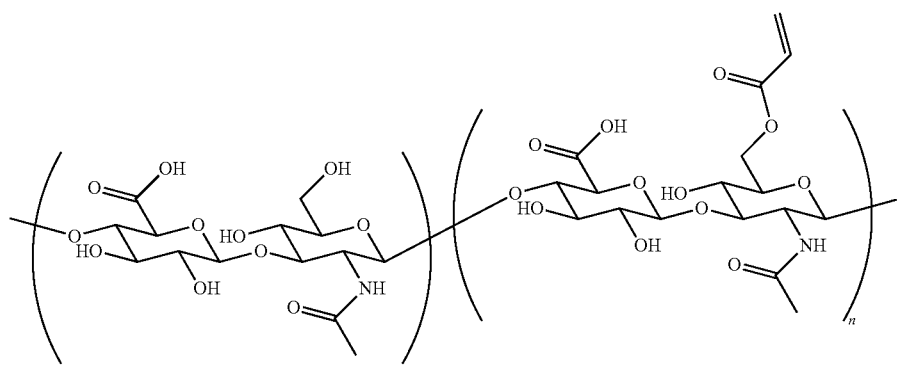

-continued
Component B-26
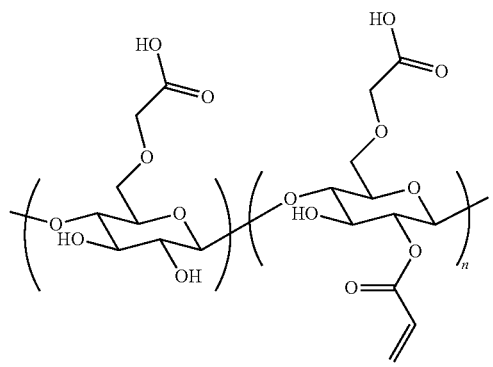
Component B-27
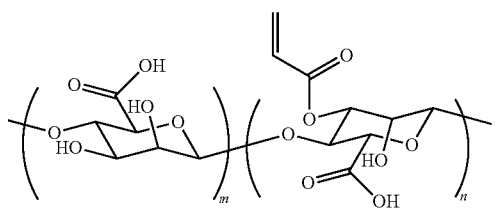
Component B-28
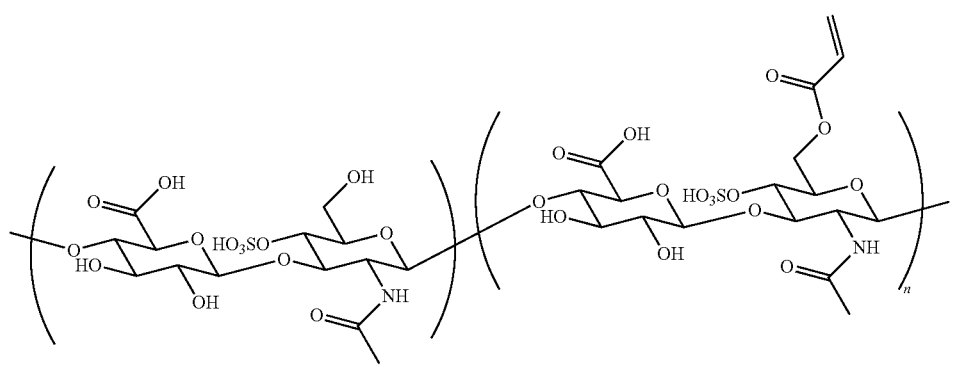
Component B-29
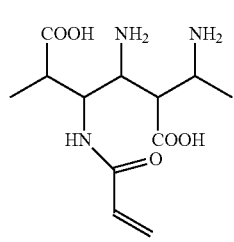
Component B-30
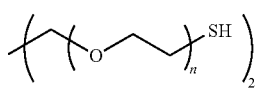
Component B-31
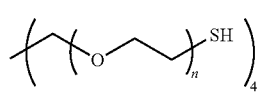
Component B-32
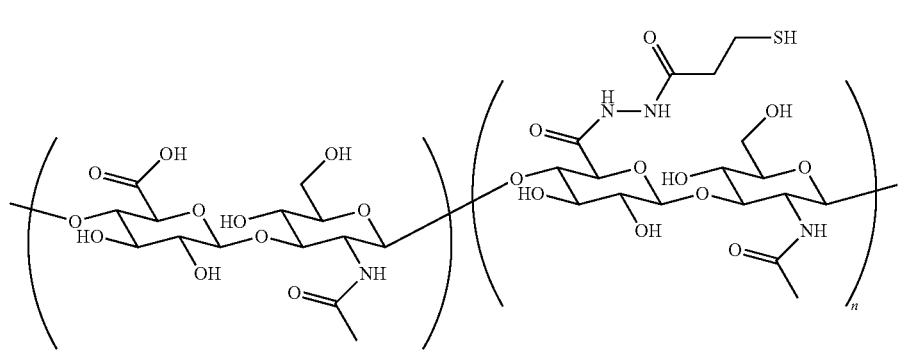

-continued
Component B-33
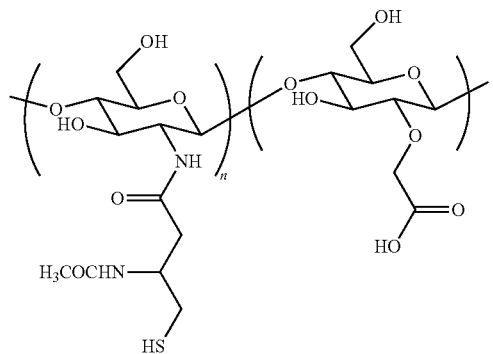
Component B-34
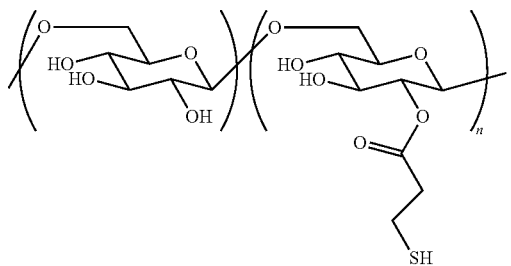
Component B-35
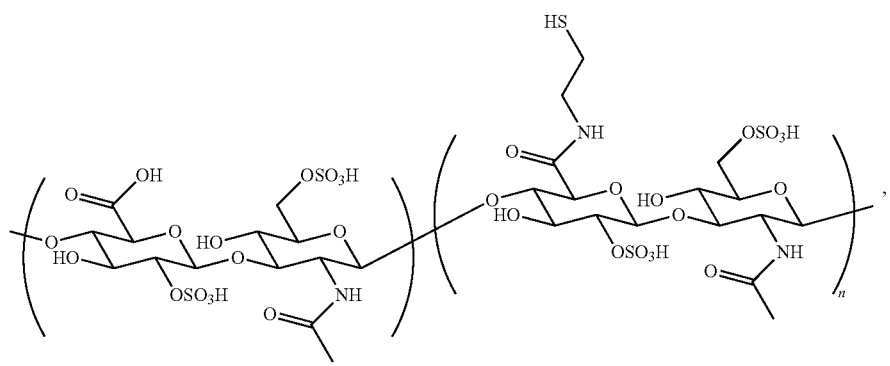
where n≥2.
* * * * *